US011527323B2

(12) United States Patent
Michuda et al.

(10) Patent No.: US 11,527,323 B2
(45) Date of Patent: Dec. 13, 2022

(54) SYSTEMS AND METHODS FOR MULTI-LABEL CANCER CLASSIFICATION

(71) Applicant: Tempus Labs, Inc., Chicago, IL (US)

(72) Inventors: Jackson Michuda, Chicago, IL (US); Kyle Ashley Beauchamp, San Mateo, CA (US); Joshuah Kapilivsky, Palo Alto, CA (US); Calvin McCarter, Chicago, IL (US); Nike Beaubier, Chicago, IL (US); Martin Christian Stumpe, Belmont, CA (US); Catherine Igartua, Chicago, IL (US); Joshua S K Bell, Chicago, IL (US); Timothy Taxter, Chicago, IL (US); Raphael Pelossof, New York, NY (US)

(73) Assignee: Tempus Labs, Inc., Chicago, IL (US)

( * ) Notice: Subject to any disclaimer, the term of this patent is extended or adjusted under 35 U.S.C. 154(b) by 0 days.

(21) Appl. No.: 15/930,234

(22) Filed: May 12, 2020

(65) Prior Publication Data
US 2020/0365268 A1 Nov. 19, 2020

Related U.S. Application Data

(60) Provisional application No. 62/983,488, filed on Feb. 28, 2020, provisional application No. 62/902,950, filed on Sep. 19, 2019, provisional application No. 62/855,750, filed on May 31, 2019, provisional application No. 62/847,859, filed on May 14, 2019.

(51) Int. Cl.
| | |
|---|---|
| *G16H 50/20* | (2018.01) |
| *G16B 20/10* | (2019.01) |
| *G16H 70/60* | (2018.01) |
| *G16H 10/40* | (2018.01) |
| *G16B 30/00* | (2019.01) |
| *G16B 20/00* | (2019.01) |

(52) U.S. Cl.
CPC ............. *G16H 50/20* (2018.01); *G16B 20/00* (2019.02); *G16B 20/10* (2019.02); *G16B 30/00* (2019.02); *G16H 10/40* (2018.01); *G16H 70/60* (2018.01)

(58) Field of Classification Search
CPC .................. G16B 20/00; G16B 20/10
See application file for complete search history.

(56) References Cited

U.S. PATENT DOCUMENTS

| | | | |
|---|---|---|---|
| 7,747,547 B1 | 6/2010 | Buturovic et al. | |
| 8,321,137 B2 | 11/2012 | Tran et al. | |
| 8,473,217 B1 | 6/2013 | Buturovic et al. | |
| 8,977,506 B2 | 3/2015 | Anderson | |
| 9,670,530 B2 | 6/2017 | Kostem et al. | |
| 10,295,540 B1 | 5/2019 | Buturovic et al. | |
| 2005/0071087 A1 | 3/2005 | Anderson | |
| 2014/0045915 A1* | 2/2014 | Skog | C12Q 1/6806 435/15 |
| 2015/0161327 A1 | 6/2015 | Anderson | |
| 2015/0294075 A1 | 10/2015 | Rinaldo | |
| 2015/0310163 A1 | 10/2015 | Kingsmore | |
| 2015/0329921 A1* | 11/2015 | Erlander | C12Q 1/6888 506/9 |
| 2018/0357372 A1 | 12/2018 | Bagaev et al. | |
| 2019/0018926 A1 | 1/2019 | Bloom et al. | |

OTHER PUBLICATIONS

Jalali et al., Interpretable per case weighted ensemble method for cancer associations, 2016, BMC Genomics, 17:501, p. 1-10 (Year: 2016).*
Pirih et al., Toward a Taxonomy for Multi-Omics Science? Terminology Development for Whole Genome Study Approaches by Omics Technology and Hierarchy, 2017, OMICS a journal of Integrative Biology, 21(1), p. 1-16 (Year: 2017).*
Affymetrix, GeneChip Human Genome Arrays, 2004, p. 1-4 (Year: 2004).*
Sun et al., Identifying and Correcting Mislabeled Training Instances, 2007, Future Generation Communication and Networking, p. 1-7 (Year: 2007).*
Rolston et al., Distinguishing de Novo Second Cancer Formation from Tumor Recurrence, 2001, Journal of Molecular Diagnostics, 3(4), p. 129-132 (Year: 2001).*
Kim et al., Synergistic effect of different levels of genomic data for cancer clinical outcome prediction, 2012, Journal of Biomedical Informatics, 45, p. 1191-1198 (Year: 2012).*
Chakraborty et al., Onco-Multi-OMICS Approach: A New Frontier in Cancer Research, BioMed Research International, 2018, p. 1-14 (Year: 2018).*
Tao et al., Classifying Breast Cancer Subtypes Using Multiple Kernel Learning Based on Omics Data, 2019, Genes, p. 1-14; (Year: 2019).*
Wang, Low-Coverage Whole Genome Sequencing: Learning from Less data, 2019, NIH, p. 1-15 (Year: 2019).*

(Continued)

*Primary Examiner* — Olivia M. Wise
*Assistant Examiner* — Kaitlyn L Minchella
(74) *Attorney, Agent, or Firm* — Morgan, Lewis & Bockius LLP

(57) ABSTRACT

Systems and methods are provided for identifying a diagnosis of a cancer condition for a somatic tumor specimen of a subject. The method receives sequencing information comprising analysis of a plurality of nucleic acids derived from the somatic tumor specimen. The method identifies a plurality of features from the sequencing information, including two or more of RNA, DNA, RNA splicing, viral, and copy number features. The method provides a first subset of features and a second subset of features from the identified plurality of features as inputs to a first classifier and a second classifier, respectively. The method generates, from two or more classifiers, two or more predictions of cancer condition based at least in part on the identified plurality of features. The method combines, at a final classifier, the two or more predictions to identify the diagnosis of the cancer condition for the somatic tumor specimen of the subject.

8 Claims, 49 Drawing Sheets
(27 of 49 Drawing Sheet(s) Filed in Color)

(56) References Cited

OTHER PUBLICATIONS

Chittenden, Statistical Classification of High-throughput Multi-omics Cancer data on Quantum Computing Architectures, 2019, WuXiNextCODE, p. 1-43 (Year: 2019).*

Healthcare Professionals "A Widely Adopted Molecular Test for Metastatic Patients with Poorly Differentiated Carcinomas and Cancer of Unknown Primary", pp. 1-2.

Healthcare Professionals "Identifying Tumor Origin with CancerTYPE ID", Biotheranostics, Inc., San Diego, CA, pp. 1-2.

Abstract for Abraham, Amy B., et al "Machine learning algorithm analysis using a commercial 592-gene NGS panel to accurately predict tumor lineage for carcinoma of unknown primary (CUP).", ASCO Meeting Library, 2019, 1 page.

Amar, David, et al. "Integrated analysis of numerous heterogeneous gene expression profiles for detecting robust disease-specific biomarkers and proposing drug targets", Aug. 10, Nucleic Acids Research, 2015, vol. 43, No. 16, pp. 7779-7789.

Bloom, Greg, et al. "Multi-Platform, Multi-Site, Microarray-Based Human Tumor Classification", American Journal of Pathology, vol. 164, No. 1, Jan. 2004, pp. 9-16.

Conway, Alicia-Marie, et al. "Molecular characterisation and liquid biomarkers in Carcinoma of Unknown Primary (CUP): taking the 'U' out of 'CUP'", Springer nature on behalf of British Journal Cancer, 2018, pp. 141-153.

Erlander, Mark G., et al. "Performance and Clinical Evaluation of the 92-Gene Real-Time PCR Assay for Tumor Classification", The Journal of Molecular Diagnostics, vol. 13, No. 5, Sep. 2011, pp. 493-503.

Flynn, Wiliam F., et al. "Pan-cancer machine learning predictors of primary site of origin and molecular subtype", bioRxiv preprint, https://doi.org/10.1101/333914, pp. 1-38.

Grewal, Jasleen K., et al. "Application of a Neural Network Whole Transcriptome-Based Pan-Cancer Method for Diagnosis of Primary and Metastatic Cancers", JAMA Network|Open, Apr. 26, 2019, pp. 1-15.

Haigis, Kevin M., et al. "Tissue-specificity in cancer: The rule, not the exception", Science, vol. 363, Issue 6432, Mar. 15, 2019, pp. 1150-1151.

Hartman, Anne-Renee, et al. "Simultaneous Multi-cancer Detection and Tissue of Origin (TOO) Localization Using Targeted Bisulfite Sequencing of Plasma Cell-free DNA (cfDNA)", 2020, GRAIL, Inc., Menlo Park, CA, p. 1.

Jaskowiak, Pablo Andretta, et al. "Clustering of RNA-Seq samples: Comparison study on cancer data", Elsevier, vol. 132, Jan. 2018, pp. 42-49.

Kerr, Sarah E., et al. "Multisite Validation Study to Determine Performance Characteristics of a 92-Gene Molecular Cancer Classifier", 2012, Clinical Cancer Research, pp. 3952-3960.

Kolesov, Anton, et al. "On Multilabel Classification Methods of Incompletely Labeled Biomedical Text Data", Computational and Mathematical Methods in Medicine, Jan. 23, 2014, pp. 1-11.

Liu, Minetta C., et al. "Genome-wide Cell-free DNA (cfDNA) Methylation Signatures and Effect on Tissue of Origin (TOO) Performance" Jun. 1, 2019, ASCO, p. 1.

Ma, Xiao-Jun, et al. "Molecular Classification of Human Cancers Using a 92-Gene Real-Time Quantitative Polymerase Chain Reaction Assay", Arch Pathol Lab Med—vol. 130, Apr. 2006, pp. 465-473.

Mobadersany, Pooya, et al. "Predicting cancer outcomes from histology and genomics using convolutional networks", PNAS, 2018, vol. 115, No. 13, pp. 2970-2979.

Oxnard, Geoffrey R., et al. "Simultaneous multi-cancer detection and tissue of origin (TOO) localization using targeted bisulfite sequencing of plasma cellfree DNA (cfDNA)" ASCO, Oct. 11, 2019, pp. 1-11.

Pakrashi, Arjun, et al. "Benchmarking Multi-label Classification Algorithms", Insight Centre for Data Analytics, University College Dublin, Ireland, p. 12.

Penson, Alexander, et al. "Development of Genome-Derived Tumor Type Prediction to Inform Clinical Cancer Care", JAMA Oncology, 2020; 6(1), pp. 84-91.

Soh, Kee Pang, et al. "Predicting cancer type from tumour DNA signatures", Genome Medicine, Nov. 28, 2017, pp. 1-11.

Stella, Giulia Maria, et al. "Cancers of unknown primary origin: current perspectives and future therapeutic strategies", Journal of Translational Medicine, 2012, pp. 1-11.

Sveen, Anita, et al. "Colorectal Cancer Consensus Molecular Subtypes Translated to Preclinical Models Uncover Potentially Targetable Cancer Cell Dependencies", Clinical Cancer Research, 24(4), Feb. 15, 2018, pp. 794-806.

Tao, Mingxin, et al. "Classifying Breast Cancer Subtypes Using Multiple Kernel Learning Based on Omics Data", Genes, 2019, 10, pp. 1-14.

Tschentscher, Frank, et al. "Tumor Classification Based on Gene Expression Profiling Shows That Uveal Melanomas with and without Monosomy 3 Represent Two Distinct Entities[1]", Cancer Research, 63, May 15, 2003, pp. 2578-2584.

Thiel, David D., et al. Abstract CT021: "Prediction of Cancer and Tissue of Origin in Individuals with Suspicion of Cancer Using a Cell-Free DNA Multi-Cancer Early Detection Test", Cancer Research, Aug. 2020, pp. 1-3.

Varadhachary, Gauri R., "Carcinoma of Unknown Primary Origin", www.myGCRonline.org, 2006/2007, vol. 1, Issue 6, pp. 229-235.

Young, Andrew N., et al. "A Method for Tumor Classification and Discovery of Diagnostic Molecular Markers", American Journal of Pathology, vol. 158, No. 5, May 2001, pp. 1639-1651.

Zhang, Min-Ling, et al. "ML-KNN: A Lazy Learning Approach to Multi-Label Learning", National Laboratory for Novel Software Technology, Nanjing University, Nanjing, China, pp. 1, 21.

Zhao, Qing, et al. "Combining multidimensional genomic measurements for predicting cancer prognosis: observations from TCGA", Briefings in Bioinformatics, vol. 16, No. 2, Mar. 13, 2014, pp. 291-303.

Yoshihara, Kosuke, et al. "Inferring tumour purity and stromal and immune cell admixture from expression data", Nature Communications, DOI: 10.1038/ncomms3612, Jul. 12, 2013, pp. 11.

Lee A. Albacker, et al. "DNA-based genomic profiling forclassification of tissue of origin forpatients with carcinoma ofunknown primary site", Abstract, Journal of Clinical Oncology, vol. 34, Issue 15, pp. 3.

Tanya G.K. Bentley, et al. "Cost effectiveness of a 92-gene assay for the diagnosis of metastatic cancer", Journal of Medical Economics, 2014, Article 0010.R1/909817, pp. 1-11.

Catherine I. Dumur, Ph.D., et al. "Clinical Verification ofthe Performance ofthe Pathwork Tissue of Origin Test", Anatomic Pathology / Utility of a Test ofr Tissue of Origin, American Society for Clinical Pathology, 2011, 136, pp. 924-933.

K. Fizazi, et al. "Cancers of unknown primary site: ESMO Clinical Practice Guidelines for diagnosis, treatment and follow-up", Annals of Oncology 26 (Supplement 5): pages: v133-v138, 2015.

John D. Hainsworth, et al. "Molecular Gene Expression Profiling to Predict the Tissue of Origin and Direct Site-Specific Therapy in Patients With Carcinoma of Unknown Primary Site: A Prospective Trial of the Sarah Cannon Research Institute", Journal of Clinical Oncology, vol. 31, No. 2, Jan. 10, 2013, pp. 217-223.

Charles R. Handorf, et al. "A Multicenter Study Directly Comparing the Diagnostic Accuracy of Gene Expression Profiling and Immunohistochemistry for Primary Site Identification in Metastatic Tumors", Am J Surg Pathol. Jul. 2013, 37(7): 1067-1075, pp. 1-18.

Federico A. Monzon, et al. "Multicenter Validation of a 1,550-Gene Expression Profile for Identification of Tumor Tissue of Origin", Journal of Clinical Oncology, vol. 27, No. 15, May 20, 2009, pp. 2503-2508.

Panagiota Economopoulou, et al. "Cancer of Unknown Primary Origin in the Genomic Era: Elucidating the dark box of cancer", Medical Oncology Unit/Dpt., Greece, pp. 1-19.

Vinita Parkash, MD, et al. "The Pathwork Tissue of Origin Test", American Society for Clinical Pathology, 2012, 138, 165-166.

(56) References Cited

OTHER PUBLICATIONS

Raji Pillai, et al. "Validation and Reproducibility of a Microarray-Based Gene Expression Test forTumor Identification in Formalin-Fixed, Paraffin-Embedded Specimens", The Journal of Molecular Diagnostics, vol. 13, No. 1, Jan. 2011, pp. 48-56.

Fernandez, Agustin F., et al. "A DNA methylation fingerprint of 1628 human samples", Cold Spring Harbor Laboratory Press, 2012, 22, pp. 407-419.

Hainsworth, John D., et al. "A Retrospective Study of Treatment Outcomes in Patients With Carcinoma of Unknown Primary Site and a Colorectal Cancer Molecular Profile", Clinical Colorectal Cancer, vol. 11, No. 2, Jun. 2012, pp. 112-118.

Horlings, Hugo M., et al. "Gene Expression Profiling to Identify the Histogenetic Origin of Metastatic Adenocarcinomas of Unknown Primary", Journal of Clinical Oncology, vol. 26, No. 27, Sep. 20, 2008, pp. 4435-4441.

Moran, Sebastian, et al. "Epigenetic profiling to classify cancer of unknown primary: a multicentre, retrospective analysis", Lancet Oncol, vol. 17, Oct. 2016, pp. 1386-1395.

Pentheroudakis, George, et al. "Novel microRNA-based assay demonstrates 92% agreement with diagnosis based on clinicopathologic and management data in a cohort of patients with carcinoma of unknown primary", Molecular Cancer, 2013, 12, pp. 1-8.

Tothill, Richard W., et al. "Development and validation of a gene expression tumour classifier for cancer of unknown primary", Anatomical Pathology, Jan. 2015, 47(1), pp. 7-12.

Varadhachary, Gauri R., et al. "Molecular Profiling of Carcinoma of Unknown Primary and Correlation With Clinical Evaluation", Journal of Clinical Oncology, vol. 26, No. 27, Sep. 20, 2008, pp. 4442-4448.

Varadhachary, Gauri R., et al. "Prospective Gene Signature Study Using microRNA to Identify the Tissue of Origin in Patients with Carcinoma of Unknown Primary", Clinical Cancer Research, Apr. 29, 2011, 17, pp. 4063-4070.

Yoon, H.H., et al. "Gene expression profiling identifies responsive patients with cancer of unknown primary treated with carboplatin, paclitaxel, and everolimus: NCCTG N0871 (alliance)", Annals of Oncology, 27, 2016, pp. 339-344.

Bray et al., Near-optimal probabilistic RNA-seq quantification, 2016, Nature Biotechnology, 34(5), p. 525-527 (Year: 2016).

Davicioni et al., Diagnostic and Prognostic Sarcoma Signatures, 2008, Mol Diag. Ther., 12(6), p. 359-374 (Year: 2008).

Thompson et al., Cross-platform normalization of microarray and RNA-seq data for machine learning applications, 2016, PeerJ, 4: e16121, p. 1-19 (Year: 2016).

Zhao et al., Comparison of RNA-Seq by poly(A) capture, ribosomal RNA depletion, and DNA microarray for expression profiling, 2014, BMC Genomics, 15:419, p. 1-11 (Year: 2014).

Losa, F. et al. "SEOM clinical guideline on unknown primary cancer (2017)", Clin Transl Oncol (2018) 20, pp. 89-96.

Qaseem, Aisha et al. "Cancer of Unknown Primary: A Review on Clinical Guidelines in the Development and Targeted Management of Patients with the Unknown Primary Site", Cureus, 11(9), Sep. 2, 2019, pp. 9.

* cited by examiner

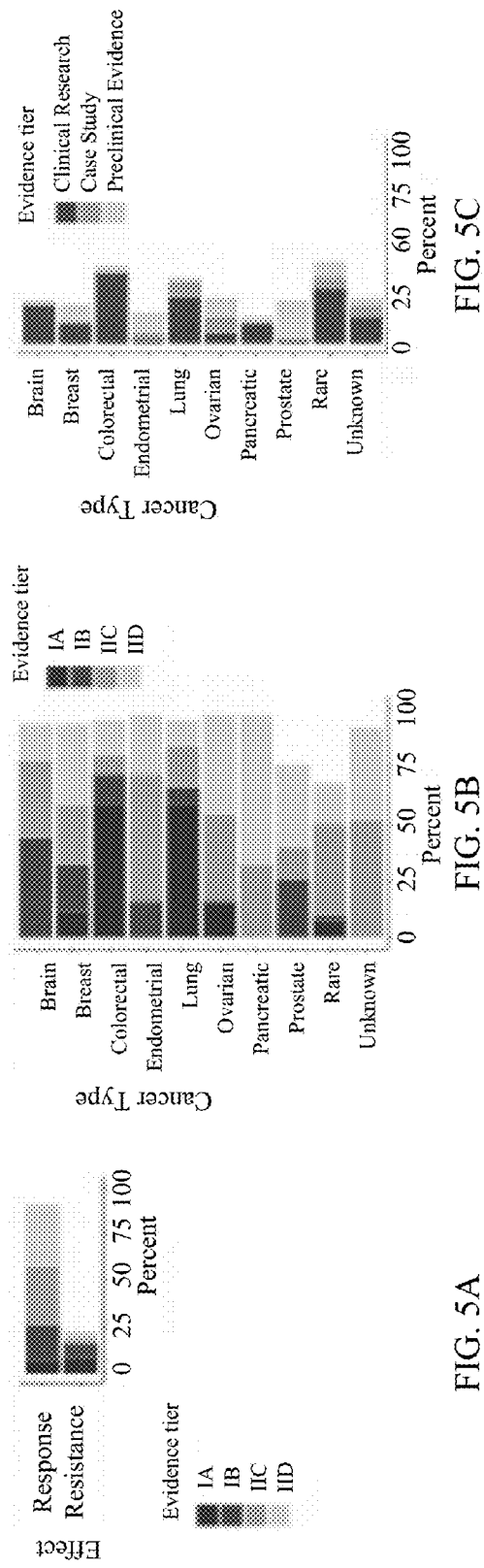
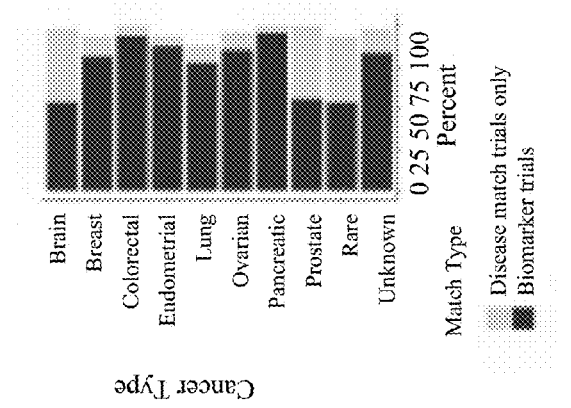
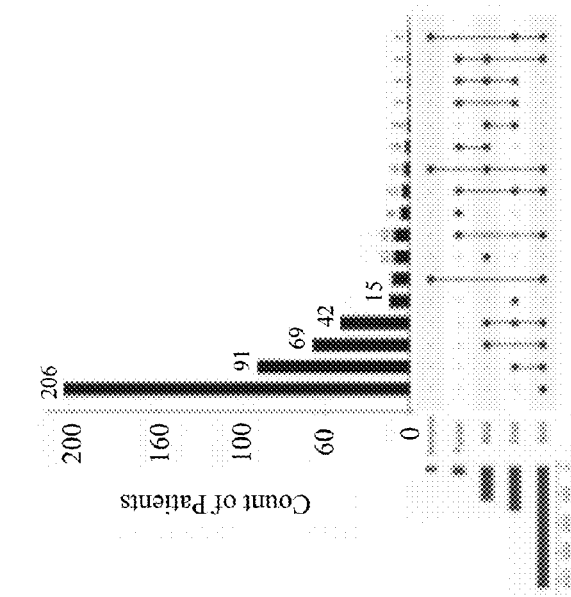
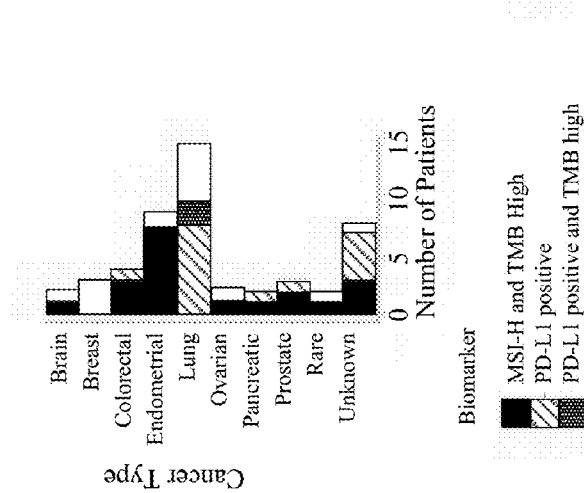
FIG. 5A  FIG. 5B  FIG. 5C  FIG. 5D  FIG. 5E  FIG. 5F Predicted Tumor

1016

TREATMENT IMPLICATIONS

WEE1 Inhibitor (AZD1775)　　　　TP53 p.R267P Loss-of-function
*Investigational drug*　　　　　　　　Clinical research, solid tumors: PMID 27601554

HDAC Inhibitors (Entinostat, Trichostatin)　　RB1 p.R7fs Loss-of-function
*Investigational drug*　　　　　　　　Preclinical, retinoblastoma: PMID 18983373

MDM2/MDMX Inhibitor (Nutlin-3a)　　RB1 p.R7fs Loss-of-function
*Investigational drug*　　　　　　　　Preclinical, retinoblastoma: PMID 21515735

1018

CLINICAL TRIALS

| Study | Details | |
|---|---|---|
| Study of COTI-2 as Monotherapy or Combination Therapy for the Treatment of Malignancies (NCT02433626) | Phase I<br>Houston, TX - 215 mi<br>✓ TP53 mutation | 1019-1 |
| OLAParib COmbinations (NCT02576444) | Phase II<br>Cleveland, OH - 914 mi<br>✓ TP53 mutation | 1019-2 |
| A Study of LY2606368 (Prexasertib) in Patients With Solid Tumors With Replicative Stress or Homologous Repair Deficiency (NCT02873975) | Phase II<br>Boston, MA - 1414 mi<br>✓ RB1 mutation | 1019-3 |

1020

VARIANTS OF UNKNOWN SIGNIFICANCE

| Somatic | Mutation effect | Variant allele fraction |
|---|---|---|
| RPS15 | c.345G>A p.K115K Splice region variant<br>NM_001308226 | 42.0% |
| MYCN | c.221C>A p.P74H Missense variant<br>NM_005378 | 39.5% |
| NRG1 | c.1165C>A p.P389T Missense variant<br>NM_013956 | 38.1% |
| AMER1 | c.2906G>T p.G969V Missense variant<br>NM_152424 | 35.8% |
| GRIN2A | c.4325C>A p.P1442H Missense variant<br>NM_001134407 | 35.1% |
| ATRX | c.5643A>T p.R1881S Missense variant<br>NM_000489 | 34.4% |
| TERT | c.-410C>G Variant<br>NM_198253 | 33.3% |
| NOTCH1 | c.6389G>T p.G2130V Missense variant<br>NM_017617 | 30.5% |
| KIT | c.1230T>C p.N410N Splice region variant<br>NM_000222 | 30.2% |
| TP63 | c.995G>T p.G332V Splice region variant<br>NM_003722 | 28.8% |

FIG. 10C

SOMATIC VARIANT DETAILS - POTENTIALLY ACTIONABLE ⌒1022

🔴 TP53  c.800_801delGGinsCT  p.R267P  NM_000546  Missense variant - LOF   VAF: 34.5%

TP53 encodes a tumor suppressor that is commonly disabled across cancer types. It normally functions to activate cellular DNA repair mechanisms, plays a role in cell cycle progression in response to DNA damage, and can initiate apoptosis. Loss of function mutations, copy number loss, and epigenetic modifications resulting in underexpression of TP53 are associated with cancer progression.

🔴 RB1  c.1944delC  p.R775fs  NM_000321  Frameshift - LOF   VAF: 20.8%

RB1 encodes the protein pRb that regulates E2F activity in the RB1/E2F pathway, a pathway responsible for the transition from the G1 to the S phase in the cell cycle. Loss of function mutations, copy number loss, epigenetic variation, and underexpression of RB1 are associated with cancer progression.

SOMATIC VARIANT DETAILS - BIOLOGICALLY RELEVANT ⌒1024

⚪ KEAP1  c.1224delC  p.M409fs  NM_012289  Frameshift - LOF   VAF: 37.5%

KEAP1 encodes a protein that interacts with NF-E2 related factor 2 in a redox-sensitive manner and functions to transport it to the nucleus of the cell. Loss of function mutations and copy number loss of KEAP1 are associated with cancer progression.

⚪ TBX3  c.739A>T  p.K247*  NM_016569  Stop gain - LOF   VAF: 21.5%

TBX3 encodes a T-box transcription factor. T-box genes are involved in the regulation of developmental processes, and TBX3 is thought to play a crucial role in anterior/posterior axial development. Loss of function mutations, copy number loss, and overexpression of TBX3 are associated with cancer progression.

⚪ ZFHX3  c.1904G>T  p.E502*  NM_006885  Stop gain - LOF   VAF: 13.5%

ZFHX3 encodes a transcription factor that regulates myogenic and neuronal differentiation and suppresses expression of alpha-fetoprotein. Loss of function mutations and copy number loss of ZFHX3 are associated with cancer progression.

⚪ PRKN  c.81C>A  NM_004562  Splice region variant - LOF   VAF: 11.7%

PRKN encodes a subunit of the E3 ubiquitin ligase complex, a complex that functions in targeting proteins in need of proteasomal degradation. Loss of function mutations and copy number loss of PRKN are associated with cancer progression.

FIG. 10D

Error rate as a function of maximum prediction probability
Tumor of Known Origin

SYSTEMS AND METHODS FOR MULTI-LABEL CANCER CLASSIFICATION

CROSS REFERENCE TO RELATED APPLICATIONS

The present application is related to and claims priority to U.S. Provisional Patent Application No. 62/983,488, filed Feb. 28, 2020, entitled "Systems and Methods for Multi-Label Cancer Classification," which is hereby incorporated by reference in its entirety.

The present application is related to and claims priority to U.S. Provisional Patent Application No. 62/855,750, filed on May 31, 2019, entitled "Systems and Methods for Multi-Label Cancer Classification," which is hereby incorporated by reference in its entirety.

The present application is related to and claims priority to U.S. Provisional Patent Application No. 62/847,859, filed on May 14, 2019, entitled "Systems and Methods for Multi-Label Cancer Classification," which is hereby incorporated by reference in its entirety.

The present application is related to and claims priority to U.S. Provisional Patent Application No. 62/902,950, filed on Sep. 19, 2019, entitled "System and Method for Expanding Clinical Options for Cancer Patients using Integrated Genomic Profiling", which is hereby incorporated by reference in its entirety.

INCORPORATION BY REFERENCE OF TABLES SUBMITTED AS TEXT FILE VIA EFS-WEB

The instant application contains a Table 2 which has been submitted as a computer readable text file in ASCII format via EFS-Web and is hereby incorporated by reference in its entirety herein. Said text file, created on May 3, 2019, is entitled TABLE-2-List-of-Genes.txt and is 144 kilobytes in size.

LENGTHY TABLES

The patent contains a lengthy table section. A copy of the table is available in electronic form from the USPTO web site (https://seqdata.uspto.gov/?pageRequest=docDetail&DocID=US11527323B2). An electronic copy of the table will also be available from the USPTO upon request and payment of the fee set forth in 37 CFR 1.19(b)(3).

TECHNICAL FIELD

The present disclosure relates generally to using nucleic acid sequencing data from cancerous tissue and pathology reports to classify patients in regards to cancer condition.

BACKGROUND

With the current advances in targeted cancer therapies, it is becoming ever more useful to determine the mutational and transcriptional status of tumors when determining patient care.

Molecular targeted therapy, including immunotherapy, is already providing improved treatment options for cancer patients. To take advantage of these advances, patients must have broad molecular tumor profiling so that optimal, personalized treatments can be selected. See Kumar-Sinha et al. 2018 Nat. Biotechnol. 36, 46-60. Therapy targeted to specific molecular alterations is already standard of care in several tumor types (e.g., as suggested in the National Comprehensive Cancer Network (NCCN) guidelines for melanoma, colorectal cancer, and non-small cell lung cancer). These few, well known mutations in the NCCN guidelines can be addressed with individual assays or small next generation sequencing (NGS) panels. However, for the largest number of patients to benefit from personalized oncology, molecular alterations that can be targeted with off-label drug indications, combination therapy, or tissue agnostic immunotherapy should be assessed. See Schwaederle et al. 2016 JAMA Oncol. 2, 1452-1459; Schwaederle et al. 2015 J Clin Oncol. 32, 3817-3825; and Wheler et al. 2016 Cancer Res. 76, 3690-3701. Large panel NGS assays also cast a wider net for clinical trial enrollment. See Coyne et al. 2017 Curr. Probl. Cancer 41, 182-193; and Markman 2017 Oncology 31, 158,168.

Genomic analysis of tumors is rapidly becoming routine clinical practice to provide tailored patient treatments and improve outcomes. See Fernandes et al. 2017 Clinics 72, 588-594. Indeed, recent studies indicate that clinical care is guided by NGS assay results for 30-40% of patients receiving such testing. See Hirshfield et al. 2016 Oncologist 21, 1315-1325; Groisberg et al. 2017 Oncotarget 8, 39254-39267; Ross et al. JAMA Oncol. 1, 40-49; and Ross et al. 2015 Arch. Pathol. Lab Med. 139, 642-649. There is growing evidence that patients who receive therapeutic advice guided by genetics have better outcomes. See, for example Wheler et al. who used matching scores (e.g., scores based on the number of therapeutic associations and genomic aberrations per patient) to demonstrate that patients with higher matching scores have a greater frequency of stable disease, longer time to treatment failure, and greater overall survival (2016 Cancer Res. 76, 3690-3701). Such methods may be particularly useful for patients who have already failed multiple lines of therapy.

Genomic analysis may include differing genes as the knowledge and accepted practice within the field of genomic sequencing advances. The NCBI publishes a listing of genes which are accepted and held out as part of the human genome based upon the best evidence at the time in the NCBI Genebank. Each new iteration of the NCBI Genebank includes removals and additions to the gene list. Removals may include replacing, withdrawing, or discontinuing genes which were once held out as part of the human genome, but later found to be discarded regions of nucleotides which are not coding genes for any gene function. As is true for most molecular biology databases, the records are a work in progress and are subject to change as scientists learn more about the genes. For example, some gene records are generated as a result of gene prediction during analysis of an organism's genome. The sequence data and/or gene prediction algorithm may change over time. That is, if new data are added in a subsequent genome build or refinements are made to the gene prediction software, some records might be discontinued. Other records, particularly those for known genes, persist from one genome build to another, but the information in the record will continue to be updated as new knowledge is acquired. What is needed is a method for identifying new genes and/or deidentifying withdrawn or discontinued genes when these advances in understanding the human genome are made from the original NGS results. For example, gene CYorf15A was replaced with gene TXLNGY (Taxilin Gamma Pseudogene, Y-Linked), and gene LOC388416 and gene LOC400951 were discontinued because new models did not predict a gene at the previously identified locations. Current NGS sequencing may not target discontinued regions as they are not currently held out in the sequencing community as predictive of a gene coding region.

Targeted therapies have shown significant improvements in patient outcomes, especially in terms of progression-free survival. See Radovich et al. 2016 *Oncotarget* 7, 56491-56500. Further, recent evidence reported from the IMPACT trial, which involved genetic testing of advanced stage tumors from 3,743 patients and where approximately 19% of patients received matched targeted therapies based on their tumor biology, showed a response rate of 16.2% in patients with matched treatments versus 5.2% in patients with non-matched treatments. See Bankhead. "IMPACT Trial: Support for Targeted Cancer Tx Approaches." *MedPageToday*. Jun. 5, 2018, available online at medpagetoday.com/meetingcoverage/asco/73291. The IMPACT study further found that the three-year overall survival for patients given a molecularly matched therapy was more than twice that of non-matched patients (15% vs. 7%). See Id. and ASCO Post. "2018 ASCO: IMPACT Trial Matches Treatment to Genetic Changes in the Tumor to Improve Survival Across Multiple Cancer conditions." *The ASCO POST*. Jun. 6, 2018, available online at ascopost.com/News/58897. Estimates of the proportion of patients for whom genetic testing changes the trajectory of their care vary widely, from approximately 10% to more than 50%. See Fernandes et al. 2017 *Clinics* 72, 588-594.

However, despite the promise of matched targeted therapies, many patients still lack access to this type of care. For example, patients with tumors of unknown origin (e.g., metastatic tumors that remain unclassified even after physician analyses) cannot be provided with targeted treatments until the primary tumor location is identified. See e.g., Varadhachary 2007 *Gastrointest Cancer Res* 1(6): 229-235. Without information regarding the primary tumor, it is difficult to provide targeted therapies and improve patient outcomes. In some instances, cancer origin classification can be performed using RNA sequencing data (e.g., RNA-Seq), which uses gene expression to identify characteristics of a tumor and can provide additional information. Most of the work using RNA-seq or microarrays is limited to differentiating between a small set of cancers. See, for example, Bloom et al. 2004 *Am J Pathol.*, 164(1):9-16; Tschentscher et al., 2003 *Can. Res.*, 63(10), 2578-84; Young et al., 2001 *Am J Pathol.*, 158(5), 1639-51; and Brueffer et al. 2018 *JCO Precision Oncology* 2, 1-18. Further, it is not always possible to determine the origin of some tumors based solely on RNA sequencing data.

The use of incomplete and/or incorrect data in classifier training sets can result in the training of poorly performing classifiers, thus complicating the problem of determining tumor of origin. This is particularly problematic when using pathology results for training, validating, and/or implementing classifiers. Pathology reports can provide invaluable information for classifying tumor of origin. See e.g., Leong et al. 2011 *Pathobiology* 78, 99-114. However, unfortunately, there is no standardized scheme for sample annotation during pathology review that is uniformly followed by all pathologists. This results in the input of many unique values during pathological review, many of which may indicate the same diagnostic conclusion by different respective pathologists. Moreover, the information that is reported can differ from one pathology report to the next. For instance, typically each pathology report will include a subset of information about the disease, stage, grade, pathology, and histology of a sample. However, the type of information included will vary. Further, the absence of a classification or label in any field of the pathology report does not necessarily indicate that the classification or label does not apply to the sample but, rather, it may have been that the particular pathologist did not consider the classification or label relevant enough to include in the report. Beyond confusion in labeling, pathology diagnoses can also be incorrect. While the rate of misdiagnoses is not well known, any mistake in cancer diagnoses can have serious repercussions for patient health and survival. See e.g., Kantola et al 2001 *British Journal of General Practice* 51, 106-111; Herreros-Villanueva et al 2012 *World J Gastroenterol* 18(23), 2902-2908; Yang et al 2015 *Cancer* 121, 3113-3121; and Xie et al 2015 *Int J Clin Exp Med* 8(5), 6762-6772.

There are additional concerns about reliability and reproducibility of sequencing data used for predicting tumor of origin. Sample handling problems (e.g., such as mislabeling, swaps, etc.) are unfortunately prevalent in all laboratory settings. See e.g., Broman et al. 2015 *Genes, Genomes, Genetics* 5, 2177-2186; Toker et al. 2016 *F1000Research* 5, 2103; and Lynch et al. 2012 *PLos ONE* 7(8), e4185. Further, it can be difficult to distinguish sample issues from simple misdiagnoses (e.g., cases where sequencing results disagree with pathology data, thus legitimately calling the pathology data into question). Multiple sample quality control methods have been proposed (see Id and also Pengelly et al. 2013 *Genome Medicine* 5, 89), but ensuring accurate data provenance remains a significant issue in using sequencing data for cancer classification.

SUMMARY

Given the background above, improved systems and methods are needed for classifying cancers, particularly those of unknown origin, for example to improve access to personalized therapies. Advantageously, the present disclosure provides solutions to these and other shortcomings in the art. For instance, in some embodiments, the systems and methods described herein leverage multiple types of information from a cancer patient, including, RNA expression data, tumor genomic sequencing, somatic genomic sequencing, and/or pathology (including digital images of pathology slides having hematoxylin and eosin and/or immunohistochemistry staining), to improve upon difficult classification, such as tumor origin. Likewise, in some embodiments, the use of multiple types of data further facilitates multi-label classification, the output of which provides additional information from which personalized treatment decisions can be made. In combination, multiple data types provide supporting evidence in resolving a diagnosis and/or validating a classification model. In some embodiments, the methods and systems described herein use classification streams. Advantageously, these streams iteratively improve poor classifier performance caused by training with incomplete, inconsistent, and/or inaccurate training data, as is commonly found in pathology reports. A particular use of the methods and systems described herein is to determine tumor origins for patients with two or more coexisting cancer diagnoses, where knowing the correct cancer to treat can improve survival rates.

One aspect of the present disclosure provides a method for determining a set of cancer conditions for a subject. The method is performed at a computer system having one or more processors, and memory storing one or more programs for execution by the one or more processors. The method proceeds by obtaining, in electronic format, one or more data structures that collectively comprise a first plurality of sequence reads. The first plurality of sequence reads is obtained from a plurality of RNA molecules or derivatives of said plurality of RNA molecules (e.g., derivatives such as cDNA, or proteins). The plurality of RNA molecules is from a somatic biopsy obtained from the subject.

The method continues by determining from the first plurality of sequence reads, a first set of sequence features for the subject. At least the first set of sequence features are applied to a trained classification model, thereby obtaining a classifier result that provides, for each respective cancer condition in the set of cancer conditions, a likelihood that the subject has or does not have the respective cancer condition.

In some embodiments, the plurality of RNA molecules is obtained by full transcriptome sequencing. In some embodiments, the one or more data structures further comprise a second plurality of sequence reads and a third plurality of sequence reads. The second plurality of sequence reads is obtained from a first plurality of DNA molecules or derivatives of said DNA molecules (e.g., derivatives from amplification methods). The third plurality of sequence reads is obtained from a second plurality of DNA molecules or derivatives of said DNA molecules. The first plurality of DNA molecules is from a somatic biopsy obtained from the subject, and the second plurality of DNA molecules is from a germline sample obtained from the subject, or is from a population of normal controls that is free of the set of cancer conditions. In such embodiments, the method further comprises determining a second set of sequence features for the subject from a comparison of the second plurality of sequence reads to the third plurality of sequence reads.

In some embodiments, the applying further comprises applying at least the first set of sequence features and the second set of sequence features to a trained classification model.

In some embodiments, the method further comprises obtaining a pathology report for the subject. The pathology report includes at least one of a first estimate of tumor cellularity (e.g., of the somatic biopsy), an indication as to whether the subject has a metastatic cancer or primary cancer, or a tissue site that is the origin of the somatic biopsy. The method includes extracting a plurality of pathology features from the pathology report for the subject including the first estimate of tumor cellularity of the somatic biopsy.

In some embodiments, the trained classification model is selected based at least in part on the plurality of pathology features.

In some embodiments, applying the features to a trained classification model further comprises applying at least the plurality of pathology features, the first set of sequence features, and the second set of sequence features to the trained classification model.

In some embodiments, the trained classification model further provides one or more treatment recommendations for the subject or a medical practitioner caring for the subject on the basis of the likelihood that the subject has or does not have each respective cancer condition in the set of cancer conditions.

An additional aspect of the present disclosure provides a method for classifying a subject to a cancer condition. The method includes obtaining, at a computer in electronic format, one or more data structures that collectively comprise a first plurality of sequence reads. The first plurality of sequence reads is obtained from a plurality of RNA molecules or derivatives of said plurality of RNA molecules (e.g., derivatives such as cDNA, or proteins). The plurality of RNA molecules is from a somatic biopsy obtained from the subject. The method continues by determining from the first plurality of sequence reads, a first set of sequence features for the subject. The method includes applying at least the first set of sequence features to a trained classification model thereby obtaining a classifier result that provides a likelihood that the subject has or does not have the cancer condition.

In some embodiments, the trained classification model further provides one or more treatment recommendations for the subject or a medical practitioner caring for the subject on the basis of the likelihood that the subject has or does not have the cancer condition.

An additional aspect of the present disclosure provides a method for classifying a subject to an expected cancer condition. The method includes obtaining, in electronic format, one or more data structures that collectively comprise a first plurality of sequence reads and an indication of the expected cancer condition of the subject. The first plurality of sequence reads is obtained from a plurality of RNA molecules or derivatives of said plurality of RNA molecules (e.g., derivatives such as cDNA, or proteins). The plurality of RNA molecules is from a somatic biopsy obtained from the subject. The method includes determining from the first plurality of sequence reads, a first set of sequence features for the subject. The method includes applying at least the first set of sequence features and the indication of expected cancer condition of the subject to a trained classification model, thereby obtaining a classifier result of a predicted cancer condition. The method further compares the predicted cancer condition to the expected cancer condition to provide a likelihood that the subject has or does not have the expected cancer condition.

In some embodiments, the trained classification model further provides one or more treatment recommendations for the subject or a medical practitioner caring for the subject on the basis of the likelihood that the subject has or does not have the expected cancer condition.

Another aspect of the present disclosure provides a classification method. The method includes obtaining, in electronic format, for each respective subject in a plurality of subjects for each respective cancer condition in the set of cancer conditions, an indication as to whether or not the respective subject has the cancer indication, a first plurality of sequence reads, and a pathology report of the respective subject. The first plurality of sequence reads is obtained from a plurality of RNA molecules or derivatives of said plurality of RNA molecules (e.g., derivatives such as cDNA, or proteins). The pathology report includes at least one of a first estimate of tumor cellularity (e.g., of the somatic biopsy), an indication as to whether the respective subject has a metastatic cancer or primary cancer, or a tissue site that is the origin of the somatic biopsy. The plurality of RNA molecules is from a somatic biopsy obtained from the respective subject The method continues by determining, for each respective subject in the plurality of subjects, from the first plurality of sequence reads of the respective subject, a corresponding first set of sequence features for the respective subject. The method includes extracting a plurality of pathology features from the pathology report for the respective subject including the first estimate of tumor cellularity of the somatic biopsy. The method then includes inputting at least the first set of sequence features, and the plurality of pathology features of each respective subject in the plurality of subjects into an untrained classification model. The method thereby trains the untrained classification model against the indication of whether or not each respective subject in the plurality of subjects has each respective cancer condition in the set of cancer conditions to obtain a trained classification model that is configured to provide, for each respective cancer condition in the set of cancer conditions, a likelihood that a test subject has or does not have the respective cancer condition.

In some embodiments, the trained classification model comprises a trained classifier stream.

In some embodiments, the method further comprises obtaining, for each respective subject in the plurality of subjects for each respective cancer condition in the set of cancer conditions, a second plurality of sequence reads and a third plurality of sequence reads. In some embodiments, the second plurality of sequence reads is obtained from a first plurality of DNA molecules or derivatives of said DNA molecules. In some embodiments, the third plurality of sequence reads is obtained from a second plurality of DNA molecules or derivatives of said DNA molecules. The first plurality of DNA molecules is from a somatic biopsy obtained from the respective subject. The second plurality of DNA molecules is from a germline sample obtained from the respective subject, or is from a population of normal controls that is free of a set of cancer conditions. In some embodiments, the method also includes determining, for each respective subject in the plurality of subjects, from a comparison of the second plurality of sequence reads to the third plurality of sequence reads of the respective subject, a second set of sequence features for the respective subject.

In some embodiments, inputting the features to the untrained classification model further comprises inputting at least the plurality of pathology features, the first set of sequence features, and the second set of sequence features of each respective subject in the plurality of subjects into an untrained classification model.

A method for identifying a diagnosis of a cancer condition for a somatic tumor specimen of a subject is provided (e.g., a somatic tumor specimen having unknown origins). The method comprises receiving sequencing information comprising analysis of a plurality of nucleic acids derived from the somatic tumor specimen. The method further comprises identifying a plurality of features from the received sequencing information, where the plurality of features include RNA features, DNA features, RNA Splicing features, viral features, and copy number features. Each RNA feature is associated with a respective target region of a first reference genome and represents a corresponding abundance of sequence reads, encompassed by the sequencing information, that map to the respective target region. Each DNA feature is associated with a respective target region of a second reference genome and represents a corresponding abundance of sequence reads, encompassed by the sequencing information, that map to the respective target region. Each RNA splicing feature is associated with a respective splicing event at a respective target region of the first reference genome and represents a corresponding abundance of sequence reads, encompassed by the sequencing information, that map to the respective target region with the respective splicing event. The first reference genome and the second reference genome may be the same reference genome or may be different reference genomes. Each viral feature is associated with a respective target region of a viral reference genome and represents a corresponding abundance of sequence reads, encompassed by the sequencing information, that map to the respective target region in the viral reference genome. Each copy number feature is associated with a target region of the second reference genome and represents a corresponding abundance of sequence reads, encompassed by the sequencing information, that map to the respective target region of the second reference genome. The method further comprises providing a first subset of features from the identified plurality of features as inputs to a first classifier. The method further comprises a second subset of features from the identified plurality of features from the identified plurality of features as inputs to a second classifier. The method further comprises generating, from two or more classifiers, two or more predictions of cancer condition based at least in part on the identified plurality of features. The two or more classifiers include at least the first classifier and the second classifier. The method further comprises combining the two or more predictions at a final classifier to identify the diagnosis of the cancer condition for the somatic tumor specimen of the subject.

In some embodiments, combining, at the final classifier, the two or more predictions further comprises scaling each prediction of the two or more predictions based at least in part on a confidence in each respective prediction, and generating a combined prediction based at least in part on each scaled prediction of the two or more predictions.

In some embodiments, the two or more predictions comprise: a first prediction from a diagnosis classifier provided with (e.g., and trained on) RNA features, a second prediction from a cohort classifier provided with RNA features, a third prediction from a tissue classifier provided with RNA features, a fourth prediction from a diagnosis classifier provided with RNA Splicing features, a fifth prediction from a cohort classifier provided with RNA Splicing features, a sixth prediction from a diagnosis classifier provided with CNV features, a seventh prediction from a cohort classifier provided with CNV features, an eighth prediction from a diagnosis classifier provided with DNA features, and a ninth prediction from a diagnosis classifier provided with viral features.

Other embodiments are directed to systems, portable consumer devices, and computer readable media associated with the methods described herein. Any embodiment disclosed herein, when applicable, can be applied to any aspect of the methods described herein.

Additional aspects and advantages of the present disclosure will become readily apparent to those skilled in this art from the following detailed description, where only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4A illustrates the distribution of genomic alteration types for the most commonly mutated genes. FIG. 4B displays a comparison of the detection assay against the MSKCC IMPACT study plotted by the prevalence of altered genes that are common hallmarks of cancer. FIG. 4C illustrates predicted TCGA cancer condition for each sample in an exemplary cohort of 500 records, in accordance with some embodiments of the present disclosure.

FIGS. 5A, 5B, 5C, 5D, 5E, and 5F collectively illustrate therapeutic and clinical trial matching, in accordance with some embodiments of the present disclosure.

FIG. 6A shows the percentage of somatic mutations, by false positive and true positive, detected in the tumor-only analysis of 50 randomly selected patient samples. FIG. 6B provides a breakdown of somatic mutation detection in tumor-normal matched DNA sequencing versus tumor-only sequencing.

FIG. 9 includes key findings and reports different tests that were performed to produce the key findings. Additional information may also be included, such as suggested immunotherapy targets and the likelihood of resistance to various treatments.

FIGS. 10A, 10B, 10C, 10D, 10E, 10F, and 10G collectively illustrate example patient reports regarding tumor of origin prediction, generated in accordance with some embodiments of the present disclosure. These figures are for illustrative purposes only, and no one FIG. 10 comprises a complete patient report in of itself.

FIG. 11B shows clusters for patients diagnosed with sarcoma, demonstrating the heterogeneity of sarcomas. FIG. 11C illustrates UMAP clusters derived for patients with testicular cancers. FIG. 11D illustrates UMAP clustering by biopsy location for neuroendocrine cancers.

Like reference numerals refer to corresponding parts throughout the several views of the drawings.

DETAILED DESCRIPTION

Figure 1:
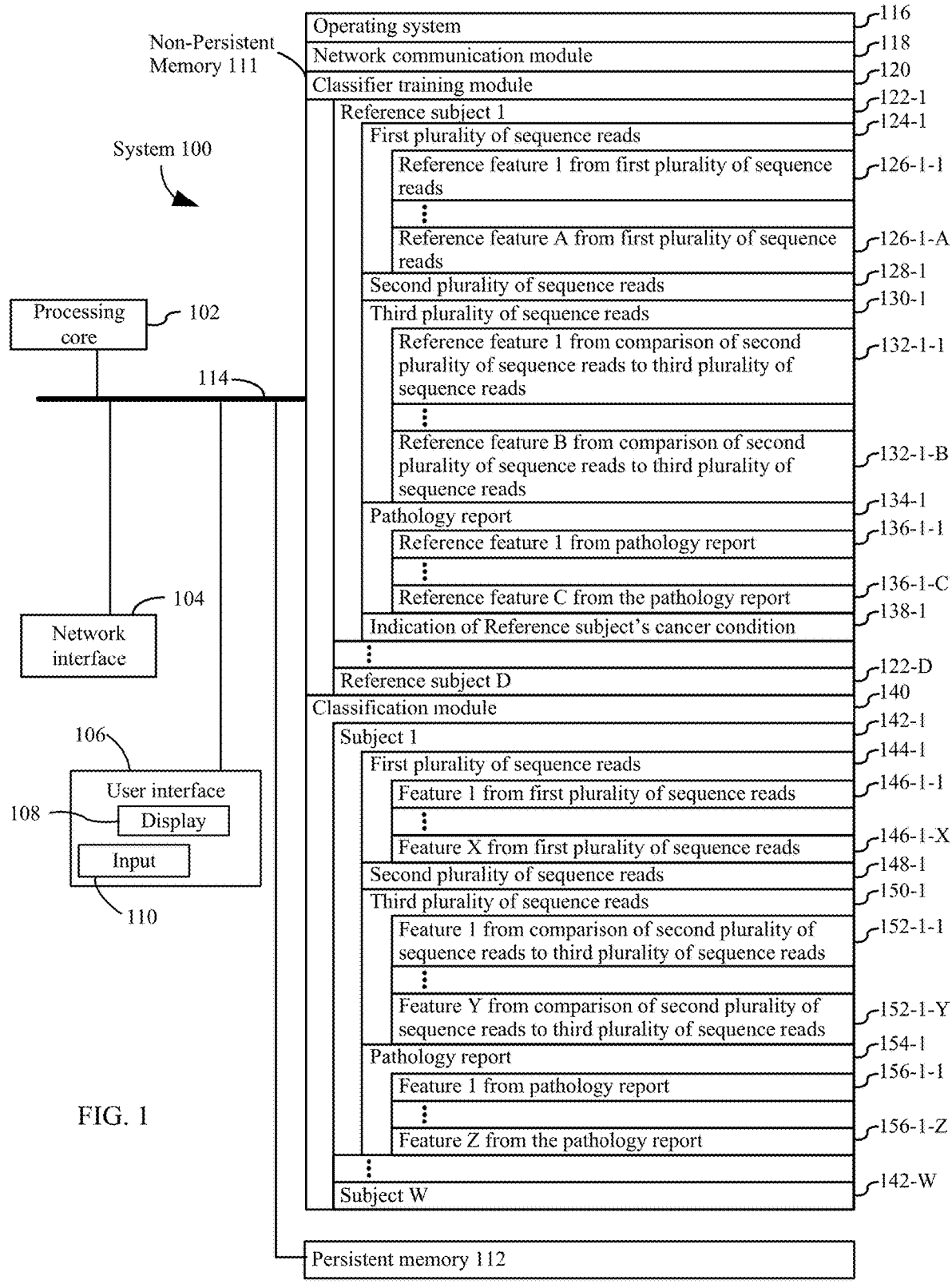
FIG. 1 illustrates a block diagram of an example computing device, in accordance with some embodiments of the present disclosure.

To make best use of newly developed targeted therapies, it is essential to determine the particular cancer condition affecting a cancer patient. The present disclosure provides systems and methods useful for determining a cancer condition of a patient using RNA sequence features and features extracted from the patient's pathology report. In some embodiments, the methods employ a multi-label classification approach, and patient samples are annotated with a combination of genomic, pathologic, and/or clinical features. The inclusion of these disparate features, which are determined from different attributes of a patient's medical history, contributes to clinically appropriate accuracy across a plurality of tumor types for the classifications disclosed herein. The present disclosure provides, in particular, improved methods for classification of tumors of unknown origin.

In some embodiments, the systems and methods described herein employ classification streams as classification models. Advantageously, this facilitates the refinement of classifiers over time, which is particularly useful when unreliable data is used to train the classifier initially, for example, data from pathology reports. In some embodiments, the systems and methods described herein employ adaptable classifier ensembles as the classification models, for example, where the output of a first classifier helps to define the structure of the downstream classification cascade (e.g., chains of classifiers). Advantageously, these classifier ensembles improve performance when input test data, for example, from pathology reports, is incorrect, inconsistent, and/or incomplete.

In one aspect, the present disclosure provides methods for training a classification model to determine a likelihood that a patient has or does not have a cancer condition. The present disclosure further provides systems and methods useful for predicting treatment type for cancer patients, based on whether the likelihood suggests that the patient has or does not have the respective cancer condition.

Benefits

In some embodiments, the present disclosure provides systems and methods for determining the cancer condition of tumor of unknown origin that leverage sequencing and pathology report data. Tumors of unknown origin comprise up to an estimated 5% of cancer patients, see e.g., Fizazi et al. 2011 Annals of Oncology 22(6), vi64-vi68 and Example 4. As discussed in Example 4, the classification methods disclosed herein enabled the classification of cancer type for 867 subjects (7.6% of the sample set) who had previously only had tumors of unknown origin. Advantageously, the combination of sequencing data and pathology report information to provide diagnoses of tumors of unknown origin, can also result in altered patient diagnoses and clinical treatment recommendations (e.g., by providing improved recommendations over and initial diagnosis). For example, as described in the case study in Example 8, using the classification methods described herein to determine tumor of origin changed the treatment strategy for a patient with two preexisting cancer diagnoses and newly detected metastatic tumors.

Standard methods of molecular classification of cancer merely use sequencing data, which results in lower accuracy of diagnosis. For example, Sveen et al. in 2017 developed an improved molecular classifier of colorectal cancer that exhibited accuracy rates of 85-92%, whereas classification methods trained in accordance with embodiments described herein have precision and recall rates of 93% and 96% for colon cancer. See Clin Cancer Res 24(4), 794-806. Similarly, another study in 2019 developed a molecular classifier of breast cancer that provided an average accuracy of 80%, while classification methods trained in accordance with embodiments described herein have precision and recall rates of 95% and 96% for breast cancer. See Tao et al 2019 *Genes* 10, 200. As described in Example 4, the methods described herein are applicable for a wide variety of patients with tumors of unknown or origin.

Diagnosis information in pathology reports is typically recorded in freeform text boxes and requires some processing before it can be incorporated in classification models. As described in Example 5, the present disclosure advantageously presents a method for performing natural language processing of diagnostic values from pathology reports. This enables the clustering of patient data in clinically and transcriptionally relevant diagnostic categories, as described in Example 6. Thus, embodiments of the current disclosure permit the incorporation of previously inaccessible data into training classification models, which helps to support the increased classification accuracy provided by these models.

In some embodiments, the present disclosure provides systems and methods for classifying cancer that leverage tumor and matched germline tissue sequencing data. For example, in some embodiments, the systems and methods provided herein use a plurality of sequence reads obtained from a somatic biopsy from a subject and another plurality of sequence reads obtained from a germline (non-cancerous) sample to classify the cancer status of the subject. Advantageously, by employing sequencing data from both tumor samples (e.g., somatic) and matched germline (e.g., non-cancerous) tissue, a more accurate portrait of the patient's tumor biology is achieved because "false positive" somatic variants are identified (e.g., as discussed in Example 3, the comparison of somatic to germline variants filtered out over 20% of the somatic variants, identifying those as false positives). The use of non-cancerous samples helps remove background mutations (e.g., those mutations that are present in a subject but are not associated with the subject's tumor). For example, as shown in Example 3 and FIG. 6B, use of sequencing data from both tumor samples and matched normal tissue reduced the false positive rate, providing more accurate classification results and improving actionable outcomes. In particular, Example 3 demonstrates that 16% of the subjects analyzed would have received a different clinical diagnosis if they had received a tumor-only test.

The methods described herein stand in contrast to conventional methods used for classifying the cancer status of a subject. Classifiers trained according to embodiments described herein provide improved prediction results for tumors of unknown origin, hence leading to improved patient outcomes as compared with other classification methods.

Definitions

The terminology used in the present disclosure is for the purpose of describing particular embodiments only and is not intended to be limiting of the invention. As used in the description of the invention and the appended claims, the singular forms "a," "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "comprising," or any variation thereof, when used in this specification, specify the presence of stated features, integers, steps, operations, elements, and/or components, but do not preclude the presence or addition of one or more other features, integers, steps, operations, elements, components, and/or groups thereof. Furthermore, to the extent that the terms "including," "includes," "having," "has," "with," or variants thereof are used in either the detailed description and/or the claims, such terms are intended to be inclusive in a manner similar to the term "comprising."

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject. Furthermore, the terms "subject," "user," and "patient" are used interchangeably herein.

As used herein, the terms "subject" or "patient" refers to any living or non-living human (e.g., a male human, female human, fetus, pregnant female, child, or the like). In some embodiments, a subject is a male or female of any stage (e.g., a man, a woman or a child).

As used herein, the terms "control," "control sample," "reference," "reference sample," "normal," and "normal sample" describe a sample from a subject that does not have a particular condition, or is otherwise healthy. In an example, a method as disclosed herein can be performed on a subject having a tumor, where the reference sample is a sample taken from a healthy tissue of said subject A reference sample can be obtained from the subject, or from a database. The reference can be, for example, a reference genome that is used to map sequence reads obtained from sequencing a sample from the subject A reference genome can refer to a haploid or diploid genome to which sequence reads from the biological sample and a constitutional sample can be aligned and compared. An example of constitutional sample can be DNA of white blood cells obtained from the subject. For a haploid genome, there can be only one nucleotide at each locus. For a diploid genome, heterozygous loci can be identified; each heterozygous locus can have two alleles, where either allele can allow a match for alignment to the locus.

As used herein, the term "locus" refers to a position (e.g., a site) within a genome, such as, on a particular chromosome. In some embodiments, a locus refers to a single nucleotide position within a genome, such as, on a particular chromosome. In some embodiments, a locus refers to a small group of nucleotide positions within a genome, for example, as defined by a mutation (e.g., substitution, insertion, or deletion) of consecutive nucleotides within a cancer genome. Because normal mammalian cells have diploid genomes, a normal mammalian genome (e.g., a human genome) will generally have two copies of every locus in the genome, or at least two copies of every locus located on the autosomal chromosomes, for example, one copy on the maternal autosomal chromosome and one copy on the paternal autosomal chromosome.

As used herein, the term "allele" refers to a particular sequence of one or more nucleotides at a chromosomal locus.

As used herein, the term "reference allele" refers to the sequence of one or more nucleotides at a chromosomal locus that is either the predominant allele represented at that chromosomal locus within the population of the species (e.g., the "wild-type" sequence), or an allele that is predefined within a reference genome for the species.

As used herein, the term "variant allele" refers to a sequence of one or more nucleotides at a chromosomal locus that is either not the predominant allele represented at that chromosomal locus within the population of the species (e.g., not the "wild-type" sequence), or not an allele that is predefined within a reference genome for the species.

As used herein, the terms "single nucleotide variant," "SNV," "single nucleotide polymorphism," or "SNP" refer to a substitution of one nucleotide to a different nucleotide at a position (e.g., site) of a nucleotide sequence, for example, a sequence read from an individual. A substitution from a first nucleobase X to a second nucleobase Y may be denoted as "X>Y." For example, a cytosine to thymine SNP may be denoted as "C>T." The term "het-SNP" refers to a heterozygous SNP, where the genome is at least diploid, and at least one—but not all—of the two or more homologous sequences exhibits the particular SNP. Similarly, a "hom-SNP" is a homologous SNP, where each homologous sequence of a polyploid genome has the same variant compared to the reference genome. As used herein, the term "structural variant" or "SV" refers to large (e.g., larger than 1 kb) regions of a genome that have undergone physical transformations such as inversions, insertions, deletions, or duplications (e.g., see review of human genome SVs by Spielmann et al., 2018, Nat Rev Genetics 19:453-467).

As used herein, the term "indel" refers to insertion and/or deletion events of stretches of one or more nucleotides, either within a single gene locus or across multiple genes.

As used herein, the term "copy number variant," "CNV," or "copy number variation" refers to regions of a genome that are repeated. These may be categorized as short or long repeats, in regards to the number of nucleotides that are repeated over the genome regions. Long repeats typically refer to cases where entire genes, or large portions of a gene, are repeated one or more times.

As used herein, the term "mutation," refers to a detectable change in the genetic material of one or more cells. In a particular example, one or more mutations can be found in, and can identify, cancer cells (e.g., driver and passenger mutations). A mutation can be transmitted from a parent cell to a daughter cell. A person having skill in the art will appreciate that a genetic mutation (e.g., a driver mutation) in a parent cell can induce additional, different mutations (e.g., passenger mutations) in a daughter cell. A mutation generally occurs in a nucleic acid. In a particular example, a mutation can be a detectable change in one or more deoxyribonucleic acids or fragments thereof. A mutation generally refers to nucleotides that are added, deleted, substituted for, inverted, or transposed to a new position in a nucleic acid. A mutation can be a spontaneous mutation or an experimentally induced mutation. A mutation in the sequence of a particular tissue is an example of a "tissue-specific allele." For example, a tumor can have a mutation that results in an allele at a locus that does not occur in normal cells. Another example of a "tissue-specific allele" is a fetal-specific allele that occurs in the fetal tissue, but not the maternal tissue.

As used herein, the term "genomic variant" may refer to one or more mutations, copy number variants, indels, single nucleotide variants, or variant alleles. A genomic variant may also refer to a combination of one or more above.

As used herein the term "cancer," "cancerous tissue," or "tumor" refers to an abnormal mass of tissue in which the growth of the mass surpasses and is not coordinated with the growth of normal tissue. In the case of hematological cancers, this includes a volume of blood or other bodily fluid containing cancerous cells. A cancer or tumor can be defined as "benign" or "malignant" depending on the following characteristics: degree of cellular differentiation including morphology and functionality, rate of growth, local invasion, and metastasis. A "benign" tumor can be well differentiated, have characteristically slower growth than a malignant tumor and remain localized to the site of origin. In addition, in some cases a benign tumor does not have the capacity to infiltrate, invade, or metastasize to distant sites. A "malignant" tumor can be a poorly differentiated (anaplasia), have characteristically rapid growth accompanied by progressive infiltration, invasion, and destruction of the surrounding tissue. Furthermore, a malignant tumor can have the capacity to metastasize to distant sites. Accordingly, a cancer cell is a cell found within the abnormal mass of tissue whose growth is not coordinated with the growth of normal tissue. Accordingly, a "tumor sample" or "somatic biopsy" refers to a biological sample obtained or derived from a tumor of a subject, as described herein.

As used herein, the term "tumor cellularity" refers to the relative proportion of tumor cells (e.g., cancer cells) to normal cells in a sample. Normal cells may include normal tissue, normal stroma, and normal immune cells. Tumor cellularity of a subject can be estimated from a biological sample of a subject and may be included in a pathology report of a subject.

As used herein, the term "somatic biopsy" refers to a biopsy of a subject. In some embodiments, the biopsy is of solid tissue. In some embodiments, it is a liquid biopsy.

As used herein, the terms "sequencing," "sequence determination," and the like as used herein refers generally to any and all biochemical processes that may be used to determine the order of biological macromolecules such as nucleic acids or proteins. For example, sequencing data can include all or a portion of the nucleotide bases in a nucleic acid molecule such as an mRNA transcript or a genomic locus.

As used herein, the term "sequence reads" or "reads" refers to nucleotide sequences produced by any sequencing process described herein or known in the art. Reads can be generated from one end of nucleic acid fragments ("single-end reads"), and sometimes are generated from both ends of nucleic acids (e.g., paired-end reads, double-end reads). The length of the sequence read is often associated with the particular sequencing technology. High-throughput methods, for example, provide sequence reads that can vary in size from tens to hundreds of base pairs (bp). In some embodiments, the sequence reads are of a mean, median or average length of about 15 bp to 900 bp long (e.g., about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, about 500 bp, or so forth). In some embodiments, the sequence reads are of a mean, median, or average length of about 1000 bp, 2000 bp, 5000 bp, 10,000 bp, or 50,000 bp or more. Nanopore sequencing, for example, can provide sequence reads that can vary in size from tens to hundreds to thousands of base pairs. Illumina parallel sequencing can provide sequence reads that do not vary as much, for example, most of the sequence reads can be smaller than 200 bp. A sequence read (or sequencing read) can refer to sequence information corresponding to a nucleic acid molecule (e.g., a string of nucleotides). For example, a sequence read can correspond to a string of nucleotides (e.g., about 20 to about 150) from part of a nucleic acid fragment, can correspond to a string of nucleotides at one or both ends of a nucleic acid fragment, or can correspond to nucleotides of the entire nucleic acid fragment. A sequence read can be obtained in a variety of ways, for example, using sequencing techniques or using probes, for example, in hybridization arrays or capture probes, or amplification techniques, such as the polymerase chain reaction (PCR) or linear amplification using a single primer or isothermal amplification.

As used herein, the term "read segment" or "read" refers to any nucleotide sequences including sequence reads obtained from an individual and/or nucleotide sequences derived from the initial sequence read from a sample obtained from an individual. For example, a read segment can refer to an aligned sequence read, a collapsed sequence read, or a stitched read. Furthermore, a read segment can refer to an individual nucleotide base, such as a single nucleotide variant.

As used herein, the term "read-depth," "sequencing depth," or "depth" refers to a total number of read segments from a sample obtained from an individual at a given position, region, or locus. The locus can be as small as a nucleotide, or as large as a chromosome arm, or as large as an entire genome. Sequencing depth can be expressed as "Y×," for example, 50×, 100×, etc., where "Y" refers to the number of times a locus is covered with a sequence read. In some embodiments, the depth refers to the average sequencing depth across the genome, across the exome, or across a targeted sequencing panel. Sequencing depth can also be applied to multiple loci, the whole genome, in which case Y can refer to the mean number of times a loci or a haploid genome, a whole genome, or a whole exome, respectively, is sequenced. When a mean depth is quoted, the actual depth for different loci included in the dataset can span over a range of values. Ultra-deep sequencing can refer to at least 100× in sequencing depth at a locus.

As used herein the term "sequencing breadth" refers to what fraction of a particular reference exome (e.g., human reference exome), a particular reference genome (e.g., human reference genome), or part of the exome or genome has been analyzed (e.g., as represented by the gene list in Table 2). The denominator of the fraction can be a repeat-masked genome, and thus 100% can correspond to all of the reference genome minus the masked parts. A repeat-masked exome or genome can refer to an exome or genome in which sequence repeats are masked (e.g., sequence reads align to unmasked portions of the exome or genome). Any parts of an exome or genome can be masked, and thus one can focus on any particular part of a reference exome or genome. Broad sequencing can refer to sequencing and analyzing at least 0.1% of the exome or genome.

As used herein, the term "reference exome" refers to any particular known, sequenced, or characterized exome, whether partial or complete, of any tissue from any organism or pathogen that may be used to reference identified sequences from a subject Exemplary reference exomes used for human subjects, as well as many other organisms, are provided in the online GENCODE database hosted by the GENCODE consortium, for instance Release 29 (GRCh38.p12) of the human exome assembly.

As used herein, the term "reference genome" refers to any particular known, sequenced, or characterized genome, whether partial or complete, of any organism or pathogen that may be used to reference identified sequences from a subject Exemplary reference genomes used for human subjects as well as many other organisms are provided in the on-line genome browser hosted by the National Center for Biotechnology Information ("NCBI") or the University of California, Santa Cruz (UCSC). A "genome" refers to the complete genetic information of an organism or pathogen, expressed in nucleic acid sequences. As used herein, a reference sequence or reference genome often is an assembled or partially assembled genomic sequence from an individual or multiple individuals. In some embodiments, a reference genome is an assembled or partially assembled genomic sequence from one or more human individuals. The reference genome can be viewed as a representative example of a species' set of genes or genetic sequences. In some embodiments, a reference genome includes sequences assigned to chromosomes. Exemplary human reference genomes include but are not limited to NCBI build 34 (UCSC equivalent: hg16), NCBI build 35 (UCSC equivalent: hg17), NCBI build 36.1 (UCSC equivalent: hg18), GRCh37 (UCSC equivalent: hg19), and GRCh38 (UCSC equivalent: hg38).

As used herein, the term "assay" refers to a technique for determining a property of a substance, for example, a nucleic acid, a protein, a cell, a tissue, or an organ. An assay (e.g., a first assay or a second assay) can comprise a technique for determining the copy number variation of nucleic acids in a sample, the methylation status of nucleic acids in a sample, the fragment size distribution of nucleic acids in a sample, the mutational status of nucleic acids in a sample, or the fragmentation pattern of nucleic acids in a sample. Any assay known to a person having ordinary skill in the art can be used to detect any of the properties of nucleic acids mentioned herein. Properties of nucleic acids can include a sequence, genomic identity, copy number, methylation state at one or more nucleotide positions, size of the nucleic acid, presence or absence of a mutation in the nucleic acid at one or more nucleotide positions, and pattern of fragmentation of a nucleic acid (e.g., the nucleotide position(s) at which a nucleic acid fragments). An assay or method can have a particular sensitivity and/or specificity, and their relative usefulness as a diagnostic tool can be measured using ROC-AUC statistics.

The term "classification" can refer to any number(s) or other characters(s) that are associated with a particular property of a sample. For example, a "+" symbol (or the word "positive") can signify that a sample is classified as having deletions or amplifications. In another example, the term "classification" can refer to an oncogenic pathogen infection status, an amount of tumor tissue in the subject and/or sample, a size of the tumor in the subject and/or sample, a stage of the tumor in the subject, a tumor load in the subject and/or sample, and presence of tumor metastasis in the subject. The classification can be binary (e.g., positive or negative) or have more levels of classification (e.g., a scale from 1 to 10 or 0 to 1). The terms "cutoff" and "threshold" can refer to predetermined numbers used in an operation. For example, a cutoff size can refer to a size above which fragments are excluded. A threshold value can be a value above or below which a particular classification applies. Either of these terms can be used in either of these contexts.

As used herein, the term "relative abundance" can refer to a ratio of a first amount of nucleic acid fragments having a particular characteristic (e.g., aligning to a particular region of the exome) to a second amount of nucleic acid fragments having a particular characteristic (e.g., aligning to a particular region of the exome). In one example, relative abundance may refer to a ratio of the number of mRNA transcripts encoding a particular gene in a sample (e.g., aligning to a particular region of the exome) to the total number of mRNA transcripts in the sample.

As used herein the term "untrained classifier" refers to a classifier that has not been trained on a training dataset or to a classifier that has been partially trained on a training dataset.

As used herein, an "effective amount" or "therapeutically effective amount" is an amount sufficient to affect a beneficial or desired clinical result upon treatment. An effective amount can be administered to a subject in one or more doses. In terms of treatment, an effective amount is an amount that is sufficient to palliate, ameliorate, stabilize, reverse or slow the progression of the disease, or otherwise reduce the pathological consequences of the disease. The effective amount is generally determined by the medical practitioner on a case-by-case basis and is within the skill of one in the art. Several factors are typically taken into account when determining an appropriate dosage to achieve an effective amount. These factors include age, sex and weight of the subject, the condition being treated, the severity of the condition and the form and effective concentration of the therapeutic agent being administered.

As used herein, the term "tumor mutation burden" (TMB) refers to the level of mutations present in a patient's tumor cells. Herein, TMB was calculated by dividing the number of non-synonymous mutations by the size of the genetic panel (e.g., 2.4 Mb). See e.g., Beaubier et al. 2019 *Oncotarget* 10, 2384-2396. All non-silent somatic coding mutations, including missense, insertions or deletions, and stop loss variants, with coverage greater than 100× and an allelic fraction greater than 5% were included in the number of non-synonymous mutations. Hypermutated tumors were considered TMB-high if the TMB was at least nine mutations per Mb. This threshold was established by testing for the enrichment of tumors with orthogonally defined hypermutation (MSI-H) in the Tempus clinical database.

Several aspects are described below with reference to example applications for illustration. It should be understood that numerous specific details, relationships, and methods are set forth to provide a full understanding of the features described herein. One having ordinary skill in the relevant art, however, will readily recognize that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

Example System Embodiments

Now that an overview of some aspects of the present disclosure and some definitions used in the present disclosure have been provided, details of an exemplary system are described in conjunction with FIG. 1. FIG. 1 is a block diagram illustrating a system 100 in accordance with some implementations. The system 100 in some implementations includes one or more processing units CPU(s) 102 (also referred to as processors), one or more network interfaces 104, a user interface 106 including (optionally) a display 108 and an input system 110, a non-persistent memory 111, a persistent memory 112, and one or more communication buses 114 for interconnecting these components. The one or more communication buses 114 optionally include circuitry (sometimes called a chipset) that interconnects and controls communications between system components. The non-persistent memory 111 typically includes high-speed random access memory, such as DRAM, SRAM, DDR RAM, ROM, EEPROM, flash memory, whereas the persistent memory 112 typically includes CD-ROM, digital versatile disks (DVD) or other optical storage, magnetic cassettes, magnetic tape, magnetic disk storage or other magnetic storage devices, magnetic disk storage devices, optical disk storage devices, flash memory devices, or other non-volatile solid state storage devices. The persistent memory 112 optionally includes one or more storage devices remotely located from the CPU(s) 102. The persistent memory 112, and the non-volatile memory device(s) within the non-persistent memory 112, comprise non-transitory computer readable storage medium. In some implementations, the non-persistent memory 111 or alternatively the non-transitory computer readable storage medium stores the following programs, modules and data structures, or a subset thereof, sometimes in conjunction with the persistent memory 112:

- an optional operating system 116, which includes procedures for handling various basic system services and for performing hardware dependent tasks;
- an optional network communication module (or instructions) 118 for connecting the system 100 with other devices and/or a communication network 104;
- an optional classifier training module 120 for training classifiers that determine a set of cancer conditions, the classifier training module including a dataset for one or more reference subjects 122, where the dataset for each reference subject includes at least a first plurality of sequence reads 124, (optionally) a second plurality of sequence reads 128, (optionally) a third plurality of sequence reads 130, (optionally) a pathology report 134, and an indication of the respective reference subject's diagnosed cancer condition 138, where the dataset for the respective reference subject further includes one or more reference features 126 derived from the first plurality of sequence reads 124, one or more reference features 132 derived from a comparison of the second plurality of sequence reads 128 and the third plurality of sequence reads 130, and one or more reference features 136 derived from the pathology report 134;
- a patient classification module 140 for classifying a test subject to a particular set of cancer conditions using DNA sequence information, RNA sequence information, and pathology report information, using a classifier, for example, as trained using classifier training module 120; and
- the patient classification module 140 further includes, for each test subject, a dataset comprising, for each test subject 142, a first plurality of sequence reads 144—including one or more features 146 derived from the first plurality of sequence reads, a second plurality of sequence reads 148 and a third plurality of sequence reads 150—including one or more features 152 from comparing the second and third plurality of sequence reads, and (optionally) a pathology report 154—including one or more features 156 derived from the pathology report.

In various implementations, one or more of the above identified elements are stored in one or more of the previously mentioned memory devices, and correspond to a set of instructions for performing a function described above. The above identified modules, data, or programs (e.g., sets of instructions) need not be implemented as separate software programs, procedures, datasets, or modules, and thus various subsets of these modules and data may be combined or otherwise re-arranged in various implementations. In some implementations, the non-persistent memory 111 optionally stores a subset of the modules and data structures identified above. Furthermore, in some embodiments, the memory stores additional modules and data structures not described above. In some embodiments, one or more of the above identified elements is stored in a computer system, other than that of visualization system 100, that is addressable by visualization system 100 so that visualization system 100 may retrieve all or a portion of such data when needed.

Although FIG. 1 depicts a "system 100," the figure is intended more as a functional description of the various features that may be present in computer systems than as a structural schematic of the implementations described herein. In practice, and as recognized by those of ordinary skill in the art, items shown separately could be combined and some items could be separated. Moreover, although FIG. 1 depicts certain data and modules in non-persistent memory 111, some or all of these data and modules instead may be stored in persistent memory 112 or in more than one memory. For example, in some embodiments, at least dataset 122 is stored in a remote storage device which can be a part of a cloud-based infrastructure. In some embodiments, at least dataset 122 is stored on a cloud-based infrastructure. In some embodiments, dataset 122, the classifier training module 120, and the patient classification module 140 can also be stored in the remote storage device(s).

Classification of Patients

Figure 2A:
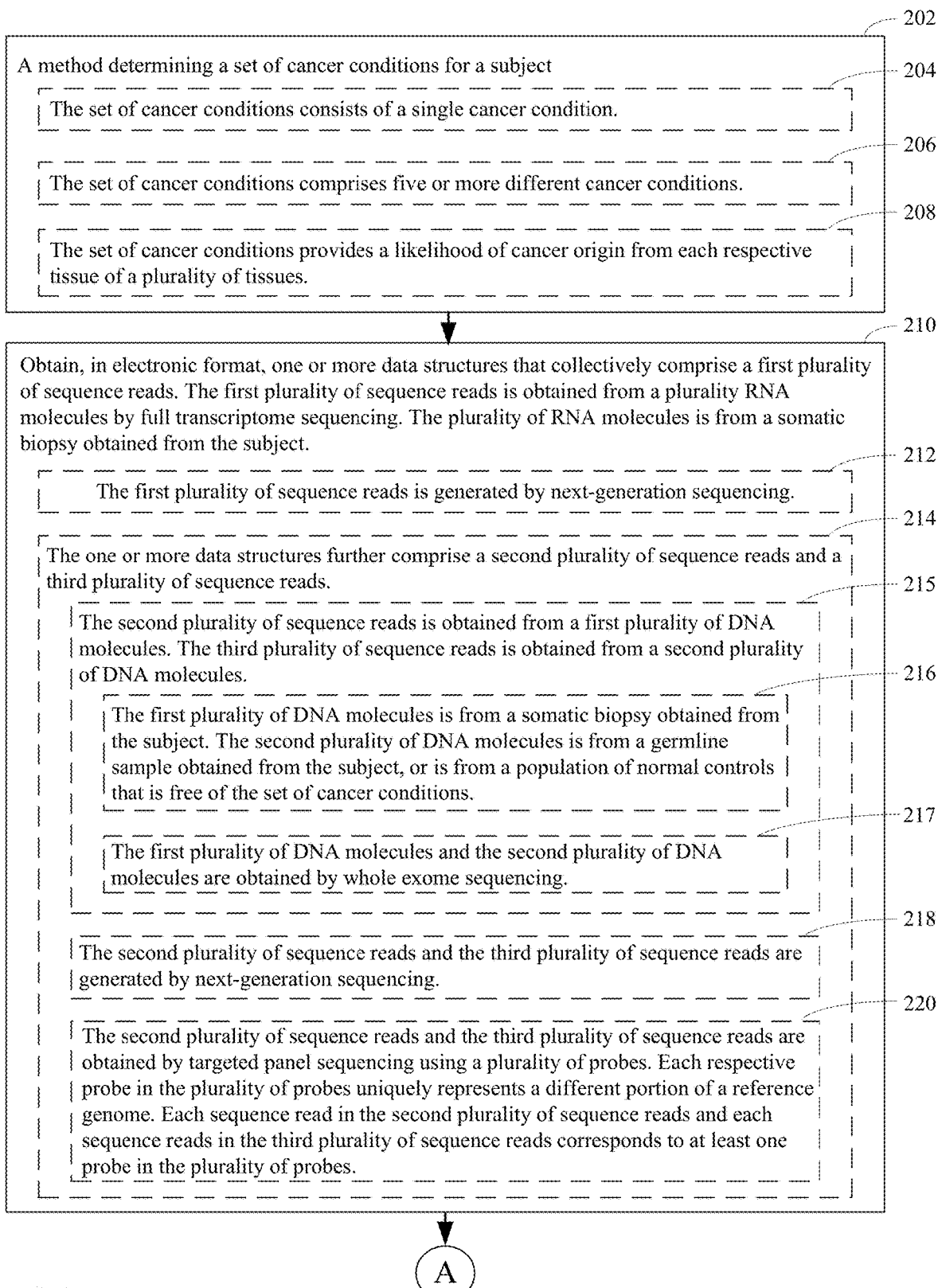
FIGS. 2A, 2B, and 2C collectively provide a flow chart of processes and features for classifying a subject to determine, for a set of cancer conditions, a likelihood that the subject has or does not have each respective cancer condition, in which optional blocks are indicated with dashed boxes, in accordance with some embodiments of the present disclosure.

While a system in accordance with the present disclosure has been disclosed with reference to FIG. 1, methods in accordance with the present disclosure are now detailed with reference to FIGS. 2 and 3.

Determining a Set of Cancer Conditions for a Subject.

Block 202. Referring to block 202 of FIG. 2A, the method determines a set of cancer conditions for a subject. Referring to block 204, in some embodiments, the set of cancer conditions consists of a single cancer condition (e.g., for determining whether a subject has a particular cancer condition). In some embodiments, the one cancer condition is selected from a pathology report or other medical record of the subject. In some embodiments, the set of cancer conditions consists of two, three, or four different cancer conditions. Referring to block 206, in some embodiments, the set of cancer conditions includes five or more different cancer conditions. Referring to block 208, in some embodiments, the set of cancer conditions comprises a likelihood of cancer origin from each respective tissue of a plurality of tissues (e.g., the set of cancer conditions provides information on the tissue of origin). In some embodiments, a cancer condition in the set of cancer conditions is a likelihood that the subject has a metastatic cancer. In some embodiments, a cancer condition in the set of cancer conditions is a likelihood that the subject has a primary cancer.

In some embodiments, the method classifies a subject to a cancer condition. In some embodiments, the cancer condition is selected from the set of cancer conditions.

In some embodiments, the method classifies a subject to an expected cancer condition. In some embodiments, the expected cancer condition is selected from the set of cancer conditions. In some embodiments, the expected cancer condition (e.g., a prediction or determination made by a pathologist) is determined from a pathology report of the subject. In some embodiments, the expected cancer condition is determined from one or more cancer conditions from a pathology report of the subject.

Figure 16:
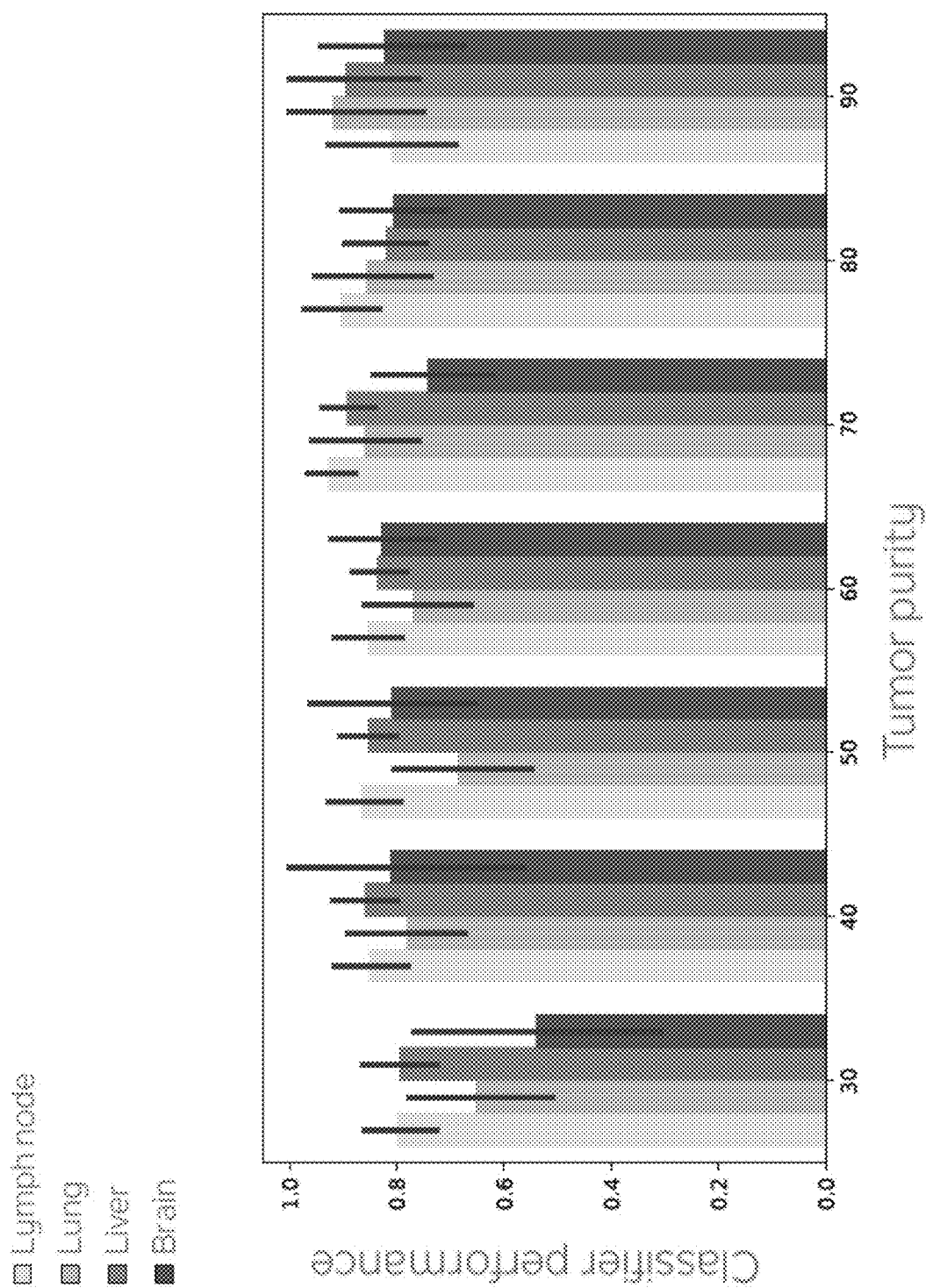
FIG. 16 illustrates the performance of classification models described herein in accordance with some embodiments of the present disclosure. For lymph node, liver, lung, and brain cancers, varying tumor cellularity (in deciles) within the range of 20-100% does not have a large impact on classifier performance, in accordance with some embodiments of the present disclosure. The disclosed methods yield similar results for samples associated with other cancer conditions.
Figure 17A:
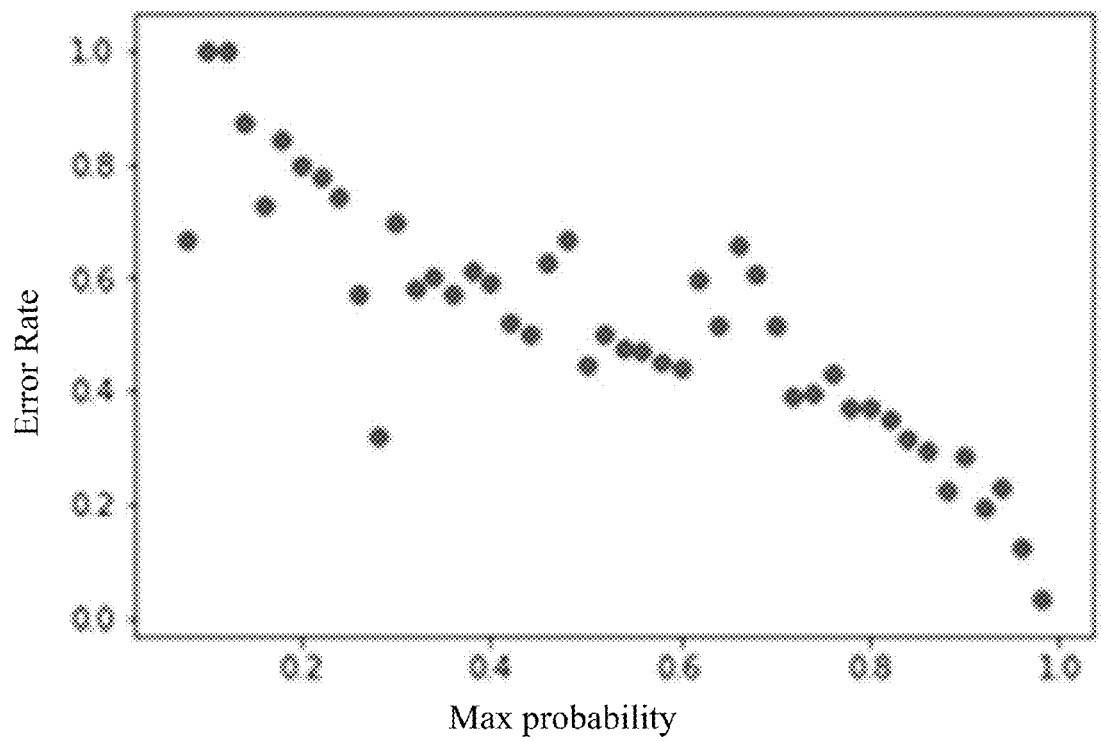
FIGS. 17A and 17B illustrate the error rate of classification models described herein in accordance with some embodiments of the present disclosure.
Figure 17A:
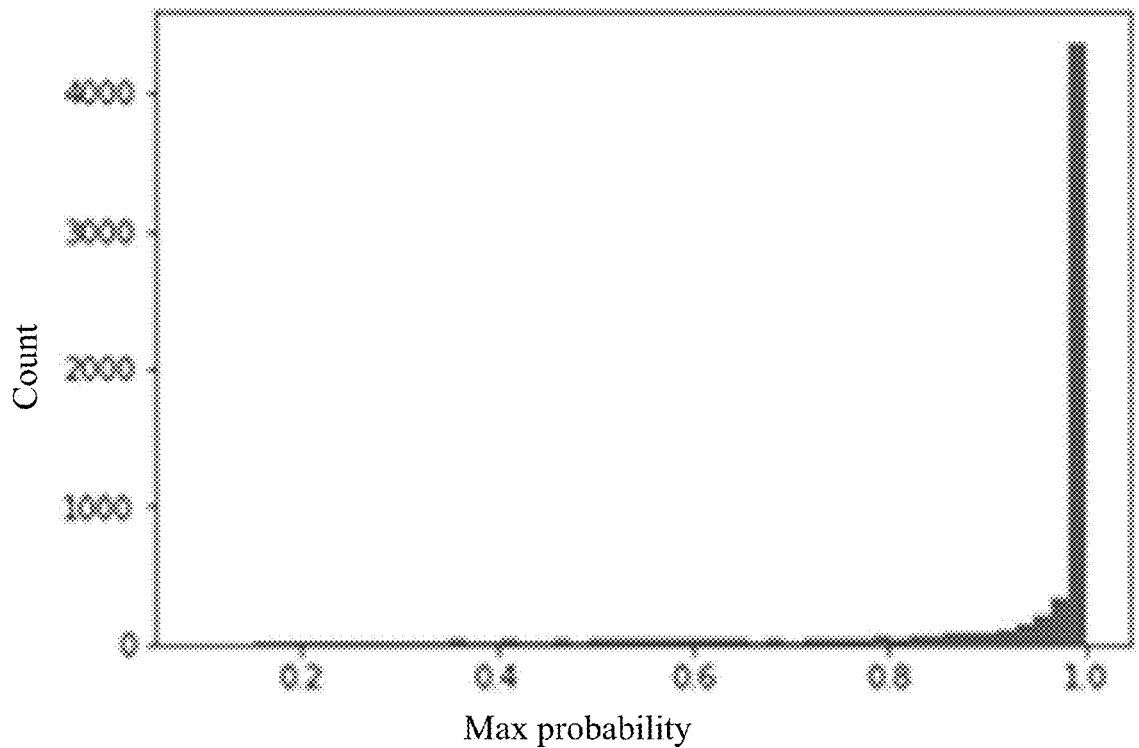
Figure 17B:
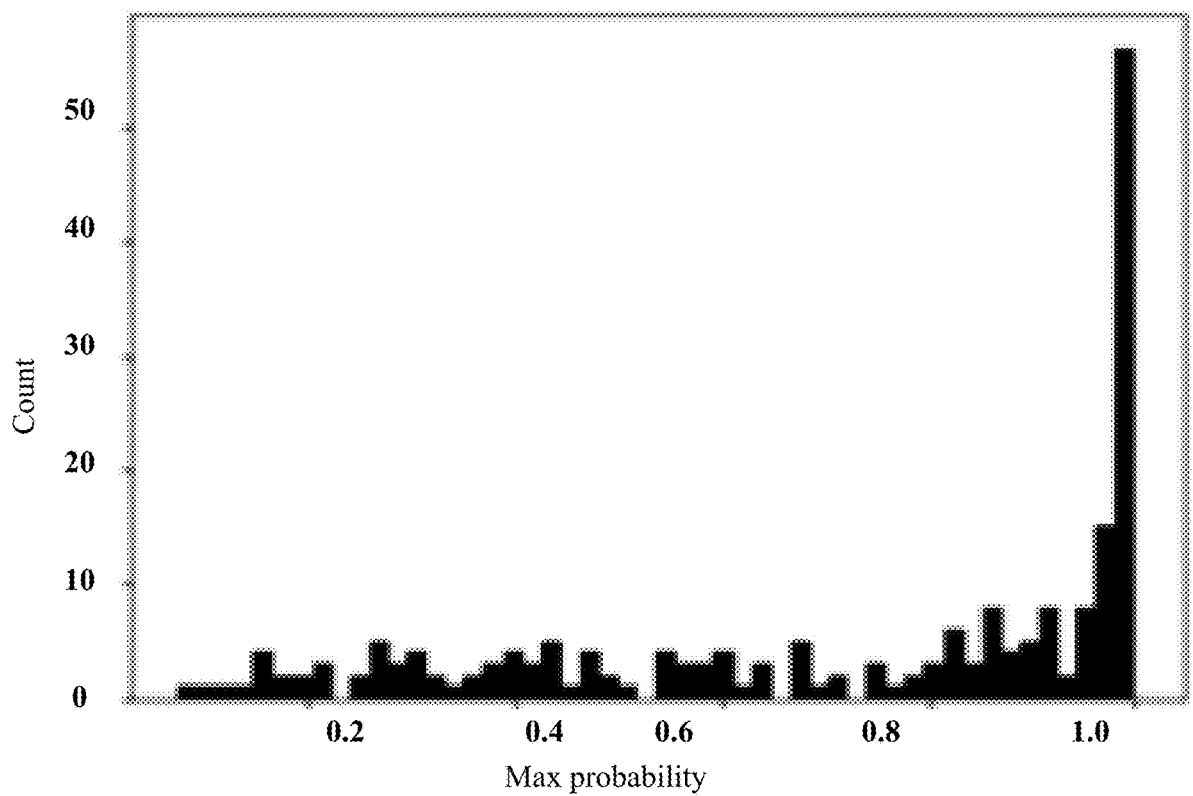

In some embodiments, as illustrated in FIG. 16, varying tumor cellularity in the range of 20-100% does not have a large impact on classification performance. The data shown in FIG. 16 are all related to liver metastatic samples. Liver is a representative type of cancer because many tumors of unknown origins may be found in that organ. This analysis exemplifies that the classification model works well in metastatic, low-purity settings. The classification of tumor of unknown origin is described in more detail in Example 4.

Block 210. Referring to block 210 of FIG. 2A, one or more data structures of the subject are obtained in electronic format. The one or more data structures collectively comprise a first plurality of sequence reads. The first plurality of sequence reads is obtained from a plurality of RNA molecules or derivatives of said plurality of RNA molecules (e.g., derivatives such as cDNA). In some embodiments, the plurality of RNA molecules is obtained by full transcriptome sequencing. In some embodiments, these sequence read are derived from RNA that has been isolated from a solid or hematological tumor (e.g., a solid biopsy).

Figure 15A:
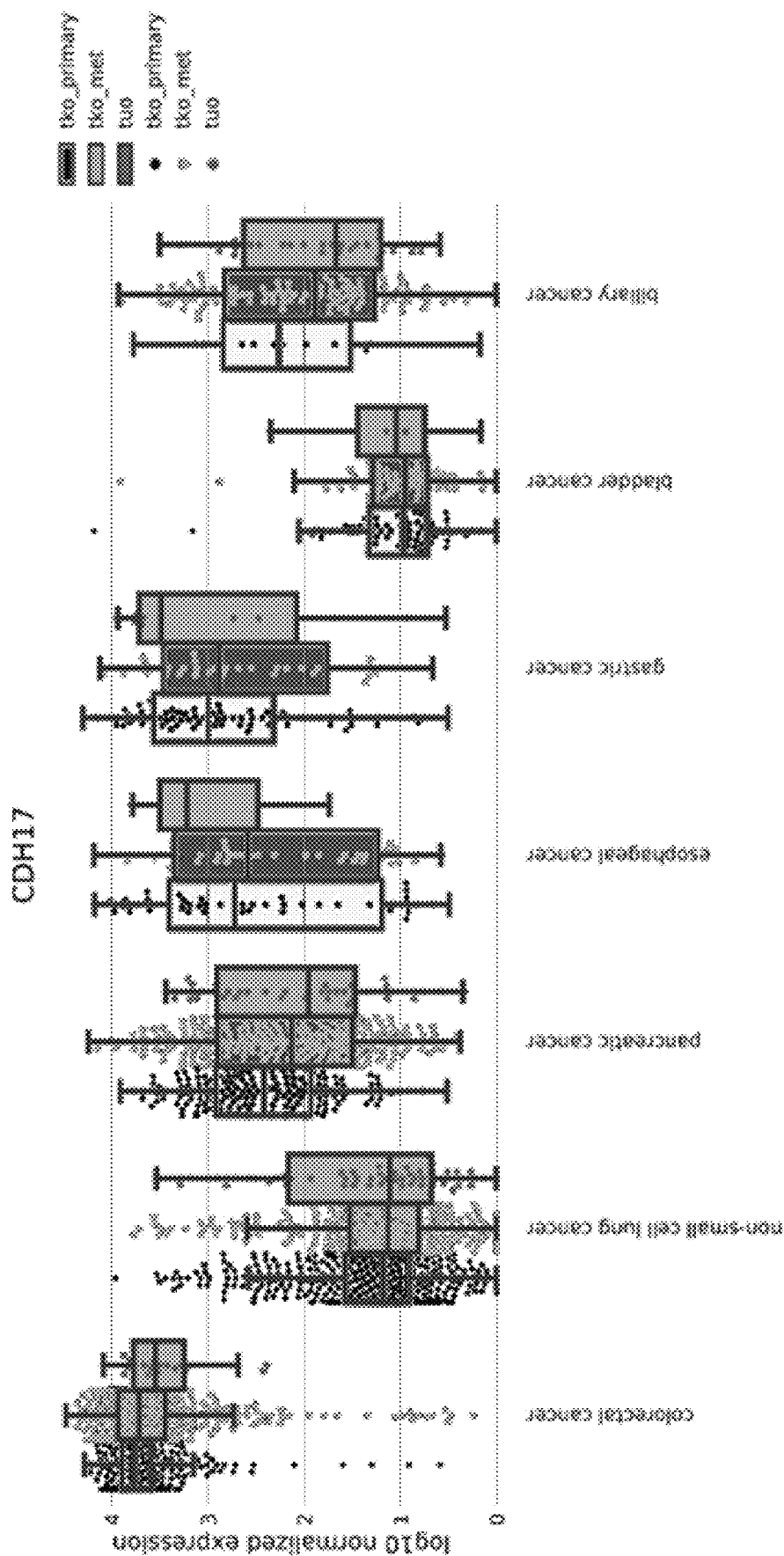
FIGS. 15A, 15B, and 15C collectively illustrate examples of correlation in RNA transcription levels between patients with tumors of known origin (tko) cancer conditions (tko_primary for primary cancers and tko_met for metastatic cancers) and patients with tumors of unknown origin organized by cancer condition, in accordance with some embodiments of the present disclosure. These results indicate that a trained model generates a cancer condition prediction (tuo) associated with RNA expression level profiles that mimics the RNA expression level profiles associated with the actual primary and/or metastatic cancer condition.
Figure 15B:
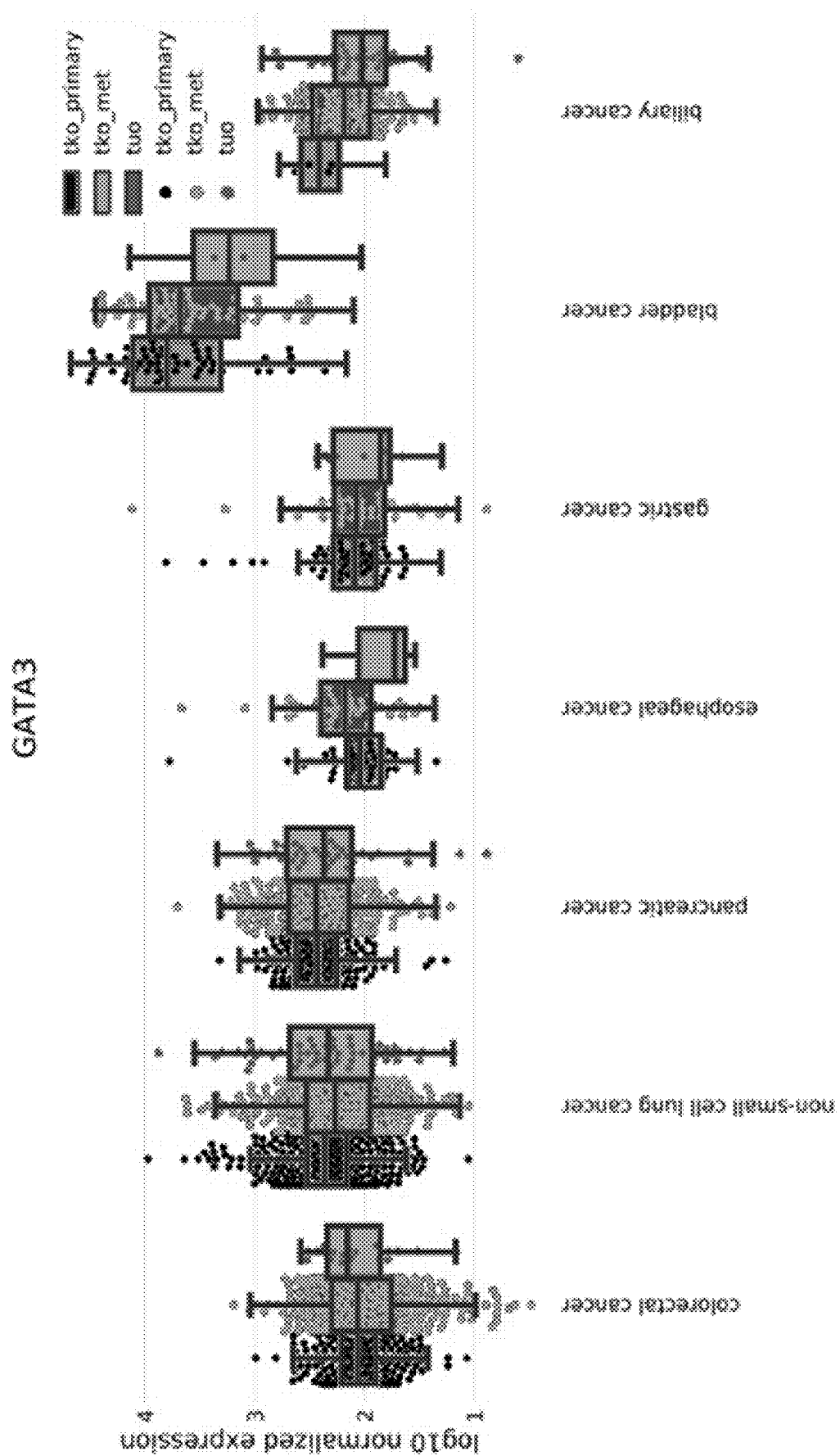
Figure 15C:
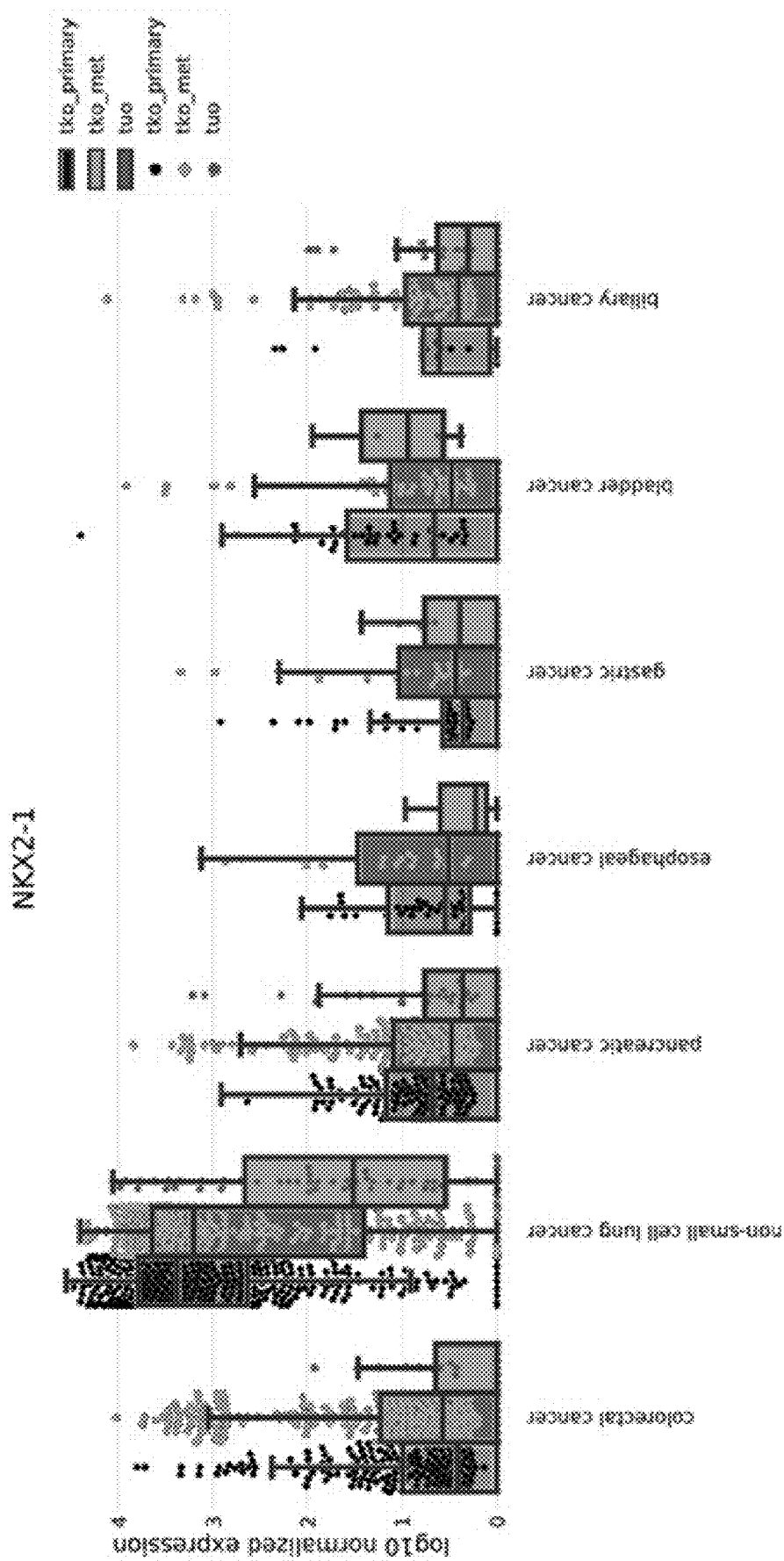

FIGS. 15A-15C show expression data (e.g., amounts of sequence reads obtained from RNA molecules, for instance, each for a specific RNA) for patients with primary tumors of known origin (tko_primary) and patients with metastatic tumors of known origin (tko_met) as compared with the expression profiles of patients with tumors of unknown origin (tuo). Each patient in these figures has one of the following cancers (as shown along the x-axes): colorectal, non-small cell lung, pancreatic, esophageal, gastric, bladder, or biliary. Each figure shows the expression levels of the patients for one gene (e.g., genes known to be associated with cancer). The tuo patients were classified to cancer condition by a classification model that was trained as described herein. As can be seen from the expression profiles, there is a general correlation between the RNA expression of patients with tumors of known origin) both metastatic and primary tumors) and patients with tumors of unknown origin. These figures illustrate that RNA data can be useful with regards to classifying patients with tumors of unknown origin.

Referring to block 214, in some embodiments, the one or more data structures further comprise a second plurality of sequence reads and a third plurality of sequence reads. In some embodiments, referring to block 215, the second plurality of sequence reads is obtained from a first plurality of DNA molecules or derivatives of said DNA molecules, and the third plurality of sequence reads is obtained from a second plurality of DNA molecules or derivatives of said DNA molecules. Referring to block 216, in some embodiments, the first plurality of DNA molecules is from a somatic biopsy obtained from the subject, and the second plurality of DNA molecules is from a germline sample obtained from the subject or is from a population of normal controls that is free of the set of cancer conditions. Referring to block 217, in some embodiments, the first plurality of DNA molecules and the second plurality of DNA molecules are obtained by whole exome sequencing.

Referring to block 218, in some embodiments, the second plurality of sequence reads and the third plurality of sequence reads are generated by next-generation sequencing. In some embodiments, the second plurality of sequence reads, and the third plurality of sequence reads are generated from short-read, paired-end next-generation sequencing. Referring to block 220, in some embodiments, the second plurality of sequence reads and the third plurality of sequence reads are obtained by targeted panel sequencing using a plurality of probes. In such embodiments, each respective probe in the plurality of probes uniquely represents a different portion of a reference genome. In such embodiments, each sequence read in the second plurality of sequence reads and each sequence reads in the third plurality of sequence reads corresponds to at least one probe in the plurality of probes.

Figure 14A:
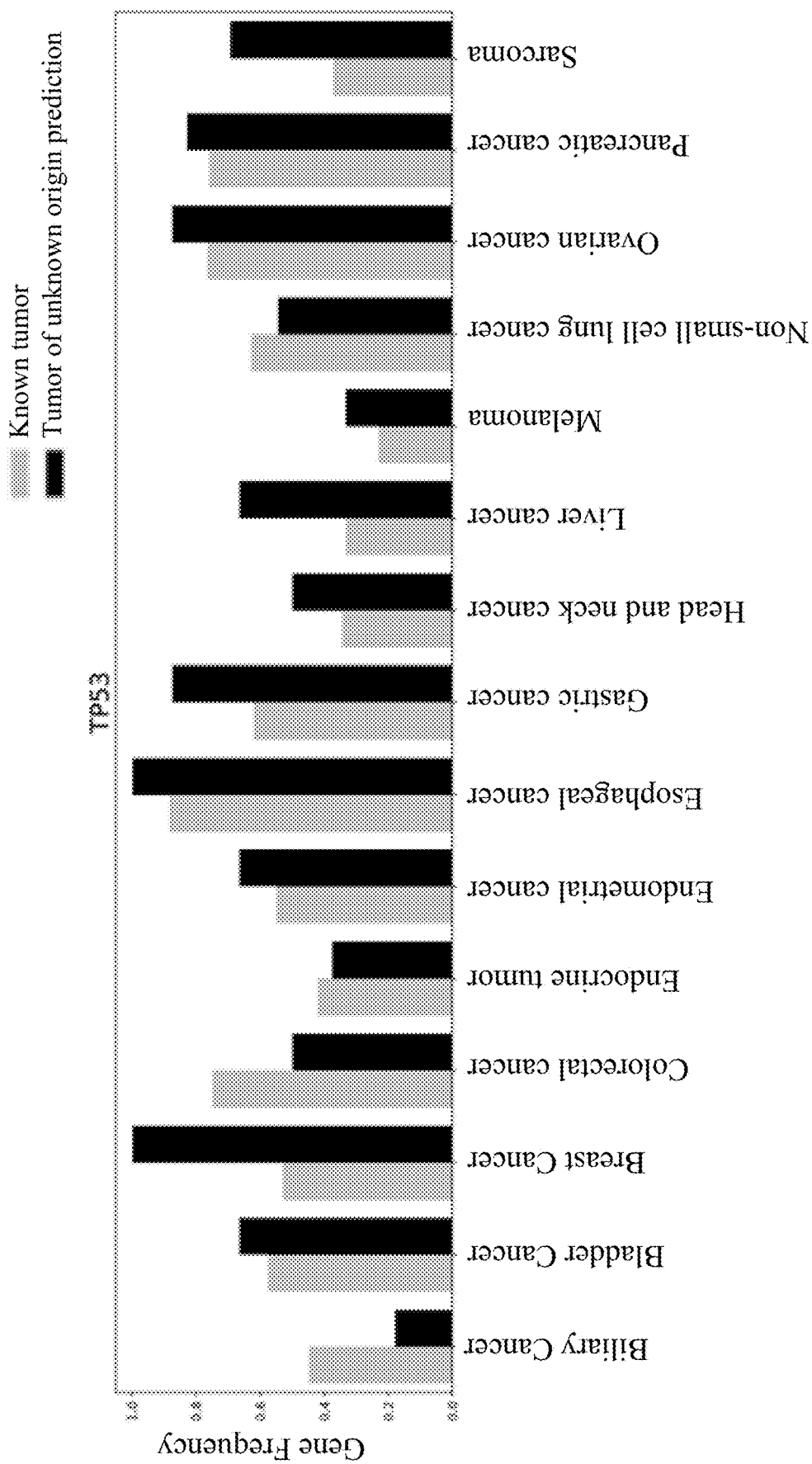
FIGS. 14A and 14B illustrate examples of correlation in the gene frequency between patients with known cancer conditions (light gray bars, "actual") and patients with predicted tumors of origin (dark gray bars, "tumor of unknown origin (tuo) prediction"), organized by actual or predicted cancer condition, in accordance with some embodiments of the present disclosure. These results indicate that a trained model generates a cancer condition prediction associated with DNA mutation profiles that mimic the DNA mutation profiles associated with the actual cancer condition.
Figure 14B:
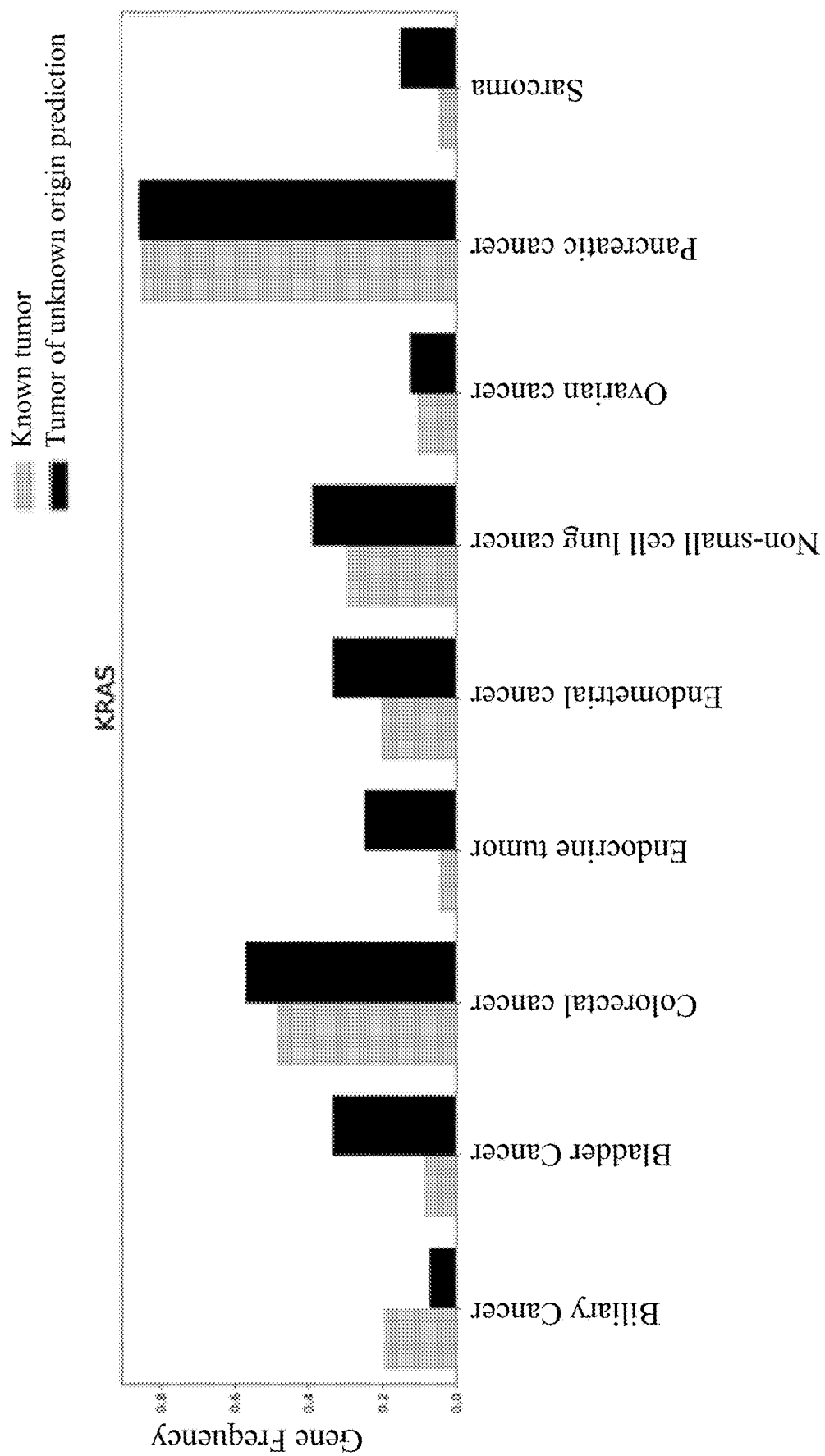

FIGS. 14A and 14B illustrate that DNA expression data can provide helpful information for classifying subjects to cancer condition. Each of FIGS. 14A and 14B illustrate expression levels for a specific gene. The amounts of sequence reads obtained from DNA molecules are often correlated between patients with known cancer conditions and patients with the same predicted tumor of origin (e.g., in particular for patients with known or predicted bladder cancer, endocrine cancer, endometrial cancer, esophageal cancer, non-small cell lung cancer, ovarian cancer, and pancreatic cancer in FIG. 14A and for patients with known or predicted colorectal cancer, non-small cell lung cancer, ovarian cancer, and pancreatic cancer in FIG. 14B)).

Referring to block 222, in some embodiments, the one or more data structures (e.g., from the data store described in more detail below) further include a pathology report for the subject (e.g., a pathology report of the subject is obtained). In some embodiments, the pathology report includes one or more of IHC protein levels of the subject, age of the subject, gender of the subject, disease diagnosis, treatment category, type of treatment, and treatment outcomes.

In some embodiments, the pathology report further includes an image file. In some embodiments, the pathology report further includes one or more extracted image features from one or more image files of the somatic biopsy (e.g., a tumor biological sample) from the subject. In some embodiments, the extracted image features include size of tumor, stage of tumor, tumor grade, tumor purity, degree of invasiveness, degree of immune infiltration into the tumor, cancer stage, anatomic origin site of the tumor, etc. In some embodiments, one or more of these extracted image features is incorporated into the pathology report. In some embodiments, image features are extracted according to methods described in U.S. Patent Application No. 62/824,039 entitled "PD-L1 Prediction Using H&E Slide Images," filed on Mar. 26, 2019.

In some embodiments, digital pathology images (e.g., image files of a somatic biopsy) of somatic biopsies provide essential clues about the population of cells from the subject that are subsequently sequenced to obtain the first plurality of sequence reads (e.g., obtained from the plurality of RNA molecules) and the second plurality of sequence reads (e.g., obtained from the first plurality of DNA molecules). Somatic biopsies are often a heterogeneous mixture of necrotic tissue, lymphocytes and other immune cells, stromal cells, and tumor cells. Imaging itself provides essential information about the cellular composition of the sample that is being sequenced. Further analysis of image files (e.g., through convolutional neural networks as described in U.S. patent application Ser. No. 16/732,242 entitled "Artificial Intelligence Segmentation of Tissue Images," filed Dec. 31, 2019), can capture higher level information about the tissue morphology of the biopsy location. Deep ranking neural networks perform retrieval tasks that can be used to find other images in the dataset that share common features, providing information about the identity of the tumor.

In some embodiments, one or more data structures further include an indication of viral status (e.g., as described in U.S. Pat. Application No. 62/810,849, entitled "Systems and Methods for Using Sequencing Data for Pathogen Detection," filed Feb. 26, 2019, which is hereby incorporated by reference in its entirety (e.g., an indication of viral status of the subject is obtained). In some embodiments, the indication of viral status comprises a count of viral-associated sequence reads (e.g., see FIG. 20 and Example 9). In such embodiments, the method further comprises applying the indication of viral status to the trained classification model.

In some embodiments, both DNA and RNA expression data are used to train a classification model. In some embodiments, one of DNA or RNA expression data is used to train a classification model. In some embodiments, both DNA and RNA expression data are used to determine a set of cancer conditions and/or a cancer condition for a patient with one or more tumors of unknown origin. In some embodiments, one of DNA or RNA expression data is used to determine a set of cancer conditions and/or a cancer condition for a patient with one or more tumors of unknown origin.

Referring to block 224, in some embodiments, the somatic biopsy comprises macrodissected formalin fixed paraffin embedded (FFPE) tissue sections, surgical biopsy, skin biopsy, punch biopsy, prostate biopsy, bone biopsy, bone marrow biopsy, needle biopsy, CT-guided biopsy, ultrasound-guided biopsy, fine needle aspiration, aspiration biopsy, fresh tissue or blood samples. In some embodiments, the germline sample comprises blood or saliva from the subject. This serves to separate the tumor sample from the normal sample (e.g., the patient's own control sample). In some embodiments, the somatic biopsy is of a breast tumor, a glioblastoma, a prostate tumor, a pancreatic tumor, a kidney tumor, a colorectal tumor, an ovarian tumor, an endometrial tumor, a breast tumor, or a combination thereof. Biopsies are typically performed after one or more less-invasive clinical tests suggest that a patient has or has a likelihood of having one or more tumors. The type of biopsy often depends on the location of the tumor. For example, biopsies of kidney tumors are frequently performed endoscopically, while biopsies of ovarian tumors frequently comprise tissue scraping.

Referring to block 226, in some embodiments, the first plurality of sequence reads is generated by next-generation sequencing with one or more spike-in controls. In some embodiments, the first plurality of sequence reads is generated from short-read paired end next-generation sequencing. In some embodiments, the second plurality and/or third plurality of sequence reads are generated by next-generation sequencing with one or more spike-in controls. In some embodiments, the first second plurality and/or third plurality of sequence reads are generated from short-read paired end next-generation sequencing Methods of next-generation sequencing for use in accordance with methods described herein are disclosed in Shendure 2008 Nat. Biotechnology 26:1135-1145 and Fullwood et al. 2009 Genome Res. 19:521-532, which are each hereby incorporated by reference. Next generation sequencing methods well known in the art include synthesis technology (Illumina), pyrosequencing (454 Life Sciences), ion semiconductor technology (Ion Torrent sequencing), single-molecule real-time sequencing (Pacific Biosciences), sequencing by ligation (SOLiD sequencing), nanopore sequencing (Oxford Nanopore Technologies), or paired-end sequencing. In some embodiments, massively parallel sequencing is performed using sequencing-by-synthesis with reversible dye terminators.

Methods for mRNA sequencing are also well known in the art. In some embodiments, the mRNA is reverse transcribed to cDNA prior to sequencing. For example, methods of RNA-seq for use in accordance with block 210 are disclosed in Nagalakshmi et al., 2008, Science 320, 1344-1349; and Finotell and Camillo, 2014, *Briefings in Functional Genomics* 14(2), 130-142, each of which is hereby incorporated by reference. In some embodiments, the mRNA sequencing is performed by whole exome sequencing (WES). In some embodiments, WES is performed by isolating RNA from a tissue sample, optionally selecting for desired sequences and/or depleting unwanted RNA molecules, generating a cDNA library, and then sequencing the cDNA library, for example, using next-generation sequencing techniques. For a review of the use of whole exome sequencing techniques in cancer diagnosis, see, Serrati et al., 2016, Onco Targets Ther. 9, 7355-7365 and Cieslik, M. et al. 2015 *Genome Res.* 25, 1372-81, the content of each of which is hereby incorporated herein by reference in its entirety, for all purposes. In some embodiments, the mRNA sequencing is performed by nanopore sequencing. A review of the use of nanopore sequencing techniques on the human genome can be found in Jain et al., 2018, Nature 36(4), 338-345. This list is not exhaustive of the RNA sequencing methods that may be used in accordance with the methods described herein. In some embodiments, the RNA sequencing is performed according to one or more sequencing methods known in the art. See e.g., a review of RNA sequencing methods Kukurba et al. 2015 *Cold Spring Harb Protoc.* 11: 951-969.

RNA-seq is a methodology for RNA profiling based on next-generation sequencing that enables the measurement and comparison of gene expression patterns across a plurality of subjects. In some embodiments, millions of short strings, called 'sequence reads,' are generated from sequencing random positions of cDNA prepared from the input RNAs that are obtained from tumor tissue of a subject. In some embodiments, RNA-seq gene expression data was generated from formalin fixed paraffin embedded tumor samples using an exome-capture based RNA-seq protocol. These reads can then be computationally mapped on a reference genome to reveal a 'transcriptional map', where the number of sequence reads aligned to each gene gives a measure of its level of expression (e.g., abundance). In some embodiments, the RNA-seq expression levels (e.g., raw read counts) are normalized (e.g., to correct for GC content, sequencing depth, and/or gene length). In some embodiments, methods of mapping raw RNA sequence reads to the transcriptome, quantifying gene counts, and normalization are performed as described in U.S. Patent Application No. 62/735,349, entitled "Methods of Normalizing and Correcting RNA Expression Data," filed on Sep. 24, 2018.

In some alternative embodiments, rather than using RNA-seq, microarrays are used to examine RNA profiling. Such microarrays are disclosed in Wang et al., 2009, *Nat Rev Genet* 10, 57-63; Roy et al., 2011, *Brief Funct Genomic* 10:135-150; Shendure, 2008 *Nat Methods* 5, 585-587; Cloonan et al., 2008, "Stem cell transcriptome profiling via massive-scale mRNA sequencing," Nat Methods 5, 613-619; Mortazavi et al., 2008, "Mapping and quantifying mammalian transcriptomes by RNA-Seq," Nat Methods 5, 621-628; and Bullard et al., 2010, "Evaluation of statistical methods for normalization and differential expression in mRNA-Seq experiments" BMC Bioinformatics 11, p. 94, each of which is hereby incorporated by reference.

The first computational step of the RNA-seq data analysis pipeline is read mapping: reads are aligned to a reference genome or transcriptome by identifying gene regions that match read sequences. Any of a variety of alignment tools can be used for this task. See, for example, Hatem et al., 2013 *BMC Bioinformatics* 14, 184; and Engstrom et al. 2013 *Nat Methods* 10, 1185-1191, each of which is hereby incorporated by reference. In some embodiments, the mapping process starts by building an index of either the reference genome or the reads, which is then used to retrieve the set of positions in the reference sequence where the reads are more likely to align. Once this subset of possible mapping locations has been identified, alignment is performed in these candidate regions with slower and more sensitive algorithms. See, for example, Flicek and Birney, 2009, *Nat Methods* 6(Suppl. 11), S6-S12, which is hereby incorporated by reference. In some embodiments, the mapping tools is a methodology that makes use of a hash table or makes use of a Burrows-Wheeler transform (BWT). See, for example, Li and Homer, 2010 *Brief Bioinformatics* 11, 473-483, which is hereby incorporated by reference.

After mapping, the reads aligned to each coding unit, such as exon, transcript, or gene, are used to compute read counts, in order to provide an estimate of its abundance (e.g., expression) level. In some embodiments, only the coding region of the genome is available for mapping, thus preventing discontinued or withdrawn genes from previous iterations of the human genome from being mapped. In some embodiments, such counting considers the total number of reads overlapping the exons of a gene. However, because in some instances some of the sequence reads map outside the boundaries of known exons, alternative embodiments consider the whole length of a gene, also counting reads from introns. Further still, in some embodiments spliced reads are used to model the abundance of different splicing isoforms of a gene. See, for example, Trapnell et al., 2010 Nat Biotechnol 28, 511-515; and Gatto et al, 2014 Nucleic Acids Res 42, p. e71, each of which is hereby incorporated by reference.

As explained above, quantification of transcript abundance from RNA-seq data is typically implemented in the analysis pipeline through two computational steps: alignment of reads to a reference genome or transcriptome, and subsequent estimation of transcript and isoform abundances based on aligned reads. Unfortunately, the reads generated by the most used RNA-Seq technologies are generally much shorter than the transcripts from which they are sampled. Consequently, in the presence of transcripts with similar sequences, it is not always possible to uniquely assign short sequence reads to a specific gene. Such sequence reads are referred to as "multireads" because they are homologous to more than one region of the reference genome. In some embodiments, such multireads are discarded, that is, they do not contribute to gene abundance counts. In some embodiments, programs such as MMSEQ or RSEM, are used to resolve the ambiguity. See examples of methodologies used to resolve multireads in Turro et al., 2011 Genome Biol 12, p. R13; and Nicolae et al., Algorithms Mol Biol 6, 9, each of which is hereby incorporated by reference.

Another aspect of RNA-seq is normalization of sequence read counts. In some embodiments, this includes normalization to take into account different sequencing depths. See, for example, Lin et al., 2011 Bioinformatics 27, 2031-2037; Robinson Oshlack, 2010 Genome Biol 11, R25; and Li et al., 2012 Biostatistics 13, 523-538, each of which is hereby incorporated by reference. In some embodiments, sequence read counts are normalized to account for gene length bias. See, Finotell and Camillo, 2014 Briefings in Functional Genomics 14(2), 130-142, which is hereby incorporated by reference.

In some embodiments, a fourth plurality of sequence reads is obtained from an additional plurality of RNA molecules, which are isolated from normal healthy tissues (e.g., the use of paired tumor/normal analysis is described in Example 3). In some embodiments, the amount of each sequence read in the first plurality of sequence reads is compared to the amount of the corresponding sequence read from the fourth plurality of sequence reads, (e.g., essentially normalizing the amounts of RNA sequence reads in the subject).

In some embodiments, the second plurality of sequence reads and the third plurality of sequence reads are obtained by targeted panel sequencing using a plurality of probes. Each respective probe in the plurality of probes uniquely targets a different portion of a reference genome (e.g., of the human reference genomes). Each sequence read in the second plurality of sequence reads and each sequence reads in the third plurality of sequence reads corresponds to least one probe in the plurality of probes. In some embodiments, whole genome sequencing is used, for example, instead of targeted panel sequencing.

In some embodiments, the second plurality of sequence reads has an average depth of at least 50× across the plurality of probes. In some embodiments, the second plurality of sequence reads has an average depth of at least 400× across the plurality of probes. In other embodiments, the second plurality of sequence reads has an average depth of at least 10×, 15×, 20×, 25×, 30×, 40×, 50×, 75×, 100×, 150×, 200×, 250×, 300×, 400×, 500×, or greater.

In some embodiments, the plurality of probes includes probes for at least three hundred different genes. In some embodiments, the plurality of probes includes probes for at least five hundred different genes. In yet other embodiments, the plurality of probes includes at least 50, 100, 150, 200, 250, 300, 400, 500, 600, 700, 800, 900, 1000, 1500, 2000, 3000, 4000, 5000, or more different genes. In some embodiments, the plurality of probes includes probes for at least 50, 100, 150, 200, 250, 300, 400, 500, or more different genes selected from the Targeted Gene List (e.g., Table 2). In some embodiments, and the plurality of probes includes probes for at least five hundred different genes selected from the Targeted Gene List. The Targeted Gene List is derived from the IDT xGen Exome Research Panel and comprises around 19,400 exons from the human genome. See e.g., information available online at idtdna.com/pages/products/next-generation-sequencing/hybridization-capture/lockdown-panels/xgen-exome-research-panel.

In some embodiments, whole exome sequencing of the cDNA library is performed using the integrated DNA technologies (IDT) XGEN® LOCKDOWN® technology with the xGen Exome Research Panel. Briefly, the xGen Exome Research Panel covers 51 Mb of end-to-end tiled probe space of the human genome, providing deep and uniform coverage for whole exome target capture. The cDNA library was hybridized to biotinylated-DNA capture probes covering a reference human exome. The hybridized probes were recovered by binding to streptavidin beads. Post-capture PCR was performed to enrich the captured sequences. The amplified products were then sequenced using sequencing by synthesis (SBS) technology (Bently et al., 2008, Nature 456(7218), 53-59, the content of which is hereby incorporated herein by reference, in its entirety, for all purposes).

In some embodiments, the metastatic cancer or the primary cancer (e.g., in some embodiments, defined as the somatic biopsy) includes a tumor from a common primary site of origin (e.g., the metastatic cancer or the primary cancer originate from one tumor of origin). In some embodiments, the metastatic cancer or the primary cancer includes a tumor originating from two or more different organs (e.g., the tumor originates from multiple organs and/or the tumor originates from either of several possible organs).

In some embodiments, the metastatic cancer or the primary cancer (e.g., in some embodiments, defined as the somatic biopsy) includes a tumor of a predetermined stage of a brain cancer, a predetermined stage of a glioblastoma, a predetermined stage of a prostate cancer, a predetermined stage of a pancreatic cancer, a predetermined stage of a kidney cancer, a predetermined stage of a colorectal cancer, a predetermined stage of an ovarian cancer, a predetermined stage of an endometrial cancer, or a predetermined stage of a breast cancer. FIG. 7B illustrates results of classification of samples from different brain cancers to a wide range of categories (e.g., distinct tumor grades), as discussed below in Example 4.

Referring to block 226, in some embodiments, the first plurality of sequence reads is generated from short-read next-generation sequencing with one or more spike-in controls. In some embodiments, the one or more spike-in controls calibrate variation in sequence reads across a population of cells (e.g., the volume of RNA reads obtained from each cell can vary significantly and spiking helps to normalize reads across a set of cells).

Figure 2B:
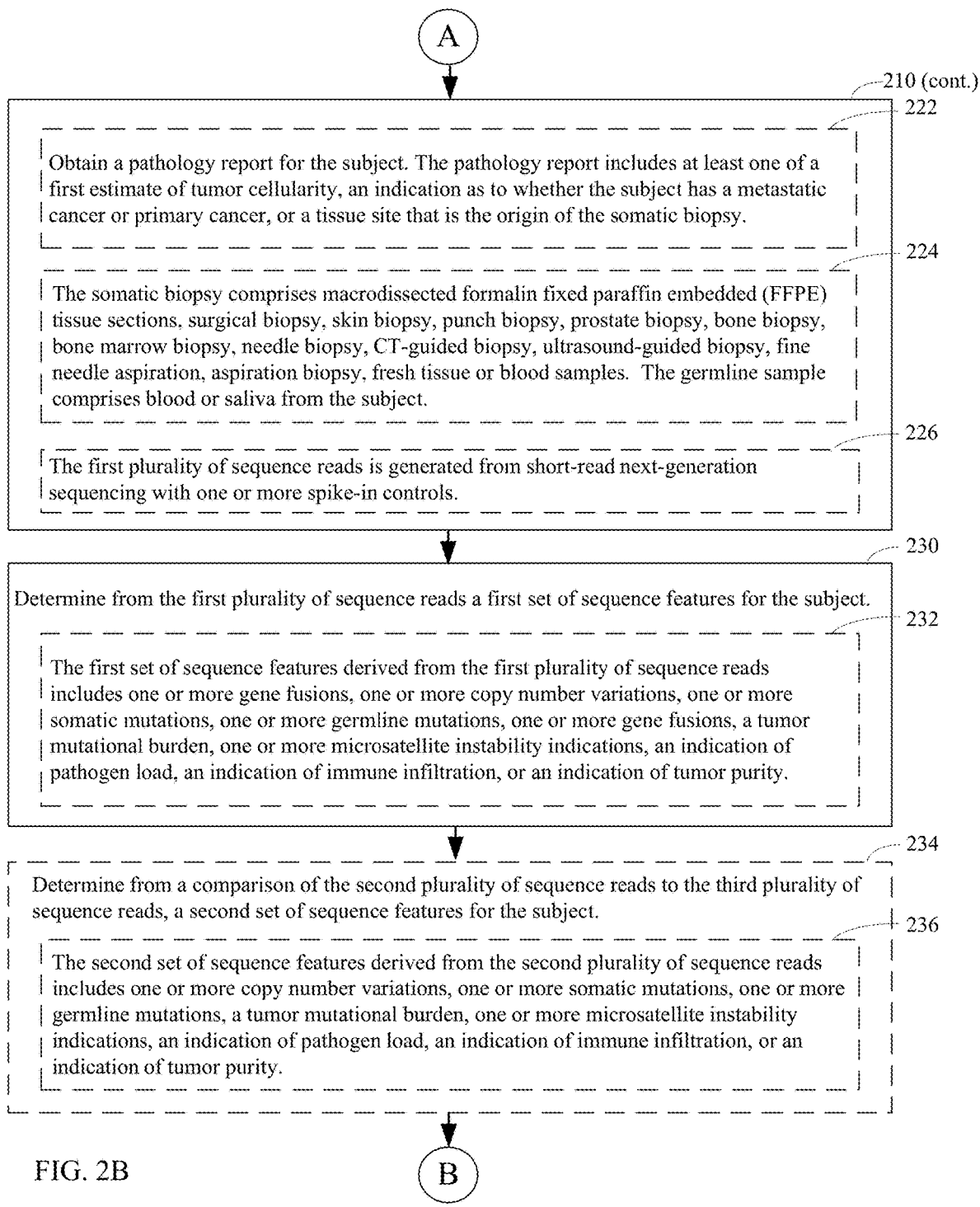
Figure 3A:
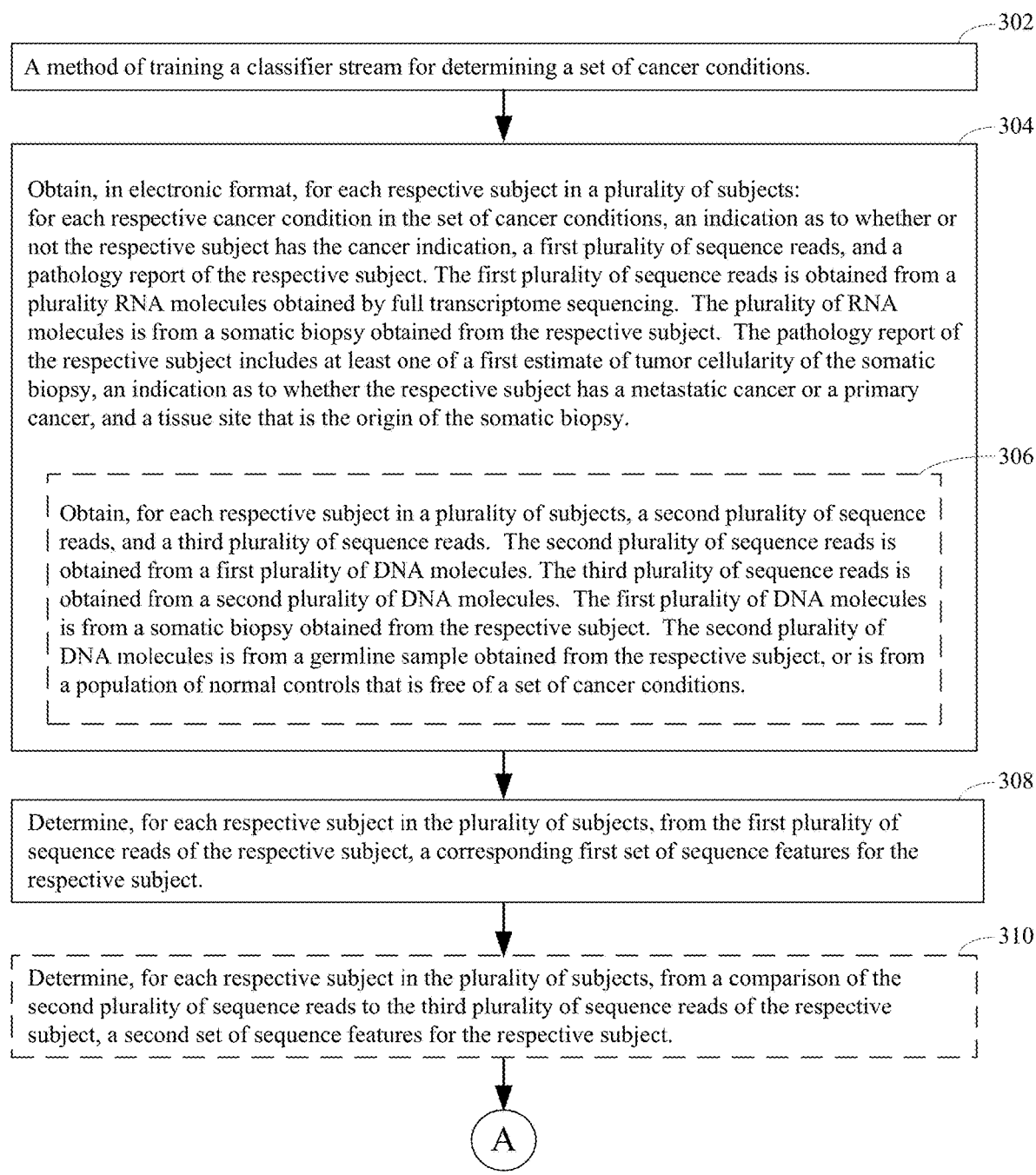
FIGS. 3A and 3B collectively provide a flow chart of processes and features for training a classifier to estimate tumor cellularity, in which optional blocks are indicated with dashed boxes, in accordance with some embodiments of the present disclosure.
Figure 3B:
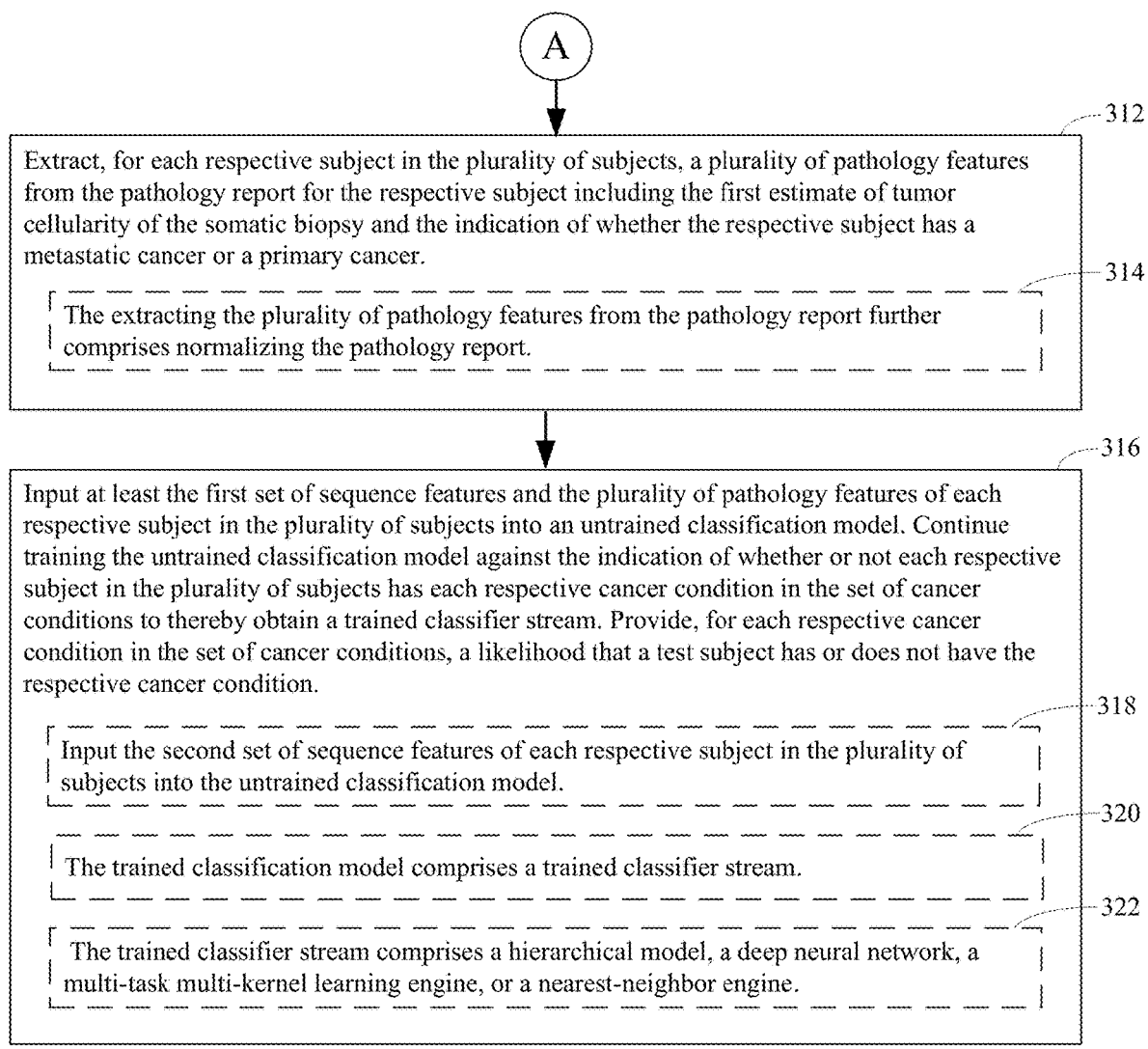

Next, in block 230 of FIG. 2B, the method continues by determining a first set of sequence features for the subject from the first plurality of sequence reads. In some embodiments, the first set of sequence features includes between 15,000 features and 22,000 features. In some embodiments, the first set of sequence features includes 20,000 RNA variables (e.g., transcriptomes). In some embodiments, features for the subject further comprise any of the features described herein (e.g., RNA features, DNA features, CNV features, viral features or any combination thereof). In some embodiments, the methods for generating features in the plurality of features may include one or more of the methods disclosed in U.S. patent application Ser. No. 16/657,804, titled "Data Based Cancer Research and Treatment Systems and Methods" (hereinafter the '804 patent), filed Oct. 18, 2019, which is hereby incorporated by reference in its entirety.

In some embodiments, the determining a first set of sequence features further comprises deconvoluting the first plurality of sequence reads by comparing the first plurality of sequence reads to a deconvoluted RNA expression model comprising at least one cluster identified as corresponding to a cancer condition. In some embodiments, the deconvolution process is performed as described by U.S. patent application Ser. No. 16/732,229, entitled "Transcriptome Deconvolution of Metastatic Tissue Samples," filed Dec. 31, 2018, which is hereby incorporated in entirety.

In some embodiments, as shown in block 232 of FIG. 2B, the first set of sequence features derived from the first plurality of sequence reads includes one or more gene fusions, one or more copy number variations, one or more somatic mutations, one or more germline mutations, one or more gene fusions, a tumor mutational burden (TMB), one or more microsatellite instability indications (MSI), an indication of pathogen load, an indication of immune infiltration, or an indication of tumor cellularity.

In some embodiments, the determining includes aligning each respective sequence read in the first plurality of sequence reads to a reference genome to determine the first set of sequence features of the subject. In some embodiments, the one or more gene fusions are determined as discussed in McPherson et al 2011 PLoS Comput Biol 7(5): e1001138. In some embodiments, the one or more copy number variations are determined as described in Shilien and Malkin 2009 Genome Med 1, 62. In some embodiments, the one or more somatic mutations and/or one or more germline mutations are discovered by comparing the second plurality of sequence reads and the third plurality of sequence reads, respectively, to a reference genome. In some embodiments, the one or more microsatellite instability indications are determined as described by Buhard et al. 2006 J Clinical Onco 24(2), 241. In some embodiments, the tumor mutational burden is determined as described in Chalmers et al 2017 Genome Med 9, 34. In some embodiments, the indication of pathogen load and/or the indication of immune infiltration are determined as described, for example, by Barber et al 2015 PLoS Pathog 11(1): e1004558 and Pages et al 2010 Oncogene 29, 1093-1102. In some embodiments, the indication of tumor cellularity is determined from a somatic biopsy by comparing a number of cancerous cells with a number of normal cells obtained in the somatic biopsy. In some embodiments, the indication of tumor cellularity is determined from one or more images of a somatic biopsy (e.g., by counting and identifying cancer vs. non-cancer cells in the one or more images).

Next, in block 234 of FIG. 2B, in some embodiments the method continues by determining a second set of sequence features for the subject from a comparison of the second plurality of sequence reads to the third plurality of sequence reads. In some embodiments, the second set of sequence features includes between 400 features and 2,000 features. In some embodiments, the second set of sequence features includes 500 DNA variables. In other embodiments, the second set of sequence features includes at least 100, 200, 300, 400, 500, 600, 700, 800, 900, 1000, 1500, 2000, 2500, 3000, 4000, 5000, 7500, 10,000, or more sequence features.

In some embodiments, as shown in block 236 of FIG. 2B, the second set of sequence features derived from the comparison of the second plurality of sequence reads to the third plurality of sequence reads includes one or more copy number variations, one or more somatic mutations, one or more germline mutations, a tumor mutational burden (TMB), one or more microsatellite instability indications (MSI), an indication of pathogen load, an indication of immune infiltration, or an indication of tumor cellularity. In some embodiments, the second set of sequence features are derived as described above with regard to FIG. 232. In some embodiments, the second set of sequence features includes one or more DNA variant patterns (e.g., as discussed in Example 9 and illustrated by FIGS. 21A-21C). In some embodiments, the one or more DNA variant patterns are determined for the subject by comparing the second and third pluralities of sequence reads to a reference set of DNA variant patterns, where each DNA variant pattern in the reference set is for a respective cancer condition in the set of cancer conditions.

In some embodiments, the determining the second set of sequence features includes aligning each respective sequence read in the second plurality of sequence reads and the third plurality of sequence reads to a reference genome to determine the second set of sequence features of the subject. The second and third plurality of sequence reads must be aligned before they can be compared to each other.

Figure 2C:
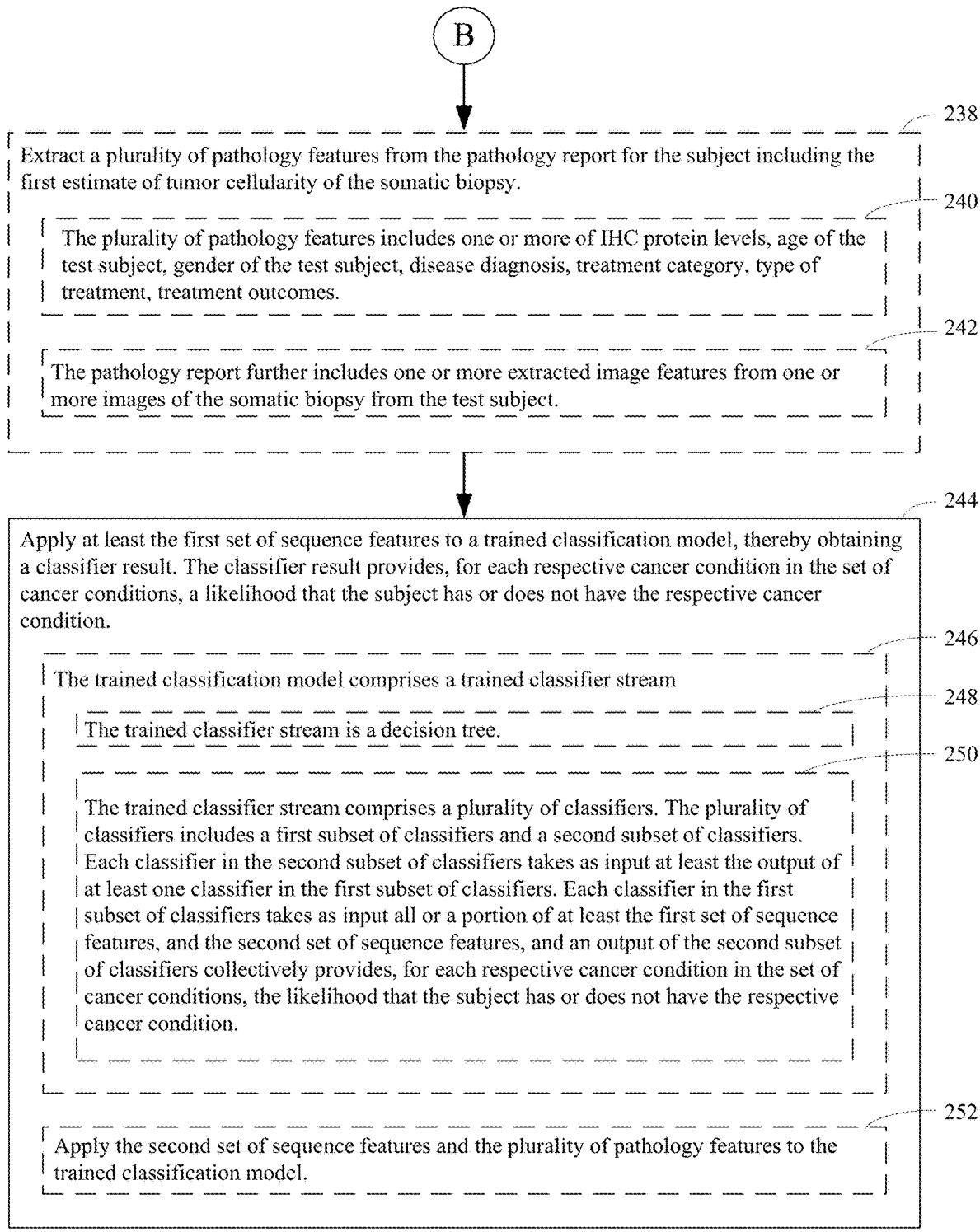

In block 238 of FIG. 2C, in some embodiments, the method continues by extracting a plurality of pathology features from the pathology report for the subject including the first estimate of tumor cellularity of the somatic biopsy and the indication of whether the subject has a metastatic cancer or a primary cancer. Referring to block 240, in some embodiments, the plurality of pathology features includes one or more of immunohistochemistry (IHC) protein levels, tissue site, tumor cellularity, extent of tumor infiltration by lymphocytes, tumor mutation burden (TMB), microsatellite status (e.g., MSI), viral status (e.g., HPV+/−), age of the subject, gender of the subject, disease diagnosis (e.g., including cancer diagnosis, cancer stage, and/or cancer subtype), treatment category (e.g., treated or not treated), type of treatment, or treatment outcomes. In some embodiments, other sections of a pathology report known in the art may also be considered. In some embodiments, a subset of the possible pathology features is considered in classifying a subject to a set of cancer conditions.

In some embodiments, the method further includes supplementing the first estimate of tumor cellularity of the somatic biopsy with a second estimate of tumor cellularity from one or more images of the somatic biopsy (e.g., one or more somatic biopsy images are analyzed to determine the extent of tumor growth and/or development). Images of the somatic biopsy may include images of histological slides generated from the somatic biopsy or radiology scans of the solid tumor or somatic biopsy. In some embodiments, the method further includes supplementing the first estimate of tumor cellularity of the somatic biopsy with a second estimate of tumor cellularity from an abundance of one or more mutations in the second plurality of sequence reads (e.g., from the sequence reads derived from the somatic biopsy).

The pathology report typically requires data cleaning (which may include natural language processing—e.g., as described in Example 5—or manual abstraction) before it is possible to extract meaningful features. Natural language processing in the pathology report is, in some embodiments, performed as described in U.S. application Ser. No. 16/702,510, entitled "Clinical Concept Identification, Extraction, and Prediction System and Related Methods," filed Dec. 3, 2019, which is hereby incorporated in its entirety. Terms in pathology reports are not necessarily standardized, and natural language processing determines which terms are synonyms and may be collapsed together for downstream analysis.

Referring to block 242, in some embodiments, the pathology report further includes one or more extracted image features from one or more images of the somatic biopsy of the test subject. In some embodiments, the plurality of pathology features is extracted from the pathology report (and any associated files, such as images) itself. In alternate embodiments, pathology features are determined or extracted from an alternate source (e.g., without the need for a pathology report). For instance, in some embodiments an electronic medical record (EMR), which is focused on pathology needs and permits pathologists to enter features (e.g., such as tumor purity), is available in a structured format, and the plurality of pathology features are parsed from the structured report (where, e.g., less data cleaning is required than for less-structured pathology reports).

In some embodiments, the plurality of pathology features includes at least two hundred pathology features. In some embodiments, the plurality of pathology features includes between 200 features and 500 features in the pathology record. In some embodiments, the plurality of pathology features includes 400 pathology features in the medical record. In other embodiments, the plurality of pathology features includes at least 10, 15, 20, 25, 30, 40, 50, 75, 100, 150, 200, 250, 300, 400, 500, 600, 700, 800, 900, 1000, or more pathology features. "Pathology features" are features derived from information typically present in pathology records or pathology images.

Next, in block 244 of FIG. 2C, the method continues by applying at least the first set of sequence features to a trained classification method, thereby obtaining a classification result. The classification result provides, for each respective cancer condition in the set of cancer conditions, a likelihood that the subject has or does not have the respective cancer condition.

Referring to block 246, in some embodiments, the trained classification method comprises a trained classifier stream. Referring to block 248, in some embodiments, by way of non-limiting example the trained classifier stream is a decision tree. Decision tree algorithms suitable for use as the classification model of block 244 are described in, for example, Duda, 2001, Pattern Classification, John Wiley & Sons, Inc., New York, 395-396, which is hereby incorporated by reference. Tree-based methods partition the feature space into a set of rectangles, and then fit a model (like a constant) in each one. In some embodiments, the decision tree is random forest regression. One specific algorithm that can be used as the classification model of block 244 is a classification and regression tree (CART). Other examples of specific decision tree algorithms that can be used as the classifier of block 244 include, but are not limited to, ID3, C4.5, MART, and Random Forests. CART, ID3, and C4.5 are described in Duda, 2001, *Pattern Classification*, John Wiley & Sons, Inc., New York. 396-408 and 411-412, which is hereby incorporated by reference. CART, MART, and C4.5 are described in Hastie et al., 2001, *The Elements of Statistical Learning*, Springer-Verlag, New York, Chapter 9, which is hereby incorporated by reference in its entirety. Random Forests are described in Breiman, 1999, "Random Forests—Random Features," Technical Report 567, Statistics Department, U. C. Berkeley, September 1999, which is hereby incorporated by reference in its entirety. In some embodiments, xgboost and/or lightgbm are additional decision tree methods that can be used as the trained classifier stream. See e.g., Chen et al. 2016 KDD '16: Proc 22nd ACM SIGKDD Int Conf Knowledge Disc. Data Mining, 785-794, and Wang et al. 2017 ICCBB: Proc 2017 Int Conf Comp Biol and Bioinform, 7-11.

In some embodiments, by way of non-limiting example the trained classifier stream comprises regression. The regression algorithm can be any type of regression. For example, in some embodiments, the regression algorithm is logistic regression. Logistic regression algorithms are disclosed in Agresti, An Introduction to Categorical Data Analysis, 1996, Chapter 5, pp. 103-144, John Wiley & Son, New York, which is hereby incorporated by reference. In some embodiments, the regression algorithm is logistic regression with lasso, L2, or elastic net regularization.

In some embodiments, by way of non-limiting example the trained classifier stream comprises a neural network. Examples of neural network algorithms, including convolutional neural network algorithms, are disclosed, for example, in Vincent et al., 2010, "Stacked denoising autoencoders: Learning useful representations in a deep network with a local denoising criterion," J Mach Learn Res 11, pp. 3371-3408; Larochelle et al., 2009, "Exploring strategies for training deep neural networks," J Mach Learn Res 10, pp. 1-40; and Hassoun, 1995, Fundamentals of Artificial Neural Networks, Massachusetts Institute of Technology, each of which is hereby incorporated by reference.

In some embodiments, by way of non-limiting example the trained classifier stream comprises a support vector machine (SVM). Examples of SVM algorithms are described, for example, in Cristianini and Shawe-Taylor, 2000, "An Introduction to Support Vector Machines," Cambridge University Press, Cambridge; Boser et al., 1992, "A training algorithm for optimal margin classifiers," in Proceedings of the 5th Annual ACM Workshop on Computational Learning Theory, ACM Press, Pittsburgh, Pa., pp. 142-152; Vapnik, 1998, Statistical Learning Theory, Wiley, New York; Mount, 2001, Bioinformatics: sequence and genome analysis, Cold Spring Harbor Laboratory Press, Cold Spring Harbor, N.Y.; Duda, Pattern Classification, Second Edition, 2001, John Wiley & Sons, Inc., pp. 259, 262-265; and Hastie, 2001, The Elements of Statistical Learning, Springer, New York; and Furey et al., 2000, Bioinformatics 16, 906-914, each of which is hereby incorporated by reference in its entirety. When used for classification, SVMs separate a given set of binary labeled data training set with a hyper-plane that is maximally distant from the labeled data. For cases in which no linear separation is possible, SVMs can work in combination with the technique of "kernels," which automatically realizes a non-linear mapping to a feature space. The hyper-plane found by the SVM in feature space corresponds to a non-linear decision boundary in the input space.

In some embodiments, the trained classifier stream includes a first classifier, a second classifier, and a third classifier. In such embodiments, the applying includes inputting all or a portion of the plurality of pathology features, the first set of sequence features, and the second set of sequence features into the first classifier to thereby obtain an intermediate result. In such embodiments, the applying further includes inputting the intermediate result to the second classifier and not the third classifier when the intermediate result satisfies a first predetermined threshold or range, to thereby obtain the likelihood that the subject has or does not have a first cancer condition in the cancer condition set. In such embodiments, the applying further includes inputting the intermediate result to the third classifier and not the second classifier when the intermediate result fails to satisfy the first predetermined threshold or range, to thereby obtain the likelihood that the subject has or does not have the first cancer condition.

In some embodiments, the first classifier, the second classifier, and the third classifier each comprise a classifier of a respective classifier type (e.g., a respective cancer condition classifier). In some embodiments, the first classifier includes a classifier of a first classifier type and the second and third classifiers each comprise a classifier of a second classifier type. In some embodiments, the first classifier includes a classifier of a first classifier type, the second classifier includes a classifier of a second classifier type, and the third classifier includes a classifier of a third classifier type.

In some embodiments, the trained classifier stream includes a first classifier and a second classifier. In such embodiments, the applying includes inputting all or a portion of the plurality of pathology features, the first set of sequence features, and the second set of sequence features into the first classifier to thereby obtain an intermediate result. In such embodiments, the applying further includes inputting the intermediate result to the second classifier when the intermediate result satisfies a first predetermined threshold or range, to thereby obtain the likelihood that the subject has or does not have a first cancer condition in the cancer condition set.

In some embodiments, the first classifier and the second classifier each comprise a classifier of a respective classifier type. In some embodiments, the first classifier includes a classifier of a first classifier type and the second classifier includes a classifier of a second classifier type.

In some embodiments, the trained classifier stream used in block 244 includes a K-nearest neighbor model, a random forest model, logistic regression, support vector machine, or a neural network.

Nearest neighbor algorithms suitable for use as the classifier of block 244 are described below. For nearest neighbors, given a query point $x_0$ (a subject), a set of k training points $x_{(r)}$, r, k (here the training subjects) closest in distance to $x_0$ are identified and then the point $x_0$ is classified using the k nearest neighbors. Here, the distance to these neighbors is a function of the expression of the discriminating gene set. In some embodiments, Euclidean distance in feature space is used to determine distance as $d_{(i)} = \|x_{(i)} - x_{(O)}\|$. Typically, when the nearest neighbor algorithm is used, the expression data used to compute the linear discriminant is standardized to have mean zero and variance 1. The nearest neighbor rule can be refined to address issues of unequal class priors, differential misclassification costs, and feature selection. Many of these refinements involve some form of weighted voting for the neighbors. For more information on nearest neighbor analysis, see Duda, *Pattern Classification*, Second Edition, 2001, John Wiley & Sons, Inc; and Hastie, 2001, The Elements of Statistical Learning, Springer, New York, each of which is hereby incorporated by reference.

Neural network algorithms, including multilayer neural network algorithms, suitable for use as the classifier of block 244 are disclosed in, for example, Vincent et al., 2010 *J Mach Learn Res* 11, 3371-3408; Larochelle et al., 2009 *J Mach Learn Res* 10, 1-40; and Hassoun, 1995, Fundamentals of Artificial Neural Networks, Massachusetts Institute of Technology, each of which is hereby incorporated by reference. A neural network has a layered structure that includes a layer of input units (and the bias) connected by a layer of weights to a layer of output units. For regression, the layer of output units typically includes just one output unit. However, some neural networks can handle multiple quantitative responses in a seamless fashion. In multilayer neural networks, there are input units (input layer), hidden units (hidden layer), and output units (output layer). There is, furthermore, a single bias unit that is connected to each unit other than the input units. Additional example neural networks suitable for use as the classifier of block 244 are disclosed in Duda et al., 2001, *Pattern Classification*, Second Edition, John Wiley & Sons, Inc., New York; and Hastie et al., 2001, *The Elements of Statistical Learning*, Springer-Verlag, New York, each of which is hereby incorporated by reference in its entirety. Additional example neural networks suitable for use as the classifier of block 244 are also described in Draghici, 2003, *Data Analysis Tools for DNA Microarrays*, Chapman & Hall/CRC; and Mount, 2001, *Bioinformatics: sequence and genome analysis*, Cold Spring Harbor Laboratory Press, Cold Spring Harbor, N.Y., each of which is hereby incorporated by reference in its entirety.

Referring to block 250, in some embodiments, the trained classifier stream includes a plurality of classifiers (e.g., a combination of classifiers). The plurality of classifiers includes a first subset of classifiers and a second subset of classifiers. Each classifier in the second subset of classifiers takes as input at least the output of at least one classifier in the first subset of classifiers. Each classifier in the first subset of classifiers takes as input all or a portion of at least the plurality of pathology features, the first set of sequence features, and the second set of sequence features. An output of the second subset of classifiers collectively provides, for each respective cancer condition in the set of cancer conditions, the likelihood that the subject has or does not have the respective cancer condition.

In some embodiments, the trained classifier stream includes a plurality of classifiers (e.g., a chain of classifiers). A first classifier in the plurality of classifiers is used to determine the likelihood that the subject has or does not have a first cancer condition in the set of cancer conditions when the tumor cellularity satisfies a predetermined threshold (e.g., in cases where the tumor cellularity is of high purity). A second classifier in the plurality of classifiers is used to determine the likelihood that the subject has or does not have the first cancer condition in the set of cancer conditions when the tumor cellularity fails to satisfy the predetermined threshold (e.g., in cases where the tumor cellularity is of low purity).

In some embodiments, each individual classifier in the classifier chains performs a binary classification on a subset of the features of the subject. In such embodiments, a classification result from an upstream classifier may be an input into downstream classifiers. In some embodiments, a hyper parameter search for an optimal sequence of classifiers may be performed. In some embodiments, an ensemble model—comprising one or more chains of classifiers—classifies subjects by majority vote (e.g., each chain of classifiers gets one vote).

In some embodiments, each classifier in the plurality of classifiers is a classifier of a respective classifier type. In some embodiments, one or more classifiers in the plurality of classifiers are classifiers of a first classifier type and one or more classifiers in the plurality of classifiers are classifiers of a second classifier type.

Referring to block 252, in some embodiments, the method further comprises applying the second set of sequence features and the plurality of pathology features (e.g., as obtained above as described with regard to blocks 234 and 238, respectively) to the trained classification model.

Figure 8A:
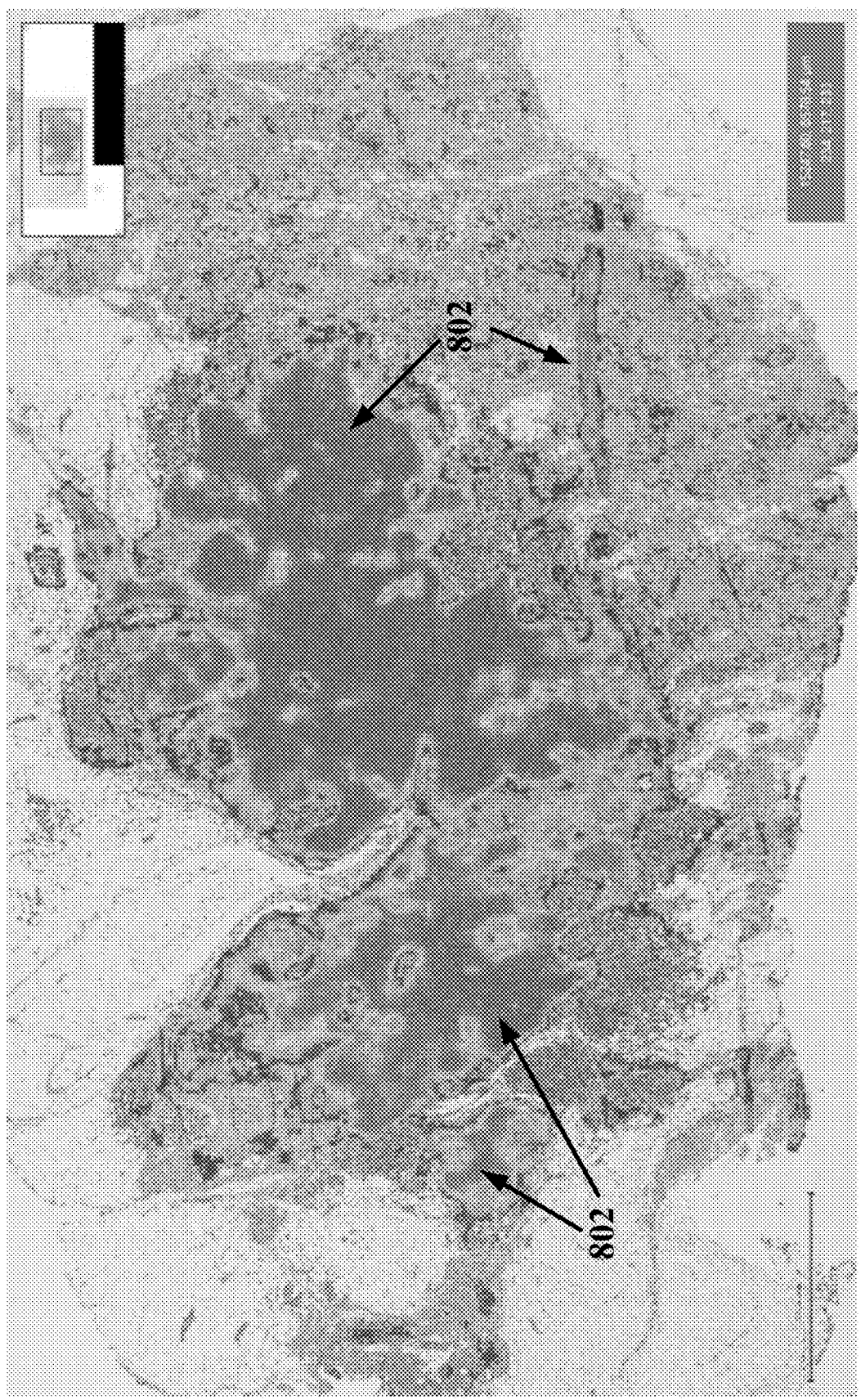
FIGS. 8A and 8B illustrate solid biopsy imaging, in accordance with some embodiments of the present disclosure.
Figure 8B:
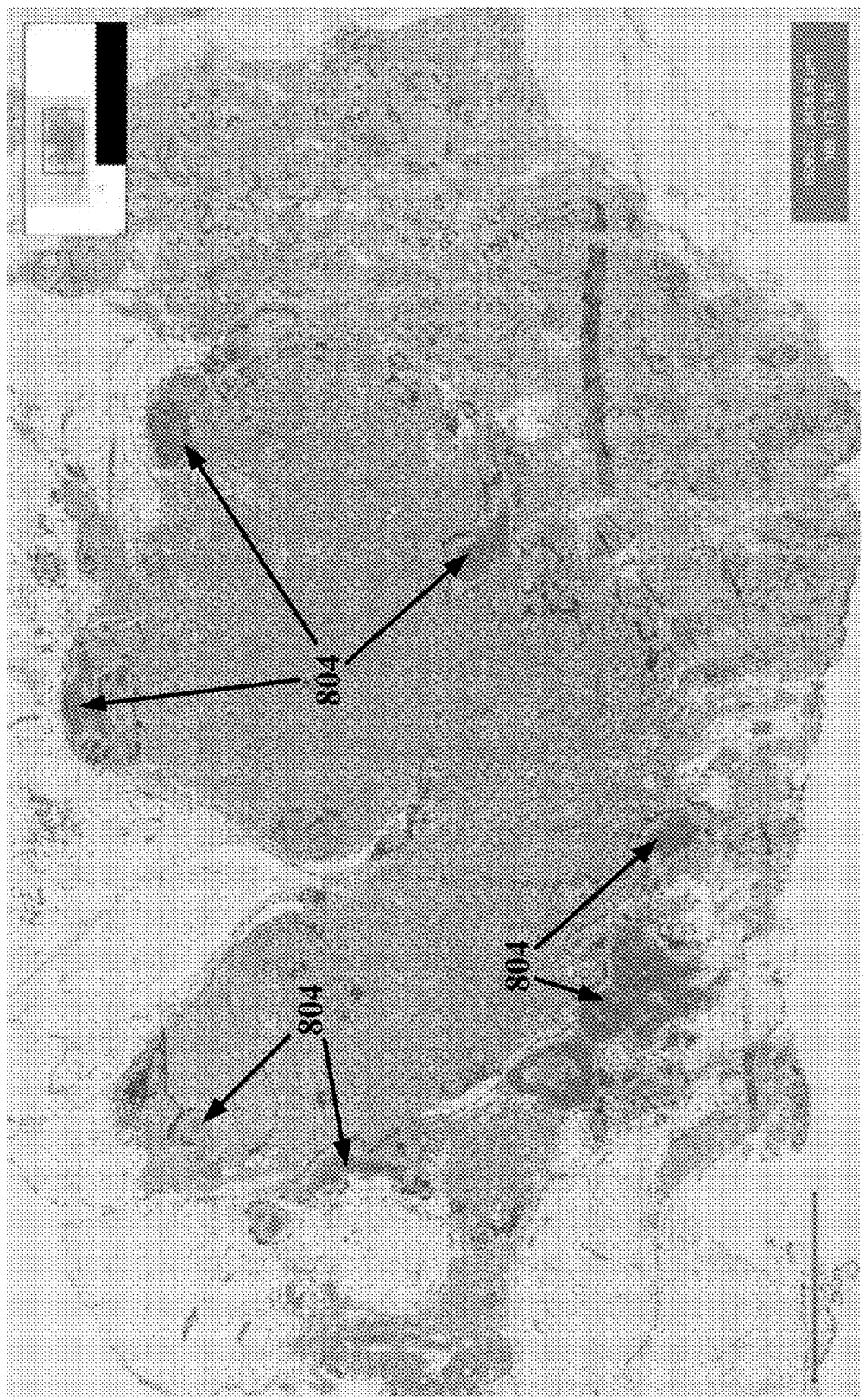
Figure 9:
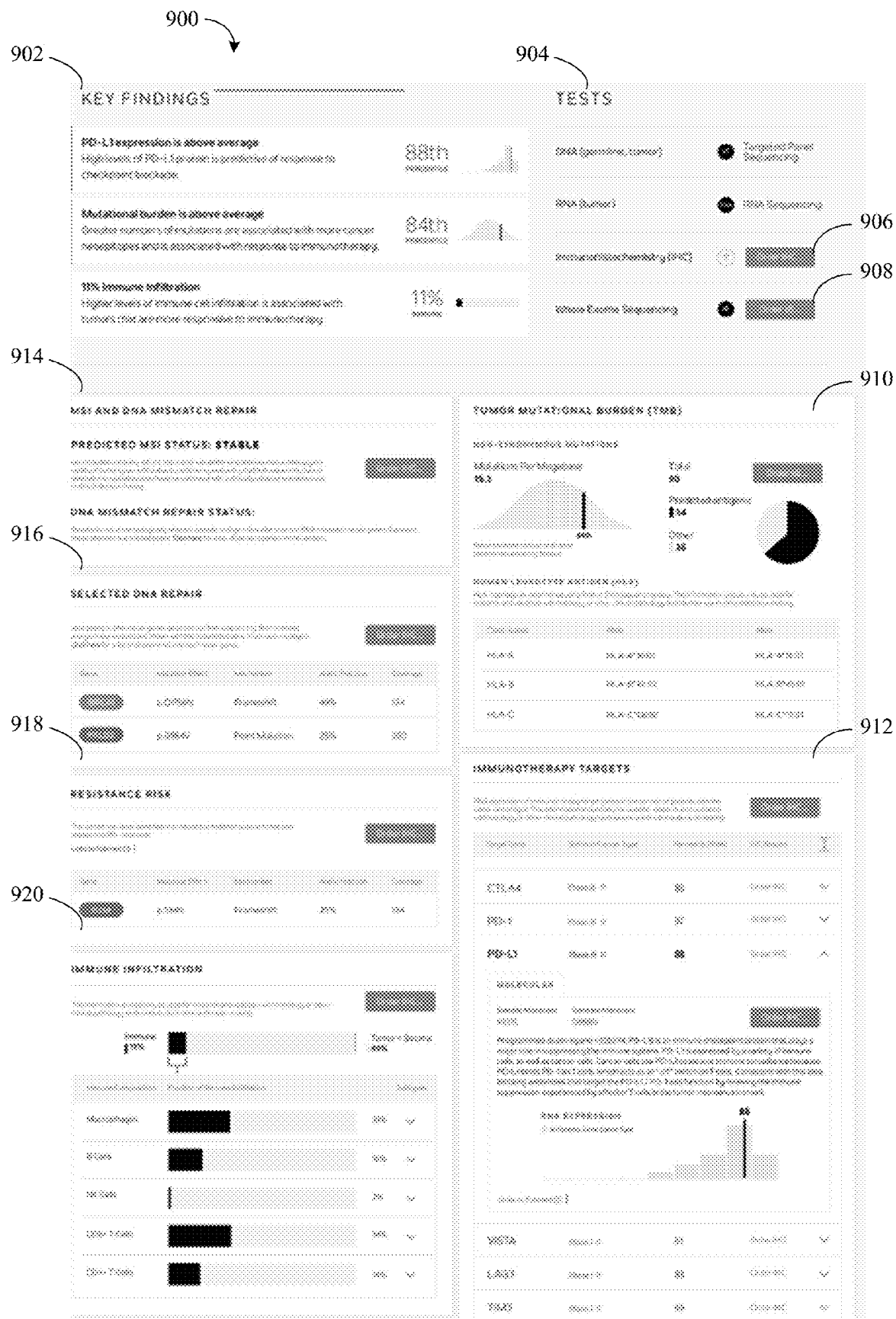
FIG. 9 illustrates an example patient report, generated in accordance with some embodiments of the present disclosure.

In some embodiments, the applying further includes applying one or more image features extracted from one or more images of the somatic biopsy from the test subject (e.g., the tumor imaging data is separate from the pathology report). FIG. 8A is an example tissue image (e.g., biopsy) being used to predict tumor versus healthy tissue, where regions 802 correspond to tissue regions that have a high likelihood of being tumorous. FIG. 8B is another image of the same example tissue sample, where regions 804 correspond to predicted lymphocytes. Tissue images such as those shown in FIGS. 8A and 8B may, in some embodiments, be used in accordance with the methods disclosed herein to estimate tumor cellularity. For example, in some embodiments, tumor cellularity can be calculated as the ratio of an area of regions predicted to be tumorous and a total area of tissue in the image. In alternate embodiments, tumor cellularity can be calculated as the ratio of a cell count for regions predicted to be tumorous and a cell count for all tissue in a respective image. In some embodiments, a respective tumor cellularity value is determined for each image in the one or more images of the somatic biopsy. In such embodiments, an overall tumor cellularity value for the subject is determined by averaging each respective tumor cellularity value.

In some embodiments, the applying further includes applying one or more epigenetic or metabolomic features of the subject obtained from the somatic sample of the subject to the trained classification model to obtain the classifier result Epigenetic modifications are known, in some cases, to contribute to the progression of cancer. See Sharma et al. 2010 *Carcinogenesis* 31:27-36. Likewise, metabolic reprogramming is also correlated with cancer diagnoses. See, for example, Yang et al. 2017 *Scientific Reports* 7:43353. In some embodiments, the applying further includes applying one or more microbiome features of the subject to the trained classification model to obtain the classifier result Recently, gut microbiota in particular have been recognized as contributing to patient response to cancer therapies. See Guglielmi 2018, available online at nature.com/articles/d41586-018-05208-8 and Gopalakrishnan et al. 2018 *Cell* 33:570-580.

In some embodiments, the classifier results are further used (e.g., by a pathologist) to provide one or more treatment recommendations (e.g., as described below for Example 2) for the subject or a medical practitioner caring for the subject on the basis of the likelihood that the subject has or does not have each respective cancer condition in the set of cancer conditions. In some embodiments, the trained classification model further provides one or more treatment recommendations for the subject or a medical practitioner caring for the subject on the basis of the likelihood that the subject has or does not have the cancer condition. In some embodiments, the trained classification model further provides one or more treatment recommendations for the subject or a medical practitioner caring for the subject on the basis of the likelihood that the subject has or does not have the expected cancer condition.

In some embodiments, the classification model changes a tumor of origin diagnosis for a subject (e.g., as described in Example 8). In some embodiments, this change further alters a treatment course recommended for the subject.

In some embodiments, as part of providing one or more treatment recommendations, results from the trained classification model are used (e.g., from a pathologist or other health care provider) to provide a patient report (e.g., as illustrated by FIGS. 10A-10G and described in Example 7). In some embodiments, the patient report includes detailed information regarding the classification result (e.g., the likelihood that the subject has or does not have each respective cancer condition in the set of cancer conditions, the likelihood that the subject has or does not have the cancer condition, or the likelihood that the subject has or does not have the expected cancer condition) and/or the treatment recommendations. An example layout of a patient report 900 is illustrated by FIG. 9, and FIGS. 10A-10G illustrate particular examples of specific sections (e.g., 902-920 in example patient report 900) of patient reports.

Details of particular example patient reports are described in Example 7 below. Briefly, these sections provide patients and medical practitioners with more information regarding their diagnoses. This serves both to improve patient treatment (e.g., by suggesting particular clinical trials—as shown in FIG. 10E—or by identifying relevant FDA-approved therapies—as shown in FIG. 10G), and to give patients a sense of control over their information and diagnosis. Studies demonstrate that there are significant limitations to doctor-patient communication in terms of effectively transmitting information about cancer diagnoses. See e.g., Cartwright et al. 2015 *J. Cancer Educ.* 29, 311-317 or Nord et al. 2003 *J. Public Health* 25(5), 313-317. Through the classification methods described herein, more accurate information is obtained about a patients' cancer, and through the corresponding patient reports this information is provided in a clear manner to patients and medical professionals.

Diagnosing a Cancer Condition for a Subject.

Each and every embodiment described with regards to FIGS. 2A, 2B, and 2C may also be applied to additional methods of diagnosing a cancer condition for a subject as described below. The method provides for identifying a diagnosis of a cancer condition for a somatic tumor specimen of a subject.

The method further comprises receiving sequencing information comprising analysis of a plurality of nucleic acids derived from the somatic tumor specimen. In some embodiments, the sequencing information comprises a plurality of DNA sequence reads (e.g., from circulating tumor DNA or a tumor biopsy). In some embodiments, the sequencing information comprises a plurality of RNA sequence reads (e.g., from circulating RNA or a tumor biopsy). In some embodiments, the sequencing information includes both DNA sequencing reads and RNA sequencing reads.

The method further comprises identifying a plurality of features from the received sequencing information, wherein the plurality of features include two or more of RNA features (e.g., RNA features 2341), DNA features (e.g., DNA features 2342), RNA splicing features (e.g., RNA splicing features 2349a), viral features, and copy number features (e.g., copy number variations 2349b). In some embodiments, the methods for generating one or more of the features described herein may include one or more of the methods of the '804 patent.

Each RNA feature (e.g., from RNA features 2341) is associated with a respective target region of a first reference genome and represents a corresponding abundance of sequence reads, encompassed by the sequencing information, that map to the respective target region. In some embodiments, each RNA feature in the RNA features is associated with coding regions of genes. In some embodiments, the RNA features are obtained from sequencing of cDNA.

Each DNA feature (e.g., from DNA features 2342) is associated with a respective target region of a second reference genome and represents a corresponding abundance of sequence reads, encompassed by the sequencing information, that map to the respective target region.

Each RNA splicing feature (e.g., from RNA splicing features 2349a) is associated with a respective splicing event at a respective target region of the first reference genome and represents a corresponding abundance of sequence reads, encompassed by the sequencing information, that map to the respective target region with the respective splicing event. In some embodiments, RNA splicing features are associated with predetermined exome-skipping events. In some embodiments, a respective RNA splicing feature is associated with two or more target regions (e.g., two or more non-contiguous exons).

Each viral feature is associated with a respective target region of a viral reference genome and represents a corresponding abundance of sequence reads, encompassed by the sequencing information, that map to the respective target region in the viral reference genome. In some embodiments, viral features are used when the subject has an indication of viral status (e.g., as described above with regards to block 222). In some embodiments, the target regions in the viral reference genome comprise viral-associated sequence reads (e.g., see FIG. 20 and Example 9). In some embodiments, the viral features are identified through DNA or RNA sequencing of a sample from the subject. In some embodiments, the viral reference genome includes one or more viral genomes (e.g., the viral reference genome represents multiple viral genomes). For example, the viral features may comprise features from one or more viruses of interest.

Each copy number feature (e.g., from copy number variations 2349b) is associated with a target region of the second reference genome and represents a corresponding abundance of sequence reads, encompassed by the sequencing information, that map to the respective target region in the second reference genome. In some embodiments, a copy number feature is associated with a structural variant of the second reference genome.

In some embodiments, the first reference genome associated with RNA features (and/or RNA splicing features) is the same as the second reference genome associated with DNA features (and/or copy number features). In some embodiments, either of the first or second reference genomes comprise a human genome (e.g., NCBI build 34 (UCSC equivalent: hg16), NCBI build 35 (UCSC equivalent: hg17), NCBI build 36.1 (UCSC equivalent: hg18), GRCh37 (UCSC equivalent: hg19), and GRCh38 (UCSC equivalent: hg38)). In some embodiments, both the first and the second reference genomes comprise a human genome.

In some embodiments, target regions are predetermined regions of a genome (e.g., the first or second reference genome). In some embodiments, the predetermined regions of the genome represent regions are known to be associated with a particular disease (e.g., with particular cancer types). In some embodiments, predetermined regions are genes. In some embodiments, each respective target region is a coding region (e.g., a gene) in a reference genome. In some embodiments, a target region is a non-coding region (e.g., an intron) in a reference genome. In some embodiments, a target region is a combination of coding and non-coding genomic regions in a reference genome. In some embodiments, a target region corresponds to a group of genomic regions in a reference genome. In some embodiments, a target region is at least two, at least three, at least four, at least five, at least six, at least seven, at least eight, at least nine, or at least 10 regions (e.g., coding and/or non-coding) in a reference genome.

In some embodiments, a respective target region corresponds to a respective feature in the plurality of features. In some embodiments, a respective feature in the plurality of features corresponds to a respective target region. In some embodiments, a respective target region corresponds to two or more features in the plurality of features. In some embodiments, a respective feature in the plurality of features corresponds to two or more target regions (e.g., the two or more target regions may be functionally linked or have similar expression patterns).

In some embodiments, target regions can be approximately the same length. In some embodiments, target regions can be different lengths. In some embodiments, target regions are of about equal length. In some embodiments, a target region is at least 100 nucleic acid bases, at least 200 nucleic acid bases, at least 300 nucleic acid bases, at least 400 nucleic acid bases, at least 500 nucleic acid bases, at least 600 nucleic acid bases, at least 700 nucleic acid bases, at least 800 nucleic acid bases, at least 900 nucleic acid bases, or at least 1,000 nucleic acid bases in length. In some embodiments, (e.g., particularly for RNA splicing features and/or structural variant copy number features) a target region is at least 1 Kb, at least 2 Kb, at least 3 Kb, at least 4 Kb, at least 5 Kb, at least 6 Kb, at least 7 Kb, at least 8 Kb, at least 9 Kb, at least 10 Kb, at least 15 Kb, at least 20 Kb, at least 25 Kb, at least 30 Kb, at least 40 Kb, at least 50 Kb, at least 60 Kb, at least 70 Kb, at least 80 Kb, at least 90 Kb, at least 100 Kb, at least 150 Kb, at least 200 Kb, at least in length. In some embodiments, (e.g., particularly for target regions corresponding to two or more genomic regions) each genomic region in a respective target region is between 100 and 500 nucleic acid bases, between 200 and 500 nucleic acid bases, between 200 and 400 nucleic acid bases, between 100 and 1000 nucleic acid bases, or between 500 and 1000 nucleic acid bases, between 100 and 10,000 nucleic acid bases, between 100 and 100,000 nucleic acid bases, between 5000 and 10,000 nucleic acid bases, between 10,000 and 50,000 nucleic acid bases, between 10,000 and 100,000 nucleic acid bases, between 50,000 and 100,000 nucleic acid bases, or between 50,000 and 150,000 in length.

In some embodiments, a predetermined number of target regions are evaluated with regards to identifying the plurality of features. In some embodiments, the predetermined number of target regions is at least 100 target regions, at least 200 target regions, at least 300 target regions, at least 400 target regions, at least 500 target regions, at least 600 target regions, at least 700 target regions, at least 800 target regions, at least 900 target regions, at least 1,000 target regions, at least 2,500 target regions, at least 5,000 target regions, at least 7,500 target regions, at least 10,000 target regions, at least 20,000 target regions, or at least 50,000 target regions.

In some embodiments, for each feature in the plurality of features, a respective abundance of sequence reads corresponds to a raw number of sequence reads associated with a respective target region of the first or second reference genome. In some embodiments, for each feature in the plurality of features, a respective abundance of sequence reads corresponds to a normalized number of sequence reads. In some embodiments, normalization of sequence reads is performed as described above with regards to block 226.

In some embodiments, the sequencing information is deconvoluted prior to feature identification. In some embodiments, deconvolution comprises identifying sequence reads in the sequencing information that originate from healthy tissue (e.g., sequence reads from normal, non-tumor cells) and removing said sequence reads from the sequencing information (e.g., to decrease background noise). In some embodiments, as described in U.S. patent application Ser. No. 16/732,229 entitled "Transcriptome Deconvolution of Metastatic Tissue Samples" and filed Dec. 31, 2018 which is hereby incorporated in its entirety, a deconvolution model comprises a supervised machine learning model, a semi-supervised machine learning model, or an unsupervised machine learning model. In some embodiments, a different deconvolution model is determined for each cancer type or set of cancer types (e.g., a liver cancer deconvolution model). In some embodiments, a deconvolution model removes expression data from cell populations that are not cell types of interest (e.g. tumor or other types of cancer tissue). In some embodiments, a deconvolution model uses machine learning algorithms such as unsupervised or supervised clustering techniques to examine gene expression data to quantify the level of tumor versus normal cell populations present in the data. In some embodiments, training a deconvolution model comprises identifying common expression characteristics shared across sequence reads from tissue normal samples, primary samples, and metastatic samples, such that the deconvolution model can predict the ratio of a metastases tumor from the background tissue and identify which portion of sequence reads is attributable to the tumor and which portion is attributable to the background tissue. In some embodiments, sequence reads attributable to background tissue are removed from the sequencing information.

In some embodiments, the plurality of features are obtained by low pass, whole genome sequencing. In some embodiments, low pass sequencing refers to the average coverage rate of a reference genome (e.g., the first, second, or viral reference genome) by the plurality of DNA or RNA sequencing reads (e.g., the sequencing information). In some embodiments, the average coverage rate of the plurality of sequence reads (either DNA or RNA sequence reads) is less than 0.25×, less than 0.5×, less than 1×, less than 2×, less than 3×, less than 4×, less than 5×, less than 6×, less than 7×, less than 8×, less than 9×, or less than 10× across a reference genome. In some embodiments, the average coverage rate of the plurality of sequence reads is between 0.1× and 1× across a reference genome. In some embodiments, the average coverage rate of the plurality of sequence reads is between 0.1× and 5× across a reference genome. In some embodiments, the average coverage rate of the plurality of sequence reads is between 0.1× and 10× across a reference genome. In some embodiments, the average coverage rate of the plurality of sequence reads is between 1× and 5× across a reference genome.

The method further comprises providing a first subset of features from the identified plurality of features as inputs to a first classifier. The method further comprises providing a second subset of features from the identified plurality of features as inputs to a second classifier. In some embodiments, the first subset of features comprises all or a portion of the identified plurality of features. In some embodiments, the second subset of features comprises all or a portion of the identified plurality of features.

In some embodiments, providing the first subset of features to the first classifier and providing the second subset of features to the second classifier comprises providing both the first and second classifiers the same subset of features. In some embodiments, the same subset of features are RNA features. In some embodiments, the same subset of features are DNA features. In some embodiments, the same subset of features are RNA splicing features. In some embodiments, the same subset of features are viral features. In some embodiments, the same subset of features are copy number features.

In some embodiments, each feature in the plurality of features is associated with a respective target region (e.g., for RNA, DNA, copy number, and/or RNA splicing features), the plurality of features collectively represent a plurality of target regions, each region in the plurality of target regions is a gene, and the plurality of target regions comprises two or more (e.g., in some embodiments, 2 or more, 3 or more, 4 or more, 5 or more, 6 or more, 7 or more, 8 or more, 9 or more, 10 or more, 15 or more, 20 or more or 50 or more) of GPM6A, CDX1, SOX2, NAPSA, CDX2, MUC12, SLAMF7, HNF4A, ANXA10, TRPS1, GATA3, SLC34A2, NKX2-1, SLC22A31, ATP10B, STEAP2, CLDN3, SPATA6, NRCAM, USH1C, SOX17, TMPRSS2, MECOM, WT1, CDHR1, HOXA13, SOX10, SALL1, CPE, NPR1, CLRN3, THSD4, ARL14, SFTPB, COL17A1, KLHL14, EPS8L3, NXPE4, FOXA2, SYT11, SPDEF, GRHL2, GBP6, PAX8, ANO1, KRT7, HOXA9, TYR, DCT, LYPD1, MSLN, TP63, CDH1, ESR1, HNF1B, HOXA10, TJP3, NRG3, TMC5, PRLR, GATA2, DCDC2, INS, NDUFA4L2, TBX5, ABCC3, FOLH1, HIST1H3G, S100A1, PTHLH, ACER2, RBBP8NL, TACSTD2, C19orf77, PTPRZ1, BHLHE41, FAM155A, MYCN, DDX3Y, FMN1, HIST1H3F, UPK3B, TRIM29, TXNDC5, BCAM, FAM83A, TCF21, MIA, RNF220, AFAP1, KRT5, SOX21, KANK2, GPM6B, C1orf116, FOXF1, MEIS1, EFHD1, and XKRX.

In some embodiments, each feature in the plurality of features is associated with a respective target region (e.g., for RNA, DNA, copy number, and/or RNA splicing features), the plurality of features collectively represent a plurality of target regions, each region in the plurality of target regions is a gene, and the plurality of target regions comprises two or more (e.g., in some embodiments, 2 or more, 3 or more, 4 or more, 5 or more, 6 or more, 7 or more, 8 or more, 9 or more, 10 or more, 15 or more, 20 or more or 50 or more) of ENSG00000150625, ENSG00000113722, ENSG00000181449, ENSG00000131400, ENSG00000165556, ENSG00000205277, ENSG00000026751, ENSG00000101076, ENSG00000109511, ENSG00000104447, ENSG00000107485, ENSG00000157765, ENSG00000136352, ENSG00000259803, ENSG00000118322, ENSG00000157214, ENSG00000165215, ENSG00000132122, ENSG00000091129, ENSG00000006611, ENSG00000164736, ENSG00000184012, ENSG00000085276, ENSG00000184937, ENSG00000148600, ENSG00000106031, ENSG00000100146, ENSG00000103449, ENSG00000109472, ENSG00000169418, ENSG00000180745, ENSG00000187720, ENSG00000179674, ENSG00000168878, ENSG00000065618, ENSG00000197705, ENSG00000198758, ENSG00000137634, ENSG00000125798, ENSG00000132718, ENSG00000124664, ENSG00000083307, ENSG00000183347, ENSG00000125618, ENSG00000131620, ENSG00000135480, ENSG00000078399, ENSG00000077498, ENSG00000080166, ENSG00000150551, ENSG00000102854, ENSG00000073282, ENSG00000039068, ENSG00000091831, ENSG00000108753, ENSG00000253293, ENSG00000105289, ENSG00000185737, ENSG00000103534, ENSG00000113494, ENSG00000179348, ENSG00000146038, ENSG00000254647, ENSG00000185633, ENSG00000089225, ENSG00000108846, ENSG00000086205, ENSG00000256018, ENSG00000160678, ENSG00000087494, ENSG00000177076, ENSG00000130701, ENSG00000184292, ENSG00000095932, ENSG00000106278, ENSG00000123095, ENSG00000204442, ENSG00000134323, ENSG00000067048, ENSG00000248905, ENSG00000256316, ENSG00000243566, ENSG00000137699, ENSG00000239264, ENSG00000187244, ENSG00000147689, ENSG00000118526, ENSG00000261857, ENSG00000187147, ENSG00000196526, ENSG00000186081, ENSG00000125285, ENSG00000197256, ENSG00000046653, ENSG00000182795, ENSG00000103241, ENSG00000143995, ENSG00000115468, and ENSG00000182489.

In some embodiments, providing the first subset of features to the first classifier and providing the second subset of features to the second classifier comprises providing both the first and second classifiers with RNA features. In some embodiments, providing the first subset of features to the first classifier and providing the second subset of features to the second classifier comprises providing the first classifier with RNA features and the second classifier with DNA features.

In some embodiments, the first classifier is a diagnosis classifier (e.g., classifier 2382a) and the second classifier is a cohort classifier (e.g., classifier 2382b). In some embodiments, the first classifier is a diagnosis classifier and the second classifier is a tissue classifier (e.g., tissue classifier 2382c).

The method further comprises generating, from two or more classifiers, two or more predictions of cancer condition based at least in part on the identified plurality of features, wherein the two or more classifiers include at least the first classifier and the second classifier.

In some embodiments, the two or more predictions comprise: a first prediction from a diagnosis classifier provided with RNA features, a second prediction from a cohort classifier provided with RNA features, a third prediction from a tissue classifier provided with RNA features, a fourth prediction from a diagnosis classifier provided with RNA splicing features, a fifth prediction from a cohort classifier provided with RNA splicing features, a sixth prediction from a diagnosis classifier provided with CNV features, a seventh prediction from a cohort classifier provided with CNV features, an eighth prediction from a diagnosis classifier provided with DNA features, and a ninth prediction from a diagnosis classifier provided with viral features.

The method further comprises combining, at a final classifier, the two or more predictions to identify the diagnosis of the cancer condition for the somatic tumor specimen (e.g., identifying a TUO classification 2382d). In some embodiments, combining, at the final classifier, the two or more predictions further comprises: scaling each prediction of the two or more predictions based at least in part on a respective confidence level in each respective prediction, and generating a combined prediction based at least in part on each scaled prediction.

In some embodiments, a corresponding confidence level for a respective prediction of the two or more predictions is at least 0.5, at least 0.6, at least 0.7, at least 0.8, or at least 0.9. In some embodiments, a confidence level for a prediction is at least 0.9, at least 0.95, or at least 0.99. In some embodiments, scaling of a respective prediction is linear (e.g., the scaling comprises a linear combination of the respective prediction and a corresponding confidence level in the respective prediction). In some embodiments, scaling of a respective prediction is non-linear (e.g., the scaling comprises a non-linear combination of the respective prediction and a corresponding confidence level in the respective prediction). In some embodiments, scaling each prediction of the two or more predictions is performed as described below with regards to features module 2340.

In some embodiments, a plurality of classifiers can be used to generate predictions of cancer condition, where each classifier is provided with a respective subset of features from the identified plurality of features. In some such embodiments, each prediction from a respective classifier in the plurality of classifiers is combined by the final classifier to determine a final diagnosis of the cancer condition of the somatic tumor specimen of the subject.

In some embodiments, the method further comprises providing a third classifier with RNA splicing features. In some such embodiments, the generating generates, from three or more classifiers, three or more predictions of cancer condition based at least in part on the identified plurality of features, where the three or more classifiers include at least the first classifier, the second classifier, and the third classifier. In some such embodiments, the combining combines the three or more predictions to identify the diagnosis of the cancer condition for the somatic tumor specimen.

In some embodiments, the method further comprises providing a third classifier with viral features. In some such embodiments, the generating generates, from three or more classifiers, three or more predictions of cancer condition based at least in part on the identified plurality of features, where the three or more classifiers include at least the first classifier, the second classifier, and the third classifier. In some such embodiments, the combining combines the three or more predictions to identify the diagnosis of the cancer condition for the somatic tumor specimen.

In some embodiments, the method further comprises providing a third classifier with copy number features. In some such embodiments, the generating generates, from three or more classifiers, three or more predictions of cancer condition based at least in part on the identified plurality of features, where the three or more classifiers include at least the first classifier, the second classifier, and the third classifier. In some such embodiments, the combining combines the three or more predictions to identify the diagnosis of the cancer condition for the somatic tumor specimen.

In some embodiments, the method further comprises providing the first classifier with RNA features, providing the second classifier with copy number features, and providing a third classifier with RNA splicing features. In some such embodiments, the generating generates, from three or more classifiers, three or more predictions of cancer condition based at least in part on the identified plurality of features, where the three or more classifiers include at least the first classifier, the second classifier, and the third classifier. In some such embodiments, the combining combines the three or more predictions to identify the diagnosis of the cancer condition for the somatic tumor specimen.

In some embodiments, the method further comprises providing the first classifier with RNA features, where the first classifier is a diagnosis classifier, providing the second classifier with RNA features, where the second classifier is a cohort classifier, and providing a third classifier with RNA features, wherein the third classifier is a tissue classifier. In some such embodiments, the generating generates, from three or more classifiers, three or more predictions of cancer condition based at least in part on the identified plurality of features, where the three or more classifiers include at least the first classifier, the second classifier, and the third classifier. In some such embodiments, the combining combines the three or more predictions to identify the diagnosis of the cancer condition for the somatic tumor specimen.

In some such embodiments, the method further comprises providing a fourth classifier with DNA features, where the fourth classifier is a diagnosis classifier, providing a fifth classifier with RNA splicing features, where the fifth classifier is a diagnosis classifier, and providing a sixth classifier with RNA splicing features, where the sixth classifier is a cohort classifier. In some such embodiments, the generating generates, from six or more classifiers, six or more predictions of cancer condition based at least in part on the identified plurality of features, where the six or more classifiers include at least the first classifier, the second classifier, the third classifier, the fourth classifier, the fifth classifier, and the sixth classifier. In some such embodiments, the combining combines the six or more predictions to identify the diagnosis of the cancer condition for the somatic tumor specimen.

In some embodiments, the final classification diagnosis differentiates between cancers of a same type (e.g., between sarcoma types). In some embodiments, the final classification diagnosis differentiates between cancers based on location of origin (e.g., to identify the origin of metastases). In some embodiments, the final classification diagnosis differentiates between two or more cancer types, three or more cancer types, four or more cancer types, five or more cancer types, six or more cancer types, seven or more cancer types, eight or more cancer types, nine or more cancer types, or ten or more cancer types.

In some embodiments, the final classification diagnosis of the cancer condition comprises differentiating between lung adenocarcinoma, lung squamous, oral adenocarcinoma, and oral adenocarcinoma. In some embodiments, the final classification diagnosis of the cancer condition comprises differentiating between general sarcomas, ependymoma, ewing sarcoma, gliosarcoma, leiomyosarcoma, meningioma, mesothelioma, and Rosai-Dorfman. In some embodiments, the final classification diagnosis of the cancer condition comprises differentiating between a liver metastasis of pancreatic origin, upper gastrointestinal origin, and cholangio origin. In some embodiments, the final classification diagnosis of the cancer condition comprises differentiating between a brain metastasis of glioblastoma, oligodendroglioma, astrocytoma, and medulloblastoma. In some embodiments, the final classification diagnosis of the cancer condition comprises differentiating between non-small cell lung cancer squamous and adenocarcinoma. In some embodiments, the final classification diagnosis of the cancer condition comprises differentiating between one or more sarcomas with carcinoma morphological features or protein expressions, and one or more carcinomas with sarcoma morphologic features or protein expressions. In some embodiments, the final classification diagnosis of the cancer condition comprises differentiating between one or more neuroendocrines, one or more carcinomas, and one or more sarcomas.

In some embodiments, the method further comprises receiving the final classifier diagnosis of the cancer condition for the somatic tumor specimen for a plurality of subjects. In some such embodiments, the method further comprises calculating an entropy score for each subject based at least in part on the respective final classifier diagnosis for each subject in the plurality of subjects. In some such embodiments, the method further comprises identifying an entropy threshold based at least in part on the accuracy of the entropy score for each subject in the plurality of subjects. In some such embodiments, the method further comprises training the final classifier with subjects from the subjects whose entropy score satisfies the entropy threshold.

In some embodiments, entropy scores provide a basis for weighting (e.g., scaling) the respective contribution from each classifier from the two or more classifiers at the final classifier. In some embodiments, entropy scores are used to remove subjects with low accuracy (e.g., high uncertainty) predictions from the plurality of subjects for the purposes of training the final classifier (e.g., as part of improving the performance of the final classifier). In some embodiments, entropy scores are between 0 and 1 (e.g., at least 0, at least 0.1, at least 0.2, at least 0.3, at least 0.4, at least 0.5, at least 0.6, at least 0.7, at least 0.8, at least 0.9, or at least 1). In some embodiments, entropy scores are between −1 and 1. In some embodiments, entropy scores are between −1 and 0. In some embodiments, entropy scores range from −5 to 5.

In some embodiments, each entropy score is associated with a classification accuracy (e.g., an accuracy of prediction as determined from the final classifier). In some embodiments, entropy scores are used to bin subjects from the plurality of subjects (e.g., subjects with a same entropy score are evaluated together). In some such embodiments, an average classification accuracy is determined for each entropy score (e.g., for each bin), and an entropy threshold is used to discard subjects with classification accuracies below a percentile of accuracy. In some embodiments, identifying an entropy threshold comprises identifying a percentile of the accuracy of the final classifier across the plurality of subjects. In some embodiments, subjects with entropy scores associated with an accuracy percentile are retained for training the final classifier. In some embodiments, the percentile of accuracy is at least 0.75, at least 0.8, at least 0.85, at least 0.9, at least 0.925, at least 0.95, at least 0.975, or at least 0.99 accuracy (e.g., subjects with predictions of a least the percentile of accuracy are used for training the final classifier).

In some embodiments, identifying the diagnosis of the cancer condition further comprises: receiving subject information comprising one or more clinical events, and differentiating the cancer condition between a new tumor and a recurrence of a previous tumor based at least in part on the one or more clinical events. In some embodiments, the one or more clinical events are received from a pathology report 134 (e.g., where the pathology report is obtained as described with regards to block 222 above). In some embodiments, the one or more clinical events comprise at least one prior disease diagnosis. In some embodiments, the one or more clinical events comprise at least one prior treatment for a disease.

In some embodiments, the subject has been treated with an agent for cancer and the method further comprises using the diagnosis to evaluate a response of the subject to the agent for cancer. In some embodiments, the agent for cancer is a hormone, an immune therapy, radiography, or a cancer drug. In some embodiments, the agent for cancer is Lenalidomid, Pembrolizumab, Trastuzumab, Bevacizumab, Rituximab, Ibrutinib, Human Papillomavirus Quadrivalent (Types 6, 11, 16, and 18) Vaccine, Pertuzumab, Pemetrexed, Nilotinib, Nilotinib, Denosumab, Abiraterone acetate, Promacta, Imatinib, Everolimus, Palbociclib, Erlotinib, Bortezomib, or Bortezomib.

In some embodiments, the method further comprises providing the identified diagnosis of the cancer condition for the somatic tumor specimen to the subject. In some embodiments, the identified diagnosis is provided to the subject as part of a patient report (e.g., patient report 900 as described with regards to FIG. 9 and FIGS. 10A-10G).

In some embodiments, the method further comprises applying a treatment regimen to the subject based at least in part, on the diagnosis. In some such embodiments, the treatment regimen comprises applying an agent for cancer (e.g., the one or more diagnosed cancers) to the subject. In some embodiments, the agent for cancer is a hormone, an immune therapy, radiography, or a cancer drug. In some embodiments, the agent for cancer is Lenalidomid, Pembrolizumab, Trastuzumab, Bevacizumab, Rituximab, Ibrutinib, Human Papillomavirus Quadrivalent (Types 6, 11, 16, and 18) Vaccine, Pertuzumab, Pemetrexed, Nilotinib, Nilotinib, Denosumab, Abiraterone acetate, Promacta, Imatinib, Everolimus, Palbociclib, Erlotinib, Bortezomib, or Bortezomib.

Training the Classifiers

To perform the classification methods for i) determining a set of cancer conditions for a test subject (e.g., the likelihoods generated for each cancer condition in the set of cancer conditions) and/or ii) classifying a subject to a cancer condition, described above and in regards to FIGS. 2A, 2B, and 2C, a classification model may be trained. Each and every embodiment described above and with regards to FIGS. 2A, 2B, and 2C may also be applied to methods of training a classification model as described below with regards to FIGS. 3A and 3B. Training a classification model may further require a dataset of data of reference subjects with known cancer conditions. Methods for providing a trained classification model are described below, and a particular example of developing a trained classifier is detailed in Example 1.

In one embodiment, a pre-training evaluation may be performed across the entire training data set to identify inputs which are best suited for training and inputs which are not suitable for training. In one example, pre-training evaluation may include calculating a subject's entropy score and including patients whose scores satisfy a threshold while excluding subjects who fail to satisfy the threshold. An entropy score may serve as a function that takes a probability vector and maps it to a single number characterizing how "uncertain" the result is. Herein, the uncertainty may be rooted in the predictions from the classifier. A probability vector with components $p_i$, the entropy may be defined as: $-\Sigma p_i \log(p_i)$. As an example, consider the case of a fair six-sided die. In that case, $p_i=[\frac{1}{6}, \frac{1}{6}, \frac{1}{6}, \frac{1}{6}, \frac{1}{6}, \frac{1}{6}]$ and so the entropy is $\log(6) \sim 1.79$. Now suppose the die is rigged so that it always gives the same answer, that is, $p_i=[1, 0, 0, 0, 0, 0]$. In this case, the entropy is 0. Entropy scores for a particular model may vary across a large range of values. In some instances, a high entropy score may be associated with increased numbers of model errors. Therefore, identifying the entropy cutoff for a particular model may include evaluating model performance at each cutoff for a range of values and selecting the cutoff with the best performance as measured by model accuracy. In one example, selecting the range of values may include grouping all hold-out model predictions from an interaction of model training by their entropy score using various cutoffs in the entropy score, for example in the negative range from [−4, −3.5, −3, −2.5, −2, −1.5, −1, −0.5, 0] and observing the accuracy of the model for each cutoff from, in one example, [0.925, 0.925, 0.927, 0.930, 0.938, 0.950, 0.972, 0.969, 0.965]. By filtering any entropy scores above −1, the highest overall model accuracy may be obtained. In other model training iterations, a differing entropy score may be identified. For each final training model one score, the best for that training set, may be used. Once identified, a subject's entropy score may be used to identify how confident the model is in predicting the subject's tumor's site of origin. In one example, a subject's TUO results may be invalidated and not reported if the entropy score is too high.

Figure 18:
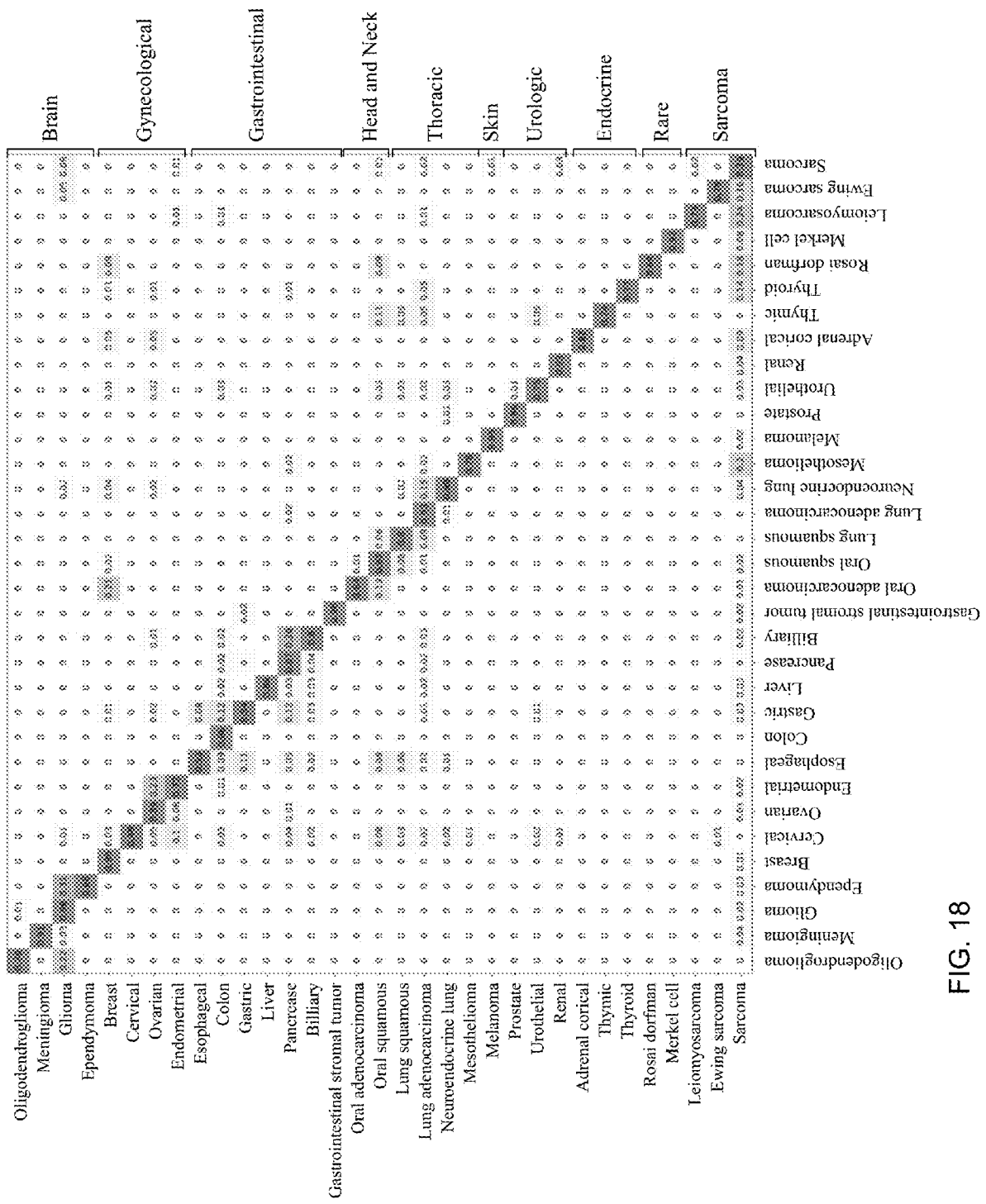
FIG. 18 illustrates the performance of an example classifier trained in accordance with some embodiments of the present disclosure.

Block 302. Referring to block 302 of FIG. 3A, a method of training a classifier stream for determining a set of cancer conditions is provided. As illustrated in FIGS. 16 and 18, the trained classification model achieves a high degree of accuracy for many cancer conditions.

Block 304. Referring to block 304 of FIG. 3A, the method obtains, in electronic format, for each respective subject in a plurality of subjects (e.g., reference subjects), for each respective cancer condition in the set of cancer conditions, an indication as to whether or not the respective subject has the cancer indication, a first plurality of sequence reads, and a pathology report for the respective subject. The corresponding first plurality of sequence reads for each subject in the plurality of subjects is obtained from a respective plurality of RNA molecules or derivatives of said plurality of RNA molecules (e.g., derivatives such as cDNA). Each respective plurality of RNA molecules is from a corresponding somatic biopsy obtained from the respective subject. The pathology report of the respective subject includes at least one of a first estimate of tumor cellularity, an indication as to whether the respective subject has a metastatic cancer or primary cancer, or a tissue site that is the origin of the somatic biopsy. In one example, the subjects of the plurality of subjects may be filtered based upon their entropy score to remove poor training subjects.

In some embodiments, the plurality of RNA molecules is obtained by full transcriptome sequencing (e.g., as described above with reference to block 226 of FIG. 2B).

Referring to block 306, in some embodiments, the method further comprises obtaining a second plurality of sequence reads and a third plurality of sequence reads for the respective subject. The second plurality of sequence reads is obtained from a first plurality of DNA molecules or derivatives of said DNA molecules. The third plurality of sequence reads is obtained from a second plurality of DNA molecules or derivatives of said DNA molecules. The first plurality of DNA molecules is from a somatic biopsy obtained from the respective subject. The second plurality of DNA molecules is from a germline sample obtained from the respective subject, or is from a population of normal controls that is free of a set of cancer conditions.

In some embodiments, the first and/or second pluralities of DNA molecules are obtained by whole genome sequencing (e.g., as described above with reference to block 226 of FIG. 2B). In some embodiments, the first and/or second pluralities of DNA molecules are obtained by targeted-panel sequencing or panel sequencing.

In some embodiments, each subject in the plurality of subjects is human. In some embodiments, the plurality of subject comprises at least 50 subjects, at least 100 subjects, at least 150 subjects, at least 200 subjects, at least 250 subjects, at least 300 subjects, at least 400 subjects, at least 500 subjects, at least 750 subjects, at least 1000 subjects, at least 1500 subjects, at least 2000 subjects, at least 3000 subjects, at least 4000 subjects, or at least 5000 subjects.

Block 308. Referring to block 308 of FIG. 3A, the method continues by determining for each respective subject in the plurality of subjects, from the first plurality of sequence reads of the respective subject, a corresponding first set of sequence features for the respective subject (e.g., as described above in reference to block 230 of FIG. 2B).

Block 310. Referring to block 310 of FIG. 3A, in some embodiments, the method continues by determining, for each respective subject in the plurality of subjects, from a comparison of the second plurality of sequence reads to the third plurality of sequence reads of the respective subject, a second set of sequence features for the respective subject (e.g., as described above with regard to blocks 234 and 236 of FIG. 2B).

Block 312. Referring to block 312 of FIG. 3B, the method continues by extracting, for each respective subject in the plurality of subjects, a plurality of pathology features from the pathology report for the respective subject including the first estimate of tumor cellularity of the somatic biopsy and the indication of whether the respective subject has a metastatic cancer or a primary cancer (e.g., as described above in reference to blocks 238-242 of FIG. 2C).

Referring to block 314, in some embodiments, extracting the plurality of pathology features from the pathology report further includes normalizing the pathology report. In some embodiments, normalizing the pathology report includes one or more data cleaning steps that enable comparisons among the pathology reports of different subjects. Various components of pathology reports are informative with regard to determining cancer of origin. Of particular use are the diagnostic labels, which provide valuable information on cancer classification, such as a patient's disease condition, disease stage and grade, pathology, and histology. In some embodiments, normalizing the pathology report includes natural language processing (NLP), which may include relabeling, performed on medical practitioner diagnostic entries. Some processing of the diagnostic labels in pathology reports is often required because there is no standardized scheme for sample annotation during pathology reviews. Instead, pathology reports include a "diagnosis" field that is a free text box, enabling medical practitioners to enter any values they choose (e.g., see the column of diagnosis field entries in Table 1 as discussed in Example 5 below).

Figure 12A:
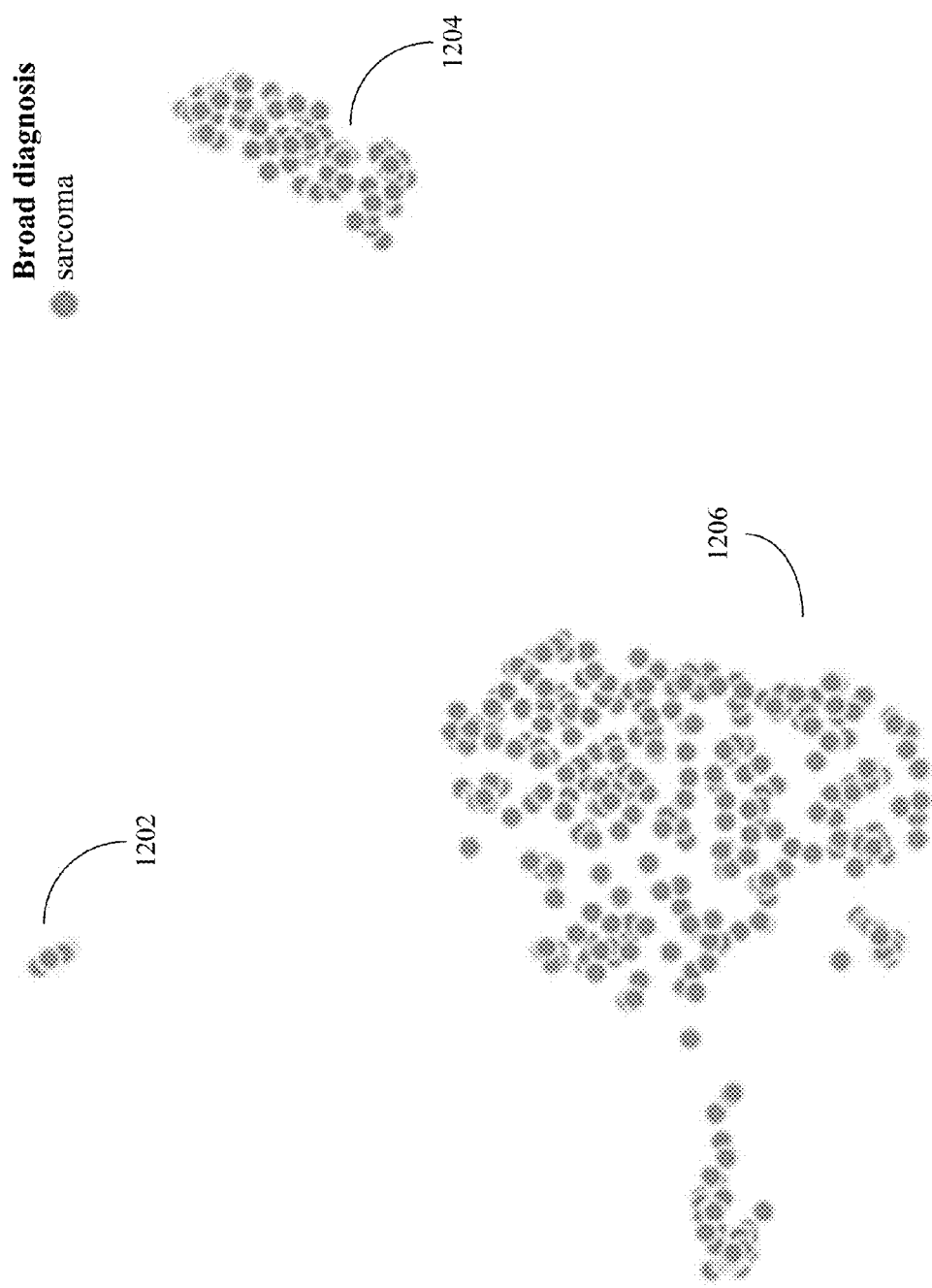
FIGS. 12A, 12B, and 12C, collectively illustrate examples of using clustering of RNA expression data to determine which cancer labels denote transcriptionally relevant divisions of data, in accordance with some embodiments of the present disclosure.
Figure 12B:
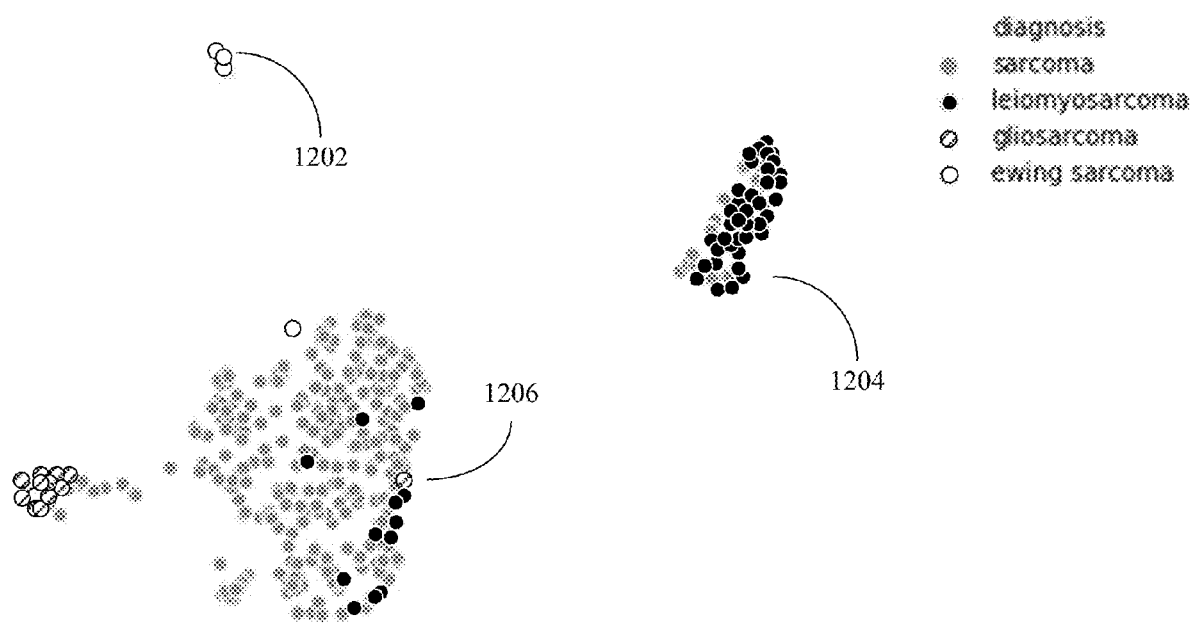

FIGS. 12A-12B illustrate the accuracy of NLP relabeling of diagnostic entries by comparing clustering performed in accordance with different set of labels determined by NLP. FIG. 12A provides an overview of the data, showing that each of the data points included in the analysis is from a respective patient with an overarching diagnosis or label of "sarcoma." As shown in FIG. 12B, using different, more specific, labels for each data point results in clusters that each associate more closely with a single label. In some embodiments, as discussed below in more detail in Example 6, when labels are highly specific (e.g., over-specific), there may be a loss of information in the resulting clusters.

Block 316. Referring to block 316 of FIG. 3B, the method continues by inputting at least the first set of sequence features and the plurality of pathology features of each respective subject in the plurality of subjects into an untrained classification model. The method continues training the untrained classification model against the indication of whether or not each respective subject in the plurality of subjects has each respective cancer condition in the set of cancer conditions to thereby obtain a trained classification model. The trained classification model is configured to provide i) for each respective cancer condition in the set of cancer conditions, a likelihood that a test subject has or does not have the respective cancer condition, ii) a likelihood that a test subject has or does not have the cancer condition, or iii) a likelihood that a test subject has or does not have the expected cancer condition.

Referring to block 318, in some embodiments, the inputting further comprises inputting the second set of sequence features of each respective subject in the plurality of subjects (e.g., alongside the first set of sequence features and the plurality of pathology features) into the untrained classification model to obtain a trained classification model.

Referring to block 320, in some embodiments, the trained classification model comprises a trained classifier stream. Referring to block 322 (and as further described below), in some embodiments, by way of a non-limiting example, the trained classifier stream includes a hierarchical model, a deep neural network, a multi-task multi-kernel learning engine, or a nearest-neighbor engine. Example, nearest-neighbor and neural network algorithms suitable for use in block 316 are described above with respect to block 244 FIG. 2C.

Multi-task multi-kernel learning engines suitable for use as the classifier of block 316 are described, for example, in Widmer et al. 2015 Framework for Multi-Task Multiple Kernel Learning and Applications in Genome Analysis. arXiv:1506.09153v1, which is hereby incorporated in its entirety by reference. The goal of multi-task multi-kernel learning methods is to identify one or more subsets of similar features in the input data, which allows for discovery of underlying structures in the input data. One specific algorithm that can be used to identify data subsets for multi-task multi-kernel learning is least absolute shrinkage and selection operator (Lasso). Additional algorithms are detailed, for example, in Yousefi et al., 2017 Multi-Task Learning Using Neighborhood Kernels. arXiv: 1707.03426v1, which is hereby incorporated by reference.

Hierarchical algorithms suitable for use as the classification model in block 316 are described in, for example, Galea et al., 2017 *Scientific Reports* 7:14981 and Silla et al. 2011 *Data Mining and Knowledge Discovery* 22:31-72, which are each hereby incorporated by reference. Hierarchical classification results are typically layered or branched, for example as in a directed acyclic graph.

Additional Embodiments Directed to Retrieving Patient Data from a Patient Data Store.

In some embodiments, artificial intelligence system 2300 retrieves features associated with a patient from a patient data store. In some embodiments, a patient data store includes one or more feature modules 2340 comprising a collection of features available for every patient in the system. In some embodiments, these features are used to generate predictions of the origin of a patient's tumor. While feature scope across all patients is informationally dense, an individual patient's feature set, in some embodiments, is sparsely populated across the entirety of the collective feature scope of all features across all patients. For example, the feature scope across all patients may expand into the tens of thousands of features while a patient's unique feature set may only include a subset of hundreds or thousands of the collective feature scope based upon the records available for that patient.

In some embodiments, feature collections may include a diverse set of fields available within patient health records. Clinical information, such as information of health records 2344, in some embodiments, are based upon fields which have been entered into an electronic medical record (EMR) or an electronic health record (EHR) 2346 by a physician, nurse, or other medical professional or representative. Other clinical information, in some embodiments, is curated 2345 from other sources, such as molecular fields from genetic sequencing reports. In some embodiments, sequencing may include next-generation sequencing (NGS) and comprises long-read, short-read, paired-end, or other forms of sequencing a patient's somatic and/or normal genome. In some embodiments, a comprehensive collection of features in additional feature modules combines a variety of features together across varying fields of medicine which may include diagnoses, responses to treatment regimens, genetic profiles, clinical and phenotypic characteristics, and/or other medical, geographic, demographic, clinical, molecular, or genetic features. For example, a subset of features may comprise molecular data features, such as features derived from an RNA feature module 2341 or a DNA feature module 2342, including sequencing results of a patient's germline or somatic specimen(s).

In some embodiments, another subset of features, imaging features 2347 from an imaging feature module, comprises features identified through review of a specimen, for example, through pathologist review, such as a review of stained H&E or IHC slides. As another example, a subset of features may comprise derivative features 2349 obtained from the analysis of the individual and combined results of such feature sets. Features derived from DNA and RNA sequencing may include genetic variants from a variant science module 2348 which are present in the sequenced tissue. Further analysis of the genetic variants may include additional steps such as identifying single or multiple nucleotide polymorphisms, identifying whether a variation is an insertion or deletion event, identifying loss or gain of function, identifying fusions, identifying splicing, calculating copy number variation (CNV), calculating microsatellite instability, calculating tumor mutational burden (TMB), or other structural variations within the DNA and RNA. Analysis of slides for H&E staining or IHC staining may reveal features such as tumor infiltration, programmed death-ligand 1 (PD-L1) status, human leukocyte antigen (HLA) status, or other immunological features.

In some embodiments, features derived from structured, curated, or electronic medical or health records may include clinical features such as diagnosis, symptoms, therapies, outcomes, patient demographics such as patient name, date of birth, gender, ethnicity, date of death, address, smoking status, diagnosis dates for cancer, illness, disease, diabetes, depression, other physical or mental maladies, personal medical history, family medical history, clinical diagnoses such as date of initial diagnosis, date of metastatic diagnosis, cancer staging, tumor characterization, tissue of origin, treatments and outcomes such as line of therapy, therapy groups, clinical trials, medications prescribed or taken, surgeries, radiotherapy, imaging, adverse effects, associated outcomes, genetic testing and laboratory information such as performance scores, lab tests, pathology results, prognostic indicators, date of genetic testing, testing provider used, testing method used, such as genetic sequencing method or gene panel, gene results, such as included genes, variants, expression levels/statuses, or corresponding dates to any of the above. Clinical features may also include imaging features.

In some embodiments, an Omics feature module 2343 comprises features derived from information from additional medical- or research-based Omics fields including proteomics, transcriptomics, epigenomics, metabolomics, microbiomics, and other multi-omic fields. In some embodiments, features derived from an organoid modeling lab include the DNA and RNA sequencing information germane to each organoid and results from treatments applied to those organoids. In some embodiments, features derived from imaging data further include reports associated with a stained slide, size of tumor, tumor size differentials over time including treatments during the period of change, as well as machine learning approaches for classifying PDL1 status, HLA status, or other characteristics from imaging data. In some embodiments, other features include the additional derivative features sets from other machine learning approaches based at least in part on combinations of any new features and/or those listed above. For example, imaging results may need to be combined with MSI calculations derived from RNA expressions to determine additional further imaging features. In some embodiments a machine learning model may generate a likelihood that a patient's cancer will metastasize to a particular organ or a patient's future probability of metastasis to yet another organ in the body. In some embodiments, other features that can extracted from medical information are also used. There are many thousands of features, and the above listing of types of features are merely representative and should not be construed as a complete or limiting listing of features.

In some embodiments, an alterations module 2350 comprises one or more microservices, servers, scripts, or other executable algorithms which generate alteration features associated with de-identified patient features from the feature collection 2305. In some embodiments, alterations modules retrieve inputs from the feature collection and may provide alterations for storage 2310. Exemplary alterations modules 2352*a*-*n* may include one or more of the following alterations as a collection of alteration modules 2353*a*-*n*.

In some embodiments, an IHC (Immunohistochemistry) module identifies antigens (proteins) in cells of a tissue section by exploiting the principle of antibodies binding specifically to antigens in biological tissues. IHC staining is widely used in the diagnosis of abnormal cells such as those found in cancerous tumors. Specific molecular markers are characteristic of particular cellular events such as proliferation or cell death (apoptosis). IHC is also widely used in basic research to understand the distribution and localization of biomarkers and differentially expressed proteins in different parts of a biological tissue. Visualizing an antibody-antigen interaction can be accomplished in a number of ways. In the most common instance, an antibody is conjugated to an enzyme, such as peroxidase, that can catalyze a color-producing reaction in immunoperoxidase staining. Alternatively, the antibody can also be tagged to a fluorophore, such as fluorescein or rhodamine in immunofluorescence. In some embodiments, approximations from RNA expression data, H&E slide imaging data, or other data are generated.

In some embodiments, a Therapies module identifies differences in cancer cells (or other cells near them) that help them grow and thrive and drugs that "target" these differences. Treatment with these drugs is called targeted therapy. For example, many targeted drugs are lethal to the cancer cells' with inner 'programming' that makes them different from normal, healthy cells, while not affecting most healthy cells. Targeted drugs may block or turn off chemical signals that tell the cancer cell to grow and divide rapidly; change proteins within the cancer cells so the cancer cells die; stop making new blood vessels to feed the cancer cells; trigger a patient's immune system to kill the cancer cells; or carry toxins to the cancer cells to kill them, without affecting normal cells. Some targeted drugs are more "targeted" than others. Some might target only a single change in cancer cells, while others can affect several different changes. Others boost the way a patient's body fights the cancer cells. This can affect where these drugs work and what side effects they cause. In some embodiments, matching targeted therapies may include identifying the therapy targets in the patients and satisfying any other inclusion or exclusion criteria that might identify a patient for whom a therapy is likely to be effective.

In some embodiments, a Trial module identifies and tests hypotheses for treating cancers having specific characteristics by matching features of a patient to clinical trials. These trials have inclusion and exclusion criteria that must be matched to enroll a patient and which may be ingested and structured from publications, trial reports, or other documentation.

In some embodiments, an Amplifications module identifies genes which increase in count (for example, the number of gene products present in a specimen) disproportionately to other genes. Amplifications may cause a gene having the increased count to go dormant, become overactive, or operate in another unexpected fashion. In some embodiments, amplifications may be detected at a gene level, variant level, RNA transcript or expression level, or even a protein level. In some embodiments, detections are performed across all the different detection mechanisms or levels and validated against one another.

In some embodiments, an Isoforms module identifies alternative splicing (AS), the biological process in which more than one mRNA type (isoform) is generated from the transcript of a same gene through different combinations of exons and introns. It is estimated by large-scale genomics studies that 30-60% of mammalian genes are alternatively spliced. The possible patterns of alternative splicing for a gene can be very complicated and the complexity increases rapidly as the number of introns in a gene increases. In silico alternative splicing prediction may find large insertions or deletions within a set of mRNA sharing a large portion of aligned sequences by identifying genomic loci through searches of mRNA sequences against genomic sequences, extracting sequences for genomic loci and extending the sequences at both ends up to 20 kb, searching the genomic sequences (repeat sequences have been masked), extracting splicing pairs (two boundaries of alignment gap with GT-AG consensus or with more than two expressed sequence tags aligned at both ends of the gap), assembling splicing pairs according to their coordinates, determining gene boundaries (splicing pair predictions are generated to this point), generating predicted gene structures by aligning mRNA sequences to genomic templates, and comparing splicing pair predictions and gene structure predictions to find alternatively spliced isoforms.

In some embodiments, an SNP (single-nucleotide polymorphism) module identifies a substitution of a single nucleotide that occurs at a specific position in the genome, where each variation is present to some appreciable degree within a population (e.g. >1%). For example, at a specific base position, or loci, in the human genome, the C nucleotide may appear in most individuals, but in a minority of individuals, the position is occupied by an A. This means that there is a SNP at this specific position and the two possible nucleotide variations, C or A, are said to be alleles for this position. SNPs underlie differences in human susceptibility to a wide range of diseases (e.g.—sickle-cell anemia, β-thalassemia, and cystic fibrosis result from SNPs). The severity of illness and the way the body responds to treatments are also manifestations of genetic variations. For example, a single-base mutation in the APOE (apolipoprotein E) gene is associated with a lower risk for Alzheimer's disease. A single-nucleotide variant (SNV) is a variation in a single nucleotide without any limitations of frequency and may arise in somatic cells. A somatic single-nucleotide variation (e.g., caused by cancer) may also be called a single-nucleotide alteration. In some embodiments, an MNP (Multiple-nucleotide polymorphisms) module identifies the substitution of consecutive nucleotides at a specific position in the genome.

In some embodiments, an Indels module may identify an insertion or deletion of bases in the genome of an organism classified among small genetic variations. While indels usually measure from 1 to 10 000 base pairs in length, a microindel is defined as an indel that results in a net change of 1 to 50 nucleotides. Indels can be contrasted with a SNP or point mutation. An indel inserts and/or deletes nucleotides from a sequence, while a point mutation is a form of substitution that replaces one of the nucleotides without changing the overall number in the DNA. Indels, being insertions and/or deletions, can be used as genetic markers in natural populations, especially in phylogenetic studies. Indel frequency tends to be markedly lower than that of single nucleotide polymorphisms (SNP), except near highly repetitive regions, including homopolymers and microsatellites.

In some embodiments, a MSI (microsatellite instability) module may identify genetic hypermutability (predisposition to mutation) that results from impaired DNA mismatch repair (MMR). The presence of MSI represents phenotypic evidence that MMR is not functioning normally. MMR corrects errors that spontaneously occur during DNA replication, such as single base mismatches or short insertions and deletions. The proteins involved in MMR correct polymerase errors by forming a complex that binds to the mismatched section of DNA, excises the error, and inserts the correct sequence in its place. Cells with abnormally functioning MMR are unable to correct errors that occur during DNA replication, which causes the cells to accumulate errors in their DNA. This causes the creation of novel microsatellite fragments. Polymerase chain reaction-based assays can reveal these novel microsatellites and provide evidence for the presence of MSI. Microsatellites are repeated sequences of DNA. These sequences can be made of repeating units of one to six base pairs in length. Although the length of these microsatellites is highly variable from person to person and contributes to the individual DNA "fingerprint," each individual has microsatellites of a set length. The most common microsatellite in humans is a dinucleotide repeat of the nucleotides C and A, which occurs tens of thousands of times across the genome. Microsatellites are also known as simple sequence repeats (SSRs).

In some embodiments, a TMB (tumor mutational burden) module may identify a measurement of mutations carried by tumor cells and is a predictive biomarker being studied to evaluate its association with response to Immuno-Oncology (I-O) therapy. Tumor cells with high TMB may have more neoantigens, with an associated increase in cancer-fighting T cells in the tumor microenvironment and periphery. These neoantigens can be recognized by T cells, inciting an anti-tumor response. TMB has emerged more recently as a quantitative marker that can help predict potential responses to immunotherapies across different cancers, including melanoma, lung cancer, and bladder cancer. TMB is defined as the total number of mutations per coding area of a tumor genome. Importantly, TMB is consistently reproducible. It provides a quantitative measure that can be used to better inform treatment decisions, such as selection of targeted or immunotherapies or enrollment in clinical trials.

In some embodiments, a CNV (copy number variation) module may identify deviations from the normal genome, especially in the number of copies of a gene, portions of a gene, or other portions of a genome not defined by a gene, and any subsequent implications from analyzing genes, variants, alleles, or sequences of nucleotides. CNV are the phenomenon in which structural variations may occur in sections of nucleotides, or base pairs, that include repetitions, deletions, or inversions.

In some embodiments, a Fusions module may identify hybrid genes formed from two previously separate genes. Hybrid genes may be a result of translocation, interstitial deletion, or chromosomal inversion. Gene fusion can play an important role in tumorigenesis. Fusion genes can contribute to tumor formation because they can produce much more active abnormal protein than non-fusion genes. Often, fusion genes are oncogenes that cause cancer; these include BCR-ABL, TEL-AML1 (ALL with t(12; 21)), AML1-ETO (M2 AML with t(8; 21)), and TMPRSS2-ERG with an interstitial deletion on chromosome 21, often occurring in prostate cancer. In the case of TMPRSS2-ERG, by disrupting androgen receptor (AR) signaling and inhibiting AR expression by oncogenic ETS transcription factor, the fusion product regulates prostate cancer. Most fusion genes are found from hematological cancers, sarcomas, and prostate cancer. BCAM-AKT2 is a fusion gene that is specific and unique to high-grade serous ovarian cancer. Oncogenic fusion genes may lead to a gene product with a new or different function from the two fusion partners. Alternatively, a proto-oncogene cay be fused to a strong promoter, and thereby the oncogenic function is set to function by an upregulation caused by the strong promoter of the upstream fusion partner. The latter is common in lymphomas, where oncogenes are juxtaposed to the promoters of the immunoglobulin genes. Oncogenic fusion transcripts may also be caused by trans-splicing or read-through events. Since chromosomal translocations play such a significant role in neoplasia, a specialized database of chromosomal aberrations and gene fusions in cancer has been created. This database is called Mitelman Database of Chromosome Aberrations and Gene Fusions in Cancer.

In some embodiments, a VUS (variant of unknown significance) module may identify variants which are detected in the genome of a patient (especially in a patient's cancer specimen) but cannot be classified as pathogenic or benign at the time of detection. VUS are catalogued from publications to identify if they may be classified as benign or pathogenic.

In some embodiments, a DNA Pathways module identifies defects in DNA repair pathways which enable cancer cells to accumulate genomic alterations that contribute to their aggressive phenotype. Cancerous tumors rely on residual DNA repair capacities to survive the damage induced by genotoxic stress which leads to isolated DNA repair pathways being inactivated in cancer cells. DNA repair pathways are generally thought of as mutually exclusive mechanistic units handling different types of lesions in distinct cell cycle phases. Recent preclinical studies, however, provide strong evidence that multifunctional DNA repair hubs, which are involved in multiple conventional DNA repair pathways, are frequently altered in cancer. Identifying pathways which may be affected may lead to important patient treatment considerations.

In some embodiments, a Raw Counts module identifies a count of the variants that are detected from the sequencing data. For DNA, in some embodiments, this comprises the number of reads from sequencing which correspond to a particular variant in a gene. For RNA, in some embodiments, this comprises the gene expression counts or the transcriptome counts from sequencing.

In some embodiments, classifications comprise classifications according to one or more trained models for generating predictions and other structural variant classification may include evaluating features from the feature collection, alterations from the alteration module, and other classifications from within itself from one or more classification modules. Structural variant classification may provide classifications to a stored classifications storage. An exemplary classification module may include a classification of a CNV as "Reportable" may mean that the CNV has been identified in one or more reference databases as influencing the tumor cancer characterization, disease state, or pharmacogenomics, "Not Reportable" may mean that the CNV has not been identified as such, and "Conflicting Evidence" may mean that the CNV has both evidence suggesting "Reportable" and "Not Reportable." Furthermore, a classification of therapeutic relevance is similarly ascertained from any reference datasets mention of a therapy which may be impacted by the detection (or non-detection) of the CNV. Other classifications may include applications of machine learning algorithms, neural networks, regression techniques, graphing techniques, inductive reasoning approaches, or other artificial intelligence evaluations within modules. In some embodiments, a classifier for clinical trials may include evaluation of variants identified from the alteration module which have been identified as significant or reportable, evaluation of all clinical trials available to identify inclusion and exclusion criteria, mapping the patient's variants and other information to the inclusion and exclusion criteria, and classifying clinical trials as applicable to the patient or as not applicable to the patient. In some embodiments, similar classifications are performed for therapies, loss-of-function, gain-of-function, diagnosis, microsatellite instability, tumor mutational burden, indels, SNP, MNP, fusions, CNV, splicing, and other alterations which may be classified based upon the results of the alteration modules. Additionally, in some embodiments, models trained to classify a type of tumor for patient with tumors of unknown origin are generated according to the disclosure herein. In some embodiments, classifications are generated and stored as part of a feature collection 2305 in a stored classifications database 2330.

In some embodiments, each of the feature collection, alteration module(s), structural variant, and feature store are communicatively coupled to a data bus to transfer data between each module for processing and/or storage. In some embodiments, each of the feature collection, alteration module(s), and classifications may be communicatively coupled to each other for independent communication without sharing the data bus.

In addition to the above features and enumerated modules, in some embodiments, feature modules may further include one or more of the following modules within their respective modules as a sub-module or as a standalone module.

In some embodiments, a germline/somatic DNA feature module comprises a feature collection associated with the DNA-derived information of a patient or a patient's tumor. These features may include raw sequencing results, such as those stored in FASTQ, BAM, VCF, or other sequencing file types known in the art; genes; mutations; variant calls; and variant characterizations. In some embodiments, genomic information from a patient's normal sample is stored as germline and genomic information from a patient's tumor sample is stored as somatic.

In some embodiments, an RNA feature module comprises a feature collection associated with the RNA-derived information of a patient, such as transcriptome information. These features may include raw sequencing results, transcriptome expressions, genes, mutations, variant calls, and variant characterizations.

In some embodiments, a metadata module comprises a feature collection associated with the human genome, protein structures and their effects, such as changes in energy stability based on a protein structure.

In some embodiments, a clinical module comprises a feature collection associated with information derived from clinical records of a patient and records from family members of the patient. These may be abstracted from unstructured clinical documents, EMR, EHR, or other sources of patient history. Information may include patient symptoms, diagnosis, treatments, medications, therapies, hospice, responses to treatments, laboratory testing results, medical history, geographic locations of each, demographics, or other features of the patient which may be found in the patient's medical record. Information about treatments, medications, therapies, and the like may be ingested as a recommendation or prescription and/or as a confirmation that such treatments, medications, therapies, and the like were administered or taken.

In some embodiments, an imaging module comprises a feature collection associated with information derived from imaging records of a patient. Imaging records may include H&E slides, IHC slides, radiology images, and other medical imaging which may be ordered by a physician during the course of diagnosis and treatment of various illnesses and diseases. These features may include TMB, ploidy, purity, nuclear-cytoplasmic ratio, large nuclei, cell state alterations, biological pathway activations, hormone receptor alterations, immune cell infiltration, immune biomarkers of MMR, MSI, PDL1, CD3, FOXP3, HRD, PTEN, PIK3CA; collagen or stroma composition, appearance, density, or characteristics; tumor budding, size, aggressiveness, metastasis, immune state, chromatin morphology; and other characteristics of cells, tissues, or tumors for prognostic predictions.

In some embodiments, an epigenome module, such as epigenome module from Omics, comprises a feature collection associated with information derived from DNA modifications which are not changes to the DNA sequence and regulate the gene expression. These modifications are frequently the result of environmental factors based on what the patient may breathe, eat, or drink. These features may include DNA methylation, histone modification, or other factors which deactivate a gene or cause alterations to gene function without altering the sequence of nucleotides in the gene.

In some embodiments, a microbiome module, such as microbiome module from Omics, comprises a feature collection associated with information derived from the viruses and bacteria of a patient. Viral genomics may be generated to identify which viruses are present in the patient's specimen(s) based upon the genomic features which map to viral DNA or RNA (e.g., a viral reference genome(s)) instead of the human genome. These features may include viral infections which may affect treatment and diagnosis of certain illnesses as well as the bacteria present in the patient's gastrointestinal tract which may affect the efficacy of medicines ingested by the patient.

In some embodiments, a proteome module, such as proteome module from Omics, comprises a feature collection associated with information derived from the proteins produced in the patient. These features may include protein composition, structure, and activity; when and where proteins are expressed; rates of protein production, degradation, and steady-state abundance; how proteins are modified, for example, post-translational modifications such as phosphorylation; the movement of proteins between subcellular compartments; the involvement of proteins in metabolic pathways; how proteins interact with one another; or modifications to the protein after translation from the RNA such as phosphorylation, ubiquitination, methylation, acetylation, glycosylation, oxidation, or nitrosylation.

In some embodiments, additional Omics module(s) are included in Omics, such as a feature collection associated with all the different field of omics, including: cognitive genomics, a collection of features comprising the study of the changes in cognitive processes associated with genetic profiles; comparative genomics, a collection of features comprising the study of the relationship of genome structure and function across different biological species or strains; functional genomics, a collection of features comprising the study of gene and protein functions and interactions including transcriptomics; interactomics, a collection of features comprising the study relating to large-scale analyses of gene-gene, protein-protein, or protein-ligand interactions; metagenomics, a collection of features comprising the study of metagenomes such as genetic material recovered directly from environmental samples; neurogenomics, a collection of features comprising the study of genetic influences on the development and function of the nervous system; pangenomics, a collection of features comprising the study of the entire collection of gene families found within a given species; personal genomics, a collection of features comprising the study of genomics concerned with the sequencing and analysis of the genome of an individual such that once the genotypes are known, the individual's genotype can be compared with the published literature to determine likelihood of trait expression and disease risk to enhance personalized medicine suggestions; epigenomics, a collection of features comprising the study of supporting the structure of genome, including protein and RNA binders, alternative DNA structures, and chemical modifications on DNA; nucleomics, a collection of features comprising the study of the complete set of genomic components which form the cell nucleus as a complex, dynamic biological system; lipidomics, a collection of features comprising the study of cellular lipids, including the modifications made to any particular set of lipids produced by a patient; proteomics, a collection of features comprising the study of proteins, including the modifications made to any particular set of proteins produced by a patient; immunoproteomics, a collection of features comprising the study of large sets of proteins involved in the immune response; phosphoproteomics, a collection of features comprising the study of phosphorylation patterns of proteins, including the modifications made to any particular set of proteins produced by a patient; nutriproteomics, a collection of features comprising the study of identifying molecular targets of nutritive and non-nutritive components of the diet including the use of proteomics mass spectrometry data for protein expression studies; proteogenomics, a collection of features comprising the study of biological research at the intersection of proteomics and genomics including data which identifies gene annotations; structural genomics, a collection of features comprising the study of 3-dimensional structure of every protein encoded by a given genome using a combination of modeling approaches; glycomics, a collection of features comprising the study of sugars and carbohydrates and their effects in the patient; foodomics, a collection of features comprising the study of the intersection between the food and nutrition domains through the application and integration of technologies to improve consumer's well-being, health, and knowledge; transcriptomics, a collection of features comprising the study of RNA molecules, including mRNA, rRNA, tRNA, and other non-coding RNA, produced in cells; metabolomics, a collection of features comprising the study of chemical processes involving metabolites, or unique chemical fingerprints that specific cellular processes leave behind, and their small-molecule metabolite profiles; metabonomics, a collection of features comprising the study of the quantitative measurement of the dynamic multiparametric metabolic response of cells to pathophysiological stimuli or genetic modification; nutrigenetics, a collection of features comprising the study of genetic variations on the interaction between diet and health with implications to susceptible subgroups; cognitive genomics, a collection of features comprising the study of the changes in cognitive processes associated with genetic profiles; pharmacogenomics, a collection of features comprising the study of the effect of the sum of variations within the human genome on drugs; pharmacomicrobiomics, a collection of features comprising the study of the effect of variations within the human microbiome on drugs; toxicogenomics, a collection of features comprising the study of gene and protein activity within particular cell or tissue of an organism in response to toxic substances; mitointeractome, a collection of features comprising the study of the process by which the mitochondria proteins interact; psychogenomics, a collection of features comprising the study of the process of applying the powerful tools of genomics and proteomics to achieve a better understanding of the biological substrates of normal behavior and of diseases of the brain that manifest themselves as behavioral abnormalities, including applying psychogenomics to the study of drug addiction to develop more effective treatments for these disorders as well as objective diagnostic tools, preventive measures, and cures; stem cell genomics, a collection of features comprising the study of stem cell biology to establish stem cells as a model system for understanding human biology and disease states; connectomics, a collection of features comprising the study of the neural connections in the brain; microbiomics, a collection of features comprising the study of the genomes of the communities of microorganisms that live in the digestive tract; cellomics, a collection of features comprising the study of the quantitative cell analysis and study using bioimaging methods and bioinformatics; tomomics, a collection of features comprising the study of tomography and omics methods to understand tissue or cell biochemistry at high spatial resolution from imaging mass spectrometry data; ethomics, a collection of features comprising the study of high-throughput machine measurement of patient behavior; and videomics, a collection of features comprising the study of a video analysis paradigm inspired by genomics principles, where a continuous image sequence, or video, can be interpreted as the capture of a single image evolving through time of mutations revealing patient insights.

In some embodiments, a sufficiently robust collection of features comprises all of the features disclosed above; however, models and predictions based from the available features comprise models which are optimized and trained from a selection of features that are much more limiting than the exhaustive feature set. In some embodiments, such a constrained feature set comprises as few as tens to hundreds of features. For example, a model's constrained feature set may include the genomic results of a sequencing of the patient's tumor, derivative features based upon the genomic results, the patient's tumor origin, the patient's age at diagnosis, the patient's gender and race, and symptoms that the patient brought to their physicians attention during a routine checkup.

In some embodiments, a feature store may enhance a patient's feature set through the application of machine learning and analytics by selecting from any features, alterations, or calculated output derived from the patient's features or alterations to those features. In some embodiments, such a feature store may generate new features from the original features found in feature module or may identify and store important insights or analysis based upon the features. In some embodiments, the selection of features is based at least upon an alteration or calculation to be generated, and comprises the calculation of single or multiple nucleotide polymorphisms insertion or deletions of the genome, a tumor mutational burden, a microsatellite instability, a copy number variation, a fusion, or other such calculations. In some embodiments, an exemplary output of an alteration or calculation generated which may inform future alterations or calculations includes a finding of hypertrophic cardiomyopathy (HCM) and variants in MYH7. In some embodiments, previous classified variants may be identified in the patient's genome which may inform the classification of novel variants or indicate a further risk of disease. An exemplary approach includes the enrichment of variants and their respective classifications to identify a region in MYH7 that is associated with HCM. Novel variants detected from a patient's sequencing localized to this region would increase the patient's risk for HCM. In some embodiments, features which may be utilized in such an alteration detection include the structure of MYH7 and classification of variants therein. In some embodiments, a model focused on enrichment may isolate such variants. An exemplary output of an alteration or calculation generated which may inform future alterations or calculations includes a finding of lung cancer and variants in EGFR, an epidermal growth factor receptor gene that is mutated in ~10% of non-small cell lung cancer and ~50% of lung cancers from non-smokers. In some embodiments, previously classified variants may be identified in the patient's genome which may inform the classification of novel variants or indicate a further risk of disease. An exemplary approach may include the enrichment of variants and their respective classifications to identify a region nearby or with evidence to interact with EGFR and associated with cancer. Novel variants detected from a patient's sequencing localized to this region or interactions with this region would increase the patient's risk. In some embodiments, features which may be utilized in such an alteration detection include the structure of EGFR and classification of variants therein. In some embodiments, a model focused enrichment may isolate such variants.

In some embodiments, the above referenced classification model may include one or more classification models 2382a-n which may be implemented as artificial intelligence engines and may include gradient boosting models, random forest models, neural networks (NN), regression models, Naive Bayes models, or machine learning algorithms (MLA). A MLA or a NN may be trained from a training data set. In an exemplary prediction profile, a training data set may include imaging, pathology, clinical, and/or molecular reports and details of a patient, such as those curated from an EHR or genetic sequencing reports. MLAs include supervised algorithms (such as algorithms where the features/classifications in the data set are annotated) using linear regression, logistic regression, decision trees, classification and regression trees, Naive Bayes, nearest neighbor clustering; unsupervised algorithms (such as algorithms where no features/classification in the data set are annotated) using Apriori, means clustering, principal component analysis, random forest, adaptive boosting; and semi-supervised algorithms (such as algorithms where an incomplete number of features/classifications in the data set are annotated) using generative approach (such as a mixture of Gaussian distributions, mixture of multinomial distributions, hidden Markov models), low density separation, graph-based approaches (such as mincut, harmonic function, manifold regularization), heuristic approaches, or support vector machines. NNs include conditional random fields, convolutional neural networks, attention based neural networks, deep learning, long short term memory networks, or other neural models where the training data set includes a plurality of tumor samples, RNA expression data for each sample, and pathology reports covering imaging data for each sample. While MLA and neural networks identify distinct approaches to machine learning, the terms may be used interchangeably herein. Thus, a mention of MLA may include a corresponding NN or a mention of NN may include a corresponding MLA unless explicitly stated otherwise. Training may include providing optimized datasets, labeling these traits as they occur in patient records, and training the MLA to predict or classify based on new inputs. Artificial NNs are efficient computing models which have shown their strengths in solving hard problems in artificial intelligence. They have also been shown to be universal approximators (can represent a wide variety of functions when given appropriate parameters). In some embodiments, some MLA may identify features of importance and identify a coefficient, or weight, to them. The coefficient may be multiplied with the occurrence frequency of the feature to generate a score, and once the scores of one or more features exceed a threshold, certain classifications may be predicted by the MLA. In some embodiments, a coefficient schema may be combined with a rule based schema to generate more complicated predictions, such as predictions based upon multiple features. For example, ten key features may be identified across different classifications. In some embodiments, a list of coefficients may exist for the key features, and a rule set may exist for the classification. In some embodiments, a rule set may be based upon the number of occurrences of the feature, the scaled weights of the features, or other qualitative and quantitative assessments of features encoded in logic known to those of ordinary skill in the art. In other MLA, features may be organized in a binary tree structure. For example, key features which distinguish between the most classifications may exist as the root of the binary tree and each subsequent branch in the tree until a classification may be awarded based upon reaching a terminal node of the tree. For example, a binary tree may have a root node which tests for a first feature. The occurrence or non-occurrence of this feature must exist (the binary decision), and the logic may traverse the branch which is true for the item being classified. Additional rules may be based upon thresholds, ranges, or other qualitative and quantitative tests. While supervised methods are useful when the training dataset has many known values or annotations, the nature of EMR/EHR documents is that there may not be many annotations provided. When exploring large amounts of unlabeled data, unsupervised methods are useful for binning/bucketing instances in the data set. A single instance of the above models, or two or more such instances in combination, may constitute a model for the purposes of models, artificial intelligence, neural networks, or machine learning algorithms, herein.

Figure 23:
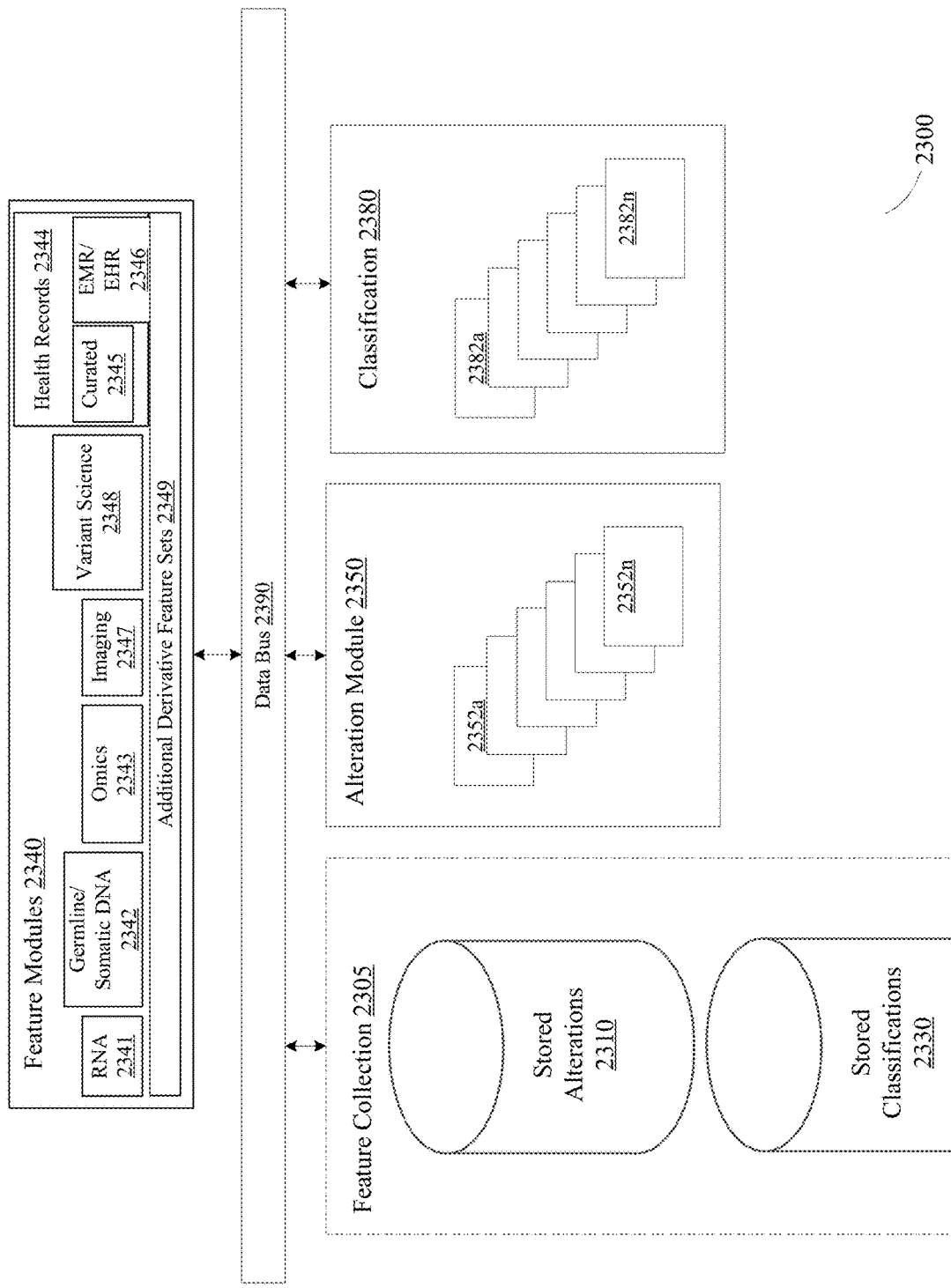
FIG. 23 illustrates an artificial intelligence system for receiving patient health information to generate a prediction of the origin of a patient's tumor, in accordance with some embodiments of the present disclosure.
Figure 24:
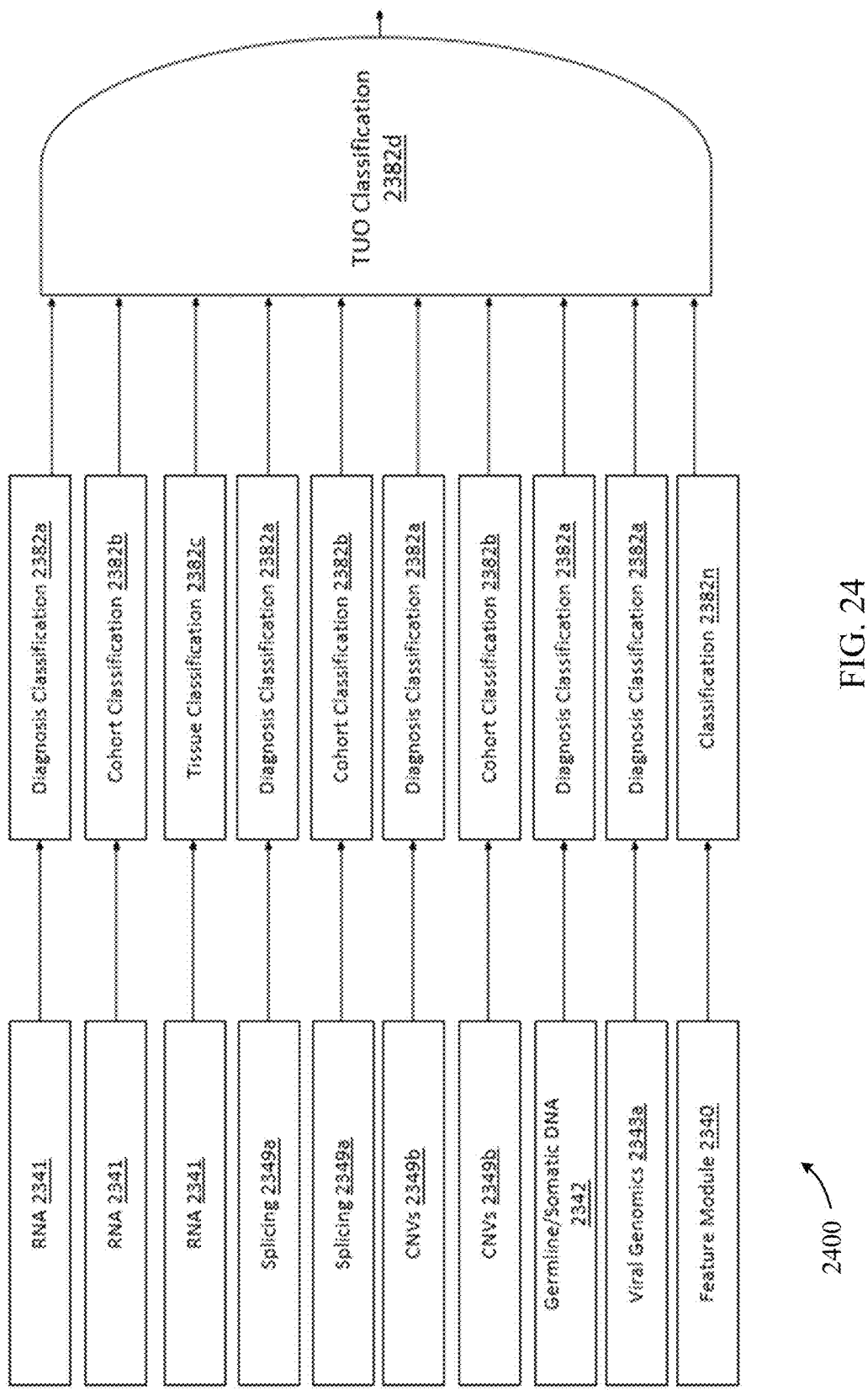
FIG. 24 illustrates a stacked TUO Classification using the artificial intelligence engine of FIG. 23 to predict cancer conditions of a patient with a tumor of unknown origin, in accordance with some embodiments of the present disclosure.

In some embodiments, Stacked TUO Classifier 2400 may receive one or more features from the artificial intelligence engine 2300 of FIG. 23 to predict cancer conditions at TUO Classification 2382 using one or more classifiers 2382a-n.

In some embodiments, the set of cancer conditions comprises diagnoses such as Acute Lymphoblastic Leukemia (ALL), Acute Myeloid Leukemia (AML), Adolescents, Cancer in, Adrenocortical Carcinoma, AIDS-Related Cancers, Kaposi Sarcoma (Soft Tissue Sarcoma), AIDS-Related Lymphoma (Lymphoma), Primary CNS Lymphoma (Lymphoma), Anal Cancer, Appendix Cancer, Astrocytomas, Childhood (Brain Cancer), Atypical Teratoid/Rhabdoid Tumor, Childhood, Central Nervous System (Brain Cancer), Basal Cell Carcinoma of the Skin, Bile Duct Cancer, Bladder Cancer, Bone Cancer (includes Ewing Sarcoma and Osteosarcoma and Malignant Fibrous Histiocytoma), Brain Tumors, Breast Cancer, Bronchial Tumors (Lung Cancer), Burkitt Lymphoma, Carcinoid Tumor (Gastrointestinal), Carcinoma of Unknown Primary, Cardiac (Heart) Tumors, Childhood, Central Nervous System, Atypical Teratoid/Rhabdoid Tumor, Childhood (Brain Cancer), Medulloblastoma and Other CNS Embryonal Tumors, Childhood (Brain Cancer), Germ Cell Tumor, Childhood (Brain Cancer), Primary CNS Lymphoma, Cervical Cancer, Childhood Cancers, Cancers of Childhood, Unusual, Cholangiocarcinoma, Chordoma, Childhood (Bone Cancer), Chronic Lymphocytic Leukemia (CLL), Chronic Myelogenous Leukemia (CML), Chronic Myeloproliferative Neoplasms, Colorectal Cancer, Craniopharyngioma, Childhood (Brain Cancer), Cutaneous T-Cell Lymphoma, Ductal Carcinoma In Situ (DCIS), Childhood (Brain Cancer), Endometrial Cancer (Uterine Cancer), Ependymoma, Childhood (Brain Cancer), Esophageal Cancer, Esthesioneuroblastoma (Head and Neck Cancer), Ewing Sarcoma (Bone Cancer), Extracranial Germ Cell Tumor, Childhood, Extragonadal Germ Cell Tumor, Eye Cancer, Intraocular Melanoma, Retinoblastoma, Fallopian Tube Cancer, Fibrous Histiocytoma of Bone, Malignant, and Osteosarcoma, Gallbladder Cancer, Gastric (Stomach) Cancer, Gastrointestinal Carcinoid Tumor, Gastrointestinal Stromal Tumors (GIST) (Soft Tissue Sarcoma), Germ Cell Tumors, Childhood Central Nervous System Germ Cell Tumors (Brain Cancer), Childhood Extracranial Germ Cell Tumors, Extragonadal Germ Cell Tumors, Ovarian Germ Cell Tumors, Testicular Cancer, Gestational Trophoblastic Disease, Hairy Cell Leukemia, Head and Neck Cancer, Heart Tumors, Childhood, Hepatocellular (Liver) Cancer, Histiocytosis, Langerhans Cell, Hodgkin Lymphoma, Hypopharyngeal Cancer (Head and Neck Cancer), Intraocular Melanoma, Islet Cell Tumors, Pancreatic Neuroendocrine Tumors, Kaposi Sarcoma (Soft Tissue Sarcoma), Kidney (Renal Cell) Cancer, Langerhans Cell Histiocytosis, Laryngeal Cancer (Head and Neck Cancer), Leukemia, Lip and Oral Cavity Cancer (Head and Neck Cancer), Liver Cancer, Lung Cancer (Non-Small Cell, Small Cell, Pleuropulmonary Blastoma, and Tracheobronchial Tumor), Lymphoma, Male Breast Cancer, Malignant Fibrous Histiocytoma of Bone and Osteosarcoma, Melanoma, Melanoma, Intraocular (Eye), Merkel Cell Carcinoma (Skin Cancer), Mesothelioma, Malignant, Metastatic Cancer, Metastatic Squamous Neck Cancer with Occult Primary (Head and Neck Cancer), Midline Tract Carcinoma With NUT Gene Changes, Mouth Cancer (Head and Neck Cancer), Multiple Endocrine Neoplasia Syndromes, Multiple Myeloma/Plasma Cell Neoplasms, Mycosis Fungoides (Lymphoma), Myelodysplastic Syndromes, Myelodysplastic/Myeloproliferative Neoplasms, Myelogenous Leukemia, Chronic (CML), Myeloid Leukemia, Acute (AML), Myeloproliferative Neoplasms, Chronic, Nasal Cavity and Paranasal Sinus Cancer (Head and Neck Cancer), Nasopharyngeal Cancer (Head and Neck Cancer), Neuroblastoma, Non-Hodgkin Lymphoma, Non-Small Cell Lung Cancer, Oral Cancer, Lip and Oral Cavity Cancer and Oropharyngeal Cancer (Head and Neck Cancer), Osteosarcoma and Malignant Fibrous Histiocytoma of Bone, Ovarian Cancer, Pancreatic Cancer, Pancreatic Neuroendocrine Tumors (Islet Cell Tumors), Papillomatosis (Childhood Laryngeal), Paraganglioma, Paranasal Sinus and Nasal Cavity Cancer (Head and Neck Cancer), Parathyroid Cancer, Penile Cancer, Pharyngeal Cancer (Head and Neck Cancer), Pheochromocytoma, Pituitary Tumor, Plasma Cell Neoplasm/Multiple Myeloma, Pleuropulmonary Blastoma (Lung Cancer), Pregnancy and Breast Cancer, Primary Central Nervous System (CNS) Lymphoma, Primary Peritoneal Cancer, Prostate Cancer, Rectal Cancer, Recurrent Cancer, Renal Cell (Kidney) Cancer, Retinoblastoma, Rhabdomyosarcoma, Childhood (Soft Tissue Sarcoma), Salivary Gland Cancer (Head and Neck Cancer), Childhood Rhabdomyosarcoma (Soft Tissue Sarcoma), Childhood Vascular Tumors (Soft Tissue Sarcoma), Ewing Sarcoma (Bone Cancer), Kaposi Sarcoma (Soft Tissue Sarcoma), Osteosarcoma (Bone Cancer), Soft Tissue Sarcoma, Uterine Sarcoma, Sézary Syndrome (Lymphoma), Skin Cancer, Small Cell Lung Cancer, Small Intestine Cancer, Soft Tissue Sarcoma, Squamous Cell Carcinoma of the Skin, Squamous Neck Cancer with Occult Primary, Metastatic (Head and Neck Cancer), Stomach (Gastric) Cancer, T-Cell Lymphoma, Lymphoma (Mycosis Fungoides and Sezary Syndrome), Testicular Cancer, Throat Cancer (Head and Neck Cancer), Nasopharyngeal Cancer, Oropharyngeal Cancer, Hypopharyngeal Cancer, Thymoma and Thymic Carcinoma, Thyroid Cancer, Tracheobronchial Tumors (Lung Cancer), Transitional Cell Cancer of the Renal Pelvis and Ureter (Kidney (Renal Cell) Cancer), Ureter and Renal Pelvis, Transitional Cell Cancer (Kidney (Renal Cell) Cancer), Urethral Cancer, Uterine Cancer, Endometrial, Uterine Sarcoma, Vaginal Cancer, Vascular Tumors (Soft Tissue Sarcoma), or Vulvar Cancer.

In some embodiments, diagnosis may include brain non-glioma (ependymoma, hemangioblastoma, medulloblastoma, meningioma), breast (breast ductal, breast lobular), colon, endometrial (endometrial, endometrial serous, endometrial stromal sarcoma), gastroesophageal (esophageal adenocarcinoma, gastric), gastrointestinal stromal tumor, glioma (Glioma, oligodendroglioma), head and neck adenocarcinoma, hematological (acute lymphoblastic leukemia, acute myeloid leukemia, b cell lymphoma, chronic lymphocytic leukemia, chronic myeloid leukemia, rosai dorfman, t cell lymphoma), hepatobiliary (cholangiocarcinoma, gallbladder, liver), lung adenocarcinoma, melanoma, mesothelioma, neuroendocrine (gastrointestinal neuroendocrine, high grade neuroendocrine lung, low grade neuroendocrine lung, pancreatic neuroendocrine, skin neuroendocrine), ovarian (ovarian clear cell, ovarian granulosa, ovarian serous), pancreas, prostate, renal (renal chromophobe, renal clear cell, renal papillary), sarcoma (chondrosarcoma, chordoma, ewing sarcoma, fibrous sarcoma, leiomyosarcoma, liposarcoma, osteosarcoma, rhabdomyosarcoma, synovial sarcoma, vascular sarcoma), squamous (cervical, esophageal squamous, head and neck squamous, lung squamous, skin squamous/basal), thymic, thyroid, or urothelial.

In some embodiments, diagnosis may include one or more entries of the ICD-10-CM, or the International Classification of Disease. The ICD provides a method of classifying diseases, injuries, and causes of death. The World Health Organization (WHO) publishes the ICDs to standardize the methods of recording and tracking instances of diagnosed disease, including cancer. For example, classifications from any chapter of the ICD or cancers from Chapter 2, C and D codes. C codes may include Neoplasm of Lip, Oral Cavity and Pharynx (C00-C14), Neoplasm of Digestive Organs (C15-C26), Neoplasm of Respiratory System and Intrathoracic Organs (C30-C39), Neoplasm of Mesothelial and Soft Tissue (C45), Neoplasm of Bones, Joints and Articular Cartilage (C40-C41), Neoplasm of Skin (Melanoma, Merkel Cell, and Other Skin Histologies) (C43, C44, C4a), Kaposi Sarcoma (46), Neoplasm of Peripheral Nerves and Autonomic nervous system, Retroperitoneum, Peritoneum, and Soft Tissues (C47, C48, C49), Neoplasm of Breast and Female Genital Organs (C50-C58), Neoplasm of Male Genital Organs (C60-C63), Neoplasm of Urinary Tract (C64-C68), Neoplasms of Eye, Brain and Other Parts of the Central Nervous System (C69-C72), Neoplasm of Thyroid, Other Endocrine Glands, and Ill-defined Sites (C73-C76), Malignant Neuroendocrine Tumors (C7a._), Secondary Neuroendocrine Tumors (C7B), Neoplasm of other and ill-defined sites (C76-80), Secondary and unspecified malignant neoplasm of lymph nodes (C77), Secondary Cancers of respiratory and digestive organs, other and unspecified sites (C78-80), Malignant Neoplasm without specification of site (C80), Malignant neoplasms of lymphoid, or hematopoietic and related tissue (C81-C96).

In some embodiments, cancer conditions may include broadly construed categorization to a cohort class. Exemplary cohort classes may include Blood Cancer, Bone Cancer, Brain Cancer, Bladder Cancer, Breast Cancer, Colon and Rectal Cancer, Endometrial Cancer, Kidney Cancer, Leukemia, Liver Cancer, Lung Cancer, Melanoma, Non-Hodgkin Lymphoma, Pancreatic Cancer, Prostate Cancer, Thyroid Cancer, or other tissue/organ-based classifications.

In some embodiments, cancer conditions may include a site of biopsy for the biopsied specimen such as one or more ICD-03 codes, including: lip, base of tongue, tongue (excluding base of tongue), gum, floor of mouth, & other mouth, salivary gland, oropharynx, nasopharynx (excluding posterior wall), posterior wall of nasopharynx, hypopharynx, pharynx, esophagus, stomach, small intestine, large intestine, (excluding appendix), appendix, rectum, anal canal & anus, liver, intrahepatic bile ducts, gallbladder & extrahepatic bile ducts, pancreas, unspecified digestive organs, nasal cavity (including nasal cartilage), middle ear, sinuses, accessory sinus, nose, larynx, trachea, lung & bronchus, thymus, heart, mediastinum, pleura, respiratory, bones & joints (excluding skull and face, mandible), bones of skull and face, mandible, blood, bone marrow, & hematopoietic sys, spleen, reticulo-endothelial, skin, peripheral nerves, retroperitoneum & peritoneum, connective & soft tissue, breast, vagina & labia, vulva, cervix uteri, corpus uteri, uterus, ovary, fallopian tube, other female genital (excluding fallopian tube), placenta, penis, prostate gland, testis, epididymis, spermatic cord, male genital, scrotum, kidney, renal pelvis, ureter, urinary bladder, other urinary organs, orbit & lacrimal gland, (excluding retina, eye, nose), retina, eyeball, eye, nose, meninges (e.g., cerebral and spinal), brain, & cranial nerves, & spinal cord, (excluding ventricle, cerebellum), ventricle, cerebellum, other nervous system, thyroid gland, adrenal glands, parathyroid gland, pituitary gland, craniopharyngeal duct, pineal gland, other endocrine glands, ill-defined, lymph nodes, and unknown.

In some embodiments, a diagnosis classifier 2382a may be trained with labels corresponding to one or more of the diagnosis cancer classifications above. Inputs to the model are a feature matrix having a plurality of patient feature vectors. For each model, a patient feature vector may include more or more of the features from the feature modules 2340, stored features of feature collection 2305, alteration module 2350, or classifications 2380. For each patient, a supervisory signal may identify which classification of the diagnosis cancer classifications the patient feature vector is labeled.

In some embodiments, a cohort classifier 2383b may be trained with labels corresponding to one or more of the cohort class cancer classifications above. In some embodiments, inputs to the model are a feature matrix having a plurality of patient feature vectors. For each model, a patient feature vector may include more or more of the features from the feature modules 2340, stored features of feature collection 2305, alteration module 2350, or classifications 2380. For each patient, a supervisory signal may identify which classification of the cohort cancer classifications the patient feature vector is labeled.

In some embodiments, a tissue classifier 2382c may be trained with labels corresponding to one or more of the site of biopsy class cancer classifications above. In some embodiments, inputs to the model are a feature matrix having a plurality of patient feature vectors. For each model, a patient feature vector may include one or more of the features from the feature modules 2340, stored features of feature collection 2305, alteration module 2350, or classifications 2380. For each patient, a supervisory signal may identify which classification of the site of biopsy cancer classifications the patient feature vector is labeled.

In some embodiments, the stacked TUO Classifier 2382d, also referred to as the final classifier, may include one or more classifiers 2382a-n.

In some embodiments, a set number of classifications may be trained and provided at the classifier. In other embodiments, a plurality of distinctive classification may be available for classification at the classifier. In one example, distinctive classifications may be made between separate tumor/tissue types having common cell lineages, one or more sarcomas and one or more carcinomas, one or more squamous and one or more carcinomas, one or more neuroendocrines and one or more carcinomas. In one example, differentiation may occur between lung adenocarcinoma, lung squamous, oral adenocarcinoma, and oral adenocarcinoma. In one example, differentiation may occur between general sarcomas, ependymoma, ewing sarcoma, gliosarcoma, leiomyosarcoma, meningioma, mesothelioma, and Rosai-Dorfman. In addition to distinguishing based on cell lineage, differentiations may be made between metastasis site of origin when tumor tissue is widely metastatic, but poorly differentiated. Examples may include distinguishing between a liver metastasis of pancreatic origin, upper gastrointestinal origin, or cholangio origin; a breast metastasis of salivary gland origin, squamous origin, or ductile origin; a brain metastasis of glioblastoma, oligodendroglioma, astrocytoma, or medulloblastoma (including Wnt, Whh, Group 3, Group 4); a lung metastasis of NSCLC adenocarcinoma or squamous; and between gynecological organs of endometrium, ovary, or fallopian tubes and between endometrioid, serous, and clear cell carcinoma. In one example, differentiation may be made between one or more sarcomas with carcinoma morphological features or protein expressions, and one or more carcinomas with sarcoma morphologic features or protein expressions In some embodiments, only a single RNA classifier may be implemented to generate a diagnosis classification 2382a, cohort classification 2382b, or tissue classification for the TUO classification 2382d. In some embodiments, inputs to the RNA classifier may include 20,000+ transcripts from a whole exome RNA sequencing or a subset of the transcripts (100, 500, 1 k, 2 k, 5 k, etc.) may be selecting on the basis of their correlation with the outcome variable or supervisory signal. In some embodiments, RNA transcripts may be deconvoluted or normalized. In some embodiments, two or more RNA classifiers, such as a combination of a diagnosis classification 2382a, cohort classification 2382b, or tissue classification may be combined to generate a diagnosis, cohort, and tissue classification 2382a-c based upon the RNA features 2341. In some embodiments, two or more classifiers based upon one or more feature modules 2340 may be combined for the TUO classification 2382d. For example, RNA features 2341 and DNA features 2342 may be received and combined to generate a diagnosis classification 2382a, cohort classification 2382b, or tissue classification for the TUO classification 2382d. Inputs to the DNA classifier may include genes, genes and their variants as represented by a protein (P dot) notation. In some embodiments, classifiers may begin operation when input features are available to the system and a refined TUO classification may be generated as each additional classification becomes available.

In some embodiments, RNA features 2341 may be normalized, such as by any of the methods disclosed in U.S. patent application Ser. No. 16/581,706, titled "Methods of Normalizing and Correcting RNA Expression Data", filed Sep. 24, 2019; and deconvoluted, such as by any of the methods disclosed in U.S. patent application Ser. No. 16/732,229, titled "Transcriptome Deconvolution of Metastatic Tissue Samples", filed Dec. 31, 2019; both of which are incorporated by reference in their entirety. RNA features which have been normalized and/or deconvoluted, may be presented as transcripts per million. In some embodiments, RNA features 2341 may be represented as an expression, such as gene expression data quantified by Kallisto, quantile normalized for GC content and length on the transcript level, followed by a library depth normalization step where a scaling factor is calculated as the median ratio of a sample's expression over its geometric mean across all references samples. Following normalization, quality control using principal component analysis may be used to filter samples with abnormal expression. RNA features may be represented as a matrix of n patients by 19147 genes, or a feature selection may be performed, such as by applying variance thresholds where a hyperparameter search may identify the optimal threshold of variance to optimize the performance on test data. In some embodiments, feature selection may reduce the number of transcripts needed to train and apply a classification model 2382a-n from 19147 transcripts to approximately 7,000 transcripts. In some embodiments, feature selection methods may select the best 250 transcripts, 1000 transcripts, or 10000 transcripts given different selection criteria or hyperparameters. In some embodiments, the methods for generating RNA features may include one or more of the methods of the '804 patent.

In some embodiments, features from genes such as GPM6A, CDX1, SOX2, NAPSA, CDX2, MUC12, SLAMF7, HNF4A, ANXA10, TRPS1, GATA3, SLC34A2, NKX2-1, SLC22A31, ATP10B, STEAP2, CLDN3, SPATA6, NRCAM, USH1C, SOX17, TMPRSS2, MECOM, WT1, CDHR1, HOXA13, SOX10, SALL1, CPE, NPR1, CLRN3, THSD4, ARL14, SFTPB, COL17A1, KLHL14, EPS8L3, NXPE4, FOXA2, SYT11, SPDEF, GRHL2, GBP6, PAX8, ANO1, KRT7, HOXA9, TYR, DCT, LYPD1, MSLN, TP63, CDH1, ESR1, HNF1B, HOXA10, TJP3, NRG3, TMC5, PRLR, GATA2, DCDC2, INS, NDUFA4L2, TBX5, ABCC3, FOLH1, HIST1H3G, S100A1, PTHLH, ACER2, RBBP8NL, TACSTD2, C19orf77, PTPRZ1, BHLHE41, FAM155A, MYCN, DDX3Y, FMN1, HIST1H3F, UPK3B, TRIM29, TXNDC5, BCAM, FAM83A, TCF21, MIA, RNF220, AFAP1, KRT5, SOX21, KANK2, GPM6B, C1orf116, FOXF1, MEIS1, EFHD1, or XKRX may be used. In some embodiments, features from genes identified by the following Ensembl gene IDs may be used: ENSG00000150625 (GPM6A), ENSG00000113722 (CDX1), ENSG00000181449 (SOX2), ENSG00000131400 (NAPSA), ENSG00000165556 (CDX2), ENSG00000205277 (MUC12), ENSG00000026751 (SLAMF7), ENSG00000101076 (HNF4A), ENSG00000109511 (ANXA10), ENSG00000104447 (TRPS1), ENSG00000107485 (GATA3), ENSG00000157765 (SLC34A2), ENSG00000136352 (NKX2-1), ENSG00000259803 (SLC22A31), ENSG00000118322 (ATP10B), ENSG00000157214 (STEAP2), ENSG00000165215 (CLDN3), ENSG00000132122 (SPATA6), ENSG00000091129 (NRCAM), ENSG00000006611 (USH1C), ENSG00000164736 (SOX17), ENSG00000184012 (TMPRSS2), ENSG00000085276 (MECOM), ENSG00000184937 (WT1), ENSG00000148600 (CDHR1), ENSG00000106031 (HOXA13), ENSG00000100146 (SOX10), ENSG00000103449 (SALL1), ENSG00000109472 (CPE), ENSG00000169418 (NPR1), ENSG00000180745 (CLRN3), ENSG00000187720 (THSD4), ENSG00000179674 (ARL14), ENSG00000168878 (SFTPB), ENSG00000065618 (COL17A1), ENSG00000197705 (KLHL14), ENSG00000198758 (EPS8L3), ENSG00000137634 (NXPE4), ENSG00000125798 (FOXA2), ENSG00000132718 (SYT11), ENSG00000124664 (SPDEF), ENSG00000083307 (GRHL2), ENSG00000183347 (GBP6), ENSG00000125618 (PAX8), ENSG00000131620 (ANO1), ENSG00000135480 (KRT7), ENSG00000078399 (HOXA9), ENSG00000077498 (TYR), ENSG00000080166 (DCT), ENSG00000150551 (LYPD1), ENSG00000102854 (MSLN), ENSG00000073282 (TP63), ENSG00000039068 (CDH1), ENSG00000091831 (ESR1), ENSG00000108753 (HNF1B), ENSG00000253293 (HOXA10), ENSG00000105289 (TJP3), ENSG00000185737 (NRG3), ENSG00000103534 (TMC5), ENSG00000113494 (PRLR), ENSG00000179348 (GATA2), ENSG00000146038 (DCDC2), ENSG00000254647 (INS), ENSG00000185633 (NDUFA4L2), ENSG00000089225 (TBX5), ENSG00000108846 (ABCC3), ENSG00000086205 (FOLH1), ENSG00000256018 (HIST1H3G), ENSG00000160678 (S100A1), ENSG00000087494 (PTHLH), ENSG00000177076 (ACER2), ENSG00000130701 (RBBP8NL), ENSG00000184292 (TACSTD2), ENSG00000095932 (C19orf77), ENSG00000106278 (PTPRZ1), ENSG00000123095 (BHLHE41), ENSG00000204442 (FAM155A), ENSG00000134323 (MYCN), ENSG00000067048 (DDX3Y), ENSG00000248905 (FMN1), ENSG00000256316 (HIST1H3F), ENSG00000243566 (UPK3B), ENSG00000137699 (TRIM29), ENSG00000239264 (TXNDC5), ENSG00000187244 (BCAM), ENSG00000147689 (FAM83A), ENSG00000118526 (TCF21), ENSG00000261857 (MIA), ENSG00000187147 (RNF220), ENSG00000196526 (AFAP1), ENSG00000186081 (KRT5), ENSG00000125285 (SOX21), ENSG00000197256 (KANK2), ENSG00000046653 (GPM6B), ENSG00000182795 (C1orf116), ENSG00000103241 (FOXF1), ENSG00000143995 (MEIS1), ENSG00000115468 (EFHD1), and ENSG00000182489 (XKRX).

Transcript isoform information associated with these genes may be selected as input features for sequencing results. For example, GPM6A may be associated with transcript isoforms GPM6A-201, GPM6A-202, GPM6A-203, GPM6A-204, GPM6A-205, GPM6A-206, GPM6A-207, GPM6A-208, GPM6A-209, GPM6A-210, GPM6A-211, GPM6A-212, GPM6A-213, GPM6A-214, GPM6A-215, GPM6A-216, GPM6A-217, GPM6A-218, GPM6A-219, GPM6A-220, GPM6A-221; CDX1 may be associated with transcript isoforms CDX1-201 and CDX1-202; SOX2 may be associated with transcript isoform SOX2-201; NAPSA may be associated with transcript isoforms NAPSA-201, NAPSA-202, NAPSA-203, NAPSA-204, NAPSA-205, NAPSA-206, and NAPSA-207; and so on for each gene. In some embodiments, the transcripts may be selected at a transcript level, so instead of each gene having all of its transcripts, only the feature selection transcripts are included for each gene. A "transcript" of a gene is the mRNA molecule associated with the gene.

In some embodiments, RNA splicing features 2349a may be generated from RNA alternative splicing such as an alternative splicing score. Alternative splicing scores may be calculated for 1500 common exon skipping events in the human genome. In some embodiments, Spliced Transcripts Alignment to a Reference (STAR), a fast RNA-Seq read mapper with support for splice-junction and fusion read detection may be applied. STAR aligns reads by finding the Maximal Mappable Prefix (MMP) hits between reads (or read pairs) and the genome, using a Suffix Array index. Different parts of a read may be mapped to different genomic positions, corresponding to splicing or RNA-fusions. The genome index includes known splice-junctions from annotated gene models, allowing for sensitive detection of spliced reads. STAR performs local alignment, automatically soft clipping ends of reads with high mismatches. STAR, or similar splicing identifier, may be used to generate a splice junction index for each RNA sample. A splice junction index may then be normalized to calculate percent spliced in (PSI) scores for common alternative splicing events and represented as a matrix of n patients by 5000 alternatively spliced transcripts. Transcript splicing may be detected at any of the RNA transcripts associated with each gene. In some embodiments, the methods for generating RNA splicing features may include one or more of the methods of the '804 patent.

In some embodiments, copy number variations (CNVs) 2349b (e.g., copy number features) may be generated from raw sequencing read data corresponding to each probe of a sequencing assay. DNA CNVs, or copy number data, may be generated using a bioinformatics pipeline that identifies structural variants from DNA sequencing by comparing a sample's read depth to a pool of normal samples. Due to variances introduced through different sequencing methods, bioinformatics procedures, or other bias introducing factors, raw sequencing may first be normalized. Normalization may include depth normalization against normal pool, GC-correction across GC percentiles for all target regions, principal components noise correction against the normal pool, log ratio computation against both the normal pool and a matched normal sample, and/or cytoband level imputation to account for discrepancies in probe targets. Following normalization, the sequencing data may be used to identify copy number data represented as the average log odds ratio for each probe within a cytoband. A log odds ratio is log ((observed number of reads)/(expected number of reads)). In some embodiments, the methods for generating CNV features may include one or more of the methods of the '804 patent. CNVs may be generated using a sliding window of a fixed width and mapped to chromosomes, genes, variants, or cytobands for each sequenced sample and represented as a matrix of n patients by 550 cytobands, alternatively n patients by approximately 600 genes. In some embodiments, other sequencing panels comprise differing numbers of genes, such as 100 genes, 300 genes, 1000 genes, or 20000 genes.

In some embodiments, cytobands for each gene include 10p11.1, 10p11.21, 10p13, 10p14, 10p15.1, 10p15.3, 10q11.21, 10q11.23, 10q21.2, 10q22.1, 10q22.3, 10q23.2, 10q23.31, 10q23.33, 10q24.2, 10q24.31, 10q24.32, 10q24.33, 10q25.2, 10q25.3, 10q26.11, 10q26.13, 10q26.2, 10q26.3, 11p11.2, 11p13, 11p14.1, 11p14.3, 11p15.1, 11p15.2, 11p15.4, 11p15.5, 11q12.1, 11q12.2, 11q12.3, 11q13.1, 11q13.2, 11q13.3, 11q13.4, 11q13.5, 11q14.1, 11q21, 11q22.2, 11q22.3, 11q23.1, 11q23.2, 11q23.3, 11q24.1, 11q24.2, 11q24.3, 11q25, 12p11.21, 12p12.1, 12p13.1, 12p13.2, 12p13.31, 12p13.32, 12p13.33, 12q12, 12q13.12, 12q13.13, 12q13.2, 12q13.3, 12q14.1, 12q14.3, 12q15, 12q21.31, 12q21.33, 12q23.1, 12q23.2, 12q23.3, 12q24.12, 12q24.13, 12q24.21, 12q24.31, 12q24.33, 13q12.11, 13q12.13, 13q12.2, 13q12.3, 13q13.1, 13q13.3, 13q14.11, 13q14.2, 13q14.3, 13q21.1, 13q22.1, 13q31.1, 13q32.1, 13q33.1, 13q34, 14q11.2, 14q12, 14q13.2, 14q13.3, 14q21.1, 14q21.2, 14q22.1, 14q23.2, 14q23.3, 14q24.1, 14q24.3, 14q31.1, 14q32.12, 14q32.13, 14q32.2, 14q32.31, 14q32.32, 14q32.33, 15q11.2, 15q13.3, 15q14, 15q15.1, 15q21.1, 15q21.2, 15q22.2, 15q22.31, 15q22.33, 15q24.1, 15q24.3, 15q25.1, 15q25.3, 15q26.1, 15q26.3, 16p11.2, 16p12.1, 16p12.2, 16p13.11, 16p13.12, 16p13.13, 16p13.2, 16p13.3, 16q12.1, 16q21, 16q22.1, 16q22.2, 16q22.3, 16q23.1, 16q23.2, 16q23.3, 16q24.1, 16q24.3, 17p11.2, 17p12, 17p13.1, 17p13.2, 17p13.3, 17q11.2, 17q12, 17q21.1, 17q21.2, 17q21.31, 17q21.32, 17q21.33, 17q22, 17q23.1, 17q23.2, 17q23.3, 17q24.1, 17q24.2, 17q24.3, 17q25.1, 17q25.3, 18p11.21, 18p11.32, 18q11.2, 18q12.3, 18q21.1, 18q21.2, 18q21.32, 18q21.33, 18q22.3, 18q23, 19p13.11, 19p13.12, 19p13.2, 19p13.3, 19q12, 19q13.11, 19q13.12, 19q13.2, 19q13.31, 19q13.32, 19q13.33, 19q13.41, 19q13.42, 19q13.43, 1p11.2, 1p12, 1p13.1, 1p13.2, 1p13.3, 1p21.3, 1p22.1, 1p22.2, 1p22.3, 1p31.1, 1p31.3, 1p32.1, 1p32.3, 1p33, 1p34.1, 1p34.2, 1p34.3, 1p35.1, 1p36.11, 1p36.12, 1p36.13, 1p36.21, 1p36.22, 1p36.23, 1p36.31, 1p36.32, 1p36.33, 1q21.1, 1q21.2, 1q21.3, 1q22, 1q23.1, 1q23.3, 1q24.2, 1q24.3, 1q25.2, 1q31.2, 1q32.1, 1q32.3, 1q41, 1q42.12, 1q42.13, 1q42.2, 1q43, 1q44, 20p11.21, 20p11.22, 20p11.23, 20p12.1, 20p13, 20q11.21, 20q11.23, 20q12, 20q13.12, 20q13.13, 20q13.2, 20q13.32, 20q13.33, 21q11.2, 21q21.1, 21q21.3, 21q22.11, 21q22.12, 21q22.2, 21q22.3, 22q11.21, 22q11.22, 22q11.23, 22q12.1, 22q12.2, 22q12.3, 22q13.1, 22q13.2, 22q13.31, 22q13.33, 2p11.2, 2p13.1, 2p13.2, 2p13.3, 2p15, 2p16.1, 2p16.3, 2p21, 2p22.2, 2p23.1, 2p23.2, 2p23.3, 2p24.1, 2p24.2, 2p24.3, 2p25.1, 2p25.3, 2q11.1, 2q11.2, 2q12.2, 2q12.3, 2q13, 2q14.2, 2q14.3, 2q22.1, 2q22.2, 2q22.3, 2q23.3, 2q24.2, 2q31.1, 2q31.2, 2q31.3, 2q32.2, 2q32.3, 2q33.1, 2q33.2, 2q34, 2q35, 2q36.1, 2q36.3, 2q37.1, 2q37.3, 3p11.1, 3p12.1, 3p13, 3p14.1, 3p14.2, 3p14.3, 3p21.1, 3p21.2, 3p21.31, 3p22.1, 3p22.2, 3p24.1, 3p25.1, 3p25.2, 3p25.3, 3p26.1, 3p26.3, 3q11.1, 3q13.11, 3q13.2, 3q13.31, 3q21.1, 3q21.2, 3q21.3, 3q22.1, 3q22.2, 3q22.3, 3q23, 3q26.1, 3q26.2, 3q26.32, 3q26.33, 3q27.1, 3q27.2, 3q27.3, 3q28, 3q29, 4p11, 4p13, 4p14, 4p15.31, 4p15.33, 4p16.1, 4p16.3, 4q11, 4q12, 4q13.2, 4q13.3, 4q21.21, 4q21.22, 4q21.23, 4q21.3, 4q24, 4q25, 4q27, 4q28.1, 4q31.1, 4q31.21, 4q31.3, 4q32.1, 4q32.3, 4q34.3, 4q35.1, 4q35.2, 5p12, 5p13.1, 5p13.2, 5p13.3, 5p15.2, 5p15.31, 5p15.33, 5q11.1, 5q11.2, 5q12.3, 5q13.1, 5q13.2, 5q14.1, 5q14.2, 5q14.3, 5q15, 5q22.2, 5q23.2, 5q23.3, 5q31.1, 5q31.2, 5q31.3, 5q32, 5q33.1, 5q33.3, 5q34, 5q35.1, 5q35.2, 5q35.3, 6p11.2, 6p21.1, 6p21.2, 6p21.31, 6p21.32, 6p21.33, 6p22.2, 6p22.3, 6p24.1, 6p25.3, 6q11.1, 6q13, 6q15, 6q16.1, 6q16.2, 6q21, 6q22.1, 6q22.31, 6q22.33, 6q23.2, 6q23.3, 6q24.1, 6q24.2, 6q25.1, 6q25.3, 6q26, 6q27, 7p11.2, 7p12.2, 7p14.1, 7p14.3, 7p15.1, 7p15.2, 7p21.1, 7p21.2, 7p22.1, 7p22.2, 7p22.3, 7q11.21, 7q21.11, 7q21.12, 7q21.2, 7q21.3, 7q22.1, 7q22.3, 7q31.1, 7q31.2, 7q31.31, 7q31.33, 7q32.1, 7q34, 7q36.1, 7q36.3, 8p11.21, 8p11.22, 8p11.23, 8p12, 8p21.2, 8p21.3, 8p22, 8p23.1, 8p23.3, 8q11.21, 8q11.23, 8q12.1, 8q13.1, 8q13.2, 8q13.3, 8q21.11, 8q21.12, 8q21.3, 8q22.2, 8q22.3, 8q23.1, 8q24.11, 8q24.13, 8q24.21, 8q24.22, 8q24.3, 9p13.1, 9p13.2, 9p13.3, 9p21.1, 9p21.3, 9p24.1, 9p24.3, 9q21.11, 9q21.2, 9q21.32, 9q21.33, 9q22.1, 9q22.2, 9q22.32, 9q22.33, 9q31.2, 9q32, 9q33.1, 9q33.2, 9q33.3, 9q34.11, 9q34.12, 9q34.13, 9q34.2, 9q34.3, Xp11.21, Xp11.22, Xp11.23, Xp11.3, Xp11.4, Xp21.2, Xp21.3, Xp22.2, Xp22.33, Xq11.2, Xq12, Xq13.1, Xq13.2, Xq21.1, Xq22.1, Xq22.3, Xq24, Xq25, Xq26.1, Xq26.2, Xq26.3, Xq27.1, and Xq28.

In some embodiments, Germline/Somatic DNA features 2342 may be represented as a gene or variant which is detected or not detected in a sample. DNA features such as DNA variants may be detected using one or more variant callers, such as freebayes and pindel. An ensemble method may allow for an improved variant detection. In some embodiments, tumor specimen sequencing results may be evaluated for variants to identify variants present in the sample. In some embodiments, a tumor specimen may be sequenced alongside a normal specimen from the same patient and compared against the normal specimen in order to identify somatic and germline alterations. For example, if a patient has a variant in both their tumor and normal specimen, it is unlikely that the variant is driving the tumor's growth, so the variant may be removed from further evaluation. In some embodiments, a variant reference set or database of all variant classifications, may be used to annotate the pathogenicity of each alteration detected in the specimen's sequencing results. In some embodiments, alterations may be represented as either the gene plus amino acid alteration (i.e. KRAS G12V) or as the gene plus the functional effect (BRAF loss-of-function). In some embodiments, pathogenic alterations may be one-hot encoded for representation in modeling. Selecting a gene and amino acid alteration representation may improve performance by reducing the number of variants in place of a nucleotide change representation because some nucleotide representation are semantically identical alterations. In some embodiments, the methods for generating DNA features may include one or more of the methods of the '804 patent. DNA features may be represented as a matrix of n patients by 20,000 variants. In some embodiments, feature selection may reduce the number of variants needed to train and apply a classification model 2382*a-n* from 20000 variants to approximately 7,000 variants. In some embodiments, feature selection methods may select the best 250, 1000, or 10000 variants given different selection criteria or hyperparameters. An exemplary feature selected gene listing is provided above with respect to the RNA feature set.

In some embodiments, viral genomic features 2343*a* may be represented as the presence or absence of a virus in the specimen results. In some embodiments, viral genomic features are determined as described in U.S. Application No. 62/978,067, entitled "Systems and Methods for Detecting Viral DNA from Sequencing," filed Feb. 18, 2020, which is hereby incorporated by reference in its entirety. Sequencing results may be matched to a human reference genome, which leaves some portion of the sequencing results unmatched. In some examples, the unmatched portion may be compared to a bacterial reference genome or a viral reference genome. Matches identify the presence of a bacteria or virus in the specimen which may affect Identification of the cancer condition for each patient's specimen. In some embodiments, identification of bacteria may include detection of *Salmonella typhi, Streptococcus bovis, Chlamydia pneumoniae, Mycoplasma,* or *Helicobacter pylori* and identification of viral presence may include detection of Hepatitis B (HBV), Hepatitis C (HCV), Human T-lymphotropic virus (HTLV), Human papillomaviruses (HPV), Kaposi's sarcoma-associated herpesvirus (HHV-8), Merkel cell polyomavirus (MCV), or Epstein-Barr virus (EBV). Viral genomic features may be represented as a matrix of n patients by 13 bacteria and viruses, x bacteria, or y viruses, such as 3 viruses. In some embodiments, the methods for generating viral features may include one or more of the methods of the '804 patent.

In some embodiments, feature module 2340 may include other features such as clinical features. Clinical features may include patient information from the patient's electronic health records, testing results, diagnosis, and treatments. In one example, clinical information may include a patient's history of diagnosis of breast cancer and subsequent note of remission. A classifier trained to identify a cancer condition of diagnosis may first identify a diagnosis using one or more of the features introduced above as RNA features, DNA features, RNA fusions, viral features, or copy number features and as a secondary step, may further include referencing clinical features to further identify if the patient had a previous diagnosis. A patient having a previous diagnosis of breast cancer which is in remission and having a cancer condition classification related to breast cancer may be further identified to have a recurrence of breast cancer noted in the cancer condition.

In some embodiments, any features of feature module 2340 may be provided to one or more classifiers 2382*a-n* for generating a TUO Classification. Combinations of features may include DNA features only, RNA features only, a combination of DNA and RNA features, any combination of DNA features and other features, any combination of RNA features and other features, any combination of DNA and RNA features with other features, including a combination of each of RNA features, DNA features, splicing features, CNV features, and Viral/Bacterial genomic features. It should be understood that one or more combinations of models may be trained and selected for each new patient based upon the combinations of features available and associated with that patient. For example, a patient who was sequenced for DNA only may have DNA features, CNV features, and viral features, but not RNA features. One or more models may receive the DNA features, CNV features, and viral features. In some embodiments, the TUO classification may receive the predicted outputs from one or more classifiers 2382a-n and combine them to generate a TUO classification to identify a diagnosis of a cancer condition for a patient. In some embodiments, each of the classifiers may be a diagnosis classifier 2382a, using a linear regression on the RNA feature set, DNA feature set, Splicing feature set, CNV feature set and viral feature set. In some embodiments, each of the classifiers may be a cohort/sub-type classifier 2382b, using a linear regression on the RNA feature set, DNA feature set, Splicing feature set, CNV feature set and viral feature set. In some embodiments, each of the classifiers may be a tissue classifier 2382c, using a linear regression on the RNA feature set, DNA feature set, Splicing feature set, CNV feature set and viral feature set. In some embodiments, each of the classifiers may be one or more, two or more, or three or more of a diagnosis classifier 2382a, a cohort classifier 2382b, and tissue classifier 2382c, using a linear regression on the RNA feature set, DNA feature set, Splicing feature set, CNV feature set and viral feature set. In some embodiments, a boosting algorithm may be used to improve the classifier for the RNA feature set, DNA feature set, Splicing feature set, CNV feature set, and viral feature sets. A boosting algorithm may identify a subset of genes that produce better similarity between subjects, given a selected label to boost. Classifiers may be boosted on RNA labels, imaging labels, DNA labels, clinical information labels, tumor grade labels, tumor staging labels, or other labels of the data sets provided for classification. In one embodiment, boosting may be implemented as described in Skurichina, M., Duin, R. Bagging, Boosting and the Random Subspace Method for Linear Classifiers. Pattern Anal Appl 5, 121-135 (2002), which is incorporated by reference herein in its entirety.

Figure 25:
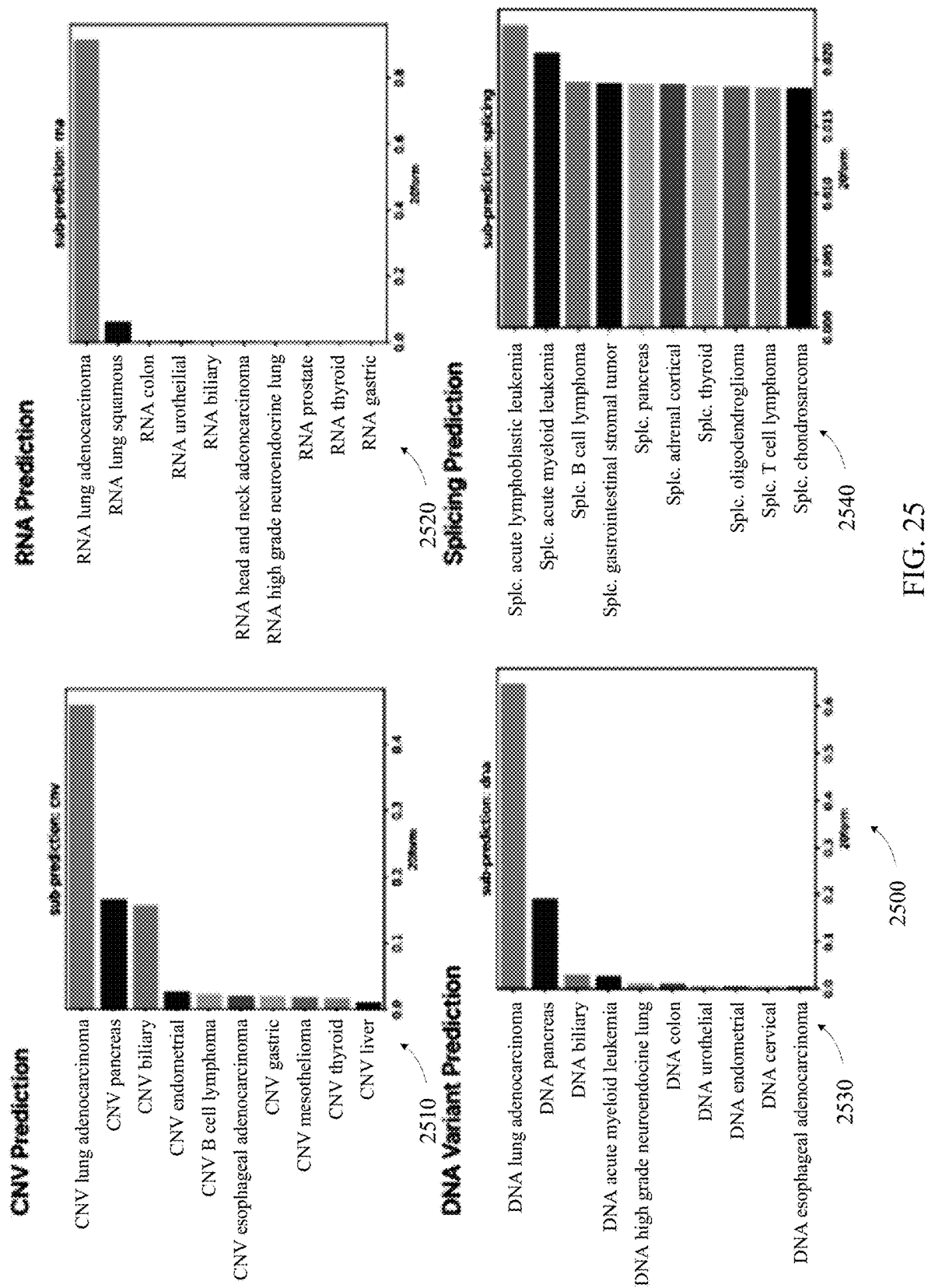
FIG. 25 illustrates classification results from four of the sub-model classifiers of FIG. 24, in accordance with some embodiments of the present disclosure.
Figure 26:
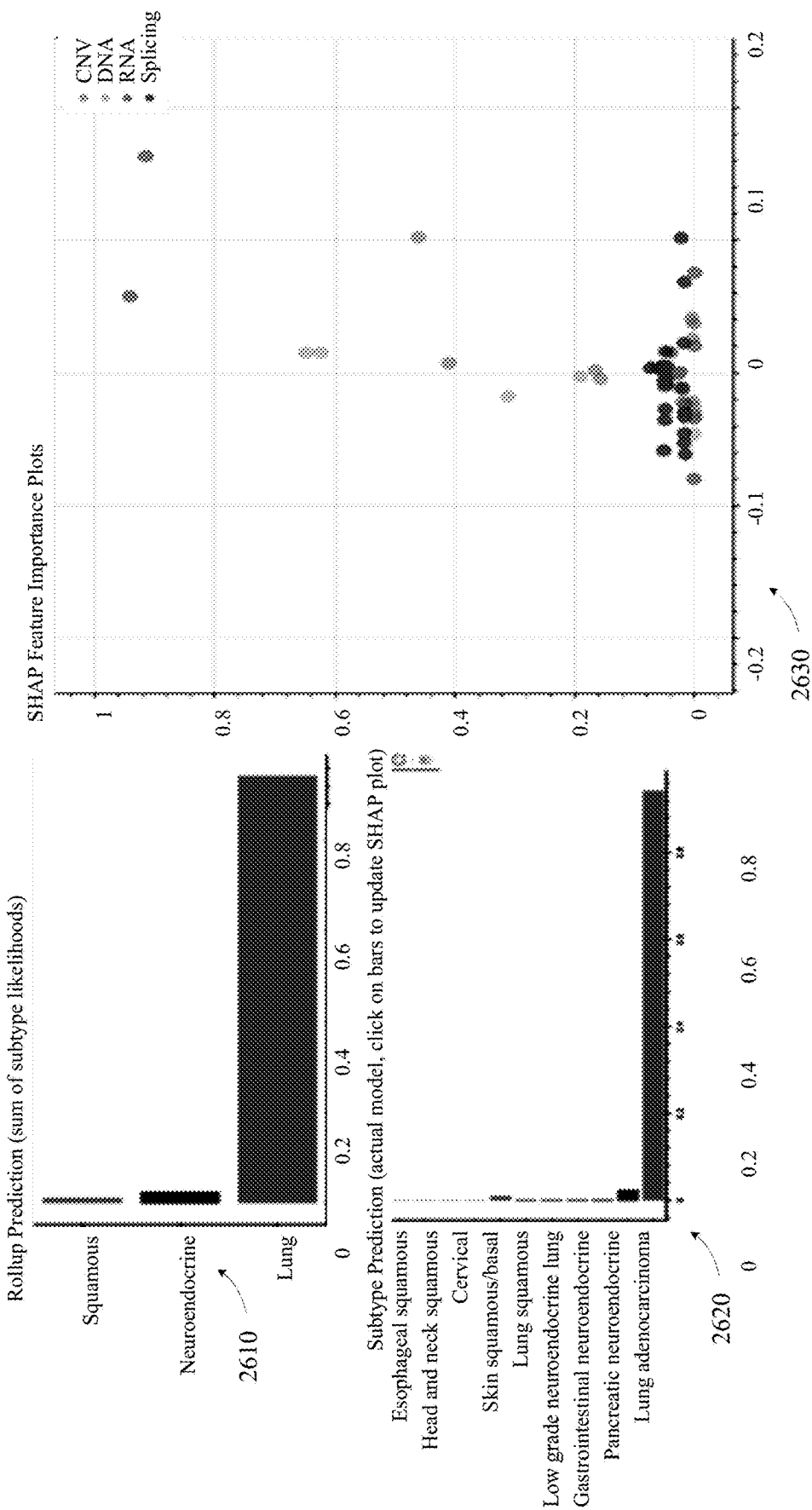
FIG. 26 illustrates meta-classification results combining the sum-model classifiers of FIG. 25, in accordance with some embodiments of the present disclosure.
Figure 27:
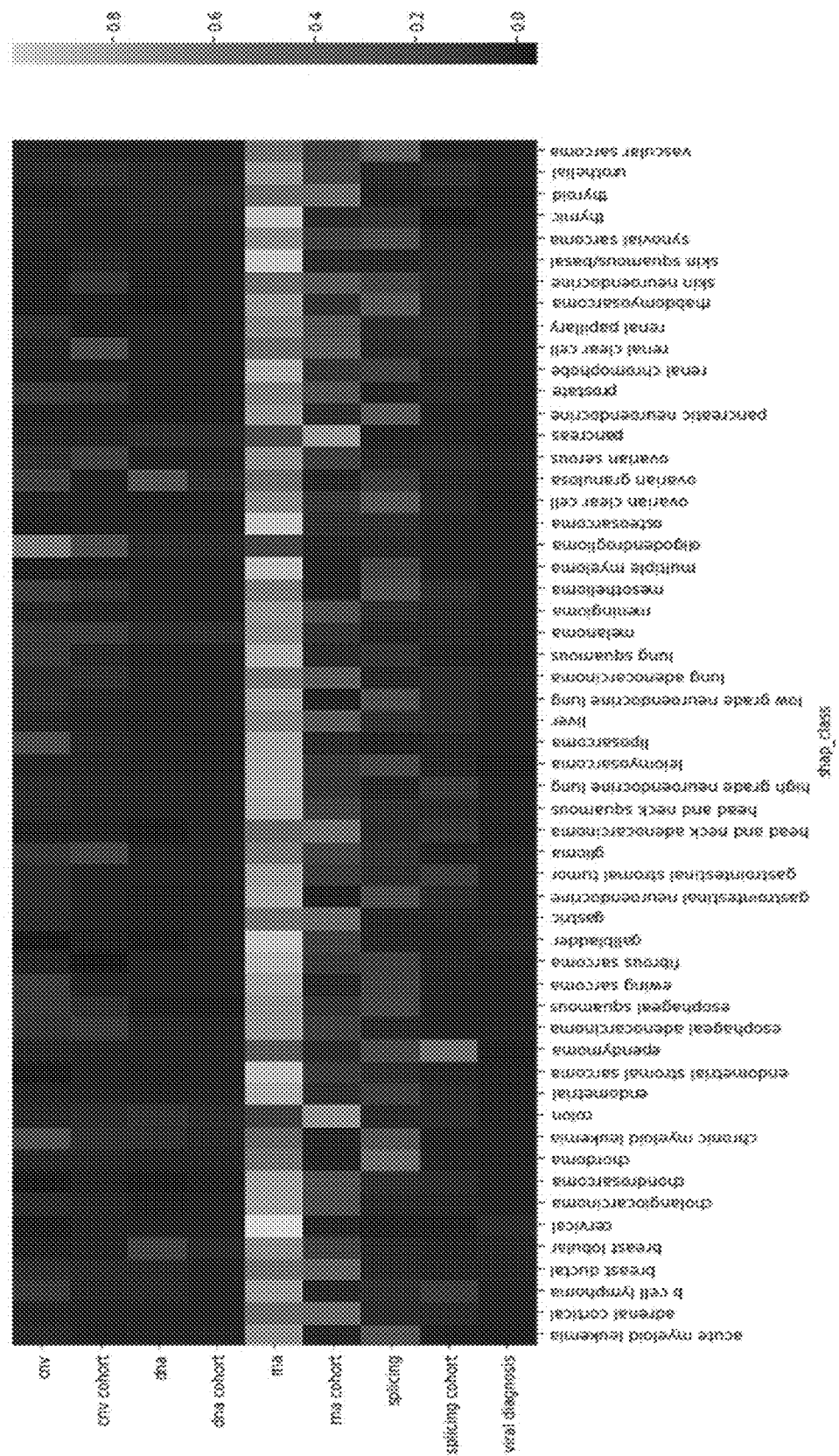
FIG. 27 illustrates an example feature importance heat map across each of the sub-model classifiers, in accordance with some embodiments of the present disclosure.

In some embodiments, classifiers 2382a-n generate classifications for a diagnosis, cohort, or tissue from the feature set(s) received as an input at each classifier. In some embodiments, a classification may also be referenced as a prediction, based upon the received features. Sub-models, models which provide predictions to the meta-classifier 2382d, may be viewed through a viewer 2500 such as a web page, application, or other display device capable of displaying graphs. In some embodiments, a web page may be accessed from a web address. A user, such as a physician, may access a patient's TUO classification results by the patient's unique, deidentified ID, or by identifying information such as patient name or medical record number. In some embodiments, a unique ID may include a combination of letters and numbers, such as "20form" as depicted in FIGS. 25 and 26. In some embodiments, the viewer 2500 may include one or more graphs 2510, 2520, 2530, and 2540 corresponding to a classifier and feature set.

In some embodiments, sub-prediction CNV illustrated in graph 2510 visually depicts the prediction/classification results for a specimen's sequencing results using copy number analysis. The top 10 classification results are arranged in ranked order. The Y-axis identifies the cancer condition and the X-axis identifies the generated likelihood of the cancer condition's presence in the sequencing results. For specimen associated with ID "20form", the classification of lung adenocarcinoma is predicted with approximately 48% likelihood, the classification of pancreas is predicted with approximately 18% likelihood, and the classification of biliary is predicted with approximately 17% likelihood.

In some embodiments, sub-prediction RNA illustrated in graph 2520 visually depicts the prediction/classification results for a specimen's sequencing results using RNA transcripts. The top 10 classification results are arranged in ranked order; however, only two results are associated with a generated likelihood of the cancer condition's presence in the sequencing results. For a specimen associated with ID "20form," the classification of lung adenocarcinoma is predicted with approximately 88% likelihood and the classification of lung squamous is predicted with approximately 6% likelihood.

In some embodiments, sub-prediction DNA illustrated in graph 2530 visually depicts the prediction/classification results for a specimen's sequencing results using DNA variants. The top 10 classification results are arranged in ranked order. For a specimen associated with ID "20form", the classification of lung adenocarcinoma is predicted with approximately 65% likelihood, the classification of pancreas is predicted with approximately 20% likelihood, and the classification of biliary is predicted with approximately 3% likelihood.

In some embodiments, sub-prediction RNA Splicing illustrated in graph 2540 visually depicts the prediction/classification results for a specimen's sequencing results using RNA splicing analysis. The top 10 classification results are arranged in ranked order. For specimen associated with ID "20form", the classification of acute lymphoblastic leukemia is predicted with approximately 0.025% likelihood, the classification of acute myeloid leukemia is predicted with approximately 0.019% likelihood, and the classification of b cell lymphomas is predicted with approximately 0.017% likelihood.

In some embodiments, physician review of each sub-prediction results may allow additional insights into the driving factors of the TUO meta-classifier classifications.

In some embodiments, meta-classifier 2382d may combine results from the one or more classifiers 2382a-n to generate a TUO classification which may be viewed through a viewer 2600 such as a web page, application, or other display device capable of displaying graphs. In some embodiments, a web page may be accessed from a web address. A user, such as a physician, may access a patient's TUO classification results by the patient's unique, deidentified ID. The viewer 2600 may include one or more graphs 2610, 2620, and 2630 for displaying the combined results of graphs 2510, 2520, 2530, and 2540 corresponding to classifier and feature sets for CNV, DNA Variants, RNA Transcripts, and RNA splicing.

In some embodiments, Rollup Prediction for CNV, DNA Variants, RNA Transcripts, and RNA splicing illustrated in graph 2610 visually depicts the sum of the sub-prediction likelihoods for each cancer classification cohort. The highest summed results are listed on the Y-axis and the accumulated likelihoods are represented along the X-axis. For specimen associated with ID "20form," the classification of lung across all sub-prediction classifiers is approximately 97% likelihood while the next closest classifications for neuroendocrine and squamous are below approximately 2% likelihood, indicating that the meta-classifier is confident that the TUO originated in the lung.

In some embodiments, Rollup Subtype Prediction for CNV, DNA Variants, RNA Transcripts, and RNA splicing illustrated in graph 2620 visually depicts the sum of the sub-prediction likelihoods for each cancer classification diagnosis. The highest summed results are listed on the Y-axis and the accumulated likelihoods are represented along the X-axis. For specimen associated with ID "20form," the classification of lung adenocarcinoma across all sub-prediction classifiers is approximately 95% likelihood while the next closest classifications for high grade neuroendocrine lung and lung squamous are below approximately 2% likelihood, indicating that the meta-classifier is confident that the TUO should be diagnosed as lung adenocarcinoma.

In some embodiments, selection of any bar of graph 2610 or any bar of graph 2620 causes graph 2630 to automatically populate with a Shapley Additive Explanations (SHAP) feature importance plot which visually depicts how each sub-prediction from CNV, DNA Variants, RNA Transcripts, and RNA splicing contributed to the rollup cancer classification diagnosis, cohort, or tissue classification (based upon which bar is selected). For example, if a user selects the lung adenocarcinoma bar of graph 2620, contributing likelihoods from each sub-prediction from graphs 2510, 2520, 2530, and 2540 are mapped to graph 2630 where the Y-axis corresponds to how much likelihood the sub-prediction contributed to the sum of likelihoods and the X-axis corresponds to whether the likelihood increased or decreased the sum of likelihoods.

In some embodiments, predicting multiple target variables in a stacked setting improves the performance of the overall model by allowing the meta-classifier to understand the semantic relationship between cohorts, tissues, and diagnoses. For example, a cancer condition cohort RNA model may predict "sarcoma" with high confidence, but the cancer condition diagnosis RNA model may be split between lung adenocarcinoma and osteosarcoma. In another example, the meta-classifier may favor osteosarcoma because of the additional cohort-level evidence weighing in favor of a sarcoma. In another example, a cancer condition tissue model may predict colon tissue as the site of biopsy, a cancer condition diagnosis RNA model may predict a diagnosis of colon cancer and liver cancer with fairly equal likelihoods. In another example, the stacked model may weight the likelihood of a diagnosis of colon cancer lower given the "pollution" of underlying colon tissue as identified by the site of biopsy, causing the meta-classifier to favor a cancer condition diagnosis of liver cancer.

In some embodiments, meta-classifier 2382d may receive classifications from 9 separate classifiers, RNA Diagnosis, RNA Cohort, RNA Splicing Diagnosis, RNA Splicing Cohort, CNV Diagnosis, CNV Cohort, DNA Variant Diagnosis, DNA Variant Cohort, and Viral Diagnosis. In some embodiments, a heat map for feature importance according to each of the features which drive the different classifiers is illustrated to provide additional clarifications as to the scaling of importance factors of the meta-classifier. While some features and their respective importance may be immediately recognizable, many importance scores determined from performance may be less easily recognized.

The examples provided herein are illustrative and are not intended to limit a feature importance scaling factor to only the provided possible examples. The Y-axis identifies the classifier, the X-axis identifies the cancer classification diagnosis, and the cell where the x and y axis meet are color coded with the importance of the classifier to accurately predicting the diagnosis from the classifier.

In some embodiments, RNA classification of diagnosis is weighted heavily across a majority of the cancer condition diagnosis as illustrated in the heat map, RNA classification of a cohort class is weighted heavily across a majority of the cancer conditions cohorts, and RNA classification of a tissue or site of biopsy is also weighted heavily across a majority of the cancer condition sites of biopsy. In some embodiments, DNA classification of diagnosis is weighted heavily when a classification includes granulosa ovarian because a majority of diagnosis for granulosa ovarian include presence of a FOXL2 alteration. In some embodiments, viral classification of diagnosis is weighted for a small number of classes. For example, HPV drives anal squamous, head and neck squamous, and cervical cancer and polyomavirus drives most Merkel Cell Carcinomas. The presence of these viral reads is a highly informative feature in some classes, but may provide less diagnostic value for samples that do not have a virally driven tumor. Therefore, the importance score for any one diagnosis is naturally lower. In some embodiments, copy number classification of diagnosis is weighted heavily for diagnosis of glioma, prostate, ovarian serous, melanoma, oligodendroglioma and leiomyosarcoma. In some embodiments, RNA Splicing classification of diagnosis is weighted heavily when a classification of prostate or breast cancer diagnosis is made.

Additional Illustrative Examples

In one example, a patient visits their physician with concerns about pain in her breast. The physician confirms a lump in the patient's breast and sends them to imaging, where a CT scan or MRI are performed, identifying additional tumors in the bone and liver of the patient. A physician biopsies the tumor of the liver, orders sequencing from a laboratory, and sends it for identification and sequencing. The pathologist is unable to confirm the tumor of the liver's origin, and labels the specimen as a Tumor of Unknown Origin (TUO). The sequencing laboratory sequences the patient's DNA and RNA from the tumor and DNA from the patient's blood. The physician receives a notification that the specimen is a TUO and orders an additional TUO classification from the laboratory in addition to the initial order for sequencing. In response to the order for TUO classification, the laboratory provides the sequencing results and other results derived from the sequencing results to an artificial intelligence engine. An artificial intelligence engine identifies that the liver tumor originated from the breast based on a multi-modal model combining classifiers for RNA, DNA, CNV, and splicing modals. A report is generated identifying the TUO classification and supporting information provided from classifier results as to why the classification is a reasonable prediction of the tissue of origin. The physician, based upon the identification as the breast as the tissue of origin for the tumor of the liver, may now select a line of therapy for the patient with FDA approved drugs/therapy for targeting breast cancer tumors over mere platinum chemotherapy that is provided to all patients having a TUO.

In another example, a sequencing laboratory includes an ordering system which provides a comprehensive breakdown of sequencing assays, reports, classifications, and predictions a physician may order. In some embodiments, a physician has one or more assay options to choose from, tumor only or matched tumor-normal sequencing, reporting TMB, MSI, CNV, fusions, splicing, and other sequencing alterations, H&E staining and/or IHC staining, predicted IHC staining from H&E staining, predicted PD-L1 or other biomarker status from H&E staining, predicted metastasis to one or more organs, predicted origin for tumors of unknown origin, and other sequencing related testing, predictions, or reporting order items. A physician may identify their preferred order by selecting one or more of the available options and paying the associated fees with each. The laboratory may receive a somatic and/or germline specimen from the patient, perform sequencing according to the ordered assay, and fulfill all ordered items before generating a report to return to the physician summarizing the sequencing results and therapeutic, treatment, clinical trial, and other insights that may influence the physician's treatment selection for the patient. "Matched Tumor-Normal", "Tumor-Normal Matched", and "Tumor-Normal Sequencing" means processing genomic information from a subject's normal, non-cancerous, germline sample, such as saliva, blood, urine, stool, hair, healthy tissue, or other collections of cells or fluids from a subject, and genomic information from a subject's tumor, somatic sample, such as smears, biopsies or other collections of cells or fluids from a subject which contain tumor tissue, cells, or DNA (especially circulating tumor DNA, ctDNA). DNA and RNA features which have been identified from a next generation sequencing (NGS) of a subject's tumor or normal specimen may be cross referenced to remove genomic mutations and/or variants which appear as part of a subject's germline from the somatic analysis. The use of a somatic and germline dataset leads to substantial improvements in mutation identification and a reduction in false positive rates. "Tumor-Normal Matched Sequencing" provides a more accurate variant calling due to improved germline mutation filtering. For example, generating a somatic variant call based at least in part on the germline and somatic specimen may include identifying common mutations and removing them. In such a manner, variant calls from the germline are removed from variant calls from the somatic as non-driver mutations. A variant call that occurs in both the germline and the somatic specimen may be presumed to be normal to the patient and removed from further bioinformatic calculations.

EXAMPLES

Example 1—Classification of an Exemplary Patient Cohort

Through the methods described herein, a classifier was developed for a targeted oncology panel using hybrid capture next generation sequencing. The classifier includes a combination of whole transcriptome RNA-seq and targeted DNA tiling probes for comprehensive gene rearrangement and microsatellite instability (MSI) detection. In addition to the clinical testing function of the classifier, the DNA- and RNA-seq assay components support a tool for evaluation of tumor immunity status, including HLA typing, neoantigen prediction, DNA repair gene analysis, MSI status, tumor mutational burden, and immune cell typing and expression.

Figure 4A:
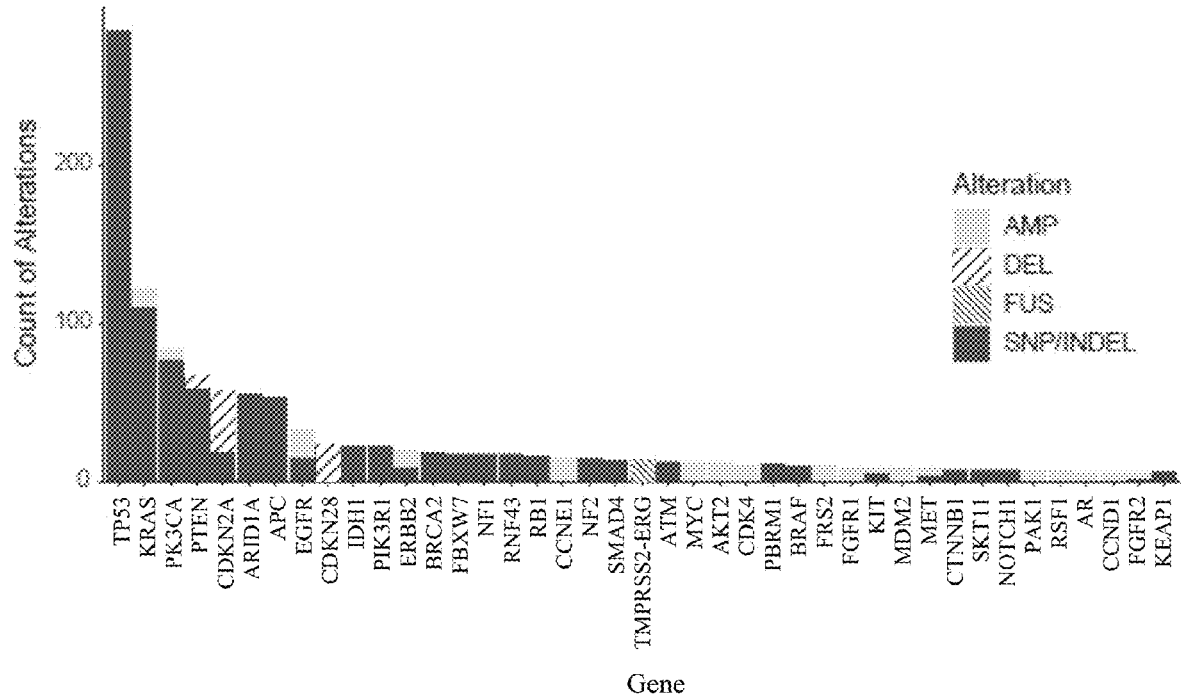
FIGS. 4A, 4B, and 4C collectively illustrate predictions of the mutational spectrum of a cohort of 500 patients, in accordance with some embodiments of the present disclosure.
Figure 4B:
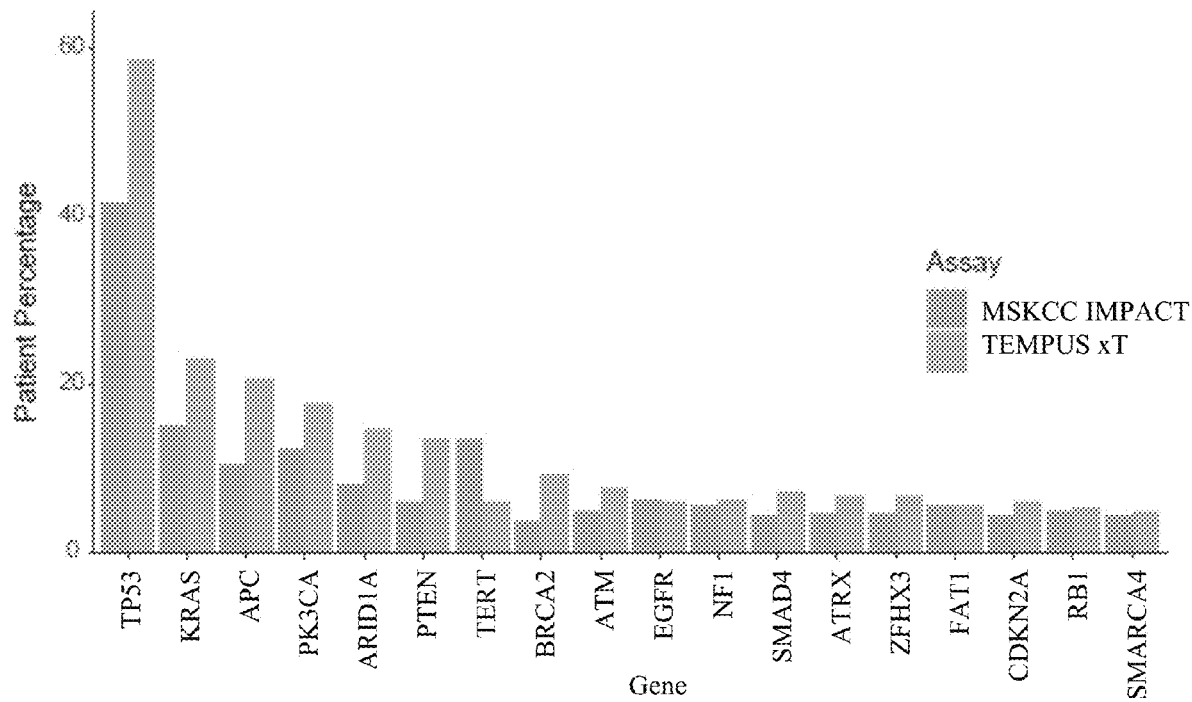
Figure 4C:
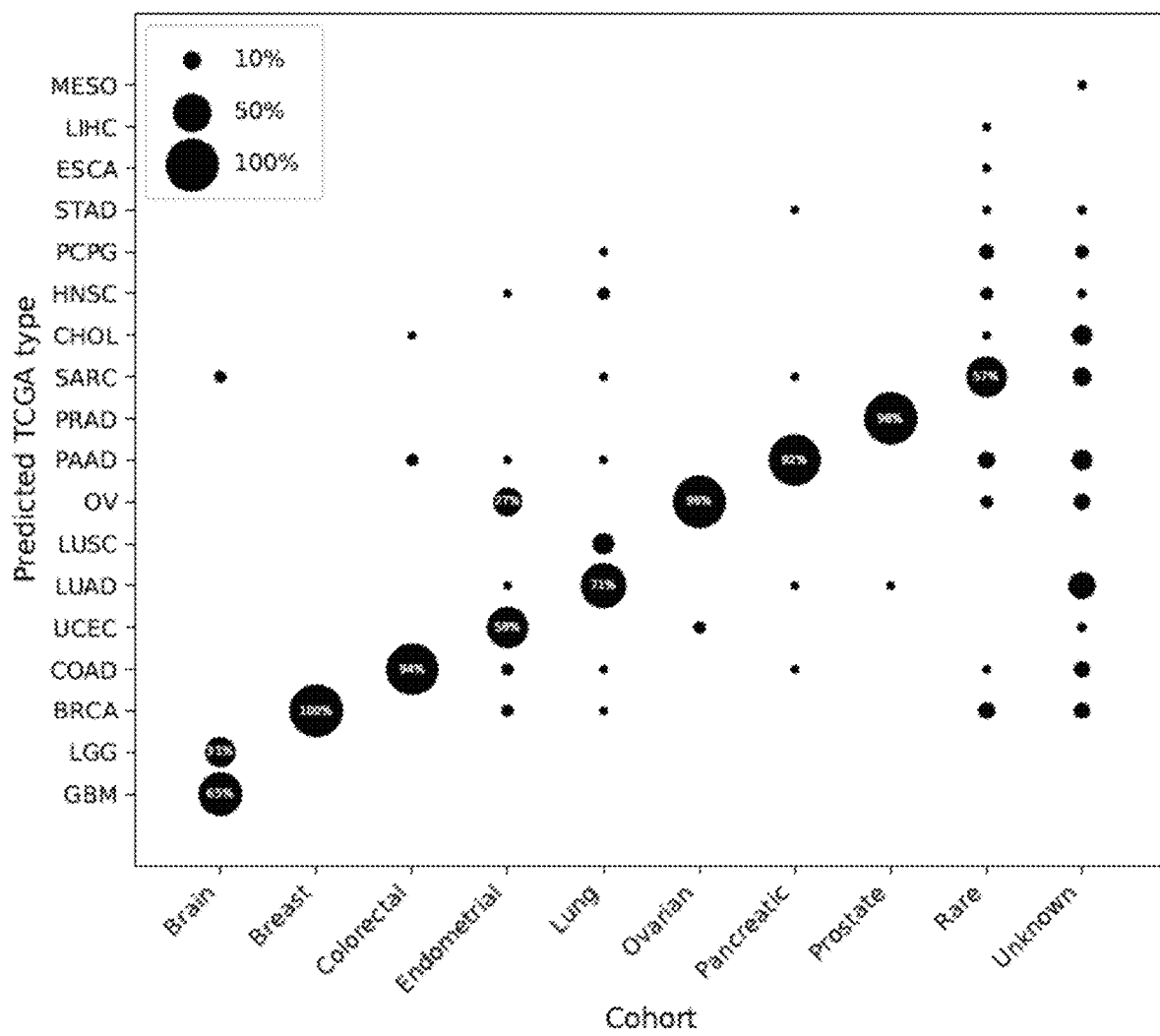

Referring to FIGS. 4A through 4C, a cohort of subjects was analyzed to examine the efficacy of using genome-wide expression patterns for cancer condition classification. A cohort of 500 patients with tumors of either known or unknown origin were examined. Analyses from tumor-normal matched sequencing on the DNA mutational spectra across cancer conditions, whole transcriptome profiling, genomic rearrangement detection, and the immunogenic landscape based on immunotherapy biomarkers in the patient cohort are described below.

The patients in the cohort of 500 patients were selected randomly from a larger patient set. In order to be eligible for inclusion in the cohort, each patient was required to have complete data elements for tumor-normal matched sequencing and clinical data. Subsequent to filtering for eligibility, a set of patients were randomly sampled via a pseudo-random number generator. Patients were divided into eight cancer conditions based on pathologic diagnosis, with 50 patients per brain, breast, colorectal, lung, ovarian, endometrial, pancreas, and prostate cancer condition. Additionally, 50 tumors from a combined set of rare malignancies and 50 tumors of unknown origin were included in the cohort, for a combined total of 500 patients.

First, the mutational spectra of the cohort of 500 patients was examined and compared to broad patterns of genomic alterations observed in large-scale studies across cancer conditions. As shown in FIG. 4A, genomic alterations by gene for all 500 patients were identified. The genomic alterations included single nucleotide polymorphisms (SNPs/indels), fusions (FUS), and a subset of copy number variants (CNVs), amplifications (AMP) and deletions (DEL). The most commonly mutated genes were well known driver mutations in solid tumors, including TP53, KRAS, PIK3CA, CDKN2A, PTEN, ARID1A, APC, ERBB2(HER2), EGFR, IDH1, and CDKN2B. Of these, CDKN2A, CDKN2B, and PTEN were most commonly found to be homozygous deletions, as expected for tumor suppressor genes. Alterations are grouped by type, and those appearing in at least 5 patients (e.g., at least 1% prevalence in the population) are plotted.

Next, the mutational spectra data illustrated in FIG. 4A were compared to a previously published pan-cancer analysis using the Memorial Sloan Kettering Cancer Center (MSKCC) IMPACT panel. See Zehir et al. 2017 Nat. Med. 23, 703-713. As shown in FIG. 4B, both the IMPACT panel and the cohort of 500 patients exhibited the same commonly mutated genes at similar relative frequencies, indicating that the mutation spectra of the cohort of 500 patients is representative of the broader population of tumors that have been sequenced in previously published large-scale studies.

Each sample included in the cohort of 500 patients was further examined by RNA-seq whole transcriptome profiling. A trained classification model was then used to predict cancer condition from each transcriptome. As shown in FIG. 4C, the classification was particularly successful at predicting breast cancer, prostate cancer, brain cancer, colorectal cancer, pancreatic cancer, and lung cancer. The bubbles in FIG. 4C indicate the percent of samples from each cohort type predicted to have a given TCGA cancer condition. In some embodiments, the accuracy of each prediction is quantified using bootstrapping.

The Cancer Genome Atlas (TCGA) dataset referenced herein is a publicly available dataset comprising more than two petabytes of genomic data for over 11,000 cancer patients, including clinical information about the cancer patients, metadata about the samples (e.g., the weight of a sample portion, etc.) collected from such patients, histopathology slide images from sample portions, and molecular information derived from the samples (e.g., mRNA/miRNA expression, protein expression, copy number, etc.). The TCGA dataset includes data on 33 different cancers: breast (breast ductal carcinoma, breast lobular carcinoma), central nervous system (glioblastoma multiforme, lower grade glioma), endocrine (adrenocortical carcinoma, papillary thyroid carcinoma, paraganglioma & pheochromocytoma), gastrointestinal (cholangiocarcinoma, colorectal adenocarcinoma, esophageal cancer, liver hepatocellular carcinoma, pancreatic ductal adenocarcinoma, and stomach cancer), gynecologic (cervical cancer, ovarian serous cystadenocarcinoma, uterine carcinosarcoma, and uterine corpus endometrial carcinoma), head and neck (head and neck squamous cell carcinoma, uveal melanoma), hematologic (acute myeloid leukemia, Thymoma), skin (cutaneous melanoma), soft tissue (sarcoma), thoracic (lung adenocarcinoma, lung squamous cell carcinoma, and mesothelioma), and urologic (chromophobe renal cell carcinoma, clear cell kidney carcinoma, papillary kidney carcinoma, prostate adenocarcinoma, testicular germ cell cancer, and urothelial bladder carcinoma).

The TCGA cancer conditions in FIG. 4C include ACC: Adrenocortical carcinoma, BRCA: Breast invasive carcinoma, COAD: Colon adenocarcinoma, GBM: Glioblastoma multiforme, HNSCC: Head and Neck squamous cell carcinoma, LGG: Brain Lower Grade Glioma, LIHC: Liver hepatocellular carcinoma, LUAD: Lung adenocarcinoma, LUSC: Lung squamous cell carcinoma, MESO: Mesothelioma, OV: Ovarian serous cystadenocarcinoma, PAAD: Pancreatic adenocarcinoma, PCPG: Pheochromocytoma and Paraganglioma, PRAD: Prostate adenocarcinoma, SARC: Sarcoma, SKCM: Skin Cutaneous Melanoma, STAD: Stomach adenocarcinoma, THYM: Thymoma, UCEC: Uterine Corpus Endometrial Carcinoma, and UCS: Uterine Carcinosarcoma.

Example 2—Therapeutic and Clinical Trial Matching

The extent to which broad molecular profiling aids patient matching to therapies was examined. Factors considered included consensus clinical guidelines to case reports for response and/or resistance to therapy. A knowledge database of therapeutic and prognostic evidence was compiled from sources including the National Comprehensive Cancer Network (NCCN), CIViC (see Griffith et al. 2017 *Nat. Genet.* 49, 170-174), and DGIdb (see Finan et al., 2017, *Sci. Transl. Med.* 9, eaag1166).

Clinically actionable entries in the knowledge database are structured by both the relevant disease and by evidence levels (e.g., tiers). The binning of somatic evidence is performed as described by the ASCO/AMP/CAP working group. See Li et al. 2017 *J. Mol. Diagnostics* 19, 4-23, which is hereby incorporated by reference. Patients are then matched to clinically actionable entries by gene, specific variant, diagnosis, and level of evidence.

Across all cancer conditions, 90.8% of patients matched to a therapeutic option based on evidence for response to therapy, and 22.6% matched to a therapeutic option based on evidence for resistance to therapy (see FIG. 5A). The maximum tier of therapeutic evidence matched varied significantly by cancer condition, as shown in FIG. 5B. For example, 58.0% of colorectal patients could be matched to Tier IA evidence, the majority of which were for resistance to therapy based on detected KRAS mutations; while no pancreatic cancer patients could be matched to Tier IA evidence. This outcome was expected, as there are several molecularly based consensus guidelines in colorectal cancer in contrast to pancreatic cancer.

Next, the contribution of each molecular assay component for patient therapy matching was determined. First, the therapeutic evidence matches that were made based on copy number variants (CNVs), single nucleotide variants (SNVs) and indels were examined. Overall, 140 patients (28%) were matched to a precision medicine option with Tier IA or Tier ID3 evidence, which together include FDA-approved and well-powered consensus therapies.

The contribution of therapy matching based on RNA-seq gene expression profiles of clinically relevant genes was next explored. The genes that were included in this analysis were selected based on their relevance to disease diagnosis, prognosis, and/or possible therapeutic intervention. In this example, up to 43 genes were evaluated for each cancer condition, based on the specific cancer condition of the sample. In order to make an expression call, the percentile of expression of the new patient was calculated relative to all cancer samples, all normal samples, matched cancer samples and matched normal samples in the TCGA and GTEx databases that had been processed. For example, a breast cancer patient's tumor expression was compared to all cancer samples, all normal samples, all breast cancer samples, and all breast normal tissue samples within the reference database. Specific thresholds used for gene expression calling have evolved during the use of the assay. Criteria specific to each gene and cancer condition at the time of reporting were used to determine gene expression calls. Therefore, the thresholds applied for specific genes may vary across this dataset.

Over or under-expression gene calls in 136 patients (28.7%) were examined for 16 genes with therapeutic evidence based on clinical studies, case studies, or preclinical studies reported in the literature (the results are shown in FIG. 5C). Metastatic cases were equally as likely to have at least one reportable expression call compared to non-metastatic tumors. The most commonly reported gene was over-expression of NGR1, which was observed in 35 cases (7.3% of tumor samples) across the cohort.

Based on the immunotherapy biomarkers identified by the assays, the percentage of the cohort would be eligible for immunotherapy was assessed. As shown in FIG. 5D, 52 patients (10.4%) would have been considered potential candidates for immunotherapy based on TMB, MSI status, and PD-L1 IHC results alone. The number of MSI-H and TMB-high cases were distributed among cancer conditions, with 22 patients (4.4%) positive for both biomarkers. PD-L1 positive IHC alone was measured in 15 patients (3%), and was found to be the highest among lung cancer patients. TMB-high status alone was measured in 13 patients (2.6%), primarily in lung and breast cancer cases. Lastly, the combination of PD-L1 positive IHC and TMB-high status was observed in the minority of cases and measured in only 2 patients (0.4%).

Taking the union of the results above, therapeutic options were matched for 455 patients (91%) using comprehensive molecular profiling (see FIG. 5E). Additionally, 1,996 clinical trial matches were reported for the cohort of 500 patients. At least one clinical trial was matched to 481 patients (96.2%). Of these patients, 77.2% matched with at least one biomarker-based clinical trial for a gene variant on their final report.

As illustrated by FIG. 5F, the frequency of biomarker-based clinical trial matches varied by diagnosis and outnumbered disease-based clinical trial matches. For example, gynecological and pancreatic cancers were typically matched to a biomarker-based clinical trial; while rare cancers had the least number of biomarker-based clinical trial matches and an almost equal ratio of biomarker-based to disease-based trial matching. The differences between biomarker versus disease-based trial matching appear to be due to the frequency of targetable alterations and heterogeneity of those cancer conditions.

The classification method described herein is unique in its use of matched tumor and normal DNA plus whole transcriptome RNA-seq to give a comprehensive view of somatic genomic alterations, including MSI status for targeted cancer therapy, immuno-oncology, and clinical trial enrollment. As described above, the method was validated with multiple testing modalities.

Example 3—Comparison of Paired Tumor/Normal Samples to Tumor Only Samples in Testing for Cancer Cancer testing assays most commonly use only tumor samples. However, there are potential advantages to using paired tumor and normal samples for diagnoses. In particular, this permits comparison of an individual patient's own germline mutations to mutations in the respective patient's tumor (e.g., the patient's somatic mutations).

Figure 6B:
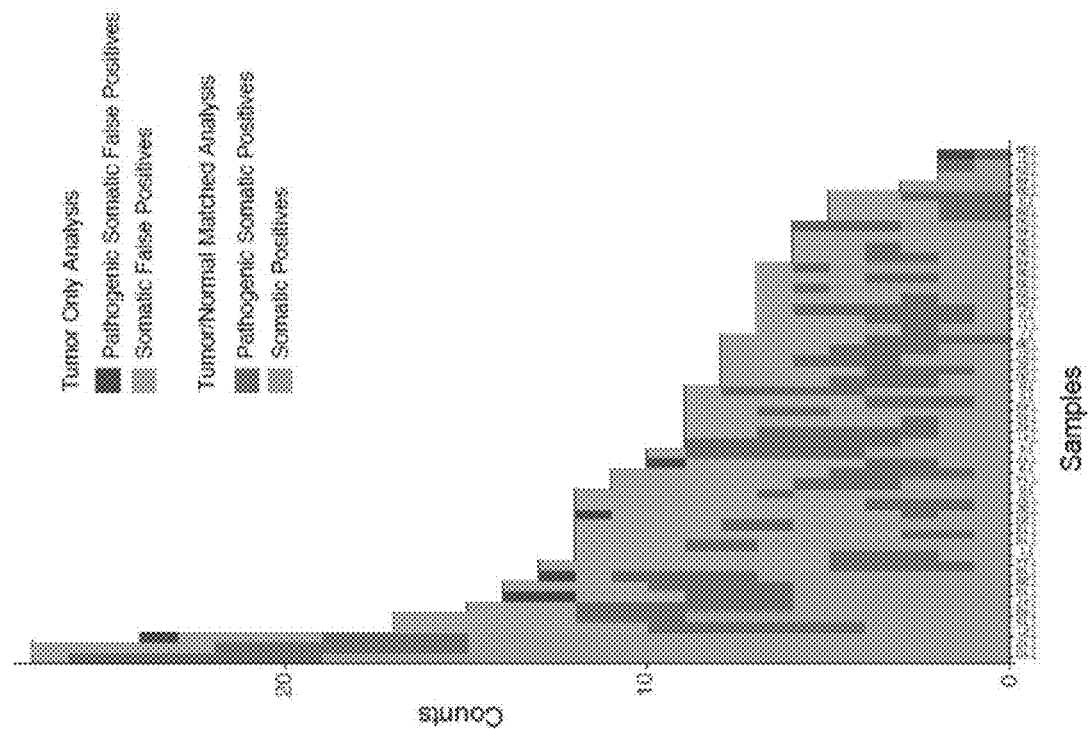
FIGS. 6A and 6B collectively illustrate a comparison of tumor-only versus tumor-normal analysis, in accordance with some embodiments of the present disclosure. The use of paired tumor/normal samples is described further in Example 3.
Figure 6A:
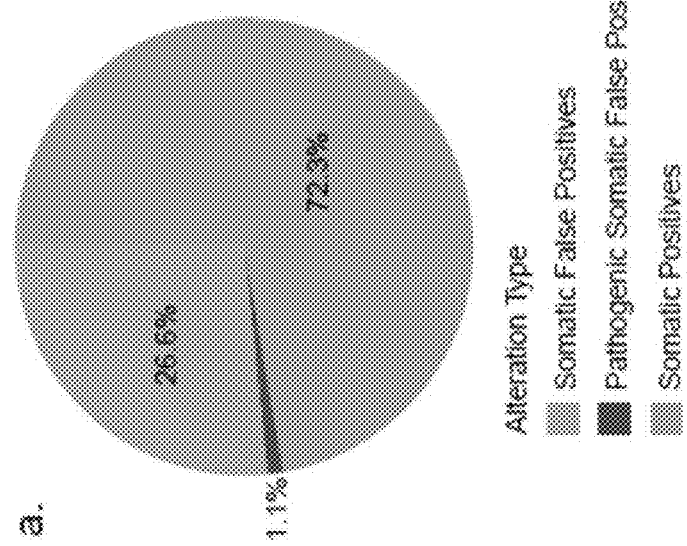

For this example, 50 cases were randomly selected from the cohort of 500 patients with a range of tumor mutational burden (TMB) profiles (e.g., as illustrated in FIG. 6A) and then re-evaluated using a tumor-only analytical pipeline. 8,557 coding variants were identified after filtering using a publicly available population database 20. By further filtering with an internally developed list of technical artifacts, an internal pool of normal samples, and classification criteria, the number of variants was reduced to 642, while still retaining all true somatic alterations (72.3%). Within the 642-filtered tumor-only variants, 27.7% of these variants were classified as somatic false positives (e.g., actually germline variants or artifacts).

To assess the therapeutic impact of a tumor-only test, and to compare to the therapeutic insights derived from the Tempus platform (e.g., from tumor-normal test plus RNA-seq and immune-oncology (TO) analyses), the therapies that would have been offered to each of these 50 patients in both scenarios were determined. Eight of the 50 patients (16%) would have been given divergent clinical recommendations if they had received a tumor-only test instead of a full Tempus test. Of these eight patients, four patients had different recommendations due to information obtained via RNA-seq, or due to the tumor having somatic mutations with low clonality, a characteristic which is hard to detect in a tumor only test. For example, in a prostate cancer patient, DNA-seq did not show any contraindication to the anti-androgen therapy the patient was receiving, but RNA-seq showed androgen receptor (AR) overexpression, indicating possible resistance. The other four had divergent therapies and also potentially would have not received genetic counseling, due to the tumor-only test reporting a germline mutation as somatic.

Finally, the therapies recommended for all DNA variants detected by the Tempus platform were compared to therapies recommended by a patient facing website, My Cancer Genome (MCG). 43 cases received recommended therapies via the Tempus tumor only test, while therapies were only found for five cases via MCG.

In the preceding analysis, the use of tumor-normal matched sequencing in the clinically reported results filtered variants and more accurately classified true somatic positives, leading to differential therapy recommendations for patients. This is illustrated by FIG. 6B, where the Tumor Only Analysis showed an increased number of false positives compared to the number of false positives produced by the Tumor/Normal Matched Analysis.

Example 4—Cancer Classification and Tumor of Unknown Origin Detection

Cancer condition classification is clinically vital to providing effective treatment to patients. Identifying tissue of origin is an important precursor to determining optimal treatment strategies. In a test set of samples analyzed in accordance with the methods described herein, 419 are in a tumor of unknown origin cohort. In addition, 41 more samples are of unknown gynecologic origin, 166 more samples are of unknown gastrointestinal origin, and 241 more samples are described as poorly differentiated. Together, these 867 samples make up 7.6% of the cancer patients in the overall sample set. Previously described methods do not suffice to determine the cancer conditions of samples in these cohorts. See e.g., Bloom et al. 2004 *Am J Pathol.*, 164(1):9-16; Tschentscher et al., 2003 *Can. Res.*, 63(10), 2578-84; Young et al., 2001 *Am J Pathol.*, 158(5), 1639-51; and Amar et al. 2015 *Nuc. Acids Res.* 43, 7779-7789. Some of the methods disclosed herein use a combination of genomic, pathologic, and clinical features in either training of classification models or as inputs to classification models to enable the classification of many tumors of unknown origin, thus providing information to patients and also improving patient outcomes (e.g., by enabling treatment appropriate to the revealed cancer condition).

Figure 7A:
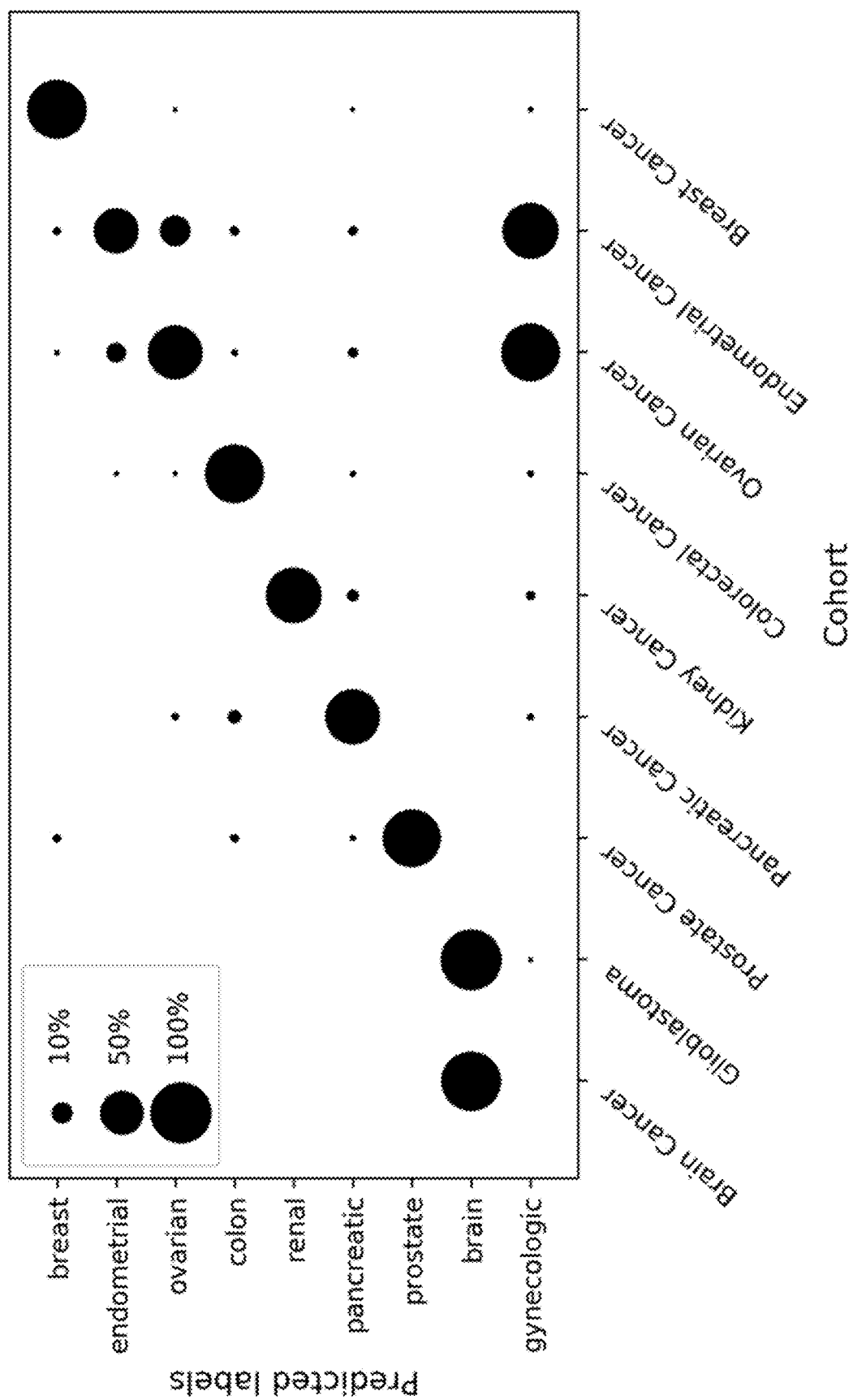
FIGS. 7A, 7B, 7C, and 7D collectively illustrate patient classifications to cancer condition, in accordance with some embodiments of the present disclosure.
Figure 7B:
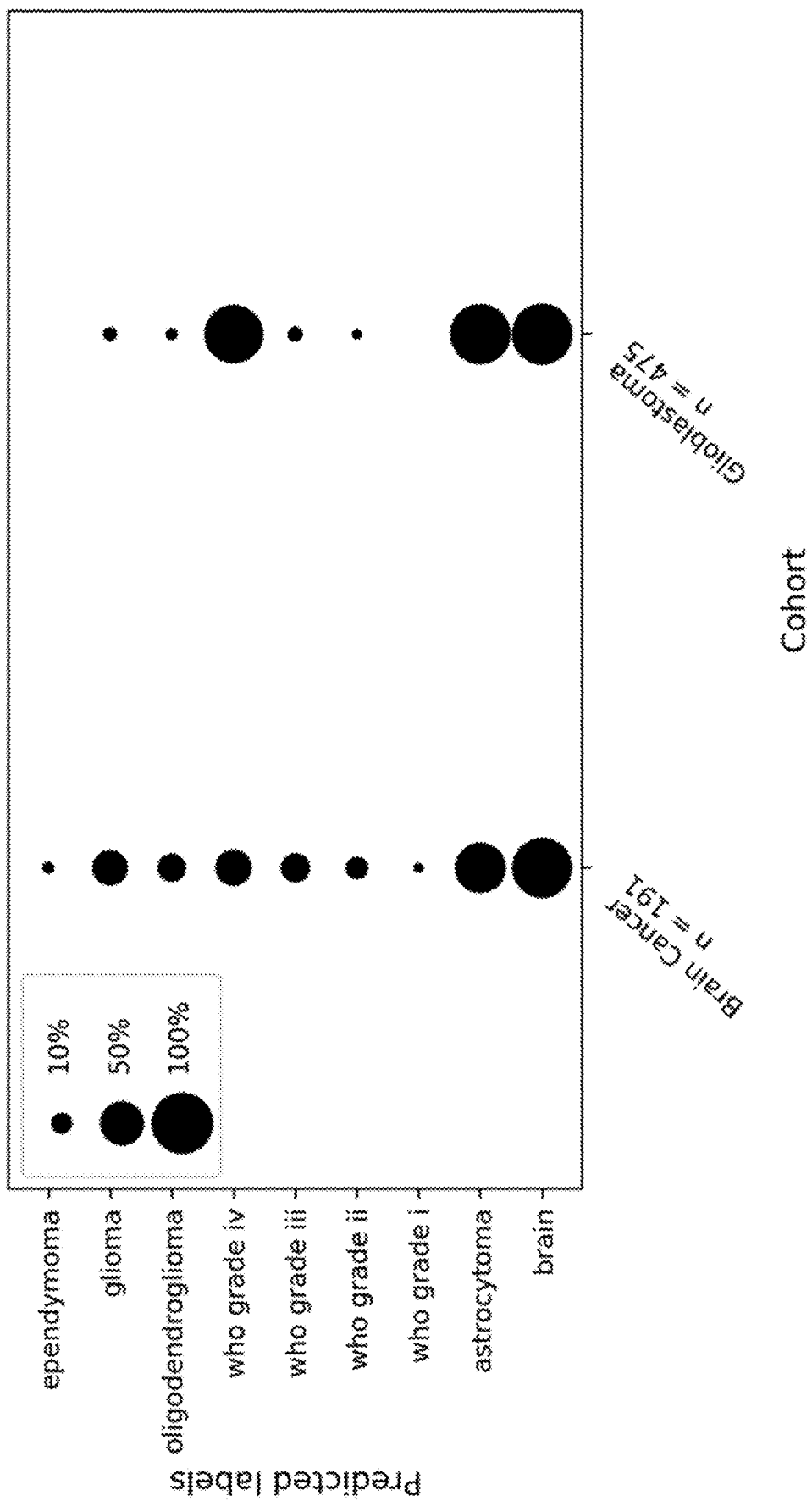

FIGS. 7A-7D illustrate examples of model classifications and demonstrate the accuracy of the methods disclosed herein. Diagnoses, cancer subtype, tissue site, and histology can all be classified correctly. FIG. 7A shows that there is a high degree of accuracy of prediction of cancer condition using the classification models described herein. Samples from different cohorts (e.g., samples with known cancer categories) were correctly categorized to their predicted labels the majority of the time (e.g., as illustrated by the sizes of the circles for each category).

FIG. 7B illustrates that tumor grades, even beyond cancer condition can also be predicted. This example shows prediction results to grades and subtype labels of brain cancer for two different cohorts of brain cancer samples. Samples that had been identified in a pathology report to be "brain cancer" (e.g., a set of "non-glioblastoma brain cancers") were classified to 9 nine different categories using the classification models trained as described herein. A similar fine-tuning of classification was also seen with samples termed "glioblastomas." Glioblastomas are grade IV astrocytomas (e.g., a specific type of brain cancer that originates in astrocytes that is highly invasive locally, but which does not usually metastasize beyond the brain and spinal cord). See e.g., Giese et al. 1996 *Int. J. Cancer* 67, 275-282. As shown in FIG. 7B, samples within the pathologist-curated glioblastoma cohort, while frequently falling into the World Health Organization (who) grade IV, can be further differentiated by classification.

Figure 7C:
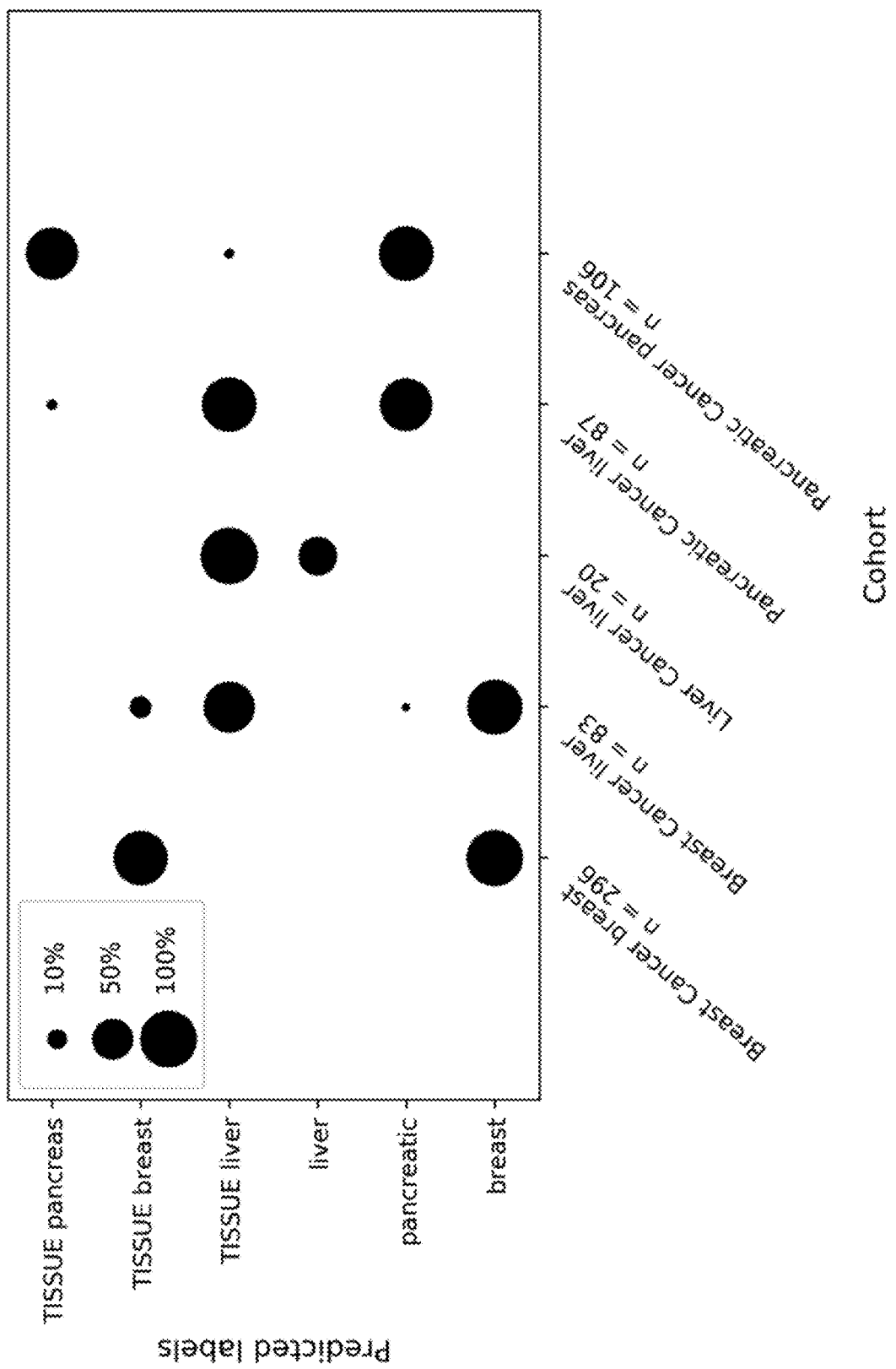

Beyond cancer condition and subtype, the classification models described herein further provide information on tissue site and histology (e.g., thus increasing the resolution in classifier results and providing important information to inform treatment options). FIG. 7C illustrates that tissue type can be accurately predicted. For example, breast cancer samples with tumors in the breast are classified to breast tissue and to breast cancer. In addition, pancreatic cancer samples that have metastasized to the liver are further classified to "pancreatic" and to "tissue liver."

Figure 7D:
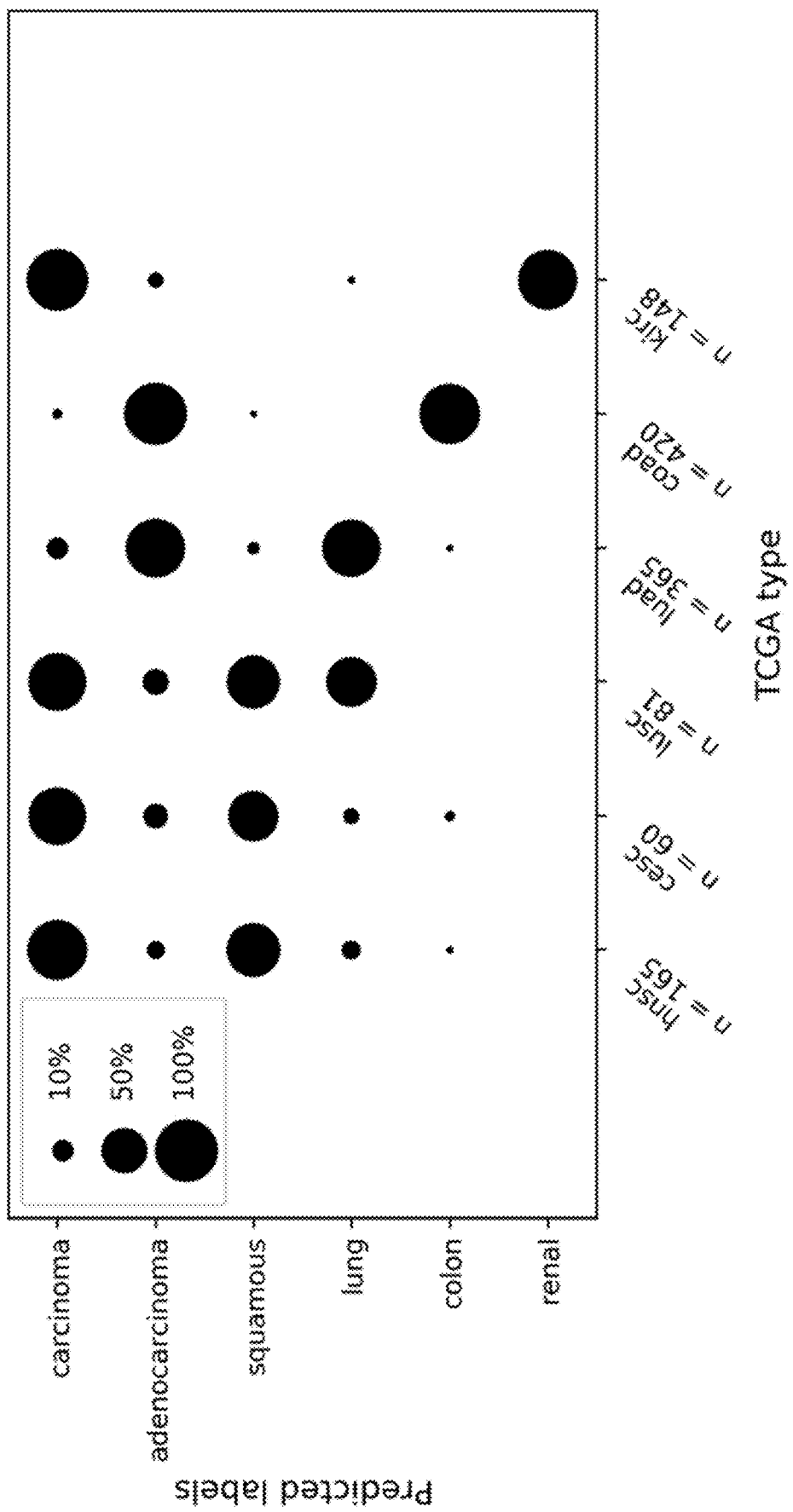

FIG. 7D illustrates that squamous and adenocarcinoma phenotypes are recapitulated with reasonable accuracy using the classification methods. The x-axis indicates TCGA types that were selected during pathology review. HNSC, CESC and LUSC samples should be classified to the squamous label. LUAD and COAD samples should be classified to the adenocarcinoma label. KIRC samples should be classified to the carcinoma label.

Example 5—Natural Language Processing of Diagnostic Values from Pathology Reports A predictive model (e.g., a classifier) trained on RNA expression levels is likely to perform better if the labels/classes that it predicts are at a degree of specificity such that the labels distinguish distinct RNA expression profiles (e.g., if the labels define sufficiently distinct clusters). There can be problems both with broad labels and with highly specific labels. For example, if the labels are too general and if many distinct RNA profiles are grouped together by being associated with the same label, the model may not recognize a meaningful pattern that can be associated with that label. The model may encounter the same obstacle if the labels are too specific and if similar RNA profiles are arbitrarily separated by such labels. In both cases, imprecise labels lead to loss of information.

Hence, providing classification algorithms with training labels that correspond to a relatively homogenous set of tumors facilitates the identification of strong expression signatures that are robust to known confounders of RNA expression including stage, tissue site, and immune infiltration. At the same time, if labels are defined overly narrowly and hence arbitrarily split an otherwise homogeneous cohort of tumors into two or more labels, then the robustness of the signature may be reduced.

Figure 11A:
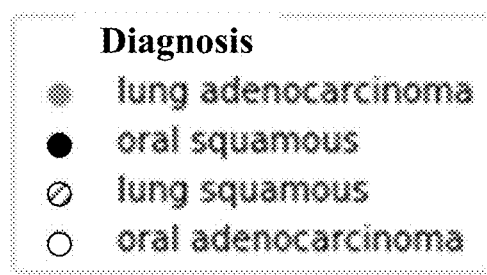
FIGS. 11A, 11B, 11C, and 11D collectively illustrate examples of transcriptionally distinct clusters of patient samples, in accordance with some embodiments. For example, 11A shows clustering of RNA expression data from patient samples where the clusters identify tissue of origin (e.g., lung vs. oral) and general cancer condition (e.g., adenocarcinoma vs. squamous) of the patient samples.
Figure 11A:
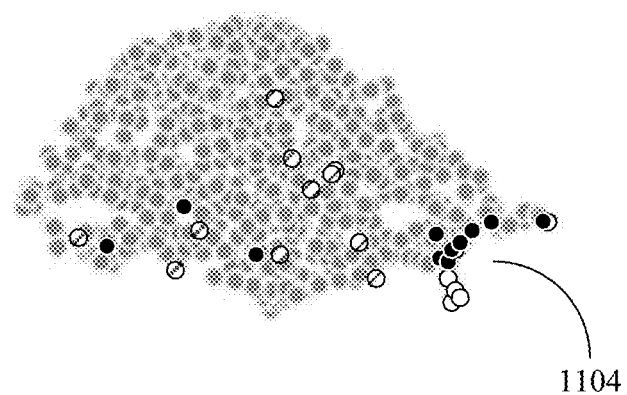
Figure 11A:
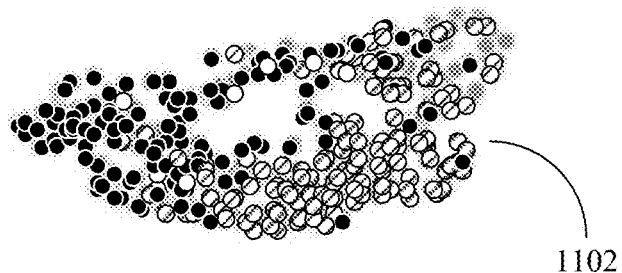
Figure 11A:
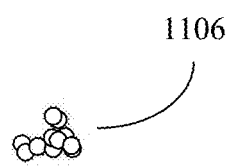

Cancer RNA expression represents the combined signal of a heterogeneous mixture of cell types present in the collected sample. Although there is tissue specificity to RNA expression (e.g., genes with expression unique to a particular cell type), the observed expression profile of a tumor may be highly confounded by the distribution of cell type(s) that are present in the sample. For example, in FIG. 11A showing clustered RNA expression data, each sample is labeled by both the sample's origin tissue (lung vs. oral) and the cohort/general cancer condition associated with the sample (adenocarcinoma vs. squamous). There are three distinct clusters in FIG. 11A: 1102, 1104, and 1106. Due to the shared transcriptional signature (e.g., as seen in cluster 1102) for some patients, oral squamous tumors appear more similar to lung squamous tumors than they are to oral adenocarcinomas, despite the biopsy tissue location.

Figure 12C:
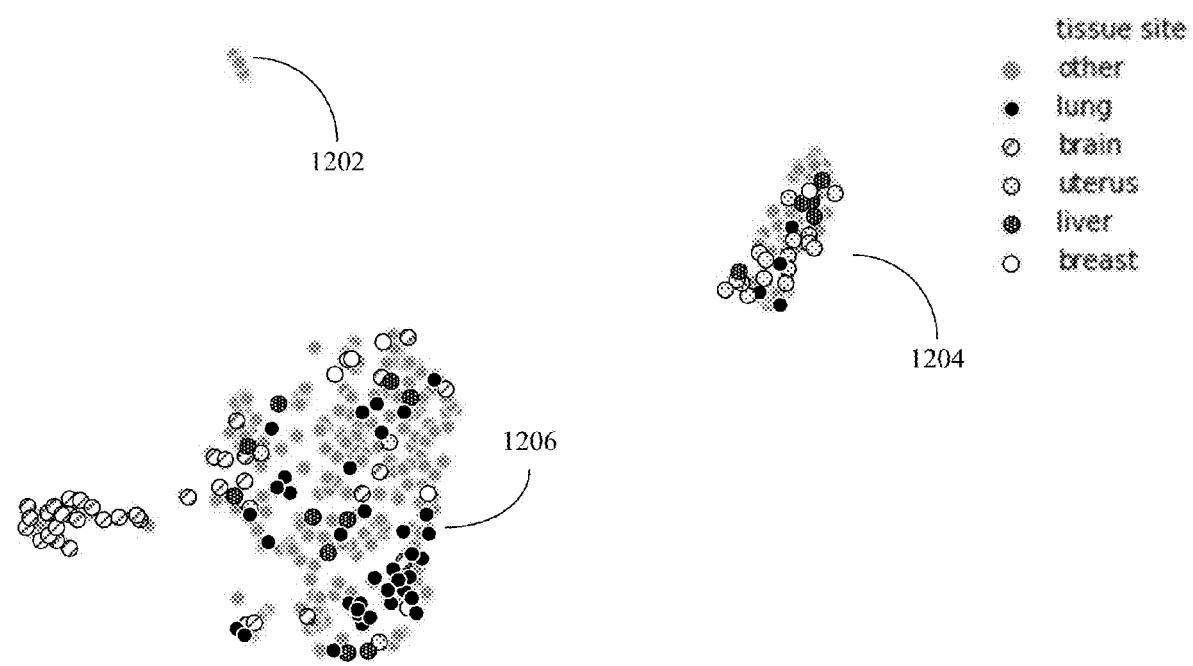

This disclosure includes a series of different tools to identify optimal cohorts (e.g., classes) for cancer classification, avoiding classes defined by confounding factors. These tools combine natural language processing, unsupervised clustering of expression data, cross validation and incorporation of known biology to identify the optimal set of labels to apply to training data. An example of clustering one data set is shown in FIGS. 12A-C, described below. The goal of clustering is that every partition (e.g., every label) will identify some biologically relevant pathological subtype of disease and provide more information to patients and/or medical practitioners. In some embodiments, multiple iterations of clustering are required to obtain clusters that accurately describe the patient data and reveal actionable information.

Natural Language Processing Prior to Clustering:

As discussed above with regard to block 314, pathology diagnosis fields typically permit unstructured entries by medical personnel such as free text boxes with pathology assessment diagnoses (e.g., in addition to histology and stage data from abstracted clinical records). Methods are described herein for defining a label set from a plurality of pathology diagnosis field entries, where the label set can then be used for analyzing the biological relevance of algorithmically defined clusters of RNA expression profile data and for annotating training data. In some embodiments, these methods also include identifying the different text patterns that would be associated with that label set (e.g., renaming the diagnostic labels).

TABLE 1

Example of relabeling of pathology diagnosis field entries

| Diagnosis field entry | Known cohort | NLP applied diagnosis |
|---|---|---|
| colonic adenocarcinoma | colorectal cancer | colon |
| prostatic adenocarcinoma | prostate cancer | prostate |
| prostatic adenocarcinoma | prostate cancer | prostate |
| colonic adenocarcinoma | colorectal cancer | colon |
| high grade serous papillary carcinoma | ovarian cancer | ovarian |
| oligoastrocytoma who grade iii | brain cancer | glioma |
| anaplastic astrocytoma who grade iii | glioblastoma | glioma |
| basal cell carcinoma | skin cancer | |
| endometrioid endometrial adenocarcinoma | endometrial cancer | endometrial |
| invasive ductal carcinoma breast | breast cancer | breast |
| glioblastoma who grade iv | glioblastoma | glioma |
| prostatic adenocarcinoma | prostate cancer | prostate |
| colorectal adenocarcinoma | colorectal cancer | colon |
| metastatic prostatic adenocarcinoma | prostate cancer | prostate |

Table 1 illustrates a variety of possible diagnostic entries found in pathology reports, the corresponding known cancer conditions associated with each diagnostic entry, and the corresponding NLP-assigned label. After natural language processing, multiple different pathology report diagnostic entries (e.g., "metastatic prostatic adenocarcinoma" and "prostatic adenocarcinoma") are mapped to the same cancer diagnostic category (e.g., "prostate"). Such normalization and data cleaning facilitates the extraction of a set of common features from a pathology report and the subsequent use of these features to refine a classifier for predicting the status/presence of a cancer condition.

In some embodiments, every label is defined by one or more of the following criteria:

The label text (e.g., 'Lung Adenocarcinoma').

A set of regular expressions that may be selected and customized to search the natural language text that indicates the presence or absence of the label (e.g., ['lung. *adeno,' 'adeno.*lung,' '^luad$').

A set of database text fields (e.g., cohort, diagnosis, histology, tissue site, etc.).

A prioritization level in order to establish a hierarchy to resolve rare situations where a single sample would be incorrectly tagged with two mutually exclusive tags such as lung adenocarcinoma and squamous lung. In some embodiments, rarer labels receive a higher priority than more general or more common labels. In some embodiments, more common labels receive a higher priority than rarer labels.

In some embodiments, a label includes at least one or more of the following: diagnosis, disease stage, histology, immune infiltration, and tissue site. In some embodiments, a set of distinct labels is determined based on the natural language processing of pathology reports.

Example 6: Iterative Clustering of RNA Expression Data

Figure 22:
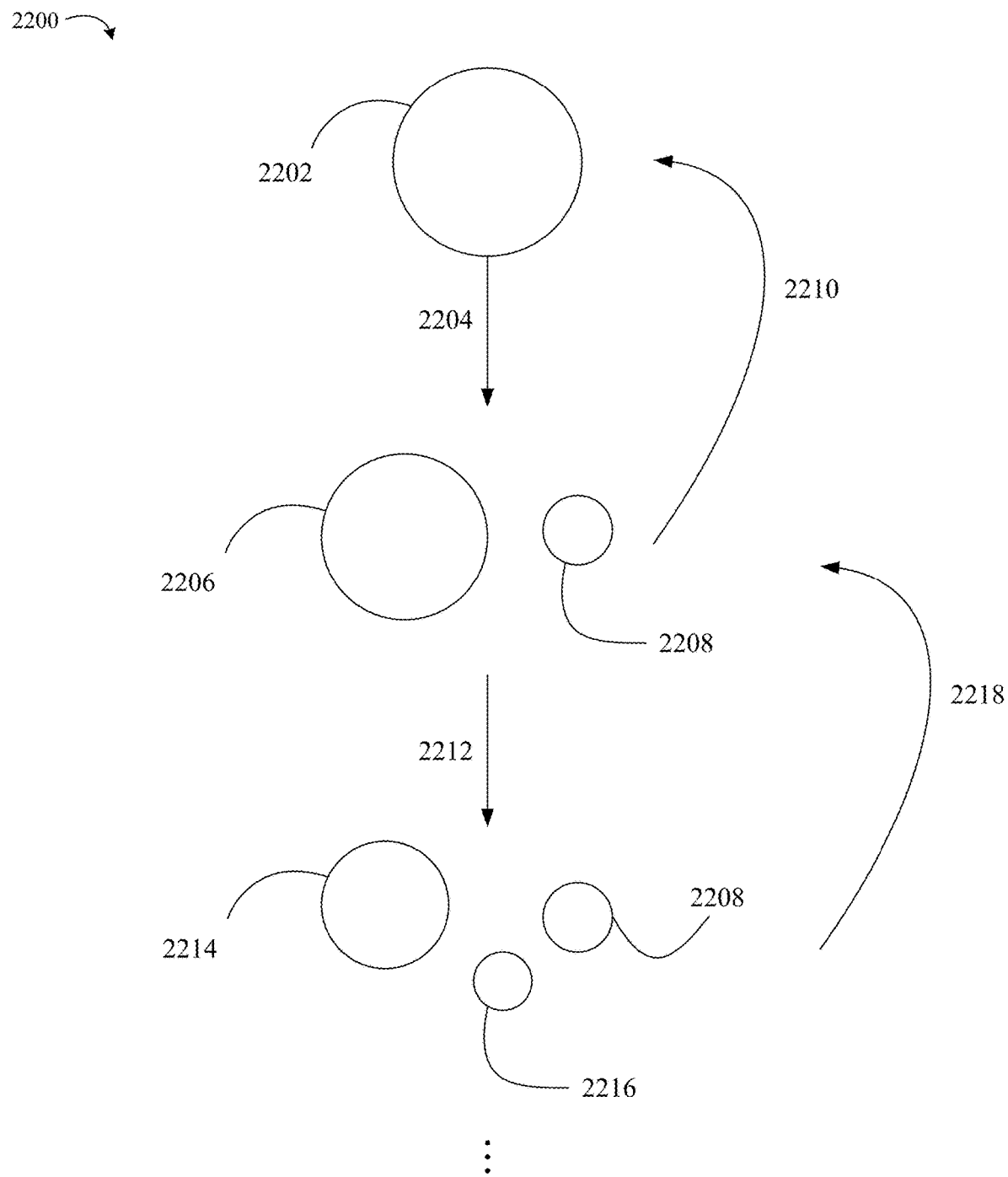
FIG. 22 illustrates an example of cancer condition label determination, in accordance with some embodiments of the present disclosure.

Iterative clustering of patient sequencing data can be performed using a determined set of labels, such as those generated by pathology report data that has been parsed as described, for example, in Example 5. In the methods disclosed here, relabeling follows an iterative process (e.g., method 2200 as illustrated in FIG. 22).

In some embodiments, the process begins with a baseline model trained on RNA expression data (from both primary and metastatic, as well as solid and hematological samples). In some embodiments, the model is xgboost. In some embodiments, the model is linear regression. Each sample in the RNA expression data is associated with one or more clinical records (including one or more pathology reports) and is labeled according to the cancer condition abstracted from those clinical records (e.g., the diagnosis from the pathology report(s)). In some embodiments, RNA expression data is formatted as a matrix of samples by genes, where each stored value in the matrix is equal to log(normalized gene expression count). In some embodiments, a matrix may contain expression values for approximately 20,000 genes representing the entire human exome, for several thousand patient samples. In some embodiments, the baseline model's performance is optionally analyzed (e.g., via 10-fold validation, confusion matrix, etc.). In some embodiments, a matrix may contain expression values for approximately 7,000 genes that represent an optimized set of values.

Figure 13:
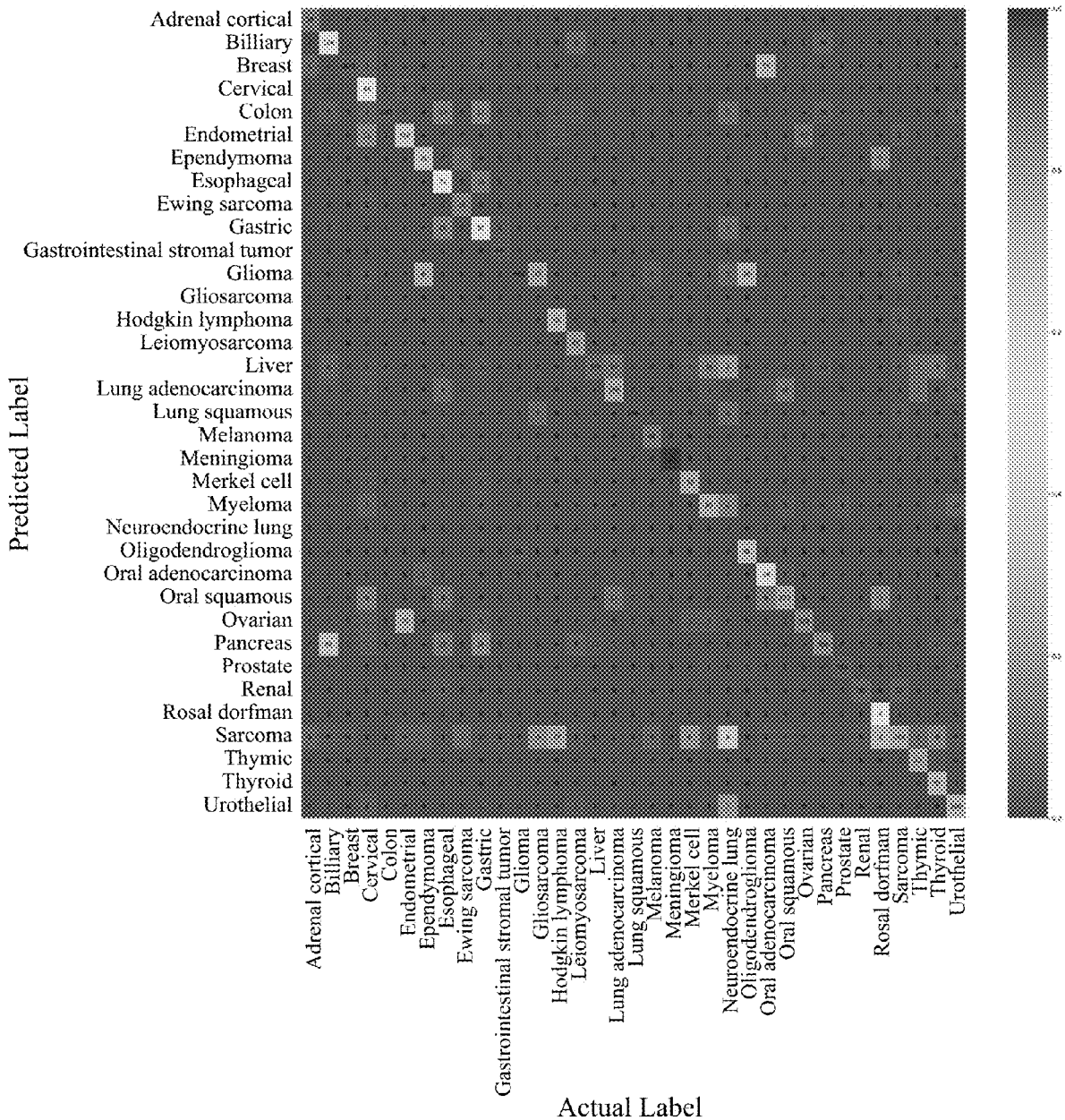
FIG. 13 is an example confusion matrix illustrating the accuracy of an example classifier trained in accordance with some embodiments of the present disclosure.

Next, cohorts are initialized with one biologically known cancer condition that may be based on origin tissue (e.g., samples with labels for lung cancer, brain cancer, breast cancer, etc. are selected). A single starting cohort 2202 is shown in FIG. 22. In some embodiments, the cohorts are selected based on a confusion matrix (e.g., FIG. 13 or FIG. 18) generated during model performance assessment. In some embodiments, cohorts are based on cancer tissue class, including sarcoma, carcinoma, adenoma, etc., or a combination of origin tissue and tissue class. After the samples are labeled by cohort, the clustering algorithm is directed to analyze only those samples within one particular cohort.

For all samples within the one selected cohort, the method performs unsupervised clustering on the RNA expression data associated with each sample in the cohort. In some embodiments, the clustering algorithm may include Uniform Manifold Approximation and Projection (UMAP) or principal component analysis (PCA) (e.g., see FIGS. 11B-11D for examples of UMAP clusters). Another way to determine the number of classes is via spectral analysis (SA) and identification of an elbow in the eigenvalue spectrum curve. In some embodiments, this unsupervised clustering is error-prone, as sources of noise in the dataset such as tissue site and stage can be the root cause of an unsupervised cluster. In some embodiments, the splitting decisions of the unsupervised clusters are manually examined with pathologist input in order to retain clinical relevance of the clusters.

FIG. 12A shows an example of initial unsupervised clustering, analyzing samples with the initial tag, "sarcoma." As demonstrated by the multiple clusters (1202, 1204, and 1206), sarcoma is a heterogeneous label (both in terms of sarcoma subtypes see e.g., FIG. 12B, and tissue of origin see e.g., FIG. 12C).

To refine the clustering, a first partition label (which may be a more specific label) associated with a portion of samples within the cohort is then selected. For example, partition label 2208 in FIG. 22 is selected. In some embodiments, after the initial partitioning 2204, the remaining samples 2206 retain the initial label 2202. The first partition label may be selected based on frequency of the label within the cohort. For example, the user may assess the number of samples in the cohort that are associated with each label, and may select the most frequently occurring label (or group of similar labels) to use as the first partition for the source of variation analysis.

Figure 11B:
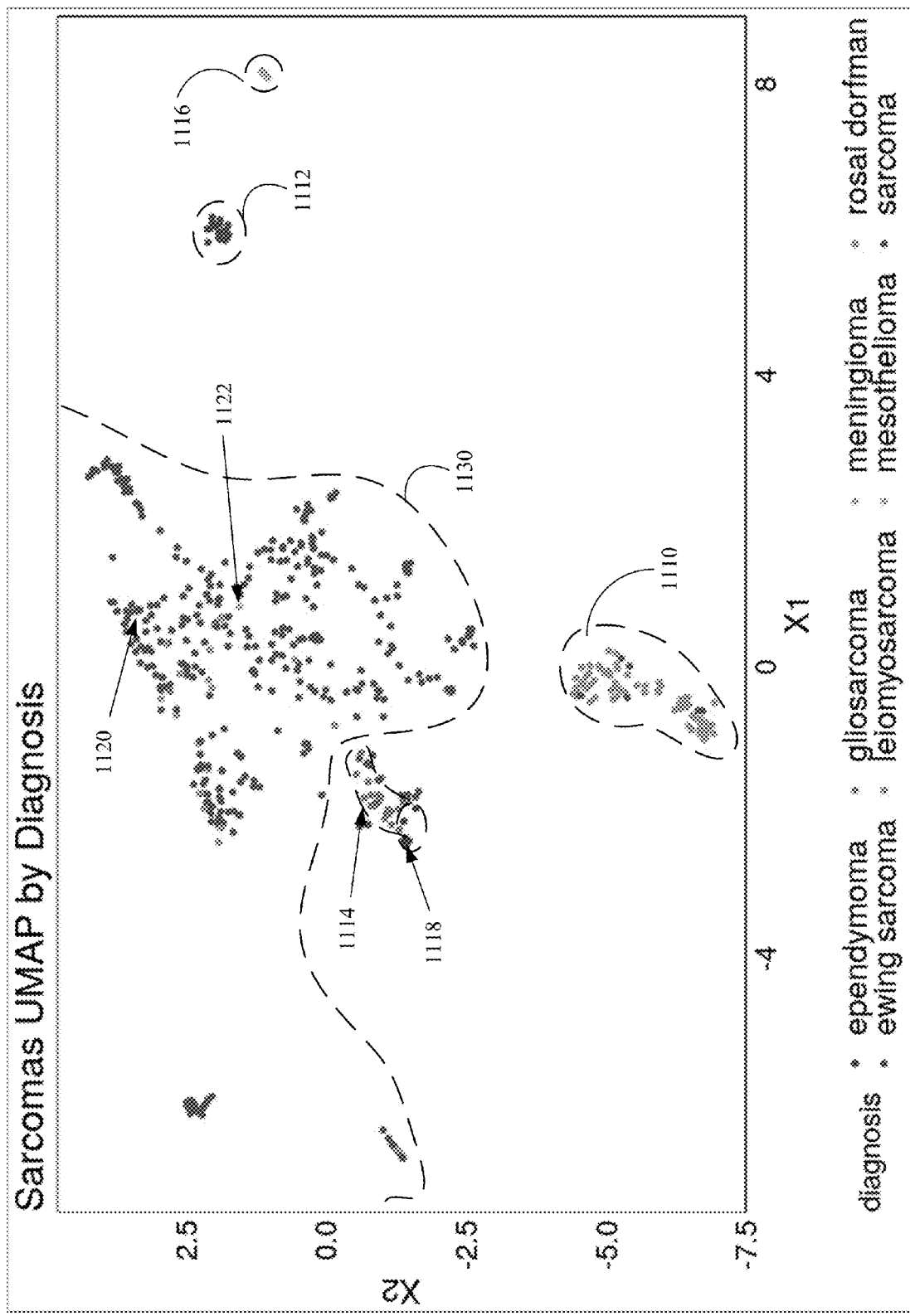

The rationale for choosing the most frequent label or label group is that the most frequent label may be more likely to be associated with a transcriptionally distinct cluster (e.g., in part due to the fact that having more data for a group makes it possible to differentiate said group). For example, as shown in FIG. 11B, there are distinct subgroups of sarcomas, some of which (e.g., leiomyosarcoma 1110, ewing sarcoma 1112, gliosarcoma 1114, meningioma 1116, and ependymoma 1118) are transcriptionally distinct (e.g., each defines a cluster). Conversely, both the rosai dorfman 1120 and mesothelioma 1122 subtypes do not define distinct clusters, instead being found within the general sarcoma 1130 cluster, and it is hence not possible to differentiate these subtypes using transcriptional data. In this example, leiomyosarcoma is the most common subtype, while mesothelioma and rosai dorfman are the least common subtypes, and it is possible that if there were more of the uncommon subtypes they would be found to form their own clusters.

The method proceeds either by i) rejecting the first partition label 2208 and returning to the previous label(s) 2210 and subsequently selecting a new first partition label, or ii) by accepting the first partition label, selecting a second partition label 2216, and proceeding with the clustering of samples 2212. Where the first partition label is accepted and a second partition label is proposed, the remaining samples 2214 may retain the initial label 2202. In some embodiments, this labeling process is repeated one or more times. In some embodiments, the labeling process is repeated a predetermined number of times.

Assessment of the similarity of labels may be based on NLP, analysis of published scientific literature, and/or consultation from physician pathologists (or any other medical practitioner). In some embodiments, more specific labels are automatically selected by the clustering method itself. In some embodiments, these more detailed labels that are selected as partitions are data that are associated with the sample. In some embodiments, these labels are text abstracted from clinical reports associated with the sample, such as other known metastatic sites (certain cancers may be more likely to metastasize to certain sites), histology (including cell composition, tissue morphology, and other features seen in pathology slides), raw/free text diagnosis, semantically related raw diagnoses, and cancer subtype. In some embodiments, additional detailed labels (especially ones used for the confounding factor analysis) include cancer stage, sample collection site/tissue type, patient age/gender/geographic location, etc. In some embodiments, the cancer subtype is a raw diagnosis from a pathology report.

Figure 11C:
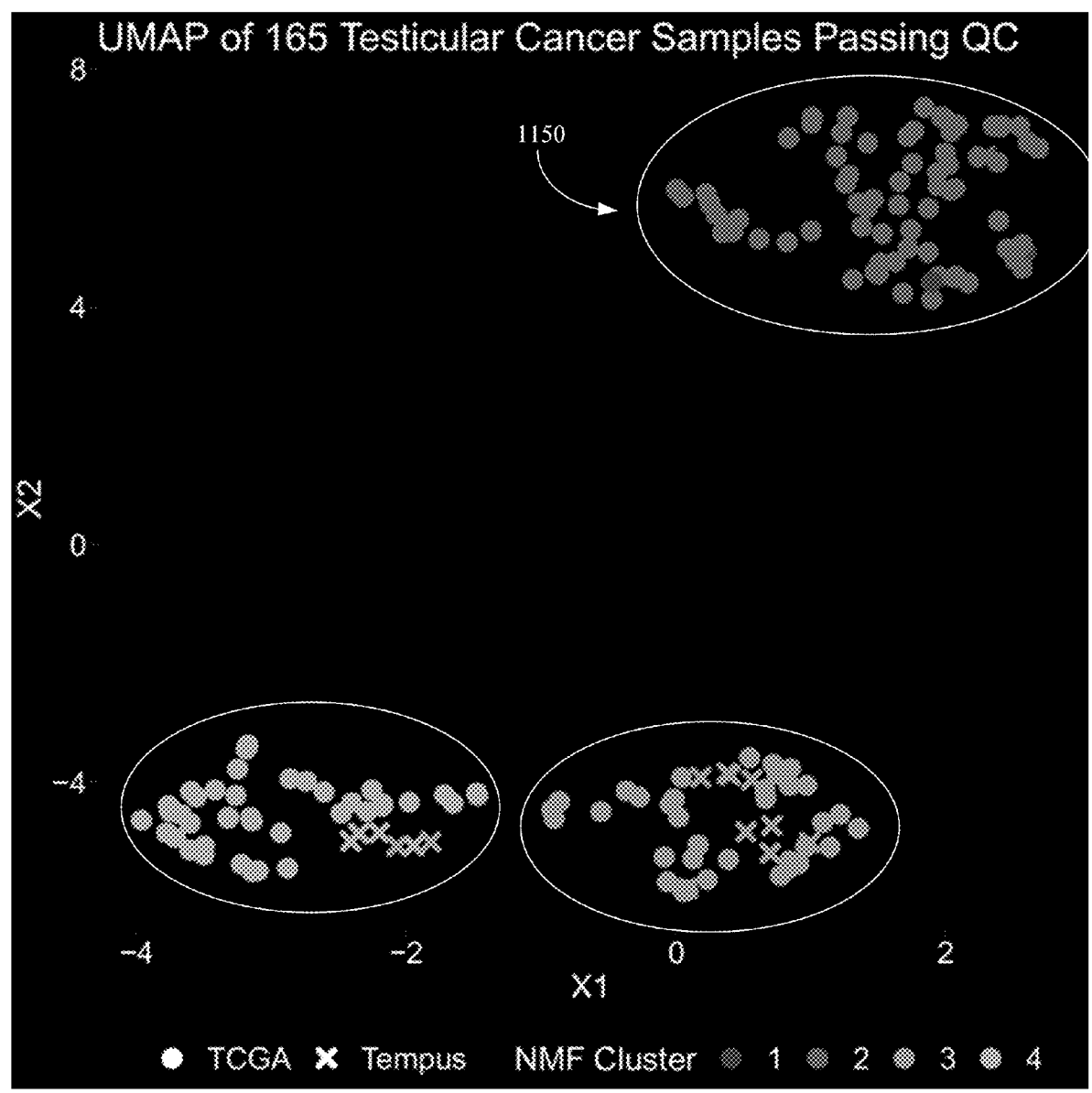

In some embodiments, clusters are evaluated by multiple clustering methods. For example, FIG. 11C shows clusters for 165 patients with testicular cancer. Both UMAP and non-negative matrix factorization (NMF) clustering methods provide similar results, thus helping to validate the overall clustering pipeline. In particular, cluster 1150 in FIG. 11C confirms that seminomas (which account for 50% of testicular cancer diagnoses) are transcriptionally distinct from other tumor types.

As illustrated in FIG. 12B, the results of repeating this cluster label analysis with multiple partition labels are somewhat more informative over classification with the broader label 'sarcoma.' Because text might be semantically related, in some embodiments, multiple sets of regular expressions are required to tag samples with associated labels (e.g., the NLP-derived labels as shown in Table 1 above).

In some embodiments, the steps involved in repeating the analysis include at least one or more of the following:

- In some embodiments, sources of variation associated with clusters are identified by labeling each sample in the figure either with the partition label or with an indication of non-label (e.g., based on whether the sample is associated with the first partition label (or another label within the group of similar labels) or not).
- In some embodiments, a correlation between the first partition label and a spatial cluster is qualitatively determined by assessing whether the majority of samples in one cluster are associated with the first partition label. In some embodiments, the majority of the samples associated with the first partition label are spatially organized into a single cluster. In some embodiments, the likelihood that a label determines the uniqueness of a cluster of RNA profiles is also quantitatively assessed (e.g., as described in the Mathematical Formulation and Cross Validation sections below).
- In some embodiments, each sample in the plurality of samples is separately labeled with one or more labels from a class of possible confounding factors (e.g., such as sample collection site, stage, etc.), as shown in FIG. 12C. In some embodiments, a qualitative assessment is made regarding whether a cluster is more closely associated with a confounding factor or with a partition label. In some embodiments, a quantitative assessment is also made regarding whether a cluster is more closely associated with a confounding factor or with a partition label.
- In some embodiments, a source of variation (e.g., a label) is associated with a pathologically distinct subtype (cluster), which is based on the clinical text associated with the cluster. In some embodiments, a label occurs frequently enough in the dataset to build one or more predictive models and is not being driven by a confounding factor, then replace the original cohort label in the training data with the partition label for samples associated with the partition label
- Retrain the model with the relabeled training data to generate a partition model
- Quantitatively assess first partition model performance
    - Perform 10-fold cross validation prediction to verify that the partition label can be accurately predicted from the expression data
    - Compare performance of partition model to performance of baseline model
    - Where a first partitioned model's performance is better than the baseline model performance, keep the partition label. In some embodiments, the performance of the first partitioned model does not exceed performance of the baseline model, samples labeled with the first partitioned label revert to broad disease type label, which may include discarding the partitioned model and reverting back to the baseline model
- Optionally: repeat the steps above to add one partition label at a time by selecting an additional partition label. The additional partition label may also be selected based on the frequency of label within the cohort, especially among samples in the cohort that are not associated with a previously added partition label
    - After selecting an additional partition label repeat cluster label/source of variation analysis by relabeling data points with additional partition label, retraining the model with relabeled data, and comparing the new model's performance to the most recent model's performance to further stratify diagnostic labels. FIG. 12B shows labeled clusters after three iterations of this process, in which the partition labels chosen for each round of analysis are leiomyosarcoma, gliosarcoma, and ewing sarcoma, respectively.

An issue with clustering is the absence of complete knowledge of all the factors informing each cluster (e.g., the presence of confounding factors). FIGS. 12B and 12C show the same clusters as in FIG. 12A. As shown in FIG. 12A, specific labels referring to sarcoma cancer conditions (e.g., leiomyosarcoma, gliosarcoma, and ewing sarcoma) are not neatly divided by transcriptional cluster (e.g., these labels do not align neatly with clusters 1202, 1204, and 1206). Likewise, in FIG. 12C, tissue site labels (e.g., lung, brain, uterus, liver, and breast) are not neatly segregated by these transcriptionally-defined clusters. Based on this analysis, leiomyosarcoma could be defined as a transcriptionally distinct cohort that should be classified separately from the rest of the sarcoma cohort; however, ewing sarcoma should be monitored, and gliosarcoma is probably not transcriptionally distinct enough to merit its own distinct diagnosis.

Figure 11D:
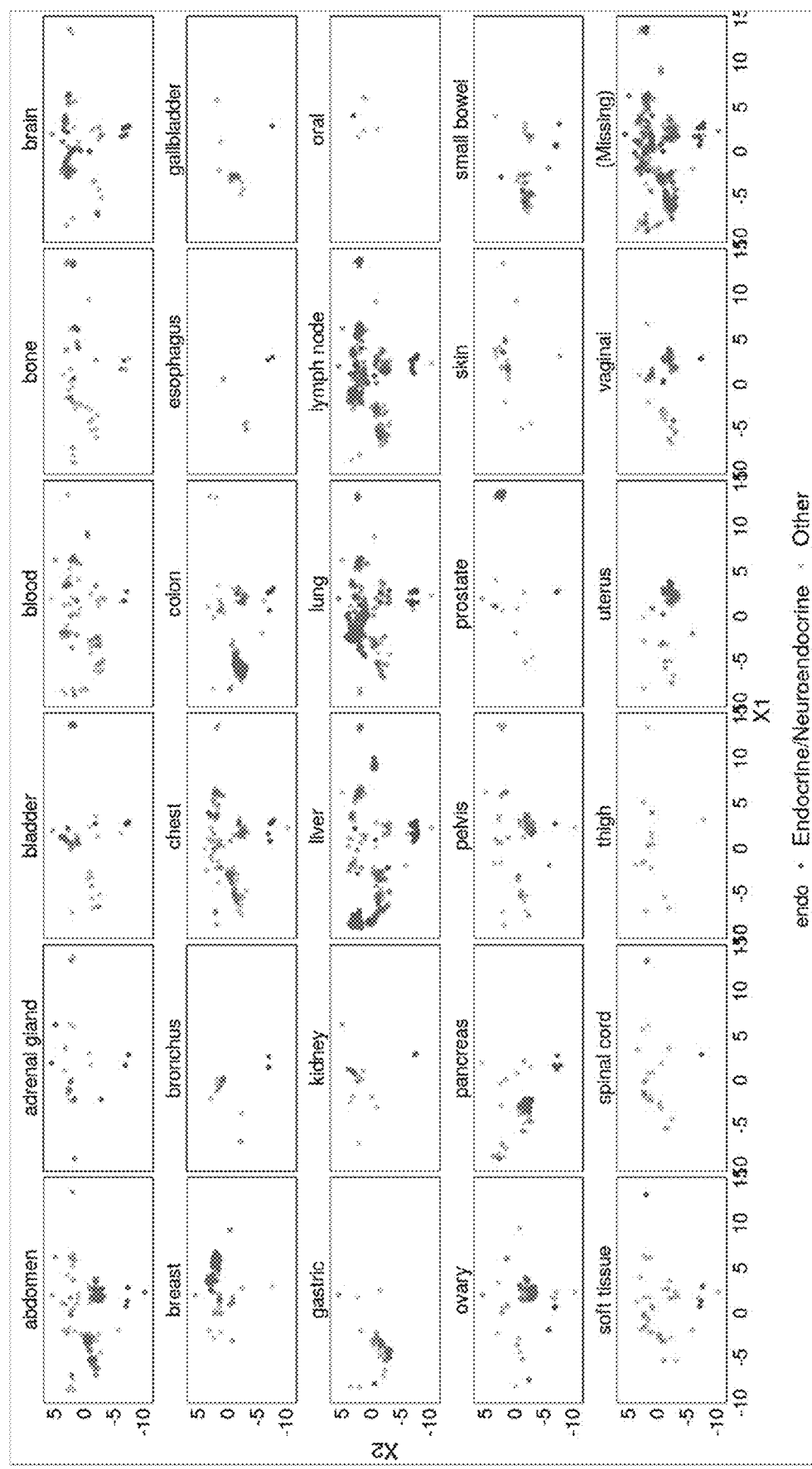

Similarly to FIG. 12C, FIG. 11D illustrates an example where biopsy location (e.g., tissue location of a tumor) is a potential confounding variable. Neuroendocrine tumors arise from specialized cells that occur throughout the body. Each UMAP plot in FIG. 11D represents transcriptome clustering of neuroendocrine tumors (e.g., the darker data points) biopsied from a particular tissue type (e.g., each panel corresponds to a particular tissue type).

This analysis reveals that these tumors are transcriptionally similar to each other (e.g., the cluster of neuroendocrine tumors is located in the same general region of each panel in FIG. 11D) regardless of their site of origin, and neuroendocrine tumors are transcriptionally distinct from other tumors (e.g., the lighter data points) from the matched site of origin.

Mathematical Formulation:

A partition label is used to define an additional cohort that improves classifier accuracy, where:

$$P(\text{class})*N(\text{class}) < P(\text{subclass 1})*N(\text{subclass 1}) + P(\text{subclass 2})*N(\text{subclass 2}).$$

In this equation, P is equal to the classification performance and N is equal to the number of samples in each class. In some embodiments, classifier performance is evaluated via F-scores, which are a measure of the sensitivity and specificity of the classes determined by a classifier in the multi-label context. If a diagnoses-associated partition (e.g., the use of an additional label describing a cancer condition) improves the performance of the dataset, then the model indicates that it is advantageous to split the dataset by stratifying the cohort into partitions or sub-cohorts. In some embodiments, the NLP-defined classes take samples from two higher order classes (which may have less specific labels), but the math remains similar.

In some embodiments, the classification model is trained using gene expression and pathology report data. The training method involves 10-fold cross validation (e.g., where each fold includes a mutually exclusive set—such as a tenth of the overall population—used for testing purposes). After training, an error analysis is performed for the classifier including at least a confusion matrix (see FIG. 13) that serves to identify potential causes for systematic errors. For example, in the specific classification model here the esophageal cancer cohort includes both squamous and epithelial cancers. The example classifier thus tends to err on these cancers, and classifies them as esophageal epithelial or other-tissue squamous. To improve this particular classification model, the esophageal cancer cohort could be divided into esophageal epithelial and esophageal squamous. In some embodiments, error analyses serve to indicate one or more disease types that are not well-determined by the classifier. As described previously, transcriptional changes can also be identified by dimensionality reduction and clustering algorithms such as non-negative matrix factorization (NMF) and clustering of UMAP embeddings.

If a confounding factor that is irrelevant to diagnosis—such as tissue site (e.g., as shown in FIG. 12C)—reduces the entropy of the dataset more than the diagnosis-associated partition for the same subset of samples, then that confounder is most likely the driver of variation and the diagnosis-based partition should not be made. In such cases, the label(s) with the potential cofounding variable (e.g., the tissue site labels in FIG. 12C) are removed from the set of labels used for clustering.

Example 7—Patient Reports and the Effect of Tumor Origin Prediction

Examples of patient reports are illustrated in FIGS. 10A-10G, each of which is a portion of a complete patient report.

FIGS. 10A-10D are sections of an example report prepared for a patient where a biopsy was taken from an epidural mass and where the tumor of origin prediction from the classification method is lung (e.g., Diagnosis 1002 "metastatic adenocarcinoma). FIG. 10E is a section from an example report prepared for a patient where a biopsy was taken from an ovary and where the tumor of origin prediction from the classification method is colorectal (e.g., Diagnosis 1026 "Mucinous adenocarcinoma, favor colorectal primary"). FIGS. 10F-10G are sections from an example report prepared for a patient where a biopsy was taken from the liver and where the tumor of origin prediction from the classification method is sarcoma (e.g., Diagnosis 1044 "Poorly-differentiated malignant neoplasm, favor sarcoma").

Figure 10A:
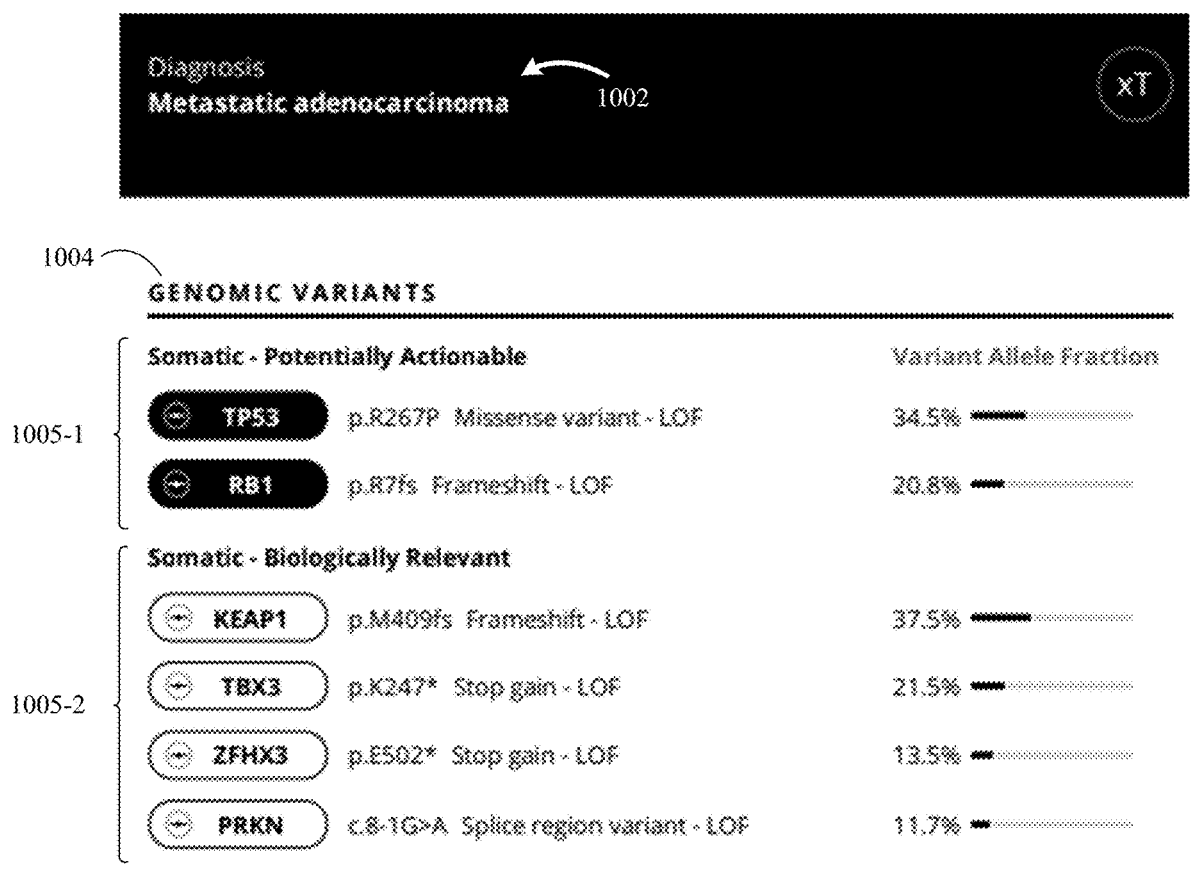
Figure 10B:
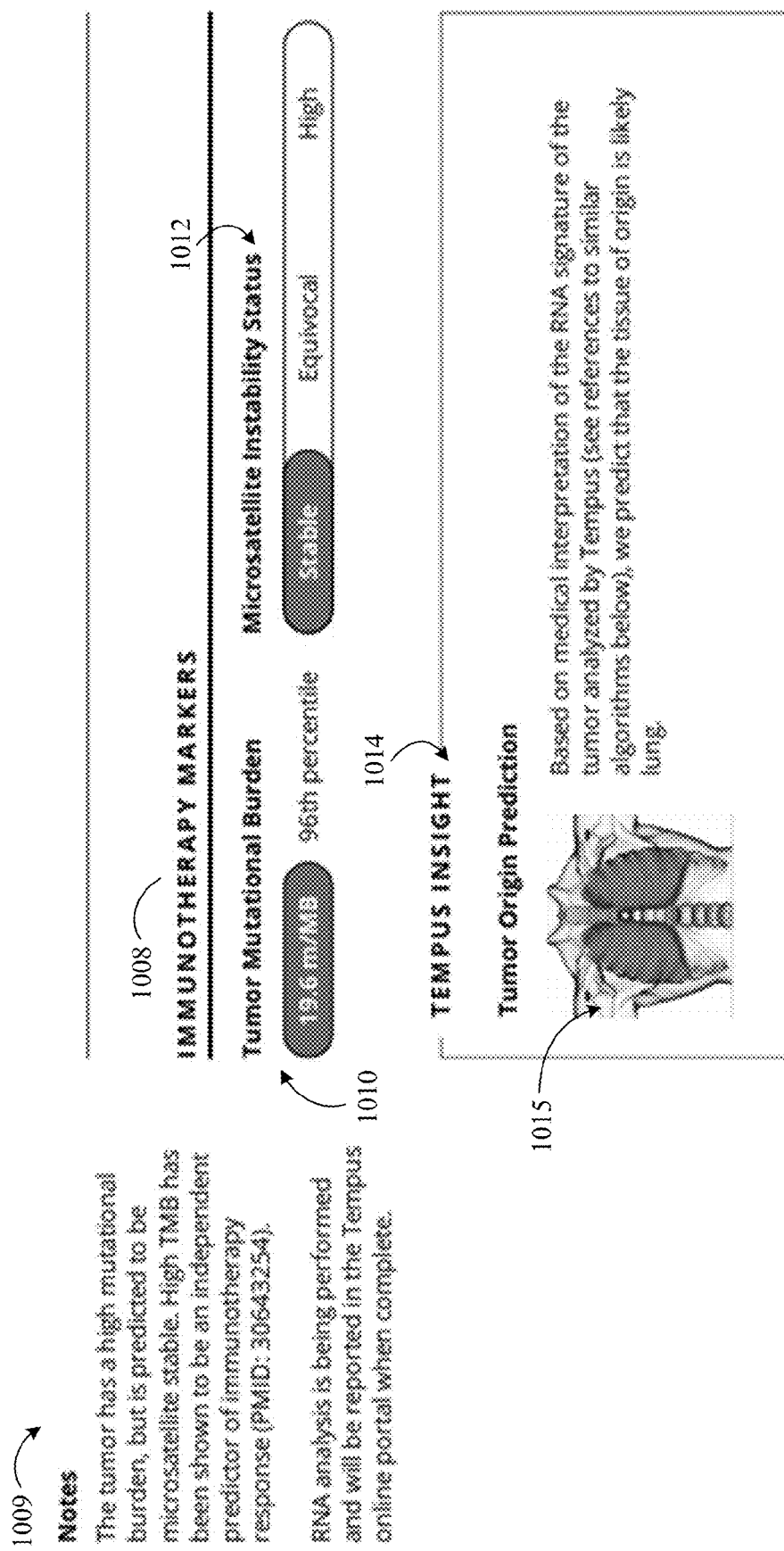
Figure 10E:
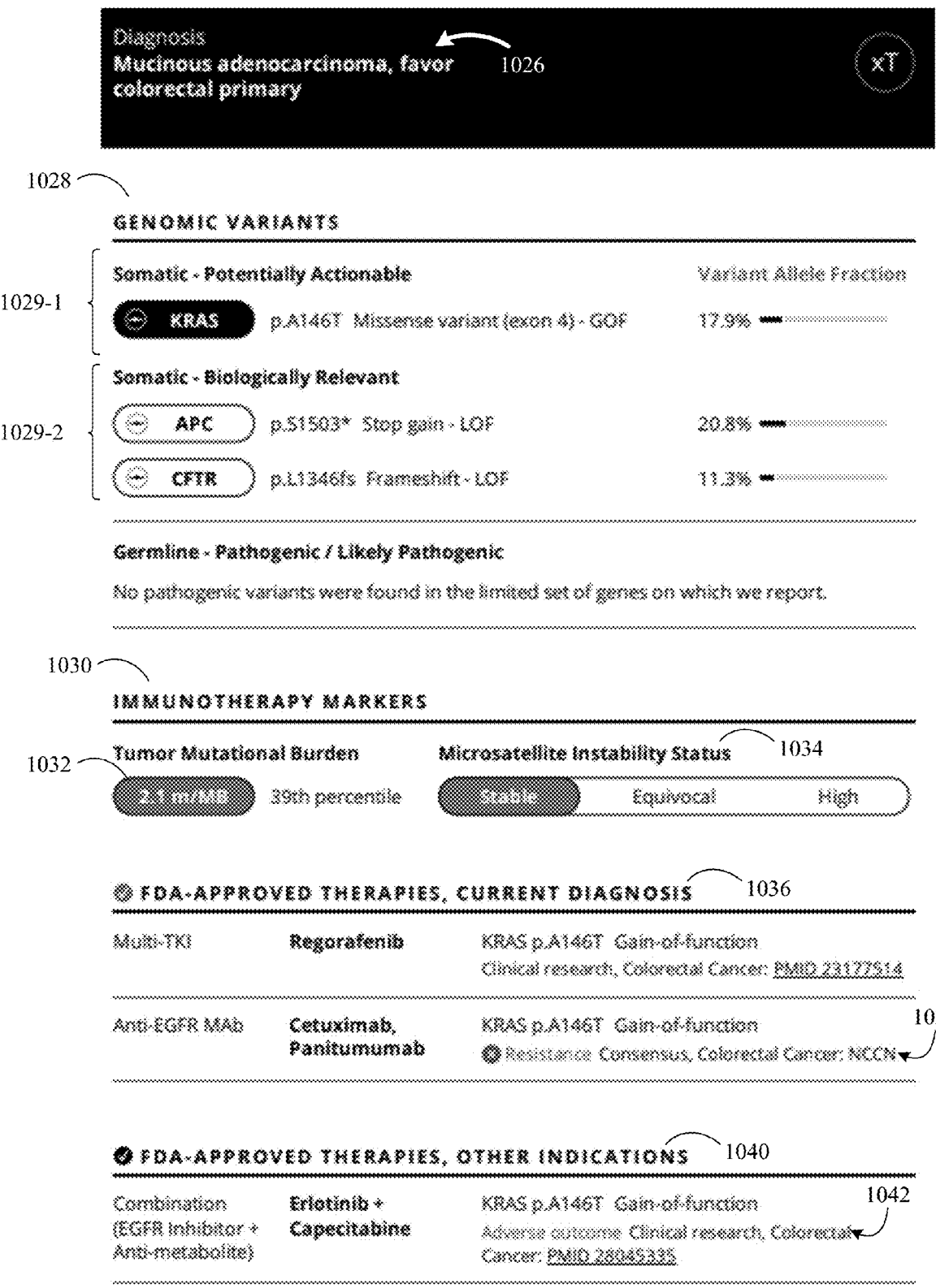
Figure 10F:
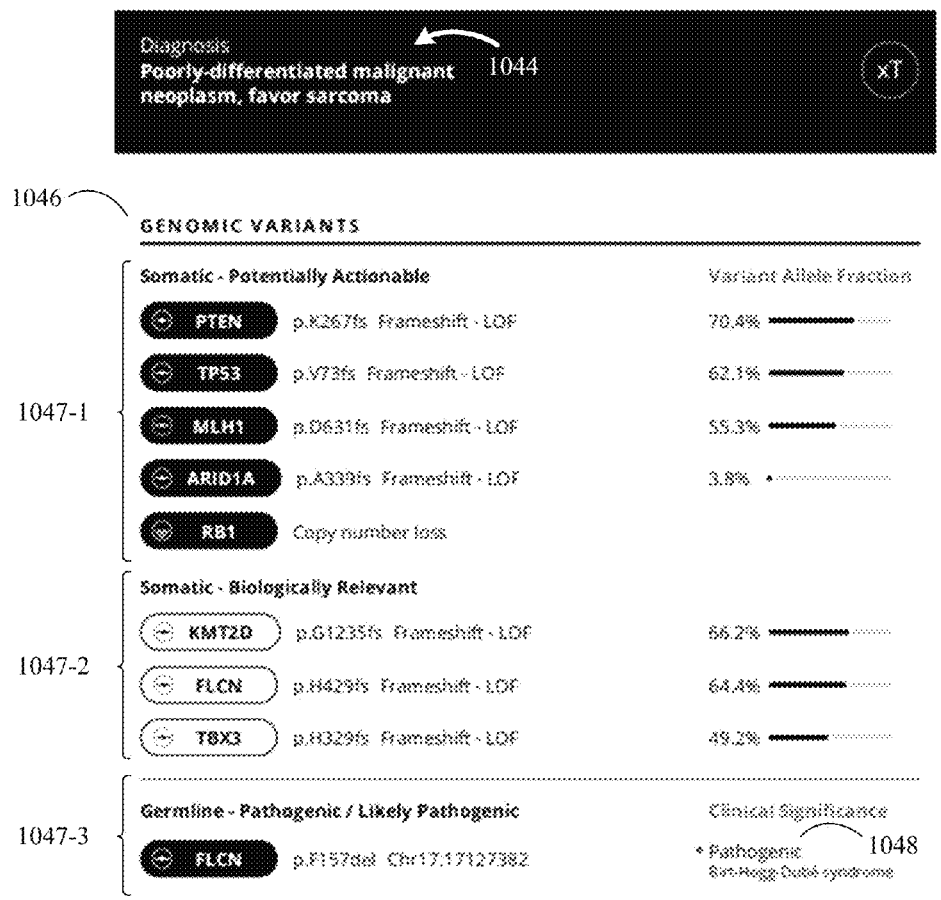
Figure 10G:
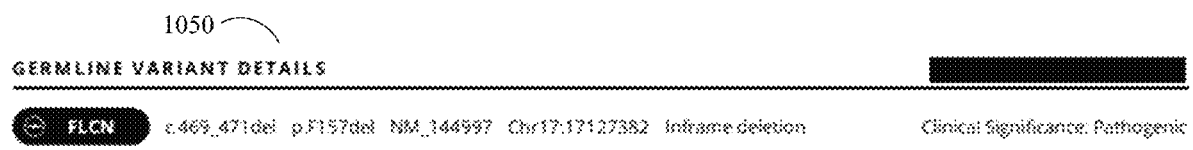

FIG. 10A includes information on genomic variants 1004: somatic variants that are potentially actionable 1005-1 (e.g., those with known treatment options), somatic, biologically relevant variants 1005-2. The report continues with FIG. 10B which includes sections on Immunotherapy markers 1008 and Tempus Insight 1014. Where appropriate, the patient report will include information regarding immunotherapy markers. The section on immunotherapy markers 1008 includes at least an indication of the tumor mutational burden 1010 and the microsatellite instability status 1012 of the subject. The Tempus Insight 1014, primarily includes a prediction of the patient's tumor origin location, which optionally includes an image illustrating the tumor origin location 1015. The report continues in FIG. 10C, which includes Treatment Implications 1016 and Clinical Trials 1018 that are relevant to the diagnosis 1026. In particular, the one or more clinical trials 1019 are determined to be relevant to the patient in accordance with the diagnosis and the genomic variants identified for the patient. The list of clinical trials may include additional information, including the phase of the trial (e.g., "Phase I"), the location of the trial (e.g., "Houston, Tex.") and characteristics of the subject that are in congruence with the requirements of each trial (e.g., the genomic requirement "TP53 mutation). The patient report in some cases includes information on genomic variants of unknown significance (e.g., the list 1020 here). Here the variants of unknown significance are all somatic. FIG. 10D continues the report with details on potentially actionable somatic variants 1022 and on biologically relevant somatic variants 1024.

FIG. 10E illustrates a second of an example report with the addition of FDA-approved therapies based either on the current diagnosis 1036 (e.g., diagnosis 1026) or on other indications 1040 (e.g., where the other indications are in some cases based on somatic or germline variants discovered for the patient). As shown here, the therapies include further information on either resistance 1038 that may arise from application of the therapy and/or adverse outcomes 1042 that may be associated with the respective therapy.

FIGS. 10F and 10G illustrate sections of an example report with a germline genomic variant (e.g., 1047-3) in addition to somatic genomic variants (e.g., lists 1047-1 and 1047-2). As shown here, the germline variant 1047-3 is pathogenic, in particular that the specific variant is indicative of Birt-Hogg-Dubé syndrome 1048. FIG. 10G provides further information 1050 on the germline variant.

By providing clear information on approved therapies, prognosis, and possible clinical trials, these patient reports give the ordering physician clinical decision-support information that the physician may choose to share with patients. As a result, patients may feel increased agency over their diagnosis and the direction of their treatment plan.

In some instances, a tumor origin prediction will alter the reported cancer condition included on the patient report. A change in the cancer condition, especially the cancer condition included in the reported diagnosis, may affect information in other sections of a patient report in significant ways. These other sections may include: the list of detected genetic variants (e.g., section 1004 in FIG. 10A) reported as biologically relevant (e.g., because the present of certain genetic variants is correlated with different cancer conditions), matched therapies (e.g., those that may be relevant for treating the patient based on the detected variants), evidence and/or strength of evidence cited for a matched therapy (e.g., where evidence includes relevant scientific publications, animal trials, clinical trials, etc.), or clinical trials reported as matching a patient case (e.g., especially if a clinical trial has inclusion/exclusion criteria that depend on cancer condition, relevant variants, or the disease status of metastatic versus non-metastatic). A change in the predicted cancer condition, will likely have implications for downstream patient treatment. For example, a clinical trial may require a patient to have breast cancer and may not accept patients who have a metastatic tumor in the breast tissue that originated in a non-breast tissue.

Establishing the tumor origin informs standard of care treatment for several NCCN targeted therapy guidelines. In some examples, a therapy may only be approved by the Food and Drug Administration (FDA) and/or National Comprehensive Cancer Network (NCCN) guidelines to target a certain gene variant in the context of specific cancer conditions. For example, the NCCN has approved the use of Dabrafenib to target BRAF specifically in the context of melanoma or non-small cell lung cancer.

The tumor origin prediction is also important for differentiating between relapse and recurrence of an established or older disease (for example, a metastatic tumor) versus a new disease (for example, a new primary tumor, or new malignancy in a patient). This is important because metastatic tumors are generally not treated with surgery or resection, and if a metastatic tumor is mistaken for a new primary tumor, a patient could lose organs to an unnecessary resection, which negatively impacts the patient's quality of life. For example, in a patient that has a history of benign kidney tumors who develops breast cancer, a new kidney tumor could cause a medical practitioner to order a nephrectomy for the patient. Later (e.g., after analysis of the extracted kidney tumor), the medical practitioner could discover that the new kidney tumor was in fact a metastatic breast tumor, implying that the tumor would have responded better to a treatment other than resection. In this case, without analyzing the origin of the tumor, the patient would lose a kidney unnecessarily. A similar hypothetical situation could result in the unnecessary resection of a lung lobe, a brain section, or any other portion of the body.

It is estimated that approximately 2-5% of all cancer samples are metastatic and thus not classifiable based merely on biopsy location (see e.g., Fizazi et al. 2011 Annals of Oncology 22(6), vi64-vi68; Stella et al. 2012 Journal of Translational Medicine 10:12; and Urban et al. 2013 British Journal of Cancer 109, 1318-1324). The methods described herein would improve the amount and quality of information available to support therapy decisions for patients with metastatic cancer.

Example 8—A Case Study of Using a Classification Model to Alter Diagnosis

In this example, a patient with multiple ongoing cancer diagnoses presented with new lesions. It was unclear from the pathology which of the ongoing cancers was responsible for the new lesions. A first treatment path, which was tailored to one of the patient's previous cancer diagnosis, was attempted but did not halt the progression of the metastatic lesions. Additional testing and classification changed the prediction of the tumor of origin of the new lesions and altered the course of treatment for the patient.

Figure 19A:
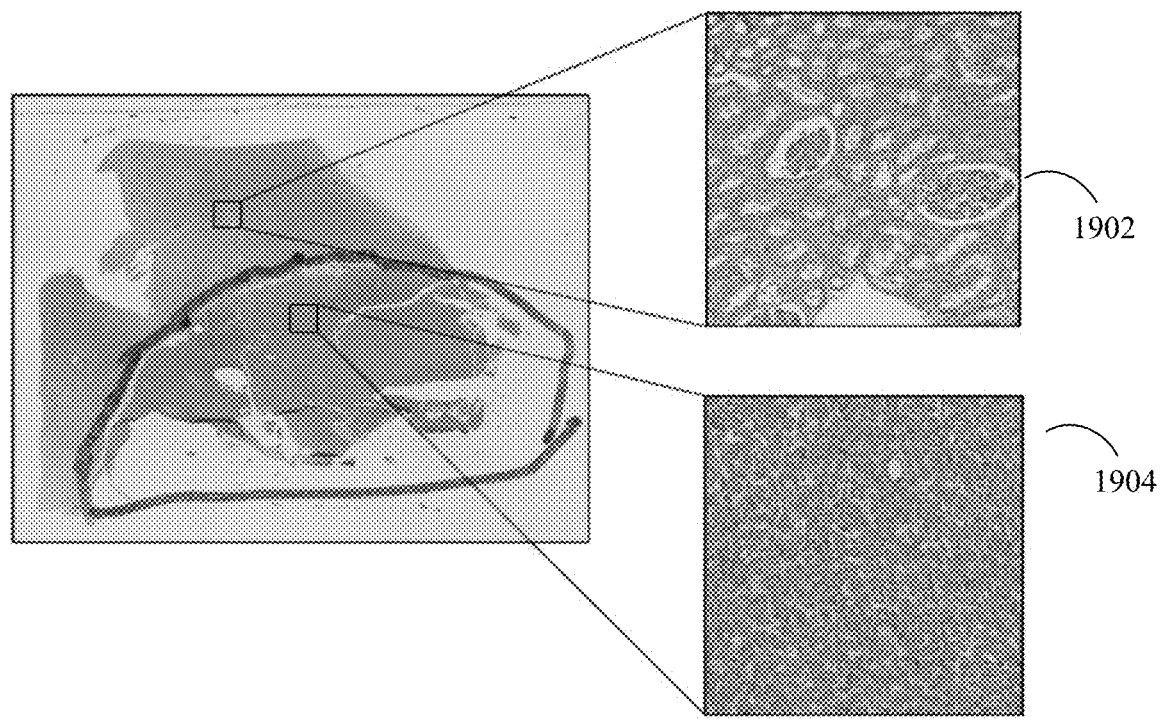
FIGS. 19A and 19B collectively illustrate a de-identified case study of an individual patient classified to a cancer condition in accordance with some embodiments of the present disclosure.

A 50 year old female was initially diagnosed with angiomyolipoma in the right kidney and subsequently diagnosed with metastatic breast cancer to the bone a year later. The initial breast cancer was treated with chemotherapy and radiation and went into remission. Angiomyolipoma is usually a benign lesion, and the patient underwent routine imaging surveillance without any growth in the lesion for sixteen years. At that point, the patient presented with splenic lesions on a routine imaging (e.g., as shown in the biopsy images 1902 and 1904 in FIG. 19A). Box 1902 shows healthy kidney cells and box 1904 shows cancerous cells from the metastatic tumor.

Pathological review of the splenic lesions showed both a GATA3 and Chromogranin A positive neoplasm with similar morphologic features to the previously diagnosed renal malignancy. This was an inconclusive result since GATA3 is a biomarker for breast cancer, and Chromogranin A is a biomarker for neuroendocrine cancer. The patient's inconclusive immunohistochemistry led to an initial diagnosis of renal neuroendocrine tumor based in part on the location of the lesions (e.g., the spleen is physically closer to the kidney than to breast tissue in the human body). The patient was subsequently treated with temozolomide, which is a treatment intended for neuroendocrine cancer, and later exhibited disease progression in the spleen and new lesions in the posterior mediastinum. The disease progression indicated that the treatment was unsuccessful, and prompted further analysis.

Figure 19B:
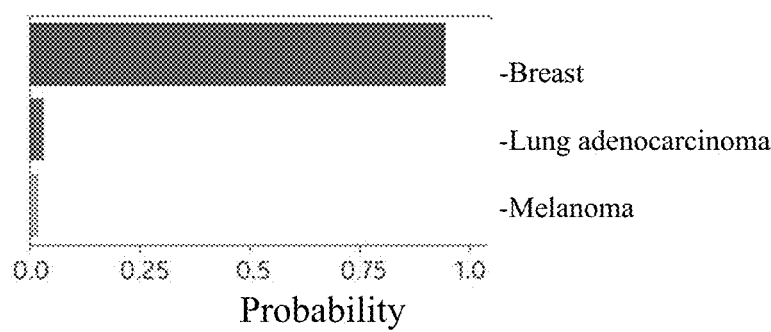

Given the aggressive clinical nature of the patient's disease, both DNA and RNA testing were performed on the patient's initial renal biopsy. The sequencing results identified activating somatic mutations in PIK3CA and GATA3. The history of a breast cancer diagnosis and uncertain histology led the pathology team to run the RNA-based classification model (e.g., as described herein in this disclosure) on the sample, which returned a prediction of breast cancer with high confidence (e.g., as shown in FIG. 19B).

The patient was subsequently enrolled in a breast cancer clinical trial, changing the course of her treatment to Tamoxifen and Alpelasib, a treatment that is tailored to her adjusted diagnosis of metastatic breast cancer and hence has a higher likelihood of impacting her cancer than any treatment targeted towards neuroendocrine neoplasm.

This example illustrates the difficulty of coming to an accurate diagnosis in cases where a patient exhibits more than one ongoing cancer condition. It demonstrates the particular value of tumor of origin detection for patients with one or more cancer diagnoses.

Example 9—Use of Viral Sequence Reads and DNA Variants in Classification

For some cases, it is possible to additional data for determining a cancer condition of a subject, and/or for training a classification model. For example, in some embodiments, DNA sequencing assays have probes that target sequences associated with oncogenic viruses such as HPV and RSV. The presence of viral DNA is a very strong biomarker for diagnosis, as viruses have high specificity in the types of cancer that they cause. In some embodiment, RNA reads associated with viruses are also detectable. In some embodiments, metagenomics pipelines determine a subset of sequencing reads from the first, second, and/or third pluralities of sequencing reads that do not map to the human transcriptome and aligns the subset of sequencing reads to viral and bacterial reference genomes. In some embodiments, this aligning determines a probable viral or bacterial source.

Figure 20:
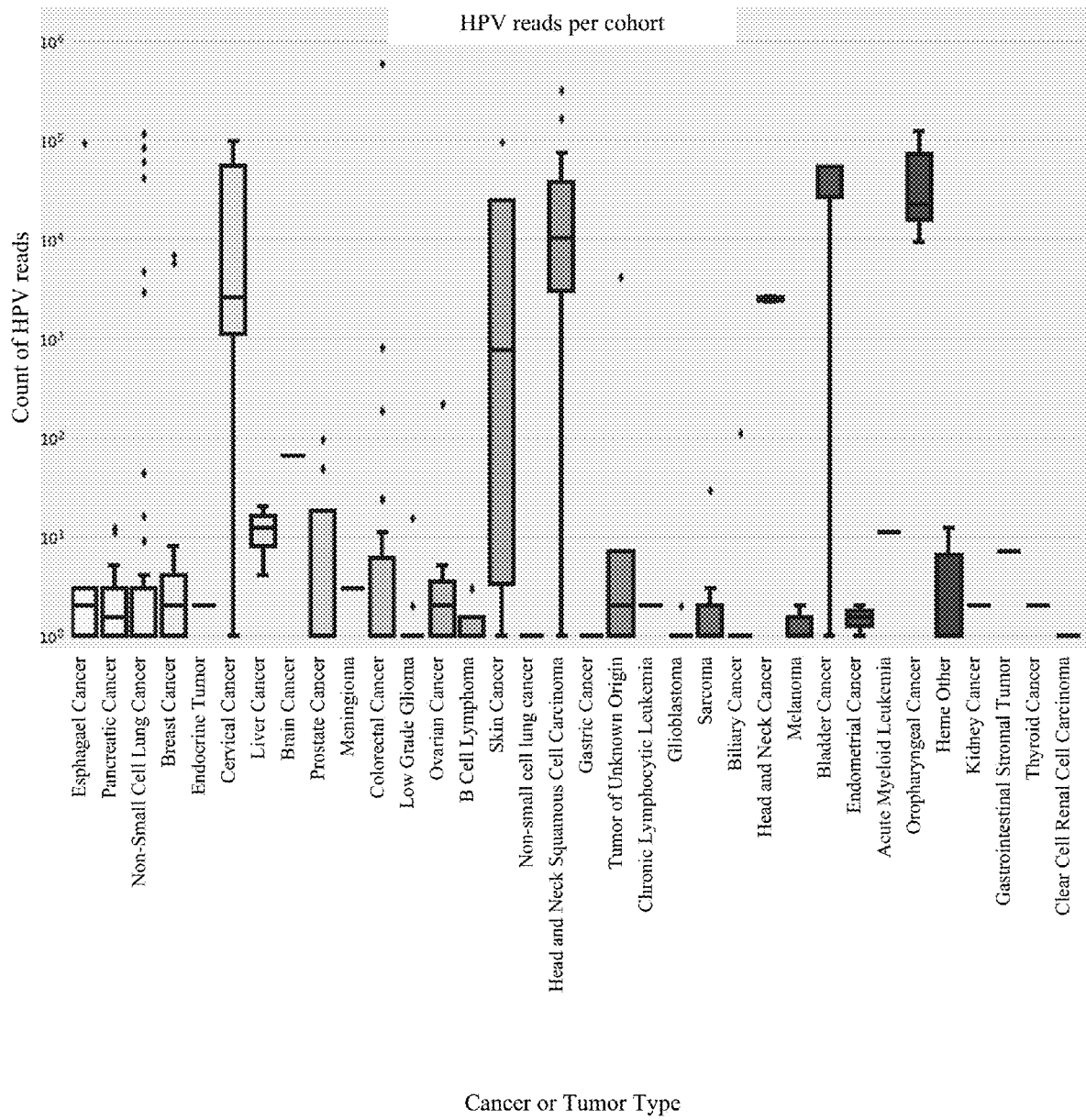
FIG. 20 illustrates an example of viral variants (e.g., viral features) associated with different cancer and tumor cohorts, in accordance with some embodiments of the present disclosure.

FIG. 20 illustrates that the number of HPV sequence reads detected in patient samples (e.g., as shown along the y-axis) may vary with the cancer condition and/or cohort associated with that sample (e.g., as arrayed along the x-axis). Here, data for training the classification model further include the number of HPV sequence reads detected in each reference subject. Including the number of HPV reads detected in a patient sample in the input data received by a model trained with these data, in some cases, improves the prediction accuracy of the model. In other cases, training and model input data instead include respective HPV infection status (for example, positive or negative) associated with each reference subject instead of the number of HPV sequence reads.

Another data type used in some embodiments for classifying a subject to a set of cancer conditions is DNA variants. Some DNA variants exhibit tissue specificity and thus provide information about organ and cell type origin of tumors. There are several ways to incorporate DNA variants into models that predict cancer type. In some embodiments, the total number of variants observed in a subject for an individual gene or locus serves as a proxy for the epigenetic state of the tumor cells (e.g., regions of open chromatin are more likely to experience mutation events).

As an example, driver variants exhibit diagnosis specificity. In particular, pancreatic and biliary cancers, despite having very similar transcriptional profiles and originating from adjacent organs, have large differences in their variant profiles. Pancreatic cancers are usually KRAS and P53 driven, whereas IDH1 variants or FGFR2 fusions are strong biomarkers for biliary (see e.g., FIGS. 21A-21C). On its own, DNA variant information is not a strong predictor of diagnosis. However, they often provide supporting evidence in the resolution of a diagnosis and are helpful for validation that the classification is working correctly.

Figure 21A:
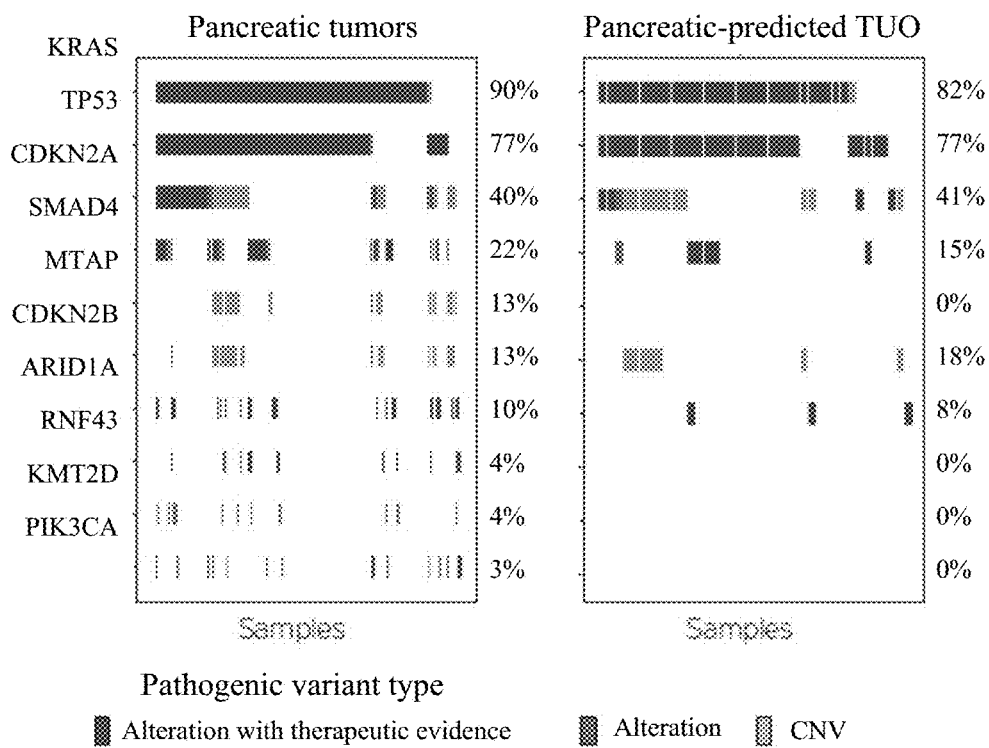
FIGS. 21A, 21B, and 21C collectively illustrate examples of genomic variant patterns associated with different cancer conditions, in accordance with some embodiments of the present disclosure.
Figure 21B:
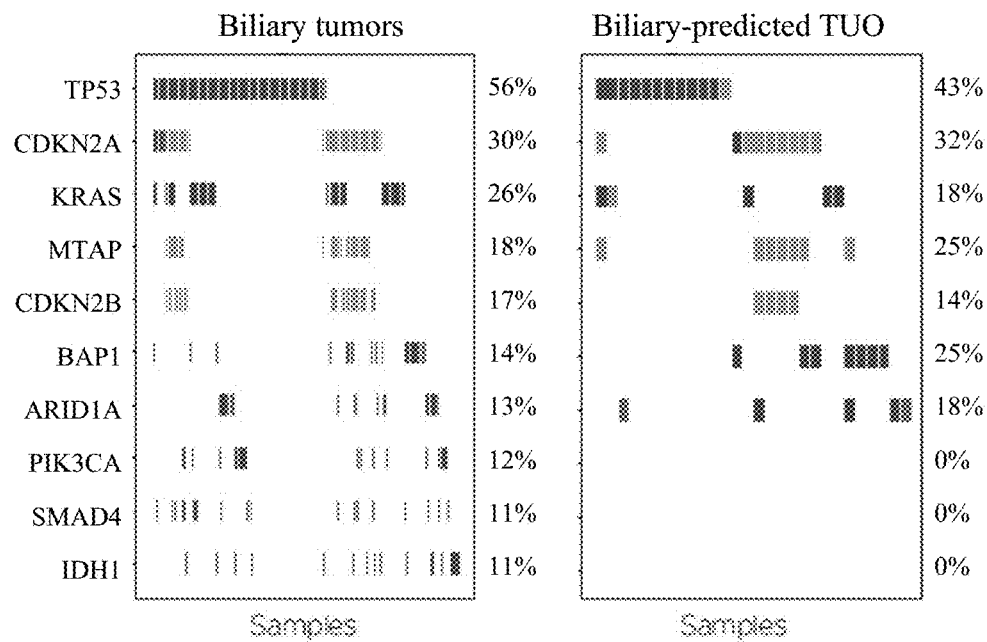
Figure 21C:
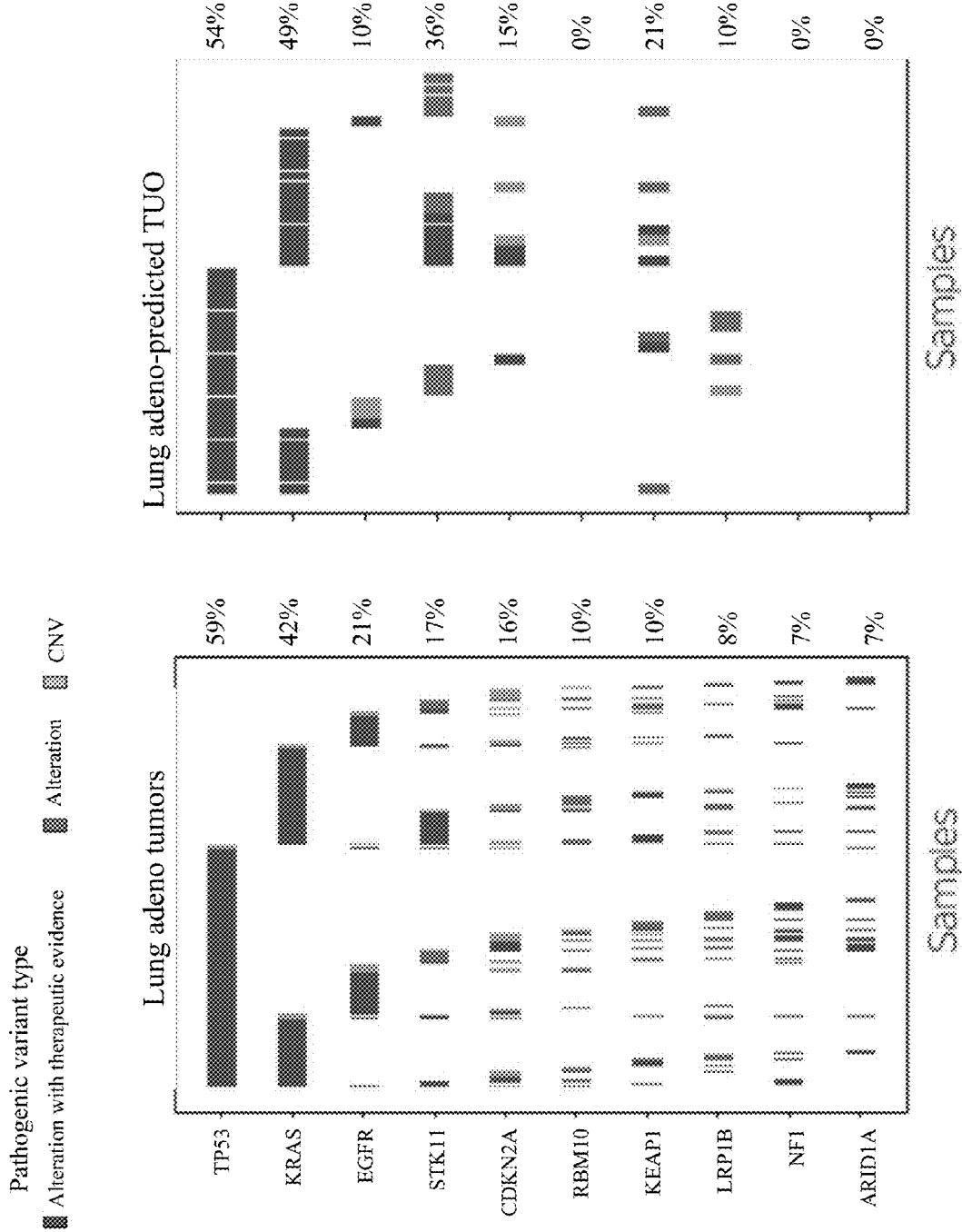

FIGS. 21A, 21B, and 21C illustrate examples of DNA variant patterns present in different cancer and tumor types. For example, FIG. 21A illustrates pancreatic tumor cancer genomic variant patterns. The pancreatic-predicted TUO (e.g., predicted tumor of origin) samples exhibit similar genomic variants. FIGS. 21B and 21C, likewise, illustrate the similarity in genomic variants for patients with known and predicted biliary cancer and known and predicted lung adenocarcinomas, respectively.

Both indications of viral infection and genomic variants are, in some embodiments, included in the classification methods described herein (e.g., for training the classification models and/or for classifying subjects).

CONCLUSION

The methods described herein provide improved cancer classification for patients. With improved accuracy and higher resolution over previous methods, the predictive algorithms provided herein can be used to resolve the diagnoses of tumors of unknown origin. With such increased resolution in the classification outputs, additional patients will receive more accurate diagnoses and more informed treatments.

REFERENCES CITED AND ALTERNATIVE EMBODIMENTS

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that comprises a computer program mechanism embedded in a non-transitory computer readable storage medium. For instance, the computer program product could contain the program modules shown in FIG. 1, and/or as described in FIGS. 2A, 2B, 2C, 3A, and 3B. These program modules can be stored on a CD-ROM, DVD, magnetic disk storage product, USB key, or any other non-transitory computer readable data or program storage product Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

What is claimed is:

1. A method for identifying a diagnosis of a cancer condition for a subject from among at least 50 different cancer conditions, the method comprising:
    sequencing a plurality of DNA molecules from a sample of a somatic tumor from the subject, thereby obtaining a first plurality of sequence reads of DNA from a somatic tumor of the subject;
    aligning each respective sequence read in the first plurality of sequence reads to a reference human genome, thereby generating a corresponding first plurality of aligned sequence reads;
    sequencing a plurality of mRNA molecules from the sample of the somatic tumor from the subject, thereby obtaining a second plurality of sequence reads of RNA from the somatic tumor of the subject;
    aligning each respective sequence read in the second plurality of sequence reads to a reference human transcriptome, thereby generating a corresponding second plurality of aligned sequence reads;
    identifying a plurality of features from the first plurality of aligned sequence reads and second plurality of aligned sequence reads, collectively, wherein the plurality of features comprises three or more subsets of features including a first subset of features comprising RNA expression features, a second subset of features comprising copy number features, and a third subset of features comprising DNA features, wherein:
        each RNA expression feature is associated with an expression level of a respective target region of the reference human transcriptome and represents a corresponding abundance of sequence reads, in the second plurality of aligned sequence reads, that map to the respective target region of the reference human transcriptome;
        each DNA feature is associated with a respective allele status in a respective target region of the reference human genome and represents a corresponding abundance of sequence reads with a corresponding reference or variant allele, in the first plurality of aligned sequence reads, that map to the respective target region of the reference human genome; and
        each copy number feature is associated with a target region of the reference human genome and represents a corresponding abundance of sequence reads, in the first plurality of aligned sequence reads, that map to the respective target region of the reference human genome; and
    evaluating the plurality of features using an ensemble classifier comprising (i) a set of intermediate classifiers that includes a first classifier, a second classifier, and a third classifier, and (ii) a final classifier, wherein
        the ensemble classifier uses the plurality of features to form:
        (a) for each respective classifier in the set of intermediate classifiers, a corresponding intermediate prediction by:
            obtaining a first intermediate prediction from among a first plurality of predictions for the cancer condition associated with the first classifier, by providing the first subset of features from the identified plurality of features as inputs to the first classifier, wherein the first classifier evaluates the first subset of features against each cancer condition in the at least 50 different cancer conditions to provide the first intermediate prediction;

obtaining a second intermediate prediction from among a second plurality of predictions for the cancer condition associated with the second classifier, by providing the second subset of features from the identified plurality of features as inputs to the second classifier; and obtaining a third intermediate prediction from among a third plurality of predictions for the cancer condition associated with the third classifier, by providing the third subset of features from the identified plurality of features as inputs to the third classifier, thereby forming a plurality of intermediate predictions; and (b) a determination of the cancer condition of the subject by combining, at the final classifier, the plurality of intermediate predictions that includes the first, second, and third intermediate predictions to identify the cancer condition for the subject from among the at least 50 different cancer conditions, wherein the determination of the cancer condition of the subject formed by the ensemble classifier comprises differentiating between general sarcomas, ependymoma, ewing sarcoma, gliosarcoma, leiomyosarcoma, meningioma, mesothelioma, and Rosai-Dorfman.

2. The method of claim 1, wherein combining, at the final classifier, the plurality of intermediate predictions further comprises:

scaling each intermediate prediction of the plurality of intermediate predictions based at least in part on a respective confidence level in each respective prediction to form a corresponding scaled prediction in a corresponding plurality of scaled predictions; and generating a combined prediction based at least in part on each scaled prediction by inputting each respective scaled prediction in the corresponding plurality of scaled predictions into the final classifier.

3. The method of claim 1, wherein:

the target regions of the reference human transcriptome associated with each RNA expression feature collectively represent a plurality of genes, and the plurality of genes comprises ten or more genes selected from the group consisting of GPM6A, CDX1, SOX2, NAPSA, CDX2, MUC12, SLAMF7, HNF4A, ANXA10, TRPS1, GATA3, SLC34A2, NKX2-1, SLC22A31, ATP10B, STEAP2, CLDN3, SPATA6, NRCAM, USH1C, SOX17, TMPRSS2, MECOM, WT1, CDHR1, HOXA13, SOX10, SALL1, CPE, NPR1, CLRN3, THSD4, ARL14, SFTPB, COL17A1, KLHL14, EPS8L3, NXPE4, FOXA2, SYT11, SPDEF, GRHL2, GBP6, PAX8, ANO1, KRT7, HOXA9, TYR, DCT, LYPD1, MSLN, TP63, CDH1, ESR1, HNF1B, HOXA10, TJP3, NRG3, TMC5, PRLR, GATA2, DCDC2, INS, NDUFA4L2, TBX5, ABCC3, FOLH1, HIST1H3G, S100A1, PTHLH, ACER2, RBBP8NL, TACSTD2, C19orf77, PTPRZ1, BHLHE41, FAM155A, MYCN, DDX3Y, FMN1, HIST1H3F, UPK3B, TRIM29, TXNDC5, BCAM, FAM83A, TCF21, MIA, RNF220, AFAP1, KRT5, SOX21, KANK2, GPM6B, C1orf116, FOXF1, MEIS1, EFHD1, and XKRX.

4. The method of claim 1, wherein the first plurality of sequence reads was generated by low pass, whole genome sequencing.

5. The method of claim 1, wherein the second plurality of sequence reads was generated from sequencing of cDNA.

6. The method of claim 1, wherein the ensemble classifier is trained by a method comprising:

obtaining, for each respective training subject in a plurality of training subjects, (i) the plurality of features, (ii) a respective training label for each respective classifier in the set of intermediate classifiers, and (iii) a respective label for the cancer condition of the respective training subject;

training, for each respective classifier in the set of intermediate classifiers, a respective initial model for the respective classifier that provides a respective initial intermediate prediction for each respective training subject based on at least, for each respective training subject in the plurality of training subjects, (i) a respective subset of features in the three or more subsets of features, and (ii) the respective training label for the respective classifier;

training a respective initial model for the final classifier that provides a corresponding initial diagnosis for the cancer condition based on at least, for each respective training subject in the plurality of training subjects,
  (i) for each respective classifier in the set of intermediate classifiers, a respective initial classification output from the respective initial model for the respective classifier for the respective training subject, and (ii) the respective label for the cancer condition of the respective training subject;

calculating, for each respective training subject in the plurality of training subjects, a respective entropy score for the respective training subject based at least in part on a respective initial diagnosis output from the initial model for the final classifier;

identifying an entropy threshold based at least in part on the accuracy of the initial model for the final classifier across the plurality of training subjects; and re-training the ensemble classifier based on respective training subjects in the plurality of training subjects whose respective entropy score satisfies the entropy threshold.

7. The method of claim 6, wherein identifying the entropy threshold comprises identifying a percentile of the accuracy of the initial model for the final classifier across the plurality of training subjects.

8. The method of claim 1, wherein identifying the diagnosis of the cancer condition further comprises:

receiving subject information comprising one or more clinical events; and differentiating the cancer condition between a new tumor and a recurrence of a previous tumor based at least in part on the one or more clinical events.

* * * * *